(12) United States Patent
Seganish et al.

(10) Patent No.: US 9,221,809 B2
(45) Date of Patent: Dec. 29, 2015

(54) AMINOPYRIMIDINONES AS INTERLEUKIN RECEPTOR-ASSOCIATED KINASE INHIBITORS

(71) Applicant: MERCK SHARP & DOHME CORP., Rahway, NJ (US)

(72) Inventors: W. Michael Seganish, Scotch Plains, NJ (US); Stephanie Nicole Brumfield, Cranbury, NJ (US); Jongwon Lim, Lexington, MA (US); Julius J. Matasi, Monmouth Junction, NJ (US); William T. McElroy, Plainfield, NJ (US); Deen B. Tulshian, Lebanon, NJ (US); Brian J. Lavey, New Providence, NJ (US); Michael D. Altman, Needham, MA (US); Craig R. Gibeau, Natick, MA (US); John William Lampe, Norfolk, MA (US); Joey Methot, Westwood, MA (US); Liang Zhu, Belmont, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/355,353

(22) PCT Filed: Oct. 26, 2012

(86) PCT No.: PCT/US2012/062016
§ 371 (c)(1),
(2) Date: Apr. 30, 2014

(87) PCT Pub. No.: WO2013/066729
PCT Pub. Date: May 10, 2013

(65) Prior Publication Data
US 2014/0329799 A1 Nov. 6, 2014

Related U.S. Application Data

(60) Provisional application No. 61/553,621, filed on Oct. 31, 2011.

(51) Int. Cl.
| | | |
|---|---|---|
| A61K 31/515 | (2006.01) | |
| C07D 417/04 | (2006.01) | |
| C07D 403/12 | (2006.01) | |
| C07D 401/14 | (2006.01) | |
| C07D 413/14 | (2006.01) | |
| C07D 491/08 | (2006.01) | |
| C07D 401/04 | (2006.01) | |
| C07D 417/14 | (2006.01) | |
| C07D 453/02 | (2006.01) | |
| C07D 471/08 | (2006.01) | |
| C07D 487/10 | (2006.01) | |
| C07D 491/10 | (2006.01) | |
| C07D 495/08 | (2006.01) | |
| C07D 513/04 | (2006.01) | |
| A61K 31/513 | (2006.01) | |
| A61K 31/5377 | (2006.01) | |
| A61K 45/06 | (2006.01) | |
| C07D 491/107 | (2006.01) | |

(52) U.S. Cl.
CPC ............ *C07D 417/04* (2013.01); *A61K 31/513* (2013.01); *A61K 31/5377* (2013.01); *A61K 45/06* (2013.01); *C07D 401/04* (2013.01); *C07D 401/14* (2013.01); *C07D 403/12* (2013.01); *C07D 413/14* (2013.01); *C07D 417/14* (2013.01); *C07D 453/02* (2013.01); *C07D 471/08* (2013.01); *C07D 487/10* (2013.01); *C07D 491/08* (2013.01); *C07D 491/10* (2013.01); *C07D 491/107* (2013.01); *C07D 495/08* (2013.01); *C07D 513/04* (2013.01)

(58) Field of Classification Search
CPC .. C07D 417/14; C07D 417/04; C07D 487/10; C07D 401/04; C07D 401/14; C07D 403/12; C07D 413/14; C07D 453/02; C07D 471/08; C07D 491/08; C07D 491/10; C07D 491/107; C07D 495/08; C07D 513/04; A61K 31/513; A61K 31/5377; A61K 45/06
See application file for complete search history.

(56) References Cited

U.S. PATENT DOCUMENTS

| | | |
|---|---|---|
| 4,910,204 A | 3/1990 | Walker et al. |
| 6,096,753 A | 8/2000 | Spohr et al. |
| 6,420,385 B1 | 7/2002 | Spohr et al. |
| 6,649,604 B2 | 11/2003 | Spohr et al. |
| 7,429,594 B2 | 9/2008 | Liu et al. |
| 2005/0038010 A1 | 2/2005 | Cao et al. |

(Continued)

FOREIGN PATENT DOCUMENTS

| | | |
|---|---|---|
| EP | 0178178 | 4/1986 |
| EP | 0156559 | 10/1986 |

(Continued)

OTHER PUBLICATIONS

B. Stanovinik et al.,91 Advances in Heterocyclic Chemistry, 1-134 (2006).*
G. Adembri et al., 45 Tetrahedron Letters, 4439-4442 (1978).*
G. Dannhardt et al., European Journal of Medicinal Chemistry, 599-604 (1991).*

(Continued)

*Primary Examiner* — Alexander R Pagano
(74) *Attorney, Agent, or Firm* — Matthew A. Leff; John C. Todaro

(57) ABSTRACT

This invention relates to aminopyrimidinone compounds of Formula (I) that are inhibitors of Interleukin receptor-associated kinases, in particular IRAK-4, and are useful in the treatment or prevention of inflammatory diseases, including rheumatoid arthritis and inflammatory bowel disease.

3 Claims, No Drawings

(56) References Cited

U.S. PATENT DOCUMENTS

2009/0042917 A1* 2/2009 Bessho et al. ............... 514/273
2009/0215801 A9    8/2009 Albert et al.

FOREIGN PATENT DOCUMENTS

| EP | 1184376 | 3/2002 |
| FR | 1381646 | 12/1964 |
| WO | WO8404040 | 10/1984 |
| WO | 8900423 A1 | 1/1989 |
| WO | WO 2006136442 A1 * | 12/2006 |
| WO | WO2008030579 | 3/2008 |
| WO | WO2009136995 A2 | 11/2009 |
| WO | 2010068863 A2 | 6/2010 |
| WO | WO2010112210 | 10/2010 |

OTHER PUBLICATIONS

J.N. Vishwakarma et al., 24B Indian Journal of Chemistry, Section B: Organic Chemistry Including Medicinal Chemistry, 466-471 (1985).*
CAS Registry No. 264610-55-1, CAS Client Services (May 12, 2000).*
http://www.cas.org/products/other-cas-products/client-services (downloaded Jan. 15, 2014).*
Li, Shyun et al, IRAK-4: A Novel member of the IRAK family with the properties of an IRAK-kinase, PNAS, Apr. 16, 2002, 5567-5572, vol. 99/Issue 8, PNAS, San Francisco.
Wang, Zhulun et al, IRAK-4 Inhibitors for Inflammation, Current Topics in Medicinal Chemistry, 2009, 724-737, vol. 9, San Francisco.
Vishwakarma et al, Organic Chemistry Including Medicinal Chemistry, Indian Journal of Chemistry, Section B, 1986, 466-471, 24.

* cited by examiner

AMINOPYRIMIDINONES AS INTERLEUKIN RECEPTOR-ASSOCIATED KINASE INHIBITORS

BACKGROUND OF THE INVENTION

This invention relates to aminopyrimidinone compounds that are inhibitors of Interleukin receptor-associated kinases, in particular IRAK-4, and are useful in the treatment or prevention of inflammatory diseases, including rheumatoid arthritis and inflammatory bowel disease.

Interleukin-1 receptor-associated kinases (IRAKs) are key components in the signal transduction pathways utilized by interleukin-1 receptor (IL-1R), interleukin-18 receptor (IL-18R), and Toll-like receptors (TLRs). Since TLRs initiate the first-wave of inflammatory signals and innate immune responses, they play a key role in many disease processes, including response to infections and auto-inflammatory disorders.

IRAK-4 belongs to a family of mammalian IRAKs that include IRAK-1, IRAK-2 and IRAK-M (also known as IRAK-3). IRAK-4 shares the domain structure of the other IRAKs and it is able to activate similar signal transduction pathways, namely NF-κB and MAPK pathways. It rapidly and transiently associates with IRAK-1 and TRAF6 in an IL-1-dependent manner but it is not functionally redundant with IRAK-1. Most strikingly, IRAK-4 is an active protein kinase and requires its kinase activity to activate NF-κB. Additionally, IRAK-4 might act upstream of IRAK-1 as an IRAK-1 activator. See Li, S. et al., "IRAK-4: a novel member of the IRAK family with the properties of an IRAK-kinase," Proc Natl Acad Sci USA. 2002 Apr. 16; 99(8):5567-72.

All four IRAK family members appear to play a role in Toll and IL-1R signaling. However, out of four members in the mammalian IRAK family, IRAK-4 is considered to be the "master IRAK", the only family member indispensable for IL-1R/TLR signaling. Mouse knock-out studies have demonstrated the essential role for IRAK-4 in IL-1R, IL-18R and most TLR signaling (see, Suzuki, N, et al, "Severe impairment of interleukin-1 and Toll-like receptor signaling in mice lacking IRAK-4," Nature, 2002, 416, 750-756). Furthermore, knock-in experiments by several groups have demonstrated that IRAK-4 requires its kinase activity for its function.

In humans, mutations resulting in IRAK-4 deficiency have been linked to susceptibility to bacterial infections, especially recurrent pyogenic bacterial infections (see, Picard, C., et al. "Pyogenic bacterial infections in humans with IRAK-4 deficiency." Science, 2003, 299, 2076-2079). While IRAK-4 deficient children are susceptible to certain pyogenic infections, adults are not prone to chronic infections. It is possible that protective immunity remains sufficiently preserved to protect against infection while modulation of IRAK-4 function through kinase inhibition may tone down inflammatory response.

Given the important role of IRAK-4 in inflammatory processes, modulation of IRAK-4 kinase activity presents an attractive therapeutic approach for the treatment of immune and inflammatory diseases. The recent success in the determination of the 3-dimensional structure of the IRAK-4 kinase domain in complex with inhibitors has facilitated the understanding of the mechanistic role of IRAK-4 in immunity and inflammation as well as the development of specific IRAK-4 kinase inhibitors. See, Wang, et al, "IRAK-4 Inhibitors for Inflammation," Current Topics in Medicinal Chemistry, 2009, 9, 724-737.

There exists a need in the art for small molecule compounds having desirable physiochemical properties as new therapeutic agents for treating or preventing inflammatory diseases, including rheumatoid arthritis and inflammatory bowel disease.

SUMMARY OF THE INVENTION

Disclosed herein are novel aminopyrimidinone compounds that are inhibitors of Interleukin receptor-associated kinases, in particular IRAK-4, and are useful for treating or preventing inflammatory diseases. The compounds disclosed herein may be illustrated by Formula (I):

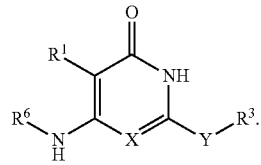

(I)

DETAILED DESCRIPTION OF THE INVENTION

The compounds disclosed herein are useful in the inhibition of Interleukin receptor-associated kinases, in particular IRAK-4, and are illustrated by a compound of Formula (I), or a pharmaceutically acceptable salt thereof:

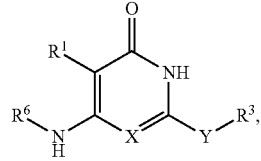

(I)

wherein X is —N= or —CH=; Y is selected from the group consisting of —NR$^2$—, —CH$_2$— and —O—;

or when Y is —NR$^2$—, R$^2$ and R$^3$ together with the nitrogen to which they are attached optionally form a 4- to 6-membered heterocyclic ring; wherein the 4- to 6-membered heterocyclic ring is optionally substituted with 1 to 3 substituents independently selected from R$^7$ groups;

R$^1$ is selected from the group consisting of:
(1) hydrogen,
(2) C$_{1-10}$ alkyl,
(3) C$_{3-8}$ cycloalkyl,
(4) aryl,
(5) heterocyclyl,
(6) halogen,
(7) —COOR$^7$,
(8) —NR$^7$,
(9) —SR$^7$,
(10) —OR$^7$,
(11) —SO$_2$R$^7$,
(12) —COR$^7$,
(13) —NCOR$^7$, and
(14) —CONR$^7$;

R$^2$ is selected from the group consisting of:
(1) hydrogen,
(2) C$_{1-10}$ alkyl, and
(3) C$_{3-4}$ cycloalkyl;

$R^3$ is selected from the group consisting of:
(1) hydrogen,
(2) $C_{1-10}$ alkyl,
(3) $C_{3-4}$ cycloalkyl,
(4) aryl,
(5) heterocyclyl, and
(6) —$COOR^7$;
$R^6$ is selected from the group consisting of:
(1) $C_{1-10}$ alkyl,
(2) $C_{3-4}$ cycloalkyl,
(3) aryl,
(4) heterocyclyl,
(5) —$COOR^7$,
(6) —$SO_2R^7$,
(7) —$COR^7$; and
$R^7$ is selected from the group consisting of:
(1) hydrogen,
(2) $C_{1-10}$ alkyl,
(3) $C_{3-4}$ cycloalkyl,
(4) aryl, and
(5) heteroaryl;
$R^8$ is selected from the group consisting of
(1) hydrogen, and
(2) $C_{1-6}$ alkyl;
wherein each of the $C_{1-10}$ alkyl, $C_{3-4}$ cycloalkyl, aryl and heterocyclyl of $R^1$, $R^3$, $R^6$ and $R^7$ is optionally substituted with 1-4 substituents independently selected from the group consisting of $C_{1-4}$ alkyl, $C_{1-4}$ alkoxy, halogen, —$SO_2R^8$ and —$OR^8$.

In one embodiment of the compounds of Formula (I), X is —N═; Y is —NH—;
$R^1$ is selected from the group consisting of:
(1) $C_{1-6}$ alkyl,
(2) $C_{3-6}$ cycloalkyl,
(3) aryl, and
(4) heterocyclyl;
$R^2$ is selected from the group consisting of:
(1) hydrogen,
(2) $C_{1-4}$ alkyl, and
$R^3$ is selected from the group consisting of:
(1) hydrogen,
(2) $C_{1-6}$ alkyl,
(3) $C_{3-6}$ cycloalkyl,
(4) aryl, and
(5) heterocyclyl;
$R^6$ is selected from the group consisting of:
(1) $C_{1-6}$ alkyl,
(2) $C_{3-6}$ cycloalkyl,
(3) aryl, and
(4) heterocyclyl;
$R^7$ is selected from the group consisting of:
(1) hydrogen,
(2) $C_{1-6}$ alkyl,
(3) $C_{3-6}$ cycloalkyl,
(4) aryl, and
(5) heteroaryl;
$R^8$ is selected from the group consisting of:
(1) hydrogen,
(2) methyl, and
(3) ethyl;
wherein each of the $C_{1-6}$ alkyl, $C_{3-6}$ cycloalkyl, aryl and heterocyclyl of $R^1$, $R^3$, $R^6$ and $R^7$ is optionally substituted with 1-3 substituents independently selected from the group consisting of $C_{1-4}$ alkyl, $C_{1-4}$ alkoxy, oxo, halogen, —$SO_2R^8$ and —$OR^8$.

In another embodiment of the compounds of Formula (I), X is —N═; Y is —NH—;

$R^1$ is selected from the group consisting of:
(1) $C_{1-6}$ alkyl,
(2) $C_{3-6}$ cycloalkyl,
(3) aryl, and
(4) heterocyclyl;
$R^2$ is selected from the group consisting of:
(1) hydrogen,
(2) $C_{1-4}$ alkyl, and
$R^3$ is selected from the group consisting of:
(1) hydrogen,
(2) $C_{1-6}$ alkyl,
(3) $C_{3-6}$ cycloalkyl,
(4) aryl, and
(5) heterocyclyl;
$R^6$ is selected from the group consisting of:
(1) $C_{1-6}$ alkyl,
(2) $C_{3-6}$ cycloalkyl,
(3) aryl, and
(4) heterocyclyl;
$R^7$ is selected from the group consisting of:
(1) hydrogen,
(2) $C_{1-6}$ alkyl,
(3) $C_{3-6}$ cycloalkyl,
(4) aryl, and
(5) heteroaryl;
$R^8$ is selected from the group consisting of:
(1) hydrogen,
(2) methyl, and
(3) ethyl;
wherein each of the $C_{1-6}$ alkyl, $C_{3-6}$ cycloalkyl, aryl and heterocyclyl of $R^1$, $R^3$, $R^6$ and $R^7$ is optionally substituted with 1-3 substituents independently selected from the group consisting of $C_{1-4}$ alkyl, $C_{1-4}$ alkoxy, oxo, halogen, —$SO_2R^8$ and —$OR^8$.

In another embodiment of the compounds of Formula (I), $R^1$ is phenyl or heterocyclyl.

In another embodiment of the compounds of Formula (I), $R^1$ is selected from the group consisting of phenyl, pyridinyl, pyrimidinyl,

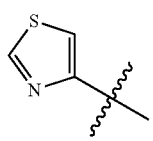 , 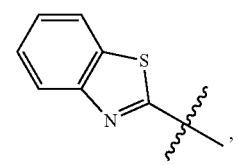 ,

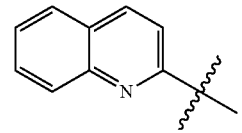 , and 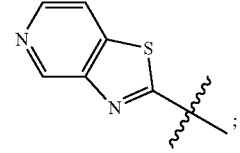 ;

wherein each of the foregoing $R^1$ group is optionally substituted with 1-3 substituents independently selected from methyl, ethyl, propyl, hydroxy, halogen, methoxy, ethoxy, oxo, phenyl optionally substituted with 1 or 2 groups independently selected from methyl and halogen.

In another embodiment of the compounds of Formula (I), $R^3$ is $C_{1-6}$ alkyl, $C_{3-6}$ cycloalkyl, aryl, a 4-7 membered monocyclic ring containing 1-3 hetero atoms selected from O, N and S, heteroaryl; wherein each of the foregoing $R^3$ group is optionally substituted with 1-3 substituents independently selected from methyl, ethyl, propyl, hydroxy, halogen, methoxy, ethoxy, oxo, —$SO_2$-methyl, heteroaryl and phenyl optionally substituted with 1 or 2 groups independently selected from methyl and halogen.

In another embodiment of the compounds of Formula (I), $R^3$ is selected from the group consisting of methyl, ethyl, propyl, butyl, cyclopropyl, cyclobutyl, cyclopentyl, cyclohexyl, phenyl, pyridinyl, pyrimidinyl,

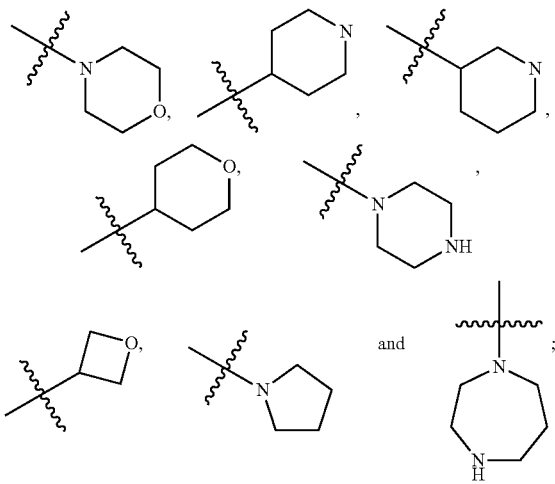

wherein each of the foregoing $R^3$ group is optionally substituted with 1-3 substituents independently selected from methyl, ethyl, propyl, hydroxy, halogen, methoxy, ethoxy, oxo, —SO$_2$-methyl, heteroaryl and phenyl optionally substituted with 1 or 2 groups independently selected from methyl and halogen.

In another embodiment of the compounds of Formula (I), $R^6$ is selected from the group consisting of $C_{1-6}$ alkyl, $C_{3-6}$ cycloalkyl, aryl and heteroaryl; wherein each of the foregoing $R^6$ group is optionally substituted with 1-3 substituents independently selected from methyl, ethyl, propyl, hydroxy, halogen, methoxy, ethoxy, oxo, —SO$_2$-methyl, heteroaryl and phenyl optionally substituted with 1 or 2 groups independently selected from methyl and halogen.

In another embodiment of the compounds of Formula (I), $R^6$ is selected from the group consisting of methyl, ethyl, propyl, butyl, cyclopropyl, cyclobutyl, cyclopentyl, cyclohexyl, phenyl, pyridinyl, pyrimidinyl,

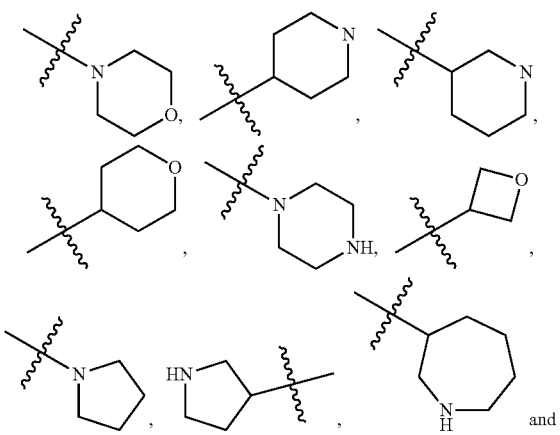

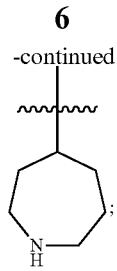

wherein each of the foregoing $R^6$ group is optionally substituted with 1-3 substituents independently selected from methyl, ethyl, propyl, hydroxy, halogen, methoxy, ethoxy, oxo, —SO$_2$-methyl, heteroaryl and phenyl optionally substituted with 1 or 2 groups independently selected from methyl and halogen.

In another embodiment of the compounds of Formula (I), $R^6$ is selected from the group consisting of cyclopropyl, cyclobutyl, cyclopentyl, cyclohexyl, phenyl, pyridinyl, pyrimidinyl,

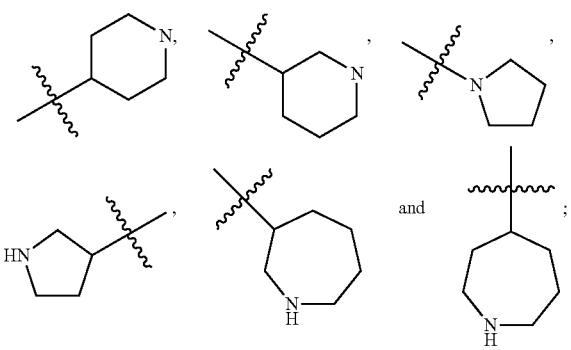

wherein each of the foregoing $R^6$ group is optionally substituted with 1-3 substituents independently selected from methyl, ethyl, propyl, hydroxy, halogen, methoxy, ethoxy, oxo, heteroaryl and phenyl optionally substituted with 1 or 2 groups independently selected from methyl and halogen.

In another embodiment of the compounds of Formula (I), X is —N═.

In another embodiment of the compounds of Formula (I), Y is selected from the group consisting of —NR$^2$—, —CH$_2$—, —CHR— and —O—, wherein R and R$^3$ optionally form a 4- to 6-membered cycloalkyl, cycloalkenyl or heterocyclic ring, wherein the 4- to 6-membered cycloalkyl, cycloalkenyl, or heterocyclic ring are optionally substituted with 1 to 3 substituents independently selected from R$^7$ groups; or when Y is —NR$^2$—, R$^2$ and R$^3$ together with the nitrogen to which they are attached optionally form a 4- to 6-membered heterocyclic ring, wherein the 4- to 6-membered heterocyclic ring is optionally substituted with 1 to 3 substituents independently selected from R$^7$ groups.

In another embodiment of the compounds of Formula (I), Y is selected from the group consisting of —NR$^2$—, —CH$_2$—, —CHR— and —O—, wherein R and R$^3$ optionally form a 4- to 6-membered heterocyclic ring, wherein the 4- to 6-membered heterocyclic ring is optionally substituted with 1 to 3 substituents independently selected from R$^7$ groups; or when Y is —NR$^2$—, R$^2$ and R$^3$ together with the nitrogen to which they are attached optionally form a 4- to 6-membered heterocyclic ring, wherein the 4- to 6-membered heterocyclic ring is optionally substituted with 1 to 3 substituents independently selected from R$^7$ groups.

In yet another embodiment, the compounds disclosed herein are illustrated by a compound of Formula (I), or a pharmaceutically acceptable salt thereof:

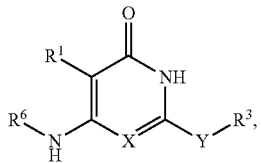

(I)

wherein
X is —N═ or —CH═;
Y is selected from the group consisting of —NR²—, —CH₂—, —CHR— and —O—, such that when Y is —CHR—, R and R³ together with the carbon to which they are attached optionally form a 4- to 6-membered cycloalkyl, cycloalkenyl or heterocyclic ring, wherein the 4- to 6-membered cycloalkyl, cycloalkenyl, or heterocyclic ring is optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸; or when Y is —NR²—, R² and R³ together with the nitrogen to which they are attached optionally form a 4- to 6-membered heterocyclic ring, wherein the 4- to 6-membered heterocyclic ring is optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸;
R¹ is selected from the group consisting of hydrogen, $C_{1-10}$ alkyl, $C_{3-8}$ cycloalkyl, aryl, heterocyclyl, halogen, —COOR⁷, —NHR⁷, —SR⁷, —OR⁷, —SO₂R⁷, —COR⁷, —NHCOR⁷, and —CONHR⁷; wherein said alkyl, cycloalkyl, aryl and heterocyclyl are optionally substituted with one to three substituents independently selected from the group consisting of $C_{1-4}$ alkyl, $C_{3-6}$ cycloalkyl, CN, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸, wherein said —NHR⁸ is optionally substituted with —N($C_{1-4}$ alkyl)NH₂ or —N($C_{3-6}$ cycloalkyl)NH₂;
R² is selected from the group consisting of hydrogen, $C_{1-10}$ alkyl, and $C_{3-8}$ cycloalkyl;
R³ is selected from the group consisting of hydrogen, $C_{1-10}$ alkyl, $C_{3-8}$ cycloalkyl, aryl, heterocyclyl, and —COOR⁷; wherein said alkyl, cycloalkyl, aryl and heterocyclyl are optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸;
R⁶ is selected from the group consisting of $C_{1-10}$ alkyl, $C_{3-8}$ cycloalkyl, aryl, heterocyclyl, —COOR⁷, —SO₂R⁷, and —COR⁷; wherein said alkyl, cycloalkyl, aryl and heterocyclyl are optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸;
R⁷ is selected from the group consisting of hydrogen, $C_{1-10}$ alkyl, $C_{3-8}$ cycloalkyl, aryl, and heteroaryl; wherein said alkyl, cycloalkyl, aryl and heterocyclyl are optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸; and
R⁸ is selected from the group consisting of hydrogen, $C_{1-6}$ alkyl and $C_{3-6}$ cycloalkyl.

In another embodiment of the compounds of Formula (I), wherein,
X is —N═;
Y is selected from the group consisting of —NR²—, —CH₂—, —CHR— and —O—, such that when Y is —CHR—, R and R³ together with the carbon to which they are attached optionally form a 4- to 6-membered heterocyclic ring, wherein the 4- to 6-membered heterocyclic ring is optionally substituted with one to three substituents independently selected from the group consisting of $C_{1-4}$ alkyl, $C_{3-4}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸; or when Y is —NR²—, R² and R³ together with the nitrogen to which they are attached optionally form a 4- to 6-membered heterocyclic ring, wherein the 4- to 6-membered heterocyclic ring is optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸;
R¹ is selected from the group consisting of hydrogen, $C_{1-10}$ alkyl, $C_{3-8}$ cycloalkyl, aryl, heterocyclyl, halogen, —COOR⁷, —NHR⁷, —SR⁷, —OR⁷, —SO₂R⁷, —COR⁷, —NHCOR⁷, and —CONHR⁷; wherein said alkyl, cycloalkyl, aryl and heterocyclyl are optionally substituted with one to three substituents independently selected from the group consisting of $C_{1-4}$ alkyl, $C_{3-6}$ cycloalkyl, CN, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸, wherein said —NHR⁸ is optionally substituted with —N($C_{1-4}$ alkyl)NH₂ or —N($C_{3-6}$ cycloalkyl)NH₂;
R² is selected from the group consisting of hydrogen, $C_{1-10}$ alkyl, and $C_{3-8}$ cycloalkyl;
R³ is selected from the group consisting of hydrogen, $C_{1-10}$ alkyl, $C_{3-8}$ cycloalkyl, aryl, heterocyclyl, and —COOR⁷; wherein said alkyl, cycloalkyl, aryl and heterocyclyl are optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸;
R⁶ is selected from the group consisting of $C_{1-10}$ alkyl, $C_{3-8}$ cycloalkyl, aryl, heterocyclyl, —COOR⁷, —SO₂R⁷, and —COR⁷; wherein said alkyl, cycloalkyl, aryl and heterocyclyl are optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸;
R⁷ is selected from the group consisting of hydrogen, $C_{1-10}$ alkyl, $C_{3-8}$ cycloalkyl, aryl, and heteroaryl; wherein said alkyl, cycloalkyl, aryl and heterocyclyl are optionally substituted with one to three substituents independently selected from the group consisting of $C_{1-4}$ alkyl, $C_{3-6}$ cycloalkyl, phenyl, $CF_3$, heterocyclyl, halogen, —COOR⁸, —NHR⁸, —SR⁸, —OR⁸, —SO₂R⁸, —COR⁸, —NHCOR⁸, and —CONHR⁸; and R⁸ is selected from the group consisting of hydrogen, C₁₋₄ alkyl and C₃₋₆ cycloalkyl.

In another embodiment of the compounds of Formula (I), wherein,

X is —N═;
Y is selected from the group consisting of —NR²— and —CHR—, such that when Y is —CHR—, R and R³ together with the carbon to which they are attached optionally form a 4- to 6-membered heterocyclic ring, wherein the 4- to 6-membered heterocyclic ring is optionally substituted with one to three substituents independently selected from the group consisting of C₁₋₄ alkyl, C₃₋₆ cycloalkyl, phenyl, CF₃, heterocyclyl, halogen, —COOR⁸, —NHR⁸, —SR⁸, —OR⁸, —SO₂R⁸, —COR⁸, —NHCOR⁸, and —CONHR⁸; or when Y is —NR²—, R² and R³ together with the nitrogen to which they are attached optionally form a 4- to 6-membered heterocyclic ring, wherein the 4- to 6-membered heterocyclic ring is optionally substituted with one to three substituents independently selected from the group consisting of C₁₋₄ alkyl, C₃₋₆ cycloalkyl, phenyl, CF₃, heterocyclyl, halogen, —COOR⁸, —NHR⁸, —SR⁸, —ORB, —SO₂R⁸, —COR⁸, —NHCOR⁸, and —CONHR⁸;
R¹ is selected from the group consisting of hydrogen, C₁₋₁₀ alkyl, C₃₋₈ cycloalkyl, aryl, heterocyclyl, halogen, —COOR⁷, —NHR⁷, —SR⁷, —OR⁷, —SO₂R⁷, —COR⁷, —NHCOR⁷, and —CONHR⁷; wherein said alkyl, cycloalkyl, aryl and heterocyclyl are optionally substituted with one to three substituents independently selected from the group consisting of C₁₋₄ alkyl, C₃₋₆ cycloalkyl, CN, phenyl, CF₃, heterocyclyl, halogen, —COOR⁸, —NHR⁸, —SR⁸, —OR⁸, —SO₂R⁸, —COR⁸, —NHCOR⁸, and —CONHR⁸, wherein said —NHR⁸ is optionally substituted with —N(C₁₋₄ alkyl)NH₂ or —N(C₃₋₆ cycloalkyl)NH₂;
R² is selected from the group consisting of hydrogen, C₁₋₁₀ alkyl, and C₃₋₈ cycloalkyl;
R³ is selected from the group consisting of hydrogen, C₁₋₁₀ alkyl, C₃₋₈ cycloalkyl, aryl, heterocyclyl, and —COOR⁷; wherein said alkyl, cycloalkyl, aryl and heterocyclyl are optionally substituted with one to three substituents independently selected from the group consisting of C₁₋₄ alkyl, C₃₋₆ cycloalkyl, phenyl, CF₃, heterocyclyl, halogen, —COOR⁸, —NHR⁸, —SR⁸, —OR⁸, —SO₂R⁸, —COR⁸, —NHCOR⁸, and —CONHR⁸;
R⁶ is selected from the group consisting of C₁₋₁₀ alkyl, C₃₋₈ cycloalkyl, aryl, heterocyclyl, —COOR⁷, —SO₂R⁷, and —COR⁷; wherein said alkyl, cycloalkyl, aryl and heterocyclyl are optionally substituted with one to three substituents independently selected from the group consisting of C₁₋₄ alkyl, C₃₋₆ cycloalkyl, phenyl, CF₃, heterocyclyl, halogen, —COOR⁸, —NHR⁸, —SR⁸, —OR⁸, —SO₂R⁸, —COR⁸, —NHCOR⁸, and —CONHR⁸;
R⁷ is selected from the group consisting of hydrogen, C₁₋₁₀ alkyl, C₃₋₈ cycloalkyl, aryl, and heteroaryl; wherein said alkyl, cycloalkyl, aryl and heterocyclyl are optionally substituted with one to three substituents independently selected from the group consisting of C₁₋₄ alkyl, C₃₋₆ cycloalkyl, phenyl, CF₃, heterocyclyl, halogen, —COOR⁸, —NHR⁸, —SR⁸, —OR⁸, —SO₂R⁸, —COR⁸, —NHCOR⁸, and —CONHR⁸; and
R⁸ is selected from the group consisting of hydrogen, C₁₋₆ alkyl and C₃₋₆ cycloalkyl.

In another embodiment of the compounds of Formula (I),

X is —N═;
Y is —NR²—, wherein R² and R³ together with the nitrogen to which they are attached form a 4- to 6-membered heterocyclic ring; wherein the 4- to 6-membered heterocyclic ring is optionally substituted with 1 to 3 substituents independently selected from R⁷ groups;
R¹ is selected from the group consisting of:
(1) C₁₋₆ alkyl,
(2) C₃₋₆ cycloalkyl,
(3) aryl, and
(4) heterocyclyl;
R⁶ is selected from the group consisting of:
(1) C₁₋₆ alkyl,
(2) C₃₋₆ cycloalkyl,
(3) aryl, and
(4) heterocyclyl;
R⁷ is selected from the group consisting of:
(1) hydrogen,
(2) C₁₋₄ alkyl,
(3) C₃₋₆ cycloalkyl,
(4) aryl, and
(5) heteroaryl;
wherein each of the C₁₋₆ alkyl, C₃₋₄ cycloalkyl, aryl and heterocyclyl of R¹, R⁶ and R⁷ is optionally substituted with 1-3 substituents independently selected from the group consisting of C₁₋₄ alkyl, C₁₋₄ alkoxy, oxo, and halogen.

In another embodiment of the compounds of Formula (I), R² and R³ together with the nitrogen to which they are attached form a 4- to 6-membered heterocyclic ring selected from

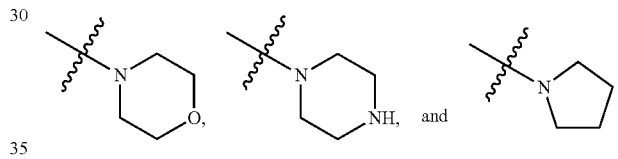

optionally substituted with 1 to 3 substituents independently selected from methyl, ethyl, propyl, hydroxy, halogen, methoxy, and ethoxy.

In another embodiment of the compounds of Formula (I), R¹ is phenyl or heterocyclyl.

In another embodiment of the compounds of Formula (I), R¹ is selected from the group consisting of phenyl, pyridinyl, pyrimidinyl,

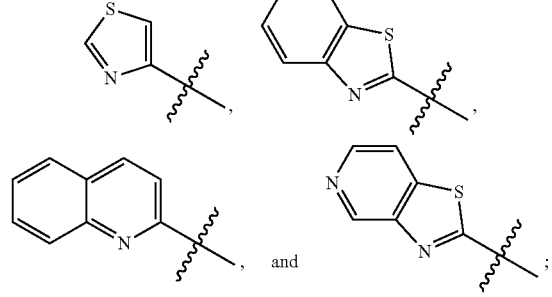

wherein each of the foregoing R¹ group is optionally substituted with 1-3 substituents independently selected from methyl, ethyl, propyl, hydroxy, halogen, methoxy, ethoxy, oxo, phenyl optionally substituted with 1 or 2 groups independently selected from methyl and halogen.

In another embodiment of the compounds of Formula (I), R¹ is selected from the group consisting of phenyl, pyridinyl, pyrimidinyl,

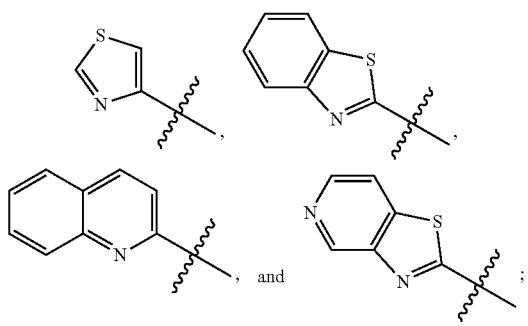

wherein each of the foregoing R¹ group is optionally substituted with 1-3 substituents independently selected from methyl, ethyl, propyl, hydroxy, halogen, methoxy, and ethoxy.

In another embodiment of the compounds of Formula (I), $R^6$ is selected from the group consisting of $C_{1-6}$ alkyl, $C_{3-6}$ cycloalkyl, aryl and heteroaryl; wherein each of the foregoing $R^6$ group is optionally substituted with 1-3 substituents independently selected from methyl, ethyl, propyl, hydroxy, halogen, methoxy, ethoxy, oxo, —SO₂-methyl, heteroaryl and phenyl optionally substituted with 1 or 2 groups independently selected from methyl and halogen.

In another embodiment of the compounds of Formula (I), $R^6$ is selected from the group consisting of methyl, ethyl, propyl, butyl, cyclopropyl, cyclobutyl, cyclopentyl, cyclohexyl, phenyl, pyridinyl, pyrimidinyl,

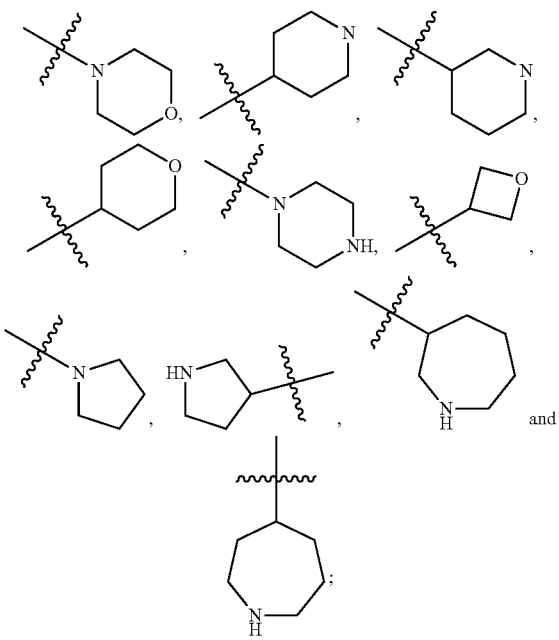

wherein each of the foregoing $R^6$ group is optionally substituted with 1-3 substituents independently selected from methyl, ethyl, propyl, hydroxy, halogen, methoxy, ethoxy, oxo, —SO₂-methyl, heteroaryl and phenyl optionally substituted with 1 or 2 groups independently selected from methyl and halogen.

In another embodiment of the compounds of Formula (I), $R^6$ is selected from the group consisting of cyclopropyl, cyclobutyl, cyclopentyl, cyclohexyl, phenyl, pyridinyl, pyrimidinyl,

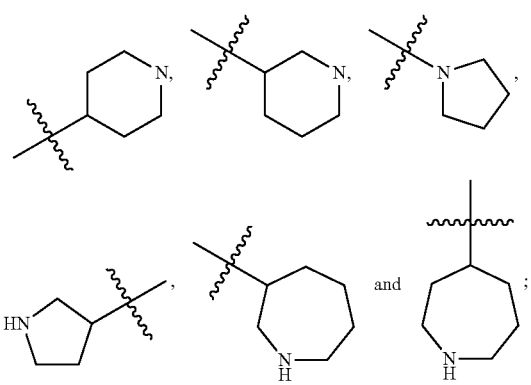

wherein each of the foregoing $R^6$ group is optionally substituted with 1-3 substituents independently selected from methyl, ethyl, propyl, hydroxy, halogen, methoxy, ethoxy, oxo, heteroaryl and phenyl optionally substituted with 1 or 2 groups independently selected from methyl and halogen.

In another embodiment of the compounds of Formula (I), $R^6$ is selected from the group consisting of cyclopropyl, cyclobutyl, cyclopentyl, cyclohexyl, phenyl, pyridinyl, pyrimidinyl,

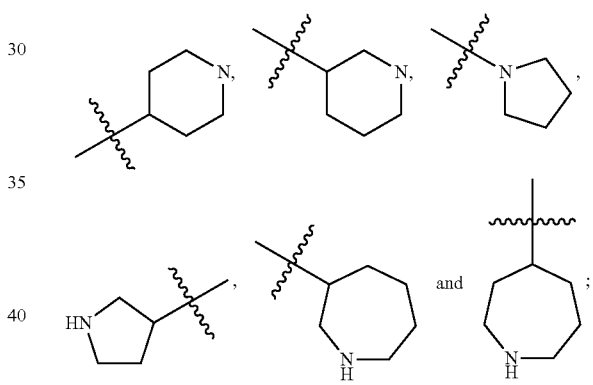

wherein each of the foregoing $R^6$ group is optionally substituted with 1-3 substituents independently selected from methyl, ethyl, propyl, hydroxy, halogen, methoxy, and ethoxy.

In another embodiment of Formula (I), $R^1$ is selected from the group consisting of phenyl, pyridinyl, pyrimidinyl,

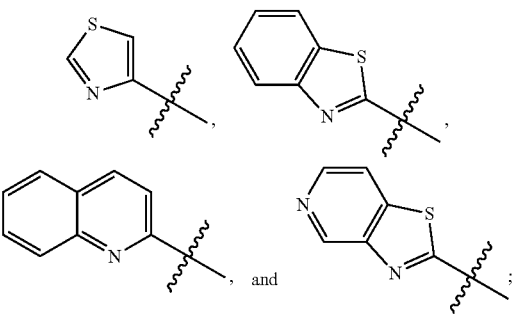

wherein each of the foregoing $R^1$ group is optionally substituted with 1-3 substituents independently selected from methyl, ethyl, propyl, hydroxy, halogen, methoxy, ethoxy, oxo, phenyl optionally substituted with 1 or 2 groups independently selected from methyl and halogen.

In another embodiment of Formula (I), $R^6$ is selected from the group consisting of $C_1$ alkyl, $C_{3-6}$ cycloalkyl, aryl and heteroaryl; wherein each of the foregoing $R^6$ group is optionally substituted with 1-3 substituents independently selected from methyl, ethyl, propyl, hydroxy, halogen, methoxy, ethoxy, oxo, —$SO_2$-methyl, heteroaryl and phenyl optionally substituted with 1 or 2 groups independently selected from methyl and halogen.

In another embodiment of Formula (I), $R^6$ is selected from the group consisting of methyl, ethyl, propyl, butyl, cyclopropyl, cyclobutyl, cyclopentyl, cyclohexyl, phenyl, pyridinyl, pyrimidinyl,

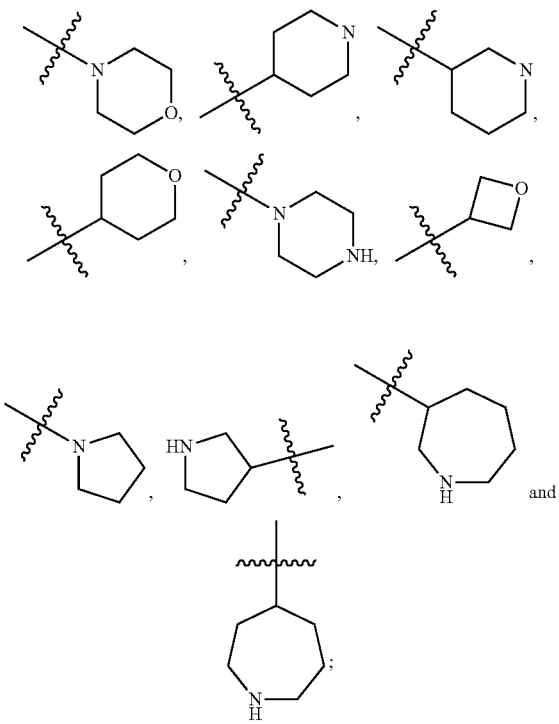

wherein each of the foregoing $R^6$ group is optionally substituted with 1-3 substituents independently selected from methyl, ethyl, propyl, hydroxy, halogen, methoxy, ethoxy, oxo, —$SO_2$-methyl, heteroaryl and phenyl optionally substituted with 1 or 2 groups independently selected from methyl and halogen.

In another embodiment of Formula (I), $R^6$ is selected from the group consisting of cyclopropyl, cyclobutyl, cyclopentyl, cyclohexyl, phenyl, pyridinyl, pyrimidinyl,

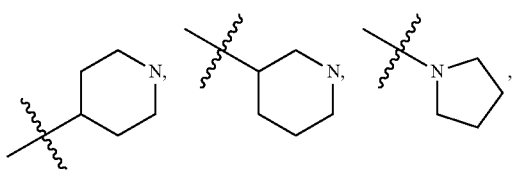

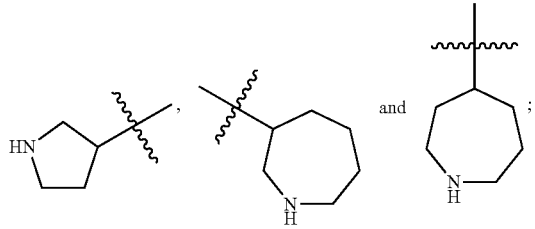

wherein each of the foregoing $R^6$ group is optionally substituted with 1-3 substituents independently selected from methyl, ethyl, propyl, hydroxy, halogen, methoxy, ethoxy, oxo, heteroaryl and phenyl optionally substituted with 1 or 2 groups independently selected from methyl and halogen.

Specific compounds of the instant inventions are:
(R)-2-(2-morpholino-6-oxo-4-(piperidin-3-ylamino)-1,6-dihydropyrimidin-5-yl)benzo[d]thiazole-5-carbonitrile,
(R)-5-(benzo[d]thiazol-2-yl)-2-morpholino-6-(piperidin-3-ylamino)pyrimidin-4(3H)-one,
6-(((1R,2S,3R,4R)-2,3-dihydroxy-4-(hydroxymethyl)cyclopentyl)amino)-5-(4-(4-fluorophenyl)thiazol-2-yl)-2-morpholinopyrimidin-4(3H)-one,
(R)-5-(benzo[d]thiazol-2-yl)-2-(4-(3-chloro-5-(trifluoromethyl)pyridin-2-yl)piperazin-1-yl)-6-(piperidin-3-ylamino)pyrimidin-4(3H)-one,
5-(benzo[d]thiazol-2-yl)-6-(((1R,2S,3R,4R)-2,3-dihydroxy-4-(hydroxymethyl)cyclopentyl)amino)-2-(4-(pyridin-3-yl)piperazin-1-yl)pyrimidin-4(3H)-one,
5-(benzo[d]thiazol-2-yl)-6-(((1R,2S,3R,4R)-2,3-dihydroxy-4-(hydroxymethyl)cyclopentyl)amino)-2-(4-(pyrimidin-5-yl)piperidin-1-yl)pyrimidin-4(3H)-one, (R)-5-(benzo[d]thiazol-2-yl)-6-(piperidin-3-ylamino)-2-(4-(5-(trifluoromethyl)pyridin-2-yl)piperazin-1-yl)pyrimidin-4(3H)-one,
8-(5-(benzo[d]thiazol-2-yl)-4-(((1R,2S,3R,4R)-2,3-dihydroxy-4-(hydroxymethyl)cyclopentyl)amino)-6-oxo-1,6-dihydropyrimidin-2-yl)-2-methyl-2,8-diazaspiro[4.5]decan-1-one, and
(R)-5-(benzo[d]thiazol-2-yl)-2-(4-(4-chloropyridin-2-yl)piperazin-1-yl)-6-(piperidin-3-ylamino)pyrimidin-4(3H)-one,
or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature.

Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When any variable (e.g. $R^1$) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

The term "optionally substituted" means "unsubstituted or substituted," and therefore, the generic structural formulas described herein encompass compounds containing the specified optional substituent as well as compounds that do not contain the optional substituent. Each variable is independently defined each time it occurs within the generic structural formula definitions.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

"Alkoxy" represents either a cyclic or non-cyclic alkyl group of indicated number of carbon atoms attached through an oxygen bridge. "Alkoxy" therefore encompasses the definitions of alkyl and cycloalkyl above.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. As with the definition of heterocyclyl below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocyclyl" as used herein is intended to mean a 3- to 10-membered aromatic or nonaromatic heterocycle containing from 1 to 4 heteroatoms selected from the group consisting of O, N and S, and includes bicyclic groups. For the purposes of this invention, the term "heterocyclic" is also considered to be synonymous with the terms "heterocycle" and "heterocyclyl" and is understood as also having the definitions set forth herein. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro, fluoro, bromo and iodo.

The alkyl, cycloalkyl, aryl, heteroaryl and heterocyclyl substituents may be substituted or unsubstituted, unless specifically defined otherwise. For example, a ($C_1$-$C_6$)alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C(=O)CH$_2$CH(OH)CH$_3$, —(C=O)OH, —CH$_2$(OH)CH$_2$CH(O), and so on.

Included in the instant invention is the free form of compounds of the instant invention, as well as the pharmaceutically acceptable salts and stereoisomers thereof. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention may potentially be internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom. An isolated compound having internally balanced charges, and thus not associated with an intermolecular counterion, may also be considered the "free form" of a compound.

Utilities

The compounds of the invention are useful to bind to and/or modulate the activity of IRAK-4. In this context, modulate means either increasing or decreasing kinase activity of IRAK-4. In an embodiment, the compounds of the instant invention inhibit the kinase activity of IRAK-4.

The compounds disclosed herein can be used to treat or prevent inflammatory diseases. In one embodiment, the inflammatory disease is selected from the group consisting of autoimmune diseases, inflammatory bowel disease, pulmonary diseases and diseases of the airway, transplant rejection, cancer, cardiovascular diseases, diseases of the central nervous system, CD14 mediated sepsis, non-CD14 mediated sepsis, osteoarthritis, osteoporosis, psoriasis, diseases of the skin, Behcet's syndrome, ankylosing spondylitis, sarcoidosis, gout, and ophthalmic diseases and conditions.

In one embodiment, the autoimmune disease is selected from the group consisting of rheumatoid arthritis, systemic lupus erythematosus, multiple sclerosis, and diabetes (e.g., type 1 diabetes mellitus). In another embodiment, the inflammatory bowel disease is selected from the group consisting of Crohn's disease and ulcerative colitis. In another embodiment, the pulmonary disease and disease of the airway is selected from the group consisting of Adult Respiratory Disease Syndrome (ARDS), Chronic Obstructive Pulmonary Disease (OPD), pulmonary fibrosis, interstitial lung disease, asthma, chronic cough, and allergic rhinitis. In another embodiment, the cancer is selected from the group consisting of solid tumors, skin cancer, and lymphoma. In another embodiment, the cardiovascular disease is selected from the group consisting of stroke and atherosclerosis. In another embodiment, the disease of the central nervous system is a neurodegenerative disease. In another embodiment, the disease of the skin is selected from the group consisting of rash, contact dermatitis, and atopic dermatitis.

The instant compounds are also useful in combination with other therapeutic agents. Combinations of the presently disclosed compounds with therapeutic agents are within the scope of the invention. A person of ordinary skill in the art would be able to discern which combinations of agents would be useful based on the particular characteristics of the drugs and the pathologies involved. The instant compounds are also useful in combination with known therapeutic agents.

The instant compounds are useful in combination with a known anti-inflammatory agent. In one embodiment, the anti-inflammatory agent is a nonsteroidal anti-inflammatory drug (NSAID). In one embodiment, the NSAID is selected from the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, and a mixture thereof.

In another embodiment, the NSAID is a selective COX-2 inhibitor. For purposes of this specification NSAID's which are selective inhibitors of COX-2 are defined as those which possess a specificity for inhibiting COX-2 over COX-1 of at least 100 fold as measured by the ratio of IC$_{50}$ for COX-2 over IC$_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344, 991, 5,134,142, 5,380,738, 5,393,790, 5,466,823, 5,633,272, and 5,932,598, all of which are hereby incorporated by reference.

Compounds that have been described as specific inhibitors of COX-2 and are therefore useful in the present invention include, but are not limited to: parecoxib, CELEBREX® and BEXTRA® or a pharmaceutically acceptable salt thereof.

The instant compounds are useful in combination with a known anti-cancer agent. Combinations of the presently disclosed compounds with anti-cancer agents are within the scope of the invention. Examples of such anti-cancer agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

In one embodiment, the anti-cancer agent is selected from the group consisting of abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®); a pharmaceutically acceptable salt thereof, and a mixture thereof.

The compounds of the instant invention are useful for the treatment and/or reducing the severity of rheumatoid arthritis.

The compounds of the instant invention are useful for the treatment and/or reducing the severity of inflammatory bowel disease.

The compounds of the instant invention are useful for the treatment and/or reducing the severity of cancer.

The compounds of the instant invention are useful for the treatment of rheumatoid arthritis.

The compounds of the instant invention are useful for the treatment of inflammatory bowel disease.

The compounds of the instant invention are useful for the treatment of cancer.

Further included within the scope of the invention is a method for treating an inflammatory disease which comprises administering to a mammal in need thereof a therapeutically effective amount of a compound of the instant invention.

Further included within the scope of the invention is a method for treating an inflammatory disease which comprises administering to a mammal in need thereof a therapeutically effective amount of a compound of the instant invention wherein the inflammatory disease is selected from rheumatoid arthritis, inflammatory bowel disease and cancer.

Further included within the scope of the invention is a method of treating an inflammatory disease which comprises administering a therapeutically effective amount of a compound of the instant invention in combination with a second therapeutic agent.

Further included within the scope of the invention is a method of treating an inflammatory disease which comprises administering a therapeutically effective amount of a compound of the instant invention in combination with a second therapeutic agent, wherein the second therapeutic agent is selected from an anti-cancer agent and an anti-inflammatory agent.

The compounds of this invention may be administered to mammals, preferably humans, either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

In a further example, compounds of the instant invention can be administered in a total daily dose of up to 1000 mg. Compounds of the instant invention can be administered once daily (QD), or divided into multiple daily doses such as twice daily (BID), and three times daily (TID). Compounds of the instant invention can be administered at a total daily dosage of up to 1000 mg, e.g., 200 mg, 300 mg, 400 mg, 600 mg, 800 mg or 1000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

The instant compounds are also useful in combination with known therapeutic agents. For example, instant compounds are useful in combination with a known anti-inflammatory agent. In one embodiment, the anti-inflammatory agent is a nonsteroidal anti-inflammatory drug (NSAID). In one embodiment, the NSAID is selected from the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, and a mixture thereof.

In another embodiment, the NSAID is a selective COX-2 inhibitor. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272, and 5,932,598, all of which are hereby incorporated by reference.

Compounds that have been described as specific inhibitors of COX-2 and are therefore useful in the present invention include, but are not limited to: parecoxib, CELEBREX® and BEXTRA® or a pharmaceutically acceptable salt thereof.

Thus, the scope of the instant invention encompasses the use of the instantly claimed compounds in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic γ-secretase inhibitors, agents that interfere with receptor tyrosine kinases (RTKs), an agent that interferes with a cell cycle checkpoint and any of the therapeutic agents listed above.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Routes of systemic administration of the compounds of the present invention described above may be utilized in the treatment of such ocular neovascular diseases. Other routes of ocular administration may also be employed, such as topical, periocular, intravitreal and the like. Intravitreal implants coated with a drug:polymer matrix may also be employed.

Ophthalmic pharmaceutical compositions that are adapted for topical administration to the eye may be in the form of solutions, suspensions, ointments, creams or as a solid insert. Ophthalmic formulations of this compound may contain from 0.01 ppm to 1% and especially 0.1 ppm to 1% of medicament. For a single dose, from between 0.01 to 5000 ng, preferably 0.1 to 500 ng, and especially 1 to 100 ng of the compound can be applied to the human eye. Formulations useful for intravitreal administration are similar to saline solutions described previously for intravenous administration.

These and other aspects of the invention will be apparent from the teachings contained herein.

SCHEMES AND EXAMPLES

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention hereinabove.

Examples provided are intended to assist in a further understanding of the invention. Particular materials employed, species and conditions are intended to be illustrative of the invention and not limiting of the reasonable scope thereof.

The abbreviations used herein have the following tabulated meanings. Abbreviations not tabulated below have their meanings as commonly used unless specifically stated otherwise.

| | |
|---|---|
| Ac = | acetyl |
| Bn = | benzyl |
| DCE = | Dichloroethylene |
| DIPEA = | N-Ethyldiisopropylamine |
| DMSO = | Dimethyl sulfoxide |
| EtOH = | ethanol |
| $Et_2O$ = | diethyl ether |
| EtOAc = | ethyl acetate |
| HCl = | hydrochloric acid |
| HPLC = | high performance liquid chromatography |
| hr = | hour |
| $K_2CO_3$ = | potassium carbonate |
| KOt-Bu = | potassium t-butoxide |
| MeOH = | methanol |
| $MgSO_4$ = | Magnesium sulfate |
| LRMS = | low resolution mass spectrometry |
| $NaHCO_3$ = | sodium bicarbonate |
| NaOH = | sodium hydroxide |
| n-BuLi = | n-butyl lithium |
| NSAID = | non-steroidal anti-inflammatory drug |
| Ph = | phenyl |
| i-PrOH = | isopropanol |
| $SOCl_2$ = | Thionyl chloride |
| r.t. = | room temperature |
| rac- = | racemic |
| THF = | tetrahydrofuran |
| TLC = | thin layer chromatography |

Alkyl Group Abbreviations

| | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

Proton NMR were acquired on a Varian 400 (400 MHz).
LC conditions: Samples were run on a Zorbox SB-C18 column (3.0×50 mm) with a 3.5 min run time (1 mL/min flow) and a gradient of 90:10 to 10:90 water:MeCN with 0.1% TFA added.
Example 1
5-(Benzo[d]thiazol-2-yl)-2-(cyclobutylamino)-6-((1R,2S,3R,4R)-2,3-dihydroxy-4-(hydroxymethyl)cyclopentylamino)pyrimidin-4(3H)-one.HCl
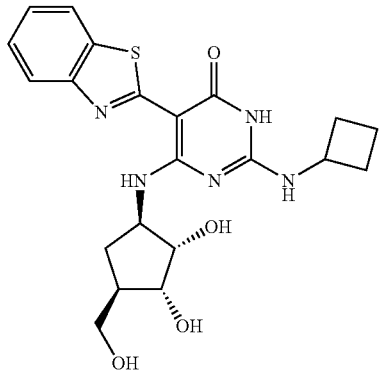
(Ex. 1)
Scheme 1
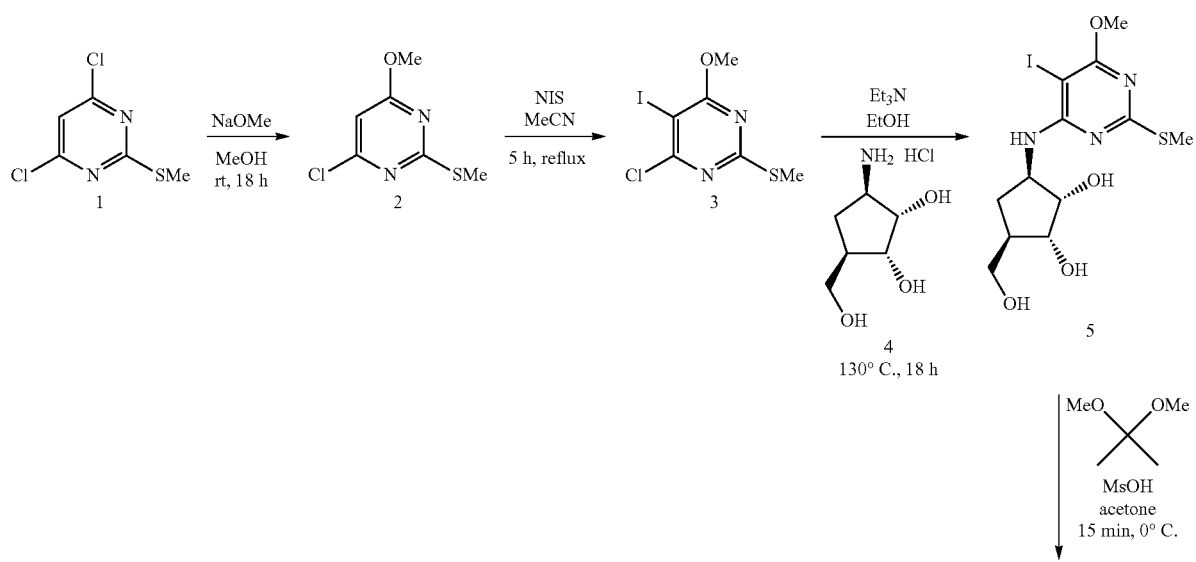

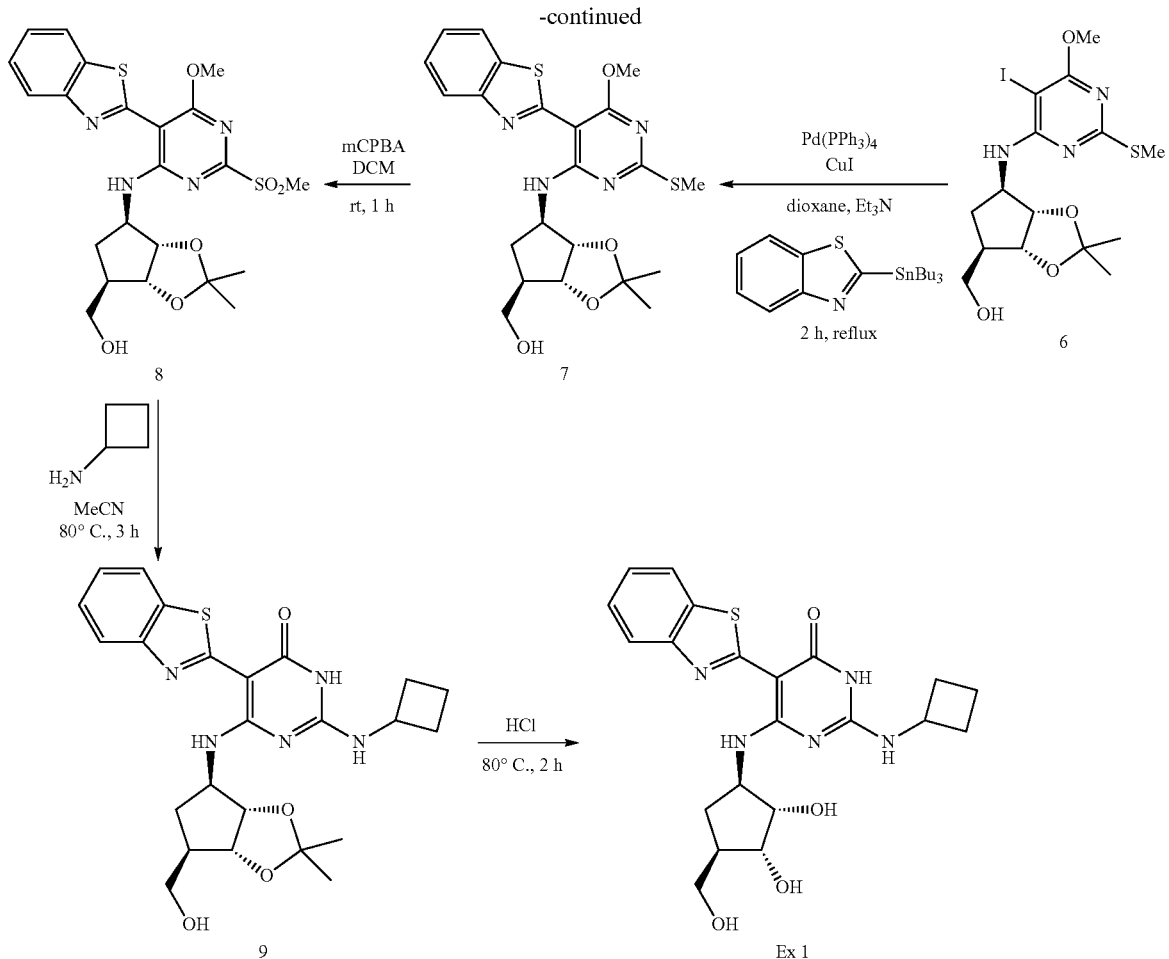

Step 1: 4-Chloro-6-methoxy-2-(methylthio)pyrimidine (Compound 2)

4,6-Dichloro-2-(methylthio)pyrimidine (40 g, 205 mmol) was dissolved in methanol (1025 mL) and cooled to 0° C. Sodium methoxide (55.4 g, 1025 mmol) was added slowly and the mixture was stirred at room temperature for 18 h. 300 mL of 3 M HCl was added and the methanol was evaporated. Additional water (500 mL) was added and the mixture was filtered, washed with water and dried to give the title compound as a white solid. $^1$H NMR (CDCl$_3$) δ 6.41 (s, 1H), 3.97 (s, 3H), 2.55 (s, 3H); LCMS 2.40 min, 191 (M+H).

Step 2: 4-Chloro-5-iodo-6-methoxy-2-(methylthio) pyrimidine (Compound 3)

Compound 2 (10 g, 52.5 mmol) was dissolved in MeCN (150 mL) and NIS (14.2 g, 62.9 mmol) was added. The solution was heated to reflux for 5 h and cooled to room temperature. The solvent was evaporated and the residue was dissolved in EtOAc. The organics were washed with sat. NaHCO$_3$ and sat. NaS$_2$O$_3$, dried (MgSO$_4$), filtered and concentrated to give the title compound as a white solid. $^1$H NMR (CDCl$_3$) δ 4.04 (s, 3H), 2.54 (s, 3H); LCMS 2.64 min, 317 (M+H).

Step 3: (1S,2R,3R,5R)-3-(Hydroxymethyl)-5-(5-iodo-6-methoxy-2-(methylthio)pyrimidin-4-ylamino) cyclopentane-1,2-diol (Compound 5)

Compound 3 (5.00 g, 15.7 mmol) and (1R,2S,3R,5R)-3-amino-5-(hydroxymethyl)cyclopentane-1,2-diol hydrochloride (Compound 4) (5.80 g, 31.6 mmol) were dissolved in EtOH (50 mL). Triethylamine (6.60 mL, 47.4 mmol) was added, the reaction was sealed, and heated to 130° C. for 18 h. The reaction mixture was cooled to room temperature and concentrated. The residue was purified via column chromatography on silica gel (EtOAc/hexanes) to give the title compound as a colorless oil. LCMS 1.23 min, 428 (M+H).

Step 4: ((3aR,4R,6R,6aS)-6-(5-Iodo-6-methoxy-2-(methylthio)pyrimidin-4-ylamino)-2,2-dimethyltetrahydro-3aH-cyclopenta[d][1,3]dioxol-4-yl)methanol (Compound 6)

Compound 5 (4.00 g, 9.36 mmol) was dissolved in acetone (10 mL) and 2,2-dimethoxypropane (5.75 mL, 46.8 mmol) was added. The solution was cooled to 0° C. and methanesulfonic acid (2 drops) was added. The solution was stirred for 15 min and Et$_3$N (1 mL) was added. The acetone was evaporated and the residue was dissolved in EtOAc, washed with water and brine, dried (MgSO$_4$), filtered and concentrated. The residue was purified via column chromatography on silica gel (EtOAc/hexanes) to give the title compound as a white solid. $^1$H NMR (CDCl$_3$) δ 6.21 (d, J=8 Hz, 1H), 4.65-4.59 (m, 2H), 4.45-4.44 (m, 1H), 3.94 (s, 3H), 3.89-3.85 (m, 1H), 3.76-3.73 (m, 1H), 2.61-2.55 (m, 1H), 2.52 (s, 3H), 2.40-2.34 (m, 1H), 1.85 (br s, 1H), 1.65-1.57 (m, 2H), 1.49 (s, 3H), 1.28 (s, 3H); LCMS 2.54 min, 468 (M+H).

Step 5: ((3aR,4R,6R,6aS)-6-(5-(Benzo[d]thiazol-2-yl)-6-methoxy-2-(methylthio)pyrimidin-4-ylamino)-2,2-dimethyltetrahydro-3 aH-cyclopenta[d][1,3]-dioxol-4-yl)methanol (Compound 7)

2-Tributylstannylbenzothiazole (1.18 g, 2.78 mmol), compound 6 (1.00 g, 2.14 mmol), Tetrakis(triphenylphosphine)palladium (0.495 g, 0.428 mmol), and CuI (0.082 g, 0.428 mmol) were combined. Dioxane (45 ml) was added followed by Et$_3$N (1.19 ml, 8.56 mmol) and the mixture was degassed and heated to reflux for 2 h. The solution was cooled to room temperature and an aqueous 10% KF solution was added and the mixture was stirred for 30 min. The mixture was diluted with EtOAc and washed with water, brine, dried (MgSO$_4$), filtered and evaporated to dryness. The residue was purified by column chromatography on silica gel, eluting with EtOAc/hexane to give the title compound as a yellow foam. $^1$H NMR (CDCl$_3$) δ 7.94 (d, J=8 Hz, 1H), 7.87 (d, J=8 Hz, 1H), 7.45 (t, J=5 Hz, 1H), 7.33 (t, J=5 Hz, 1H), 4.70-4.59 (m, 3H), 4.15 (s, 3H), 3.86-3.83 (m, 2H), 2.61 (s, 3H), 2.59-2.52 (m, 1H), 2.45-2.42 (m, 2H). 1.83-1.78 (m, 1H), 1.67-1.66 (m, 1H), 1.53 (s, 3H), 1.31 (s, 3H); LCMS 2.77 min, 475 (M+H).

Step 6: ((3aR,4R,6R,6aS)-6-(5-(Benzo[d]thiazol-2-yl)-6-methoxy-2-(methylsulfonyl)pyrimidin-4-ylamino)-2,2-dimethyltetrahydro-3aH-cyclopenta[d][1,3]dioxol-4-yl)methanol (Compound 8)

Compound 7 (600 mg. 1.27 mmol) was dissolved in DCM (25 mL). mCPBA (711 mg, 3.18 mmol, 77% wt/wt) was added in one portion and the solution was stirred at room temperature for 1 h. A saturated aqueous solution of NaHCO$_3$ was added and the mixture was stirred for 10 min. The layers were separated and the organics were dried (MgSO$_4$), filtered and concentrated to give 640 mg of the title compound as a yellow solid. MS 507 (M+H).

Step 7: 5-(Benzo[d]thiazol-2-yl)-2-(cyclobutylamino)-6-((3aS,4R,6R,6aR)-6-(hydroxymethyl)-2,2-dimethyltetrahydro-3aH-cyclopenta[d][1,3]dioxol-4-ylamino)pyrimidin-4(3H)-one (Compound 9)

Compound 8 (100 mg, 0.197 mmol) was dissolved in MeCN (2 mL) and cyclobutylamine (168 µL, 1.97 mmol) was added. The reaction was heated to 80° C. for 1 h. The solvent was evaporated and the residue was purified by column chromatography on silica gel, eluting with EtOAc/hexane to give the title compound as a yellow solid. MS 498 (M+H).

Step 8: 5-(Benzo[d]thiazol-2-yl-2-(cyclobutylamino)-6-((1R,2S,3R,4R)-2,3-dihydroxy-4-(hydroxymethyl)cyclopentylamino)pyrimidin-4(3H)-one.HCl (Example 1)

Compound 9 (48.0 mg, 0.096 mmol) was suspended in concentrated HCl (2 mL) and heated to 100° C. for 8 h. The solution was evaporated to dryness to give the title compound as a white solid. $^1$H NMR (DMSO) δ 7.89 (d, J=8 Hz, 1H), 7.74 (d, J=8 Hz, 1H), 7.36 (t, J=5 Hz, 1H), 7.21 (t, J=5 Hz, 1H), 4.73-4.65 (m, 2H), 4.53-4.50 (m, 1 H), 4.36-4.34 (m, 2H), 3.81-3.77 (m, 2H), 3.52-3.45 (m, 3H), 2.36-30 (m, 3H), 2.00-1.96 (m, 3H), 1.69 (m, 2H), 1.29-1.25 (m, 1H); LCMS 1.98 min, 444 (M+H)

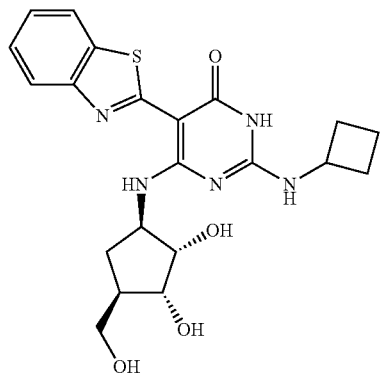

(Ex. 1)

IRAK4 IC50 is 20 nM for the compound of Example 1. The kinase activity of IRAK4 is determined by its ability to catalyze the phosphorylation of a fluorescent polypeptide substrate. The extent of phosphorylation is measured using IMAP technology (Molecular Devices) where the phosphorylated fluorescent substrate binds to the large M(III)-based nanoparticles which reduces the rotational speed of the substrate and thus increases its fluorescent polarization (FP).

Assay Procedure: A 20 µl reaction mixture contains 10 mM TriHCl, pH 7.2, 0.5 nM GST tagged IRAK4 (SignalChem), 100 nM fluorescent peptide substrate (RP7030, Molecular Devices), 100 µM ATP, 1 mM DTT, 1 mM MgCl$_2$, and 0.01% Tween 20. The reaction is initiated by the addition of ATP. After incubation for 30 minutes at 25° C., 60 µl of Progressive IMAP Reagent (Molecular Devices) is added to stop the reaction. Change in RP7030's FP is determined by a FP reader (Analyst HT, LJL BioSystems)

Using a similar synthetic scheme as described for Example 1, Examples 2-49 were prepared, as described in more detail below.

Example 2

2-Amino-5-(benzo[d]thiazol-2-yl)-6-((1R,2S,3R,4R)-2,3-dihydroxy-4-(hydroxymethyl)cyclopentylamino)pyrimidin-4(3H)-one.HCl Prepared as in Scheme 1, except ammonium hydroxide was used in Step 7 in place of cyclobutylamine.

¹H NMR (DMSO) δ 7.90 (d, J=8 Hz, 1H), 7.89 (d, J=8 Hz, 1H), 7.44 (t, J=5 Hz, 1H), 7.28 (t, J=5 Hz, 1H), 4.32-4.26 (m, 1 H), 4.09-4.05 (m, 2 H), 3.68-3.66 (m, 2H), 2.55-2.48 (m, 1H), 2.25-2.24 (m, 1H), 1.71-1.63 (m, 1H), 1.25-1.23 (m, 1H); LCMS 2.46 min, 390 (M+H)

IRAK4 IC50 is 694 nM for Example 2.

Example 3

5-(Benzo[d]thiazol-2-yl)-2-(cyclopropylamino)-6-((1R,2S,3R,4R)-2,3-dihydroxy-4-(hydroxymethyl)cyclopentylamino)pyrimidin-4(3H)-one.HCl Prepared as in Scheme 1, except cyclopropylamine was used in Step 7 in place of cyclobutylamine.

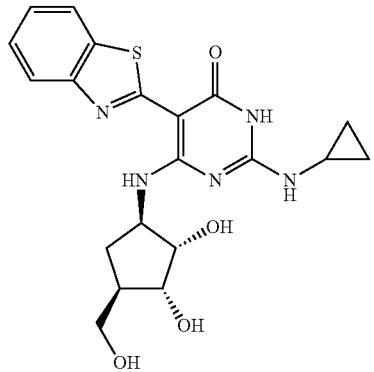 [SMILES: O=c1[nH]c(NC2CC2)nc(N[C@@H]2C[C@H](CO)[C@@H](O)[C@H]2O)c1-c1nc2ccccc2s1]

¹H NMR (DMSO) δ 7.90 (d, J=8 Hz, 1H), 7.74 (d, J=8 Hz, 1H), 7.37 (t, J=5 Hz, 1H), 7.21 (t, J=5 Hz, 1H), 4.76 (s, 1H), 4.65 (m, 1H), 4.49, (s, 1H), 4.39-4.36 (m, 1H), 3.80-3.76 (m, 2H), 3.49-3.32 (m, 2H), 2.74-2.71 (m, 1H), 2.39-2.31 (m, 2H), 1.97 (m, 1H), 1.24-1.21 (m, 2H), 0.76 (d, J=5.2, 2H), 0.55 (d, J=5.2, 2H); LCMS 1.96 min, 430 (M+H)

IRAK4 IC50 is 25 nM for Example 3.

Example 4

5-(Benzo[d]thiazol-2-yl)-2-(cyclopentylamino)-6-((1R,2S,3R,4R)-2,3-dihydroxy-4-(hydroxymethyl)cyclopentylamino)pyrimidin-4(3H)-one.HCl Prepared as in Scheme 1, except cyclopentylamine was used in Step 7 in place of cyclobutylamine.

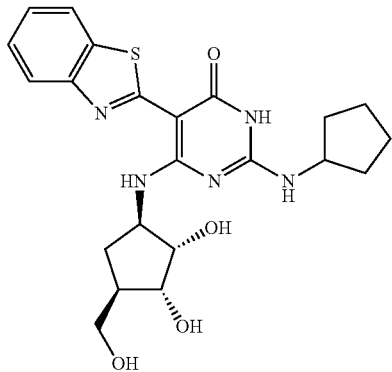 [SMILES: O=c1[nH]c(NC2CCCC2)nc(N[C@@H]2C[C@H](CO)[C@@H](O)[C@H]2O)c1-c1nc2ccccc2s1]

¹H NMR (DMSO) δ 7.90 (d, J=8 Hz, 1H), 7.74 (d, J=8 Hz, 1H), 7.38 (t, J=5 Hz, 1H), 7.23 (t, J=5 Hz, 1H), 4.35-4.31 (m, 1H), 4.23-4.00 (m, 1H), 3.92-3.83 (m, 2H), 3.55-3.42 (m, 2H), 2.43-2.30 (m, 1H), 1.98-1.95 (m, 2H), 1.66-1.45 (m, 7H), 1.29-1.21 (m, 2); LCMS 1.79 min, 458 (M+H)

IRAK4 IC50 is 92 nM for Example 4.

Example 5

5-(Benzo[d]thiazol-2-yl)-6-((1R,2S,3R,4R)-2,3-dihydroxy-4-(hydroxymethyl)cyclopentylamino)-2-(isopropylamino)pyrimidin-4(3H)-one.HCl Prepared as in Scheme 1, except isopropylamine was used in Step 7 in place of cyclobutylamine.

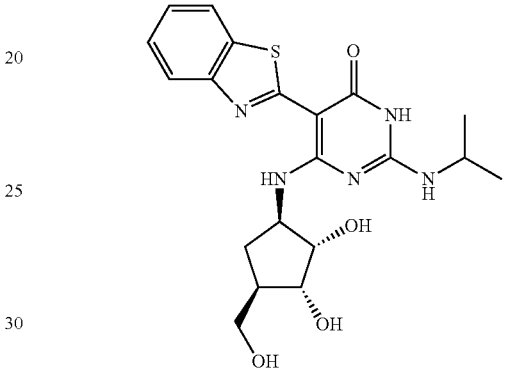

¹H NMR (DMSO) δ 7.87 (d, J=8 Hz, 1H), 7.81 (d, J=8 Hz, 1H), 7.44 (t, J=5 Hz, 1H), 7.30 (t, J=5 Hz, 1H), 4.39 (br s, 1H), 4.18-4.16 (m, 1H), 4.06-3.99 (m, 2H), 3.69-3.68 (m, 2H), 2.59-2.48 (m, 1H), 2.24-2.22 (m, 1H), 1.58 (m, 1H), 1.29 (d, J=2.4, 6H); LCMS 1.70 min, 432 (M+H)

IRAK4 IC50 is 151 nM for Example 5.

Example 6

5-(Benzo[d]thiazol-2-yl)-2-(cyclohexylamino)-6-((1R,2S,3R,4R)-2,3-dihydroxy-4-(hydroxymethyl)cyclopentylamino)pyrimidin-4(3H)-one.HCl Prepared as in Scheme 1, except cyclohexylamine was used in Step 7 in place of cyclobutylamine.

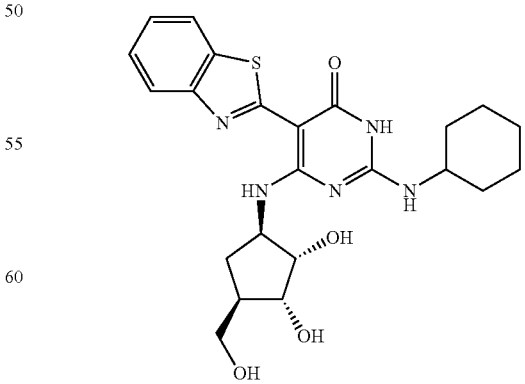

¹H NMR (DMSO) δ 7.89 (d, J=8 Hz, 1H), 7.74 (d, J=8 Hz, 1H), 7.36 (t, J=5 Hz, 1H), 7.22 (t, J=5 Hz, 1H), 3.82-3.74 (m,

3H), 3.55-3.41 (m, 2H), 2.37-2.30 (m, 1H), 1.98-1.89 (m, 3H), 1.66 (m, 2H), 1.53 (m, 1H), 1.30-1.23 (m, 7H); LCMS 1.85 min, 472 (M+H)

IRAK4 IC50 is 636 nM for Example 6.

Example 7

5-(Benzo[d]thiazol-2-yl)-6-((1R,2S,3R,4R)-2,3-dihydroxy-4-(hydroxymethyl)cyclopentylamino)pyrimidine-2,4(1H,3H)-dione.HCl Prepared as in Scheme 1, except sodium methoxide was used in Step 7 in place of cyclobutylamine.

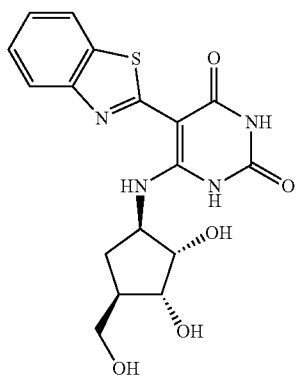 [SMILES: O=c1[nH]c(N[C@@H]2C[C@H](CO)[C@@H](O)[C@H]2O)c(-c2nc3ccccc3s2)c(=O)[nH]1]

$^1$H NMR (DMSO) δ 7.94 (d, J=8 Hz, 1H), 7.77 (d, J=8 Hz, 1H), 7.40 (t, J=5 Hz, 1H), 7.26 (t, J=5 Hz, 1H), 4.17-4.13 (m, 1H), 3.49-3.42 (m, 3H), 2.36-2.89 (m, 1H), 2.01-2.00 (m, 1H), 1.41-1.36 (m, 1H); LCMS 1.87 min, 391 (M+H)

IRAK4 IC50 is 1487 nM for Example 7.

Example 8

5-(Benzo[d]thiazol-2-yl)-6-((1R,2S,3R,4R)-2,3-dihydroxy-4-(hydroxymethyl)cyclopentylamino)-2-(tetrahydro-2H-pyran-4-ylamino)pyrimidin-4(3H)-one.HCl Prepared as in Scheme 1, except 4-aminotetrahydropyran was used in Step 7 in place of cyclobutylamine.

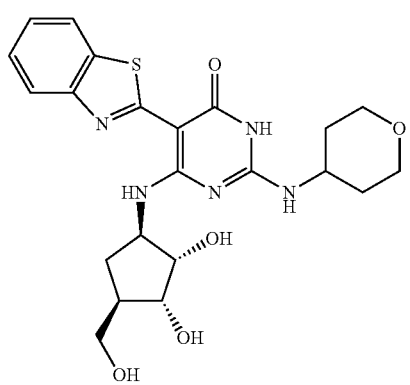 [SMILES: O=c1[nH]c(NC2CCOCC2)nc(N[C@@H]2C[C@H](CO)[C@@H](O)[C@H]2O)c1-c1nc2ccccc2s1]

$^1$H NMR (DMSO) δ 10.85 (s, 1H), 10.27 (br s, 1H), 7.87 (d, J=8 Hz, 1H), 7.74 (d, J=8 Hz, 1H), 7.36 (t, J=5 Hz, 1H), 7.21 (t, J=5 Hz, 1H), 6.90 (br s, 1H), 3.82-3.74 (m, 5H), 3.50-3.41 (m, 5H), 2.45-2.31 (m, 2H), 1.92-1.73 (m, 4H), 1.29-1.25 (m, 2H), 1.21-1.15 (m, 2H); LCMS 1.60 min, 474 (M+H)

IRAK4 IC50 is 575 nM for Example 8.

Example 9

5-(Benzo[d]thiazol-2-yl)-2-(3,3-difluorocyclobutylamino)-6-((1R,2S,3R,4R)-2,3-dihydroxy-4-(hydroxymethyl)cyclopentylamino)pyrimidin-4(3H)-one.HCl Prepared as in Scheme 1, except 3-amino-1,1-difluorocyclobutane was used in Step 7 in place of cyclobutylamine.

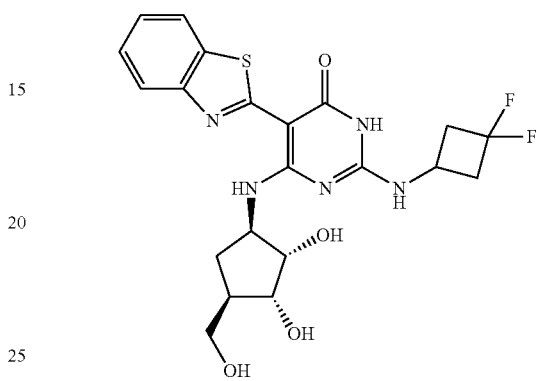

$^1$H NMR (DMSO) δ 10.90 (d, J=7.2 Hz, 1H), 10.73 (br s, 1H), 7.90 (d, J=8 Hz, 1H), 7.76 (d, J=8 Hz, 1H), 7.37 (t, J=5 Hz, 1H), 7.22 (t, J=5 Hz, 1H), 4.34-4.22 (m, 2H), 3.78-3.77 (m, 2H), 3.54-3.44 (m, 2H), 3.11-2.97 (m, 2H), 2.71-2.67 (m, 2H), 2.37-2.29 (m, 1H), 2.06-2.00 (m, 1H), 1.31-1.26 (m, 1H); LCMS 1.71 min, 480 (M+H)

IRAK4 IC50 is 324 nM for Example 9.

Example 10

5-(Benzo[d]thiazol-2-yl)-6-((1R,2S,3R,4R)-2,3-dihydroxy-4-(hydroxymethyl)cyclopentylamino)-2-(1-(methylsulfonyl)piperidin-4-ylamino)pyrimidin-4(3H)-one.HCl Prepared as in Scheme 1, except 1-(methylsulfonyl)piperidin-4-amine was used in Step 7 in place of cyclobutylamine.

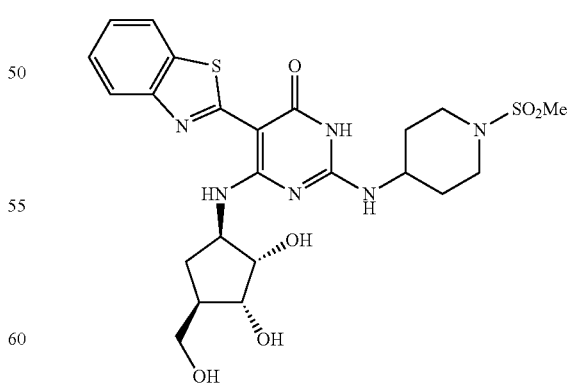

$^1$H NMR (DMSO) δ 10.86 (d, J=7.2 Hz, 1H), 10.35 (br s, 1H), 7.89 (d, J=8 Hz, 1H), 7.75 (d, J=8 Hz, 1H), 7.37 (t, J=5 Hz, 1H), 7.21 (t, J=5 Hz, 1H), 7.05 (br s, 1H), 4.28 (br s, 1H), 3.92 (br s, 1H), 3.82-3.76 (m, 2H), 3.55-3.44 (m, 4H), 2.91

(m, 1H), 2.88 (s, 3H), 2.37-2.29 (m, 2H), 2.01-1.99 (m, 3H), 1.59-1.53 (m, 2H), 1.50-1.33 (m, 1H); LCMS 0.79 min, 551 (M+H)

IRAK4 IC50 is 545 nM for Example 10.

Example 11

5-(Benzo[d]thiazol-2-yl)-6-((1R,2S,3R,4R)-2,3-dihydroxy-4-(hydroxymethyl)cyclopentylamino)-2-(oxetan-3-ylamino)pyrimidin-4(3H)-one.HCl Prepared as in Scheme 1, except oxetan-3-amine was used in Step 7 in place of cyclobutylamine.

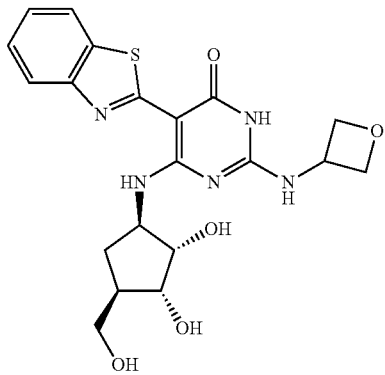 [SMILES: O=c1[nH]c(NC2COC2)nc(N[C@@H]2C[C@H](CO)[C@@H](O)[C@H]2O)c1-c1nc2ccccc2s1]

¹H NMR (DMSO) δ 11.07 (d, J=5.2 Hz, 1H), 8.62 (s, 1H), 7.90 (d, J=8 Hz, 1H), 7.74 (d, J=8 Hz, 1H), 7.36 (t, J=5 Hz, 1H), 7.21 (t, J=5 Hz, 1H), 4.36-4.35 (m, 1H), 4.08-3.77 (m, 5H), 3.52-3.42 (m, 4H), 2.32-2.24 (m, 1H), 1.95 (m, 1H), 1.27-1.21 (m, 1H); LCMS 1.49 min, 446 (M+H)

IRAK4 IC50 is 892 nM for Example 11.

Example 12

5-(Benzo[d]thiazol-2-yl)-6-((1R,2S,3R,4R)-2,3-dihydroxy-4-(hydroxymethyl)cyclopentylamino)-2-(4-(methylsulfonyl)piperazin-1-yl)pyrimidin-4(3H)-one.HCl Prepared as in Scheme 1, except 1-(methylsulfonyl)piperazine was used in Step 7 in place of cyclobutylamine.

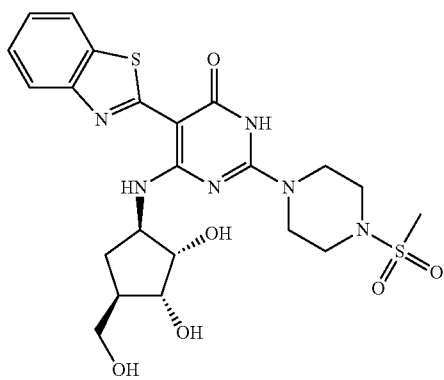 [SMILES: CS(=O)(=O)N1CCN(c2nc(N[C@@H]3C[C@H](CO)[C@@H](O)[C@H]3O)c(-c3nc4ccccc4s3)c(=O)[nH]2)CC1]

¹H NMR (DMSO) δ 11.13 (s, 1H), 10.81 (d, J=6.8 Hz, 1H), 9.10 (br s, 1H) 7.91 (d, J=8 Hz, 1H), 7.70 (d, J=8 Hz, 1H), 7.37 (t, J=5 Hz, 1H), 7.23 (t, J=5 Hz, 1H), 4.34-4.31 (m, 1H), 3.69-3.66 (m, 1H), 3.54-3.44 (m, 3H), 3.34-3.32 (m, 3H), 3.26-3.16 (m, 5H), 2.97 (s, 3H), 2.38 (m, 1H), 2.09-1.99 (m, 1H), 1.34-1.27 (m, 1H); LCMS 1.77 min, 537 (M+H)

IRAK4 IC50 is 25 nM for Example 12.

Example 13

5-(Benzo[d]thiazol-2-yl)-6-((1R,2S,3R,4R)-2,3-dihydroxy-4-(hydroxymethyl)cyclopentylamino)-2-(2-oxa-6-azaspiro[3.3]heptan-6-yl)pyrimidin-4(3H)-one.HCl Prepared as in Scheme 1, except 2-oxa-6-azaspiro[3.3]heptane was used in Step 7 in place of cyclobutylamine.

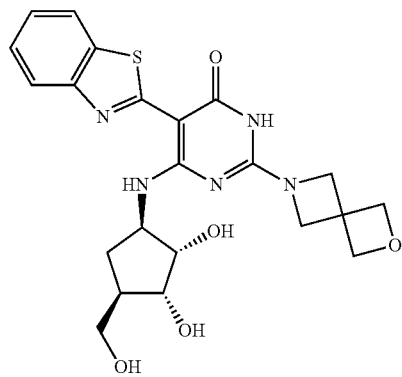 [SMILES: O=c1[nH]c(N2CC3(COC3)C2)nc(N[C@@H]2C[C@H](CO)[C@@H](O)[C@H]2O)c1-c1nc2ccccc2s1]

¹H NMR (DMSO) δ 10.88 (d, J=6.4 Hz, 1H), 7.89 (d, J=8 Hz, 1H), 7.74 (d, J=8 Hz, 1H), 7.36 (t, J=5 Hz, 1H), 7.21 (t, J=5 Hz, 1H), 4.76 (s, 1H), 4.68 (s, 4H), 4.51 (s, 1H), 4.28 (s, 4H), 3.85-3.79 (m, 2H), 3.48-3.45 (m, 2H), 2.36-2.30 (m, 1H), 1.98 (m, 1H), 1.29-1.21 (m, 1H), 1.04-1.02 (m, 1H); LCMS 1.73 min, 472 (M+H)

IRAK4 IC50 is 8.9 nM for Example 13.

Example 14

5-(Benzo[d]thiazol-2-yl)-6-((1R,2S,3R,4R)-2,3-dihydroxy-4-(hydroxymethyl)cyclopentylamino)-2-(6-(methylsulfonyl)-2,6-diazaspiro[3.3]heptan-2-yl)pyrimidin-4(3H)-one.HCl Prepared as in Scheme 1, except 2-(methylsulfonyl)-2,6-diazaspiro[3.3]heptane was used in Step 7 in place of cyclobutylamine.

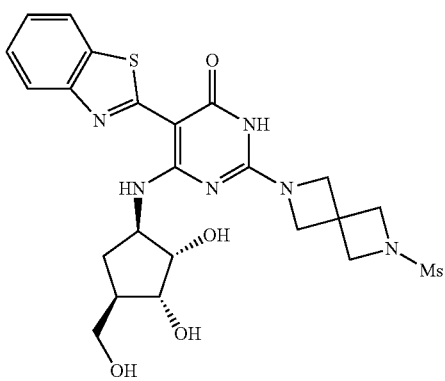 [SMILES: CS(=O)(=O)N1CC2(CN(c3nc(N[C@@H]4C[C@H](CO)[C@@H](O)[C@H]4O)c(-c4nc5ccccc5s4)c(=O)[nH]3)C2)C1]

¹H NMR (DMSO) δ 11.27 (s, 1H), 10.89 (d, J=6.8 Hz, 1H), 7.89 (d, J=8 Hz, 1H), 7.76 (d, J=8 Hz, 1H), 7.37 (t, J=5 Hz, 1H), 7.22 (t, J=5 Hz, 1H), 4.74 (d, J=5.2 Hz, 1H), 4.65 (t, J=5.2 Hz, 1H), 4.31 (d, J=6.4 Hz, 1H), 4.28 (s, 4H), 4.03 (s, 4H), 3.82-3.75 (m, 2H), 3.50-3.44 (m, 1H), 2.99 (s, 3H), 2.38-2.31 (m, 1H), 1.98-1.97 (m, 1H), 1.28-1.21 (m, 1H); LCMS 1.78 min, 549 (M+H)

IRAK4 IC50 is 5.6 nM for Example 14.

Example 15

5-(Benzo[d]thiazol-2-yl)-2-cyclobutoxy-6-((1R,2S,3R,4R)-2,3-dihydroxy-4-(hydroxymethyl)cyclopentylamino)pyrimidin-4(3H)-one.HCl Prepared as in Scheme 1, except hydroxycyclobutane was used in Step 7 in place of cyclobutylamine.

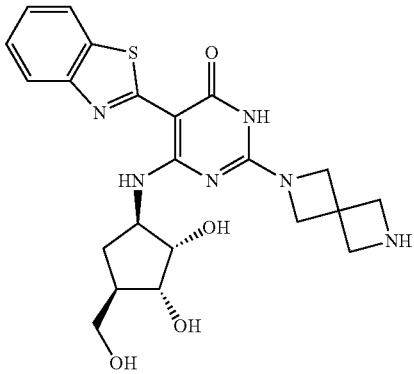

¹H NMR (DMSO) δ 11.25 (s, 1H), 10.88 (d, J=6.8 Hz, 1H), 9.07 (br s, 1H), 7.89 (d, J=8 Hz, 1H), 7.74 (d, J=8 Hz, 1H), 7.35 (t, J=5 Hz, 1H), 7.21 (t, J=5 Hz, 1H), 4.19 (s, 4H), 4.11 (s, 4H), 3.80-3.78 (m, 2H), 3.51-3.41 (m, 2H), 2.35-2.30 (m, 1H), 1.99 (br s, 1H), 1.27-1.20 (m, 1H); LCMS 1.33 min, 471 (M+H)

IRAK4 IC50 is 6.5 nM for Example 16.

Example 17

5-(Benzo[d]thiazol-2-yl)-6-((1R,2S,3R,4R)-2,3-dihydroxy-4-(hydroxymethyl)cyclopentylamino)-2-(1-methylcyclobutylamino)pyrimidin-4(3H)-one.HCl Prepared as in Scheme 1, except 1-methylcyclobutanamine was used in Step 7 in place of cyclobutylamine.

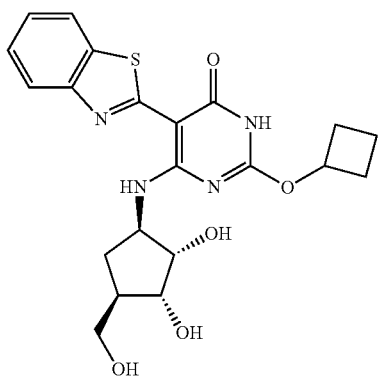 [SMILES: O=c1[nH]c(OC2CCC2)nc(N[C@@H]2C[C@H](CO)[C@@H](O)[C@H]2O)c1-c1nc2ccccc2s1]

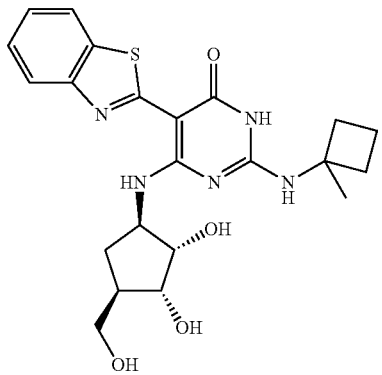 [SMILES: CC1(Nc2nc(N[C@@H]3C[C@H](CO)[C@@H](O)[C@H]3O)c(-c3nc4ccccc4s3)c(=O)[nH]2)CCC1]

¹H NMR (DMSO) δ 11.07 (s, 1H), 10.96 (s, 1H), 7.96-7.84 (m, 1H); 7.82-7.76 (m, 1H), 7.41-7.38 (m, 1H), 7.26-7.24 (m, 1H), 4.35-4.33 (m, 1H), 4.15-4.13 (m, 2H), 3.82-3.77 (m, 2H), 3.51-3.45 (m, 2H), 3.29-3.26 (m, 2H), 2.39-2.31 (m, 1H), 2.17-2.13 (m, 2H), 1.86-1.68 (m, 2H); LCMS 2.00 min, 445 (M+H)

IRAK4 IC50 is 1686 nM for Example 15.

Example 16

5-(Benzo[d]thiazol-2-yl)-6-((1R,2S,3R,4R)-2,3-dihydroxy-4-(hydroxymethyl)cyclopentylamino)-2-(2,6-diazaspiro[3.3]heptan-2-yl)pyrimidin-4(3H)-one.HCl Prepared as in Scheme 1, except tert-butyl 2,6-diazaspiro[3.3]heptane-2-carboxylate was used in Step 7 in place of cyclobutylamine.

¹H NMR (DMSO) δ 7.89 (d, J=8 Hz, 1H), 7.74 (d, J=8 Hz, 1H), 7.38 (t, J=5 Hz, 1H), 7.21 (t, J=5 Hz, 1H), 6.90 (s, 1H), 4.33-4.28 (m, 1H), 3.82-3.77 (m, 2H), 3.53-3.43 (m, 2H), 2.40-2.29 (m, 3H), 2.05-2.03 (m, 3H), 1.86-1.80 (m, 2H), 1.53 (s, 3H), 1.28-1.23 (m, 1H); LCMS 1.33 min, 471 (M+H)

IRAK4 IC50 is 1693 nM for Example 17.

Example 18

6-((1R,2S,3R,4R)-2,3-Dihydroxy-4-(hydroxymethyl)cyclopentylamino)-2-morpholino-5-(quinolin-2-yl)pyrimidin-4(3H)-one.HCl Prepared as in Scheme 1, except 2-(tributylstannyl)quinoline was used in place of 2-(tributylstannyl)benzo[d]thiazole in Step 5 and morpholine was used in Step 7 in place of cyclobutylamine.

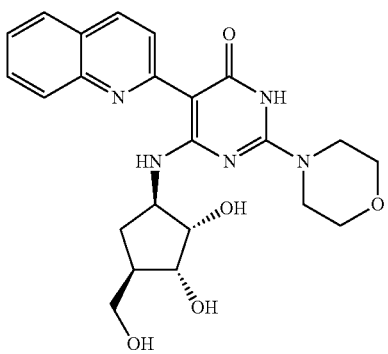 [SMILES: O=c1[nH]c(N2CCOCC2)nc(N[C@@H]2C[C@H](CO)[C@@H](O)[C@H]2O)c1-c1ccc2ccccc2n1]

¹H NMR (DMSO) δ 11.03 (br s, 1H), 8.44-8.37 (m, 2H), 8.04-7.98 (m, 2H), 7.84-7.80 (m, 1H), 7.62-7.60 (m, 1H), 4.67-4.60 (m, 2H), 3.80-3.68 (m, 9H), 3.43-3.34 (m, 2H), 2.31-2.20 (m, 1H), 1.96-1.94 (m, 1H), 1.21-1.17 (m, 1H); LCMS 1.71 min, 454 (M+H)

IRAK4 IC50 is 9.5 nM for Example 18.

Example 19

6-((1R,2S,3R,4R)-2,3-Dihydroxy-4-(hydroxymethyl) cyclopentylamino)-2-(piperidin-1-yl)-5-(quinolin-2-yl)pyrimidin-4(3H)-one.HCl Prepared as in Scheme 1, except 2-(tributylstannyl)quinoline was used in place of 2-(tributylstannyl)benzo[d]thiazole in Step 5 and piperidine was used in Step 7 in place of cyclobutylamine.

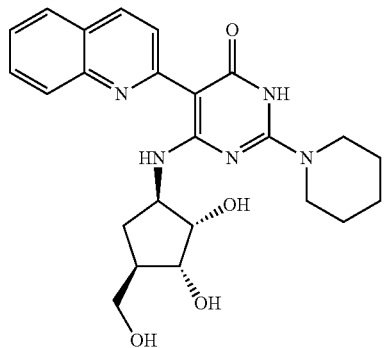 [SMILES: O=c1[nH]c(N2CCCCC2)nc(N[C@@H]2C[C@H](CO)[C@@H](O)[C@H]2O)c1-c1ccc2ccccc2n1]

¹H NMR (DMSO) δ 8.99 (d, J=9.2 Hz, 1H), 8.09 (d, J=8.8 Hz, 1H), 7.82-7.77 (m, 2H), 7.62 (t, J=8 Hz, 1H), 7.40 (t, J=8 Hz, 1H), 4.65-4.60 (m, 2H), 4.53 (d, J=4.8 Hz, 1H), 4.25-4.22 (m, 1H), 3.82-3.77 (m, 2H), 3.65 (m, 4H), 3.47-3.42 (m, 2H), 2.39-2.30 (m, 1H), 2.05-1.98 (m, 1H), 1.59-1.53 (m, 6H), 1.20-1.18 (m, 1H); LCMS 1.68 min, 452 (M+H)

IRAK4 IC50 is 23 nM for Example 19.

Example 20

2-(Cyclobutylamino)-6-((1R,2S,3R,4R)-2,3-dihydroxy-4-(hydroxymethyl)cyclopentylamino)-5-(quinolin-2-yl)pyrimidin-4(3H)-one.HCl Prepared as in Scheme 1, except 2-(tributylstannyl)quinoline was used in place of 2-(tributylstannyl)benzo[d]thiazole in Step 5.

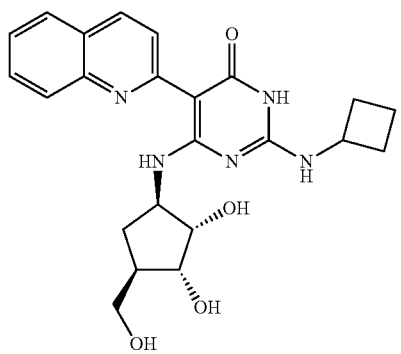 [SMILES: O=c1[nH]c(NC2CCC2)nc(N[C@@H]2C[C@H](CO)[C@@H](O)[C@H]2O)c1-c1ccc2ccccc2n1]

¹H NMR (DMSO) δ 8.37 (br s, 2H), 7.97-7.94 (m, 2H), 7.78-7.76 (m, 1H), 7.59-7.54 (m, 1H), 4.42-4.40 (m, 3H), 3.40-3.36 (m, 3H), 2.30-2.95 (m, 3H), 2.01-1.96 (m, 3H), 1.73-1.70 (m, 2H), 1.21-1.16 (m, 3H); LCMS 1.47 min, 438 (M+H)

IRAK4 IC50 is 19 nM for Example 20.

Example 21

2-(Cyclobutylamino)-6-((1R,2S,3R,4R)-2,3-dihydroxy-4-(hydroxymethyl)cyclopentylamino)-5-(pyridin-2-yl)pyrimidin-4(3H)-one.HCl Prepared as in Scheme 1, except 2-(tributylstannyl)pyridine was used in place of 2-(tributylstannyl)benzo[d]thiazole in Step 5.

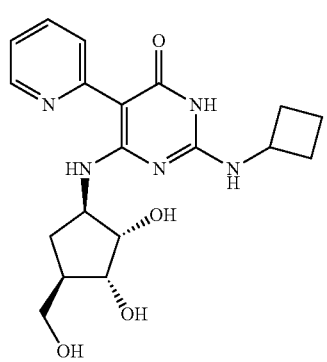 [SMILES: O=c1[nH]c(NC2CCC2)nc(N[C@@H]2C[C@H](CO)[C@@H](O)[C@H]2O)c1-c1ccccn1]

¹H NMR (DMSO) δ 10.82 (s, 1H), 8.50 (s, 1H), 8.20-7.86 (m, 3H), 7.59-7.44 (m, 4H), 4.31 (m, 2H), 3.74-3.69 (m, 2H), 3.34 (m, 2H), 2.27-2.15 (m, 2H), 1.96-1.69 (m, 4H), 1.13 (m, 2H); LCMS 1.24 min, 388 (M+H)

IRAK4 IC50 is 590 nM for Example 21.

Example 22

2-(Cyclobutylamino)-6-((1R,2S,3R,4R)-2,3-dihydroxy-4-(hydroxymethyl)cyclopentylamino)-5-(thiazol-2-yl)pyrimidin-4(3H)-one.HCl Prepared as in Scheme 1, except 2-(tributylstannyl)thiazole was used in place of 2-(tributylstannyl)benzo[d]thiazole in Step 5.

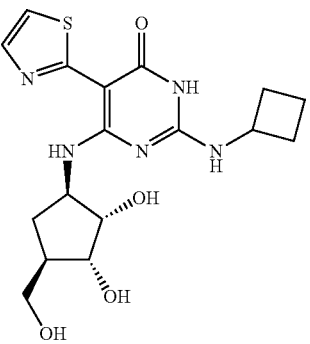 [SMILES: O=c1[nH]c(NC2CCC2)nc(N[C@@H]2C[C@H](CO)[C@@H](O)[C@H]2O)c1-c1nccs1]

¹H NMR (CD₃OD) δ 7.71 (d, J=3.6 Hz, 1H), 7.23 (d, J=3.6 Hz, 1H), 4.46 (br s, 1H), 3.89-3.93 (m, 2H), 3.65-3.57 (m, 2H), 2.49-2.41 (m, 3H), 2.21-2.16 (m, 1H), 2.11-2.02 (m, 2H), 1.86-1.79 (m, 2H), 1.45-1.43 (m, 1H); LCMS 1.79 min, 394 (M+H)

IRAK4 IC50 is 1114 nM for Example 22.

Example 23

2-(Cyclobutylamino)-6-((1R,2S,3R,4R)-2,3-dihydroxy-4-(hydroxymethyl)cyclopentylamino)-5-(thiazol-4-yl)pyrimidin-4(3H)-one.HCl Prepared as in Scheme 1, except 4-(tributylstannyl)thiazole was used in place of 2-(tributylstannyl)benzo[d]thiazole in Step 5.

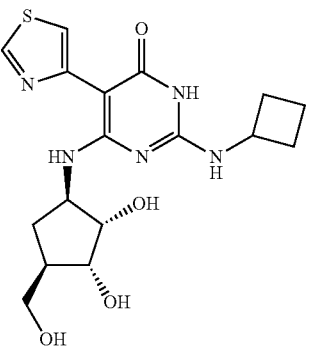 [SMILES: O=c1[nH]c(NC2CCC2)nc(N[C@@H]2C[C@H](CO)[C@@H](O)[C@H]2O)c1-c1cscn1]

¹H NMR (DMSO) δ 9.13 (s, 1H), 8.19 (s, 1H), 4.41 (m, 1H), 4.30-4.16 (m, 1H), 3.87-3.80 (m, 2H), 3.64-3.55 (m, 2H), 2.45-2.20 (m, 4H), 2.10-2.90 (m, 4H), 1.84 (m, 2H), 1.53 (m, 1H), 1.35-1.28 (m, 1H); LCMS 1.73 min, 394 (M+H)

IRAK4 IC50 is 1791 nM for Example 23.

Example 24

5-(Benzo[d]thiazol-2-yl)-6-(((1R,2S,3R,4R)-2,3-dihydroxy-4-(hydroxymethyl)cyclopentyl)amino)-2-morpholinopyrimidin-4(3H)-one.HCl Prepared as in Scheme 1, except morpholine was used in Step 7 in place of cyclobutylamine.

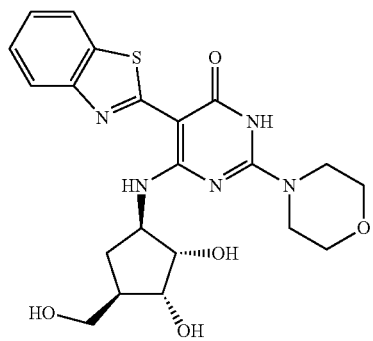 [SMILES: O=c1[nH]c(N2CCOCC2)nc(N[C@@H]2C[C@H](CO)[C@@H](O)[C@H]2O)c1-c1nc2ccccc2s1]

¹H NMR (DMSO) δ 10.99 (s, 1H), 10.81 (d, J=6.8 Hz, 1H), 7.91 (d, J=8 Hz, 1H), 7.76 (d, J=7.6 Hz, 1H), 7.37 (t, J=8 Hz, 1H), 7.22 (t, J=7.6 Hz, 1H), 4.30 (m, 1H), 3.80 (m, 2H), 3.75-3.40 (m, 10H), 2.32 (m, 1H), 1.99 (m, 1H), 1.26 (m, 1H); LCMS: 1.98 min., 460.2 (M+H)

IRAK4 IC50 is 11 nM for Example 24.

Example 25

5-(Benzo[d]thiazol-2-yl)-6-(((1R,2S,3R,4R)-2,3-dihydroxy-4-(hydroxymethyl)cyclopentyl)amino)-2-(pyrrolidin-1-yl)pyrimidin-4(3H)-one.HCl Prepared as in Scheme 1, except pyrrolidine was used in Step 7 in place of cyclobutylamine.

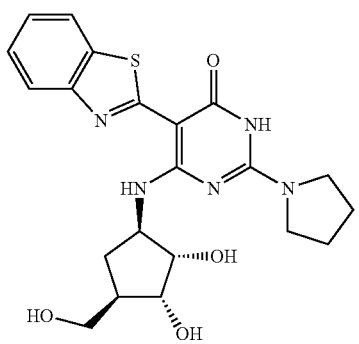 [SMILES: O=c1[nH]c(N2CCCC2)nc(N[C@@H]2C[C@H](CO)[C@@H](O)[C@H]2O)c1-c1nc2ccccc2s1]

¹H NMR (DMSO) δ 10.99 (s, 1H), 10.81 (d, J=6.4 Hz, 1H), 7.91 (d, J=8 Hz, 1H), 7.76 (d, J=8 Hz, 1H), 7.37 (dd, J=8, 7.2 Hz, 1H), 7.23 (dd, J=8, 7.2 Hz, 1H), 4.30 (m, 1H), 3.85-3.20 (m, 12H), 2.34 (m, 1H), 1.99 (m, 1H), 1.30 (m, 1H); LCMS: 2.05 min., 444.2 (M+H)

IRAK4 IC50 is 18 nM for Example 25.

Example 26

5-(Benzo[d]thiazol-2-yl)-6-(((1R,2S,3R,4R)-2,3-dihydroxy-4-(hydroxymethyl)cyclopentyl)amino)-2-(piperidin-1-yl)pyrimidin-4(3H)-one.HCl Prepared as in Scheme 1, except piperidine was used in Step 7 in place of cyclobutylamine.

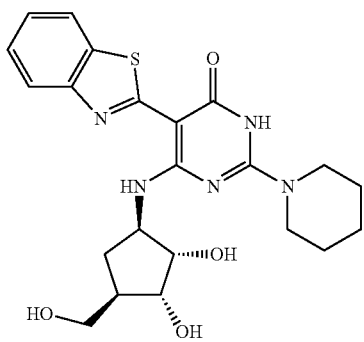 [SMILES: O=c1[nH]c(N2CCCCC2)nc(N[C@@H]2C[C@H](CO)[C@@H](O)[C@H]2O)c1-c1nc2ccccc2s1]

¹H NMR (DMSO) δ 10.6 (s, 1H), 10.76 (d, J=7.2 Hz, 1H), 7.90 (d, J=8 Hz, 1H), 7.74 (d, J=7.6 Hz, 1H), 7.36 (t, J=7.6 Hz, 1H), 7.21 (t, J=8 Hz, 1H), 4.29 (m, 1H), 3.82-3.75 (m, 2H), 3.69-3.68 (m, 4H), 3.53-3.42 (m, 2H), 2.33 (m, 1H), 1.99 (m, 1H), 1.63-1.45 (m, 5H), 1.26 (m, 1H); LCMS: 1.77 min, 458.3 (M+H)

IRAK4 IC50 is 43 nM for Example 26.

Example 27

5-(Benzo[d]thiazol-2-yl)-2-(4,4-difluoropiperidin-1-yl)-6-(((1R,2S,3R,4R)-2,3-dihydroxy-4-(hydroxymethyl)cyclopentyl)amino)pyrimidin-4(3H)-one.HCl Prepared as in Scheme 1, except 4,4-difluoropiperidine was used in Step 7 in place of cyclobutylamine.

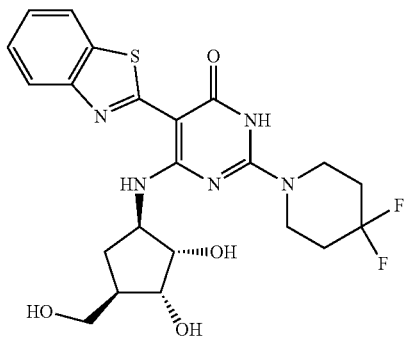 [SMILES: O=c1[nH]c(N2CCC(F)(F)CC2)nc(N[C@@H]2C[C@H](CO)[C@@H](O)[C@H]2O)c1-c1nc2ccccc2s1]

¹H NMR (DMSO) δ 11.15 (s, 1H), 10.81 (d, J=6.8 Hz, 1H), 7.91 (d, J=7.6 Hz, 1H), 7.76 (d, J=7.6 Hz, 1H), 7.38 (t, J=8 Hz, 1H), 7.23 (t, J=8 Hz, 1H), 4.30 (m, 1H), 3.95-3.20 (m, 7H), 2.34 (m, 1H), 2.15-1.88 (m, 5H), 1.30 (m, 1H); LCMS: 1.92 min, 493.8 (M+H)

IRAK4 IC50 is 134.8 nM for Example 27.

Example 28

5-(Benzo[d]thiazol-2-yl)-6-(((1R,2S,3R,4R)-2,3-dihydroxy-4-(hydroxymethyl)cyclopentyl)amino)-2-(4-methylpiperazin-1-yl)pyrimidin-4(3H)-one.HCl Prepared as in Scheme 1, except 1-methylpiperazine was used in Step 7 in place of cyclobutylamine.

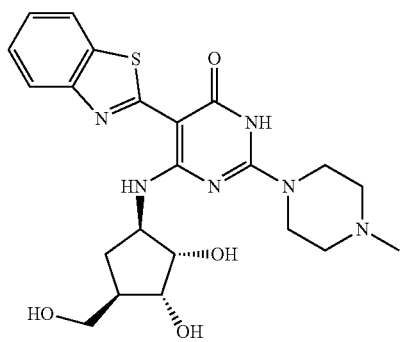 [SMILES: CN1CCN(c2nc(N[C@@H]3C[C@H](CO)[C@@H](O)[C@H]3O)c(-c3nc4ccccc4s3)c(=O)[nH]2)CC1]

¹H NMR (DMSO) δ 11.23 (s, 1H), 10.85 (d, J=7.2 Hz, 1H), 10.60 (m, 1H), 7.92 (d, J=8 Hz, 1H), 7.78 (d, J=8 Hz, 1H), 7.37 (t, J=8.3 Hz, 1H), 7.24 (t, J=8.3 Hz, 1H), 4.57 (m, 1H) 4.30 (m, 1H), 3.80 (m, 2H), 3.60-3.20 (m, 8H), 3.10 (m, 1H), 2.78 (s, 3H), 2.33 (m, 1H), 2.02 (m, 1H), 1.32 (m, 1H); LCMS: 1.81 min., 473.2 (M+H)

IRAK4 IC50 is 43 nM for Example 28.

Example 29

5-(Benzo[d]thiazol-2-yl)-2-(3,4-dihydroisoquinolin-2(H)-yl)-6-(((1R,2S,3R,4R)-2,3-dihydroxy-4-(hydroxymethyl)cyclopentyl)amino)pyrimidin-4(3H)-one.HCl Prepared as in Scheme 1, except 1,2,3,4-tetrahydroisoquinoline was used in Step 7 in place of cyclobutylamine.

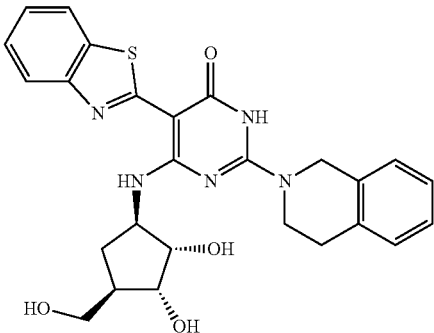 [SMILES: O=c1[nH]c(N2CCc3ccccc3C2)nc(N[C@@H]2C[C@H](CO)[C@@H](O)[C@H]2O)c1-c1nc2ccccc2s1]

¹H NMR (DMSO) δ 11.03 (s, 1H), 10.81 (d, J=6.8 Hz, 1H), 7.91 (d, J=7.2 Hz, 1H), 7.76 (d, J=8 Hz, 1H), 7.37 (dd, J=8, 7.2 Hz, 1H), 7.25-7.15 (m, 5H), 4.87 (s, 2H), 4.36 (m, 1H), 3.95-3.40 (m, 6H), 2.92 (t, J=6.2 Hz, 2H), 2.38 (m, 1H), 2.03 (m, 1H), 1.32 (m, 1H); LCMS: 2.10 min., 505.6 (M+H)

IRAK4 IC50 is 27.5 nM for Example 29.

Example 30

5-(Benzo[d]thiazol-2-yl)-6-(((1R,2S,3R,4R)-2,3-dihydroxy-4-(hydroxymethyl)cyclopentyl)amino)-2-(dimethylamino)pyrimidin-4(3H)-one.HCl Prepared as in Scheme 1, except dimethylamine was used in Step 7 in place of cyclobutylamine.

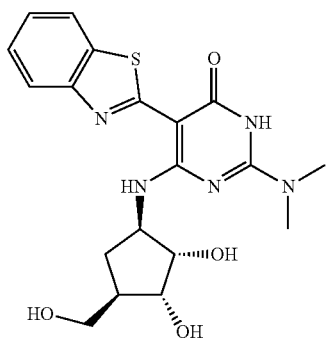 [SMILES: CN(C)c1nc(N[C@@H]2C[C@H](CO)[C@@H](O)[C@H]2O)c(-c2nc3ccccc3s2)c(=O)[nH]1]

¹H NMR (DMSO) δ 10.78 (m, 2H), 7.90 (d, J=8 Hz, 1H), 7.74 (d, J=7.6 Hz, 1H), 7.36 (t, J=8.2 Hz, 1H), 7.20 (t, J=8.2 Hz, 1H), 4.25 (m, 1H), 3.84-3.73 (m, 2H), 3.55-3.40 (m, 2H), 3.16 (s, 6H), 2.34 (m, 1H), 1.99 (m, 1H), 1.27 (m, 1H); LCMS: 1.61 min., 418.2 (M+H)

IRAK4 IC50 is 542 nM for Example 30.

Example 31

2-(Azetidin-1-yl)-5-(benzo[d]thiazol-2-yl)-6-(((1R,2S,3R,4R)-2,3-dihydroxy-4-(hydroxymethyl)cyclopentyl)amino)pyrimidin-4(3H)-one.HCl Prepared as in Scheme 1, except azetidine was used in Step 7 in place of cyclobutylamine.

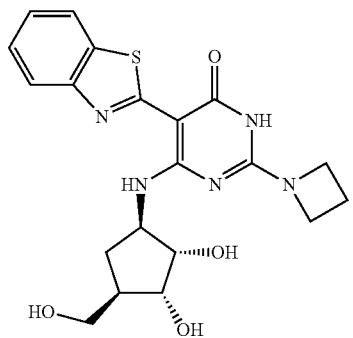 [SMILES: O=c1[nH]c(N2CCC2)nc(N[C@@H]2C[C@H](CO)[C@@H](O)[C@H]2O)c1-c1nc2ccccc2s1]

¹H NMR (DMSO) δ 11.08 (s, 1H), 10.88 (d, J=7.2 Hz, 1H), 7.89 (d, J=7.6 Hz, 1H), 7.74 (d, J=8 Hz, 1H), 7.36 (t, J=8.4 Hz, 1H), 7.21 (t, J=8 Hz, 1H), 4.30 (m, 1H), 4.11 (t, J=7.6 Hz, 4H), 3.81-3.75 (m, 2H), 3.51-3.40 (m, 2H), 2.40-2.24 (m, 2H), 2.06-180 (m, 2H), 1.25 (m, 1H); LCMS: 2.01 min., 430.2 (M+H)

IRAK4 IC50 is 67 nM for Example 31.

Example 32

6-(((1R,2S,3R,4R)-2,3-Dihydroxy-4-(hydroxymethyl)cyclopentyl)amino)-5-(4-methylthiazol-2-yl)-2-morpholinopyrimidin-4(3H)-one.HCl Prepared as in Scheme 1, except 4-methyl-2-(tributylstannyl)thiazole was used in place of 2-(tributylstannyl)benzo[d]thiazole in Step 5 and morpholine was used in Step 7 in place of cyclobutylamine.

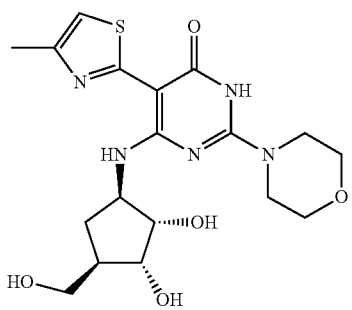 [SMILES: Cc1csc(-c2c(N[C@@H]3C[C@H](CO)[C@@H](O)[C@H]3O)nc(N3CCOCC3)[nH]c2=O)n1]

¹H NMR (DMSO) δ 10.83 (s, 1H), 10.59 (d, J=7.2 Hz, 1H), 6.78 (s, 1H), 4.65-4.48 (m, 3H), 4.23 (m, 1H), 3.73-3.60 (m, 7H), 3.50-3.32 (m, 2H), 2.33 (s, 3H), 2.29 (m, 1H), 1.96 (m, 1H), 1.18 (m, 1H); LCMS: 1.58 min., 424.2 (M+H)

IRAK4 IC50 is 26.6 nM for Example 32.

Example 33

6-(((1R,2S,3R,4R)-2,3-Dihydroxy-4-(hydroxymethyl)cyclopentyl)amino)-5-(4-methylthiazol-2-yl)-2-(4-(trifluoromethyl)piperidin-1-yl)pyrimidin-4(3H)-one.HCl Prepared as in Scheme 1, except 4-methyl-2-(tributylstannyl)thiazole was used in place of 2-(tributylstannyl)benzo[d]thiazole in Step 5 and 4-(trifluoromethyl)piperidine was used in Step 7 in place of cyclobutylamine.

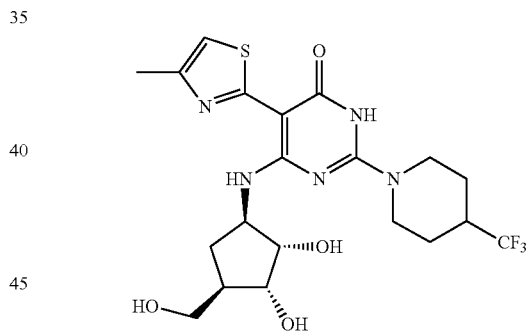

¹H NMR (DMSO) δ 10.86 (s, 1H), 10.57 (d, J=6 Hz, 2H), 6.78 (s, 1H), 4.53-4.50 (m, 2H), 3.73-3.65 (m, 2H), 3.49-3.14 (m, 2H), 2.96 (t, J=12.8 Hz, 2H), 2.63 (m, 1H), 2.32 (s, 3H), 1.96 (m, 1H), 1.86 (m, 2H), 1.84 (m, 2H), 1.16 (m, 2H); LCMS: 1.86 min., 490.2 (M+H)

IRAK4 IC50 is 93.6 nM for Example 33.

Example 34

6-(((1R,2S,3R,4R)-2,3-Dihydroxy-4-(hydroxymethyl)cyclopentyl)amino)-5-(6-methylpyridin-2-yl)-2-morpholinopyrimidin-4(3H)-one.HCl Prepared as in Scheme 1, except 2-(tributylstannyl)pyridine was used in place of 2-(tributylstannyl)benzo[d]thiazole in Step 5 and morpholine was used in Step 7 in place of cyclobutylamine.

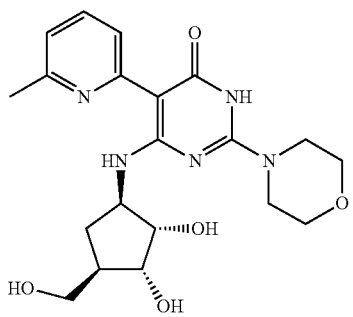 [SMILES: Cc1cccc(-c2c(N[C@@H]3C[C@H](CO)[C@@H](O)[C@H]3O)nc(N3CCOCC3)[nH]c2=O)n1]

¹H NMR (DMSO) δ 10.58 (br.s, 1H), 8.50 (br.s, 1H), 7.65 (m, 1H), 6.96 (m, 1H), 4.19 (m, 1H), 3.75-3.20 (m, 12H), 2.47 (s, 3H), 2.24 (m, 1H), 1.93 (m, 1H), 1.12 (m, 1H); LCMS: 1.39 min., 416.2 (M+H)

IRAK4 IC50 is 213.5 nM for Example 34.

Example 35

6-(((1R,2S,3R,4R)-2,3-Dihydroxy-4-(hydroxymethyl)cyclopentyl)amino)-5-(6-methylpyridin-2-yl)-2-(piperidin-1-yl)pyrimidin-4(3H)-one.HCl Prepared as in Scheme 1, except 2-(tributylstannyl)pyridine was used in place of 2-(tributylstannyl)benzo[d]thiazole in Step 5 and piperidine was used in Step 7 in place of cyclobutylamine.

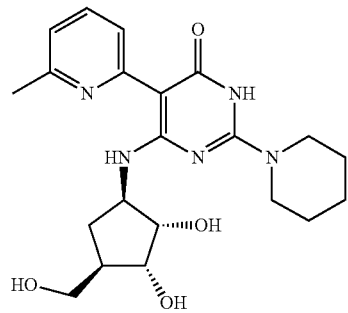 [SMILES: Cc1cccc(-c2c(N[C@@H]3C[C@H](CO)[C@@H](O)[C@H]3O)nc(N3CCCCC3)[nH]c2=O)n1]

¹H NMR (DMSO) δ 11.62 (br.s, 1H), 10.32 (s, 1H), 8.61 (d, J=9.2 Hz, 1H), 7.53 (t, J=7.6 Hz, 1H), 6.83 (d, J=6.8 Hz, 1H), 4.55-4.45 (m, 2H), 4.10 (m, 1H), 3.70-3.50 (m, 5H), 3.43 (m, 1H), 2.43 (s, 3H), 2.30 (m, 1H), 1.95 (m, 1H), 1.60-1.45 (m, 6H), 1.13 (m, 1H); LCMS: 1.39 min., 416.2 (M+H)

IRAK4 IC50 is 296.4 nM for Example 35.

Example 36

2-(Azetidin-3-ylamino)-5-(benzo[d]thiazol-2-yl)-6-(((1R,2S,3R,4R)-2,3-dihydroxy-4-(hydroxymethyl)cyclopentyl)amino)pyrimidin-4(3H)-one.HCl Prepared as in Scheme 1, except tert-butyl 3-aminoazetidine-1-carboxylate was used in Step 7 in place of cyclobutylamine.

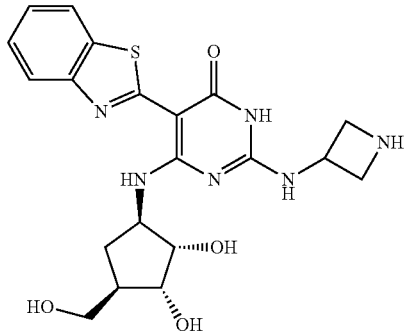 [SMILES: O=c1[nH]c(NC2CNC2)nc(N[C@@H]2C[C@H](CO)[C@@H](O)[C@H]2O)c1-c1nc2ccccc2s1]

¹H NMR (DMSO) δ 11.12 (s, 1H), 10.92 (d, J=7.2 Hz, 1H), 9.20-8.99 (m, 2H), 7.91 (d, J=8 Hz, 1H), 7.77 (d, J=8 Hz, 1H), 7.37 (t, J=8 Hz, 1H), 7.23 (t, J=8 Hz, 1H), 4.72 (m, 1H), 4.32-4.05 (m, 5H), 3.80-3.77 (m, 2H), 3.55-3.45 (m, 2H), 2.31 (m, 1H), 2.02 (m, 1H), 1.34 (m, 1H); LCMS: 1.86 min., 445.2 (M+H)

IRAK4 IC50 is 656 nM for Example 36.

Example 37

5-(Benzo[d]thiazol-2-yl)-6-(((1R,2S,3R,4R)-2,3-dihydroxy-4-(hydroxymethyl)cyclopentyl)amino)-2-(pyrrolidin-3-ylamino)pyrimidin-4(3H)-one.HCl Prepared as in Scheme 1, except tert-butyl 3-aminopyrrolidine-1-carboxylate was used in Step 7 in place of cyclobutylamine.

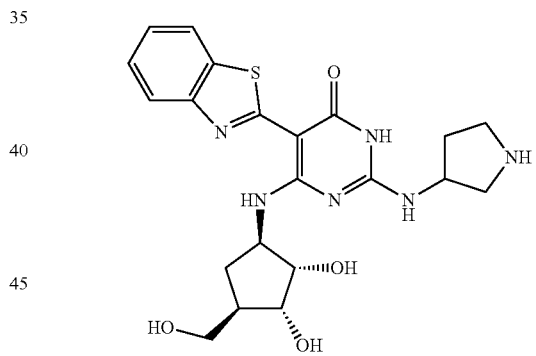

¹H NMR (DMSO) δ 10.92 (t, J=7 Hz, 1H), 10.73 (s, 1H), 9.30-9.10 (br.s, 2H), 7.90 (d, J=8 Hz, 1H), 7.76 (d, J=8.4 Hz, 1H), 7.68 (br.s, 1H), 7.37 (dd, J=8, 7.6 Hz, 1H), 7.22 (dd, J=8, 7.2 Hz, 1H), 4.50 (m, 1H), 4.33 (m, 1H), 3.83-3.78 (m, 2H), 3.55-3.40 (m, 3H), 3.35-3.14 (m, 2H), 2.40-2.15 (m, 2H), 2.10-1.85 (m, 2H), 1.33 (m, 1H); LCMS: 1.89 min., 459.2 (M+H)

IRAK4 IC50 is 2000 nM for Example 37.

Example 38

5-(Benzo[d]thiazol-2-yl)-6-(((1R,2S,3R,4R)-2,3-dihydroxy-4-(hydroxymethyl)cyclopentyl)amino)-2-((R)-piperidin-3-ylamino)pyrimidin-4(3H)-one.HCl Prepared as in Scheme 1, except (R)-tert-butyl 3-aminopiperidine-1-carboxylate was used in Step 7 in place of cyclobutylamine.

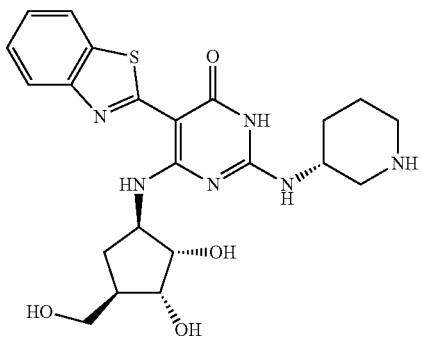 [SMILES: O=c1[nH]c(N[C@@H]2CCCNC2)nc(N[C@@H]2C[C@H](CO)[C@@H](O)[C@H]2O)c1-c1nc2ccccc2s1]

¹H NMR (DMSO) δ 7.84 (m, 1H), 7.39 (dd, J=8, 7.6 Hz, 1H), 7.25 (t, J=7.6 Hz, 1H), 4.68 (m, 1H), 4.30 (m, 1H), 4.02 (m, 1H), 3.83-3.708 (m, 3H), 3.39-3.30 (m, 3H), 3.10-2.90 (m, 2H), 2.50 (m, 1H), 2.30-2.05 (m, 3H), 1.90 (m, 1H), 1.76 (m, 1H), 1.53 (m, 1H); LCMS: 1.92 min., 473.2 (M+H)

IRAK4 IC50 is 5123 nM for Example 38.

Example 39

5-(Benzo[d]thiazol-2-yl)-6-(((1R,2S,3R,4R)-2,3-dihydroxy-4-(hydroxymethyl)cyclopentyl)amino)-2-((S)-piperidin-3-ylamino)pyrimidin-4(3H)-one.HCl Prepared as in Scheme 1, except (S)-tert-butyl 3-aminopiperidine-1-carboxylate was used in Step 7 in place of cyclobutylamine.

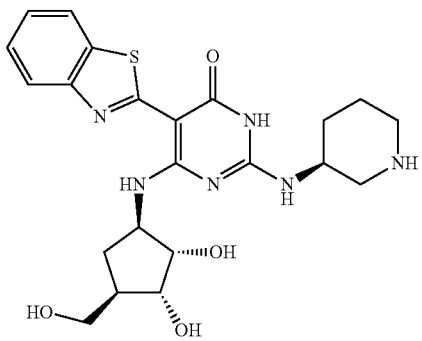 [SMILES: O=c1[nH]c(N[C@H]2CCCNC2)nc(N[C@@H]2C[C@H](CO)[C@@H](O)[C@H]2O)c1-c1nc2ccccc2s1]

¹H NMR (DMSO) δ 7.87-7.81 (m, 2H), 7.44-7.39 (m, 1H), 7.31-7.25 (m, 1H), 4.70-4.50 (m, 1H), 4.40-4.20 (m, 1H), 4.00 (m, 1H), 3.80-3.60 (m, 3H), 3.50-3.23 (m, 2H), 3.17-3.00 (m, 2H), 2.52-2.40 (m, 1H), 2.30-2.00 (m, 3H), 1.93 (m, 1H), 1.77 (m, 1H), 1.53 (m, 1H); LCMS: 1.87 min., 473.2 (M+H)

IRAK4 IC50 is 4260 nM for Example 39.

Example 40

5-(Benzo[d]thiazol-2-yl)-6-(((1R,2S,3R,4R)-2,3-dihydroxy-4-(hydroxymethyl)cyclopentyl)amino)-2-((3-methoxypropyl)amino)pyrimidin-4(3H)-one HCl Prepared as in Scheme 1, except 3-methoxypropan-1-amine was used in Step 7 in place of cyclobutylamine.

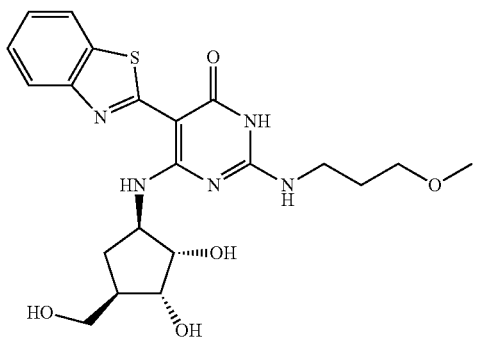 [SMILES: COCCCNc1nc(N[C@@H]2C[C@H](CO)[C@@H](O)[C@H]2O)c(-c2nc3ccccc3s2)c(=O)[nH]1]

¹H NMR (DMSO) δ 10.88 (d, J=6.4 Hz, 1H), 10.57 (s, 1H), 7.89 (d, J=7.6 Hz, 1H), 7.74 (d, J=8 Hz, 1H), 7.36 (t, J=8.4 Hz, 1H), 7.21 (t, J=8 Hz, 1H), 6.84 (m, 1H), 4.33 (m, 1H), 3.84-3.70 (m, 2H), 3.50-3.35 (m, 6H), 3.24 (s, 3H), 2.34 (m, 1H), 1.98 (m, 1H), 1.79-1.76 (m, 2H), 1.23 (m, 1H); LCMS: 1.64 min., 462.0 (M+H)

IRAK4 IC50 is 60 nM for Example 40.

Example 41

5-(Benzo[d]thiazol-2-yl)-2-(cyclobutylamino)-6-((1R,2S,3R,4R)-2,3-dihydroxy-4-(hydroxymethyl)-2-methylcyclopentylamino)pyrimidin-4(3H)-one-.HCl Prepared as in Scheme 1, except ((3aR,4R,6R,6aS)-6-amino-2,2,6a-trimethyltetrahydro-3aH-cyclopenta[d][1,3]dioxol-4-yl)methanol (synthesized according to Arasappan, A.; et. al in WO2010022121) was used in place of (1R,2S,3R,5R)-3-amino-5-(hydroxymethyl)cyclopentane-1,2-diol hydrochloride for Step 3.

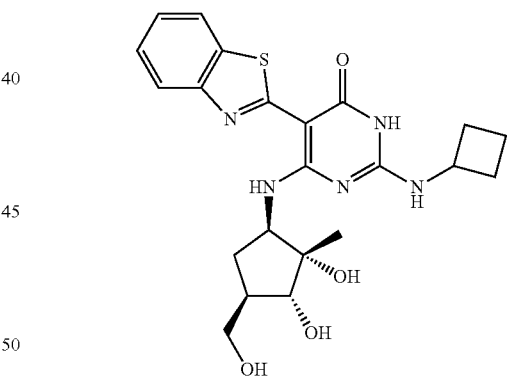

¹H NMR (DMSO) δ 10.91 (br s, 1H), 7.92-7.89 (m, 1H), 7.72-7.70 (m, 1H), 7.38-7.37 (m, 1H), 7.25-7.20 (m, 1H), 4.71-4.62 (m, 1H), 4.43-4.34 (m, 2H), 3.59-3.14 (m 5H), 2.48-2.30 (m, 2H), 1.99-1.97 (m, 2H), 1.76-1.69 (m, 2H), 1.28-1.16 (m, 3H); LCMS 1.80 min, 458 (M+H)

IRAK4 IC50 is 459 nM for Example 41.

Example 42

5-(Benzo[d]thiazol-2-yl)-6-((1R,2S,3R,4R)-2,3-dihydroxy-4-isopropylcyclopentylamino)-2-morpholinopyrimidin-4(3H)-one.HCl Prepared as in Scheme 1, except (3aS,4R,6R,6aR)-2,2-dimethyl-6-(prop-1-en-2-yl)tetrahydro-3aH-cyclopenta[d]

[1,3]dioxol-4-amine (synthesized according to Girijavallabhan, V.; et al. *J. Org. Chem.* 2011, 76, 6442) was used in place of (1R,2S,3R,5R)-3-amino-5-(hydroxymethyl)cyclopentane-1,2-diol hydrochloride for Step 3 and morpholine was used in place of cyclobutylamine for Step 7.

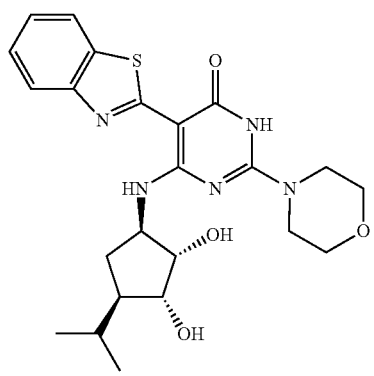 [SMILES: CC(C)[C@H]1C[C@@H](Nc2nc(N3CCOCC3)[nH]c(=O)c2-c2nc3ccccc3s2)[C@H](O)[C@@H]1O]

$^1$H NMR (DMSO) δ 10.98 (s, 1H), 10.76 (d, J=5.6 Hz, 1H), 7.91 (d, J=7.6 Hz, 1H), 7.70 (d, J=7.6 Hz, 1H), 7.38 (t, J=7.2 Hz, 1H), 7.25 (t, J=7.2 Hz, 1H), 4.38-4.27 (m, 2H), 3.77-3.67 (m, 10H), 2.30-2.29 (m, 1H), 1.68 (s, 1H), 1.22-1.13 (m, 2H), 0.94 (m, 6H); LCMS 2.25 min, 472 (M+H)

IRAK4 IC50 is 72 nM for Example 42.

Example 43

5-(Benzo[d]thiazol-2-yl)-6-((1R,2S,3R,4R)-2,3-dihydroxy-4-isopropylcyclopentylamino)pyrimidin-4(3H)-one.HCl Prepared as in Scheme 1, except (3aS,4R,6R,6aR)-2,2-dimethyl-6-(prop-1-en-2-yl)tetrahydro-3aH-cyclopenta[d][1,3]dioxol-4-amine (synthesized according to Girijavallabhan, V.; et al. *J. Org. Chem.* 2011, 76, 6442) was used in place of (1R,2S,3R,5R)-3-amino-5-(hydroxymethyl)cyclopentane-1,2-diol hydrochloride for Step 3.

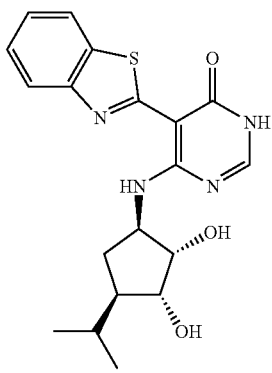 [SMILES: CC(C)[C@H]1C[C@@H](Nc2nc[nH]c(=O)c2-c2nc3ccccc3s2)[C@H](O)[C@@H]1O]

$^1$H NMR (DMSO) δ 10.76 (d, J=7.2 Hz, 1H), 8.01 (d, J=7.6 Hz, 1H), 7.88 (d, J=7.6 Hz, 1H), 7.46 (t, J=7.2 Hz, 1H), 7.33 (t, J=7.2 Hz, 1H), 4.42 (m, 2H), 3.79-3.71 (m, 2H), 2.26-2.22 (m 1H), 1.89-1.89 (m, 1H), 1.66-1.63 (m, 1H), 1.16-1.12 (m, 1H), 0.90 (m, 6H); LCMS 2.23 min, 387 (M+H)

IRAK4 IC50 is 850 nM for Example 43.

Example 44

5-(Benzo[d]thiazol-2-yl)-6-((1R,2S,3R,4R)-2,3-dihydroxy-4-isopropylcyclopentylamino)-2-(4-(pyrimidin-5-yl)piperidin-1-yl)pyrimidin-4(3H)-one.HCl Prepared as in Scheme 1, except (3aS,4R,6R,6aR)-2,2-dimethyl-6-(prop-1-en-2-yl)tetrahydro-3aH-cyclopenta[d][1,3]dioxol-4-amine (synthesized according to Girijavallabhan, V.; et al. *J. Org. Chem.* 2011, 76, 6442) was used in place of (1R,2S,3R,5R)-3-amino-5-(hydroxymethyl)cyclopentane-1,2-diol hydrochloride for Step 3 and 5-(piperidin-4-yl)pyrimidine was used in place of cyclobutylamine for Step 7.

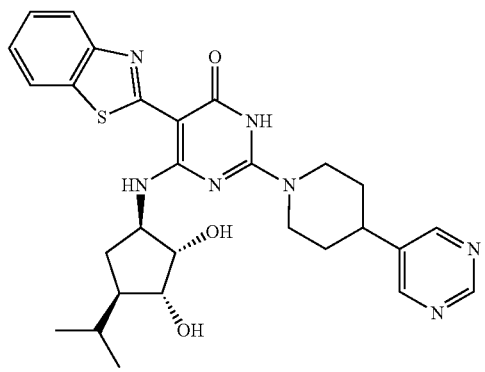 [SMILES: CC(C)[C@H]1C[C@@H](Nc2nc(N3CCC(c4cncnc4)CC3)[nH]c(=O)c2-c2nc3ccccc3s2)[C@H](O)[C@@H]1O]

$^1$H NMR (DMSO) δ 10.98 (br s, 1H), 10.74 (d, J=6.4 Hz, 1H), 9.06 (s, 1H), 8.79 (s, 2H), 7.93-7.87 (m, 2H), 7.71-7.68 (m, 1H), 7.38 (t, J=7.2 Hz, 1H), 7.22 (t, J=7.2 Hz, 1H), 4.65-4.65 (m, 2H), 4.29-4.24 (m, 1H), 3.81-3.55 (m, 2H), 3.09-3.92 (m, 2H), 2.34-2.27 (m, 1H), 1.97-1.88 (m, 2H), 1.79-1.65 (m, 4H), 1.21-1.11 (m, 2H), 1.97-0.81 (m, 6H); LCMS 1.87 min, 548 (M+H)

IRAK4 IC50 is 23 nM for Example 44.

Example 45

5-(Benzo[d]thiazol-2-yl)-2-(cyclobutylamino)-6-((1R,2S,3R,4S)-2,3-dihydroxy-4-(2-hydroxypropan-2-yl)cyclopentylamino)pyrimidin-4(3H)-one.HCl Prepared as in Scheme 1, except 2-((3aR,4S,6R)-6-amino-2,2-dimethyltetrahydro-3aH-cyclopenta[d][1,3]dioxol-4-yl)propan-2-ol (synthesized according to Arasappan, A.; et. al in WO2010022121) was used in place of (1R,2S,3R,5R)-3-amino-5-(hydroxymethyl)cyclopentane-1,2-diol hydrochloride for Step 3.

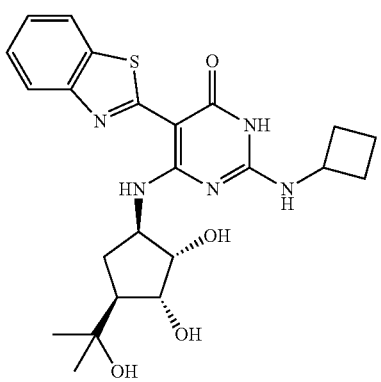 [SMILES: CC(C)(O)[C@H]1C[C@@H](Nc2nc(NC3CCC3)[nH]c(=O)c2-c2nc3ccccc3s2)[C@H](O)[C@@H]1O]

¹H NMR (CD₃OD) δ 7.88 (d, J=7.6 Hz, 1H), 7.82 (d, J=7.6 Hz, 1H), 7.49-7.41 (m, 1H), 7.33-7.28 (m, 1H), 4.43 (br s, 2H), 4.12-4.10 (m, 1H), 3.93-3.90 (m, 1H), 2.51-2.35 (m, 3H), 2.11-2.04 (m, 3H), 1.87-1.79 (m, 2H), 1.70-1.65 (br s, 1H), 1.33-1.26 (m, 6H); LCMS 0.89 min, 472 (M+H)

IRAK4 IC50 is 65 nM for Example 45.

Example 46

6-((1R,2S,3R,4S)-2,3-Dihydroxy-4-methylcyclopentylamino)-2-morpholino-5-(quinolin-2-yl)pyrimidin-4(3H)-one.HCl Prepared as in Scheme 1, except (3aS,4R,6S,6aR)-2,2,6-trimethyltetrahydro-3aH-cyclopenta[d][1,3]dioxol-4-amine (synthesized according to Arasappan, A.; et. al in WO2010022121) was used in place of (1R,2S,3R,5R)-3-amino-5-(hydroxymethyl)cyclopentane-1,2-diol hydrochloride in Step 3, 2-(tributylstannyl)quinoline was used in place of 2-(tributylstannyl)benzo[d]thiazole in Step 5 and morpholine was used in Step 7 in place of cyclobutylamine.

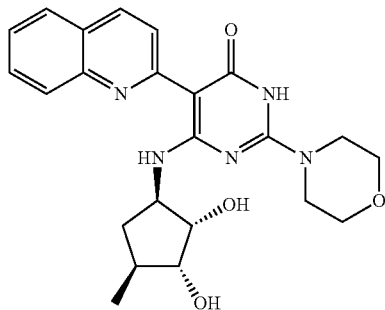 [SMILES: C[C@H]1C[C@@H](Nc2nc(N3CCOCC3)[nH]c(=O)c2-c2ccc3ccccc3n2)[C@H](O)[C@@H]1O]

¹H NMR (DMSO) δ 12.25 (s, 1H), 10.55 (s, 1H), 8.91 (d, J=9.2 Hz, 1H), 8.11 (d, J=9.2 Hz, 1H), 7.79-7.74 (m, 2H), 7.67-7.64 (m, 1H), 7.42-7.40 (m, 1H), 4.64-4.62 (m, 2H), 3.21-3.20 (m, 1H), 3.86 (s, 1H), 3.66 (m, 8H), 3.66 (s, 1H), 1.90-1.87 (m, 1H), 1.06-1.04 (4H); LCMS 1.73 min, 438 (M+H)

IRAK4 IC50 is 5 nM for Example 46.

Example 47

5-(Benzo[d]thiazol-2-yl)-6-((1R,2S,3R,4S)-2,3-dihydroxy-4-methylcyclopentylamino)-2-morpholinopyrimidin-4(3H)-one.HCl Prepared as in Scheme 1, except (3aS,4R,6S,6aR)-2,2,6-trimethyltetrahydro-3aH-cyclopenta[d][1,3]dioxol-4-amine (synthesized according to Arasappan, A.; et. al in WO2010022121) was used in place of (1R,2S,3R,5R)-3-amino-5-(hydroxymethyl)cyclopentane-1,2-diol hydrochloride in Step 3, and morpholine was used in Step 7 in place of cyclobutylamine.

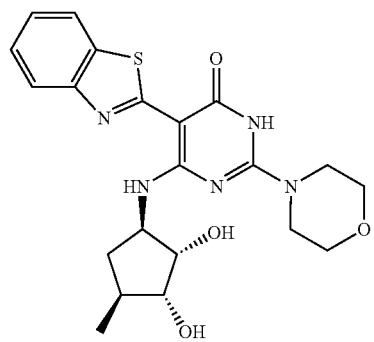 [SMILES: C[C@H]1C[C@@H](Nc2nc(N3CCOCC3)[nH]c(=O)c2-c2nc3ccccc3s2)[C@H](O)[C@@H]1O]

¹H NMR (DMSO) δ 11.00 (br s, 1H), 10.81 (d, J=7.2 Hz, 1H), 7.91 (d, J=8 Hz, 1H), 7.73 (d, J=8 Hz, 1H), 7.42-7.36 (m, 1H), 7.28-7.29 (m, 1H), 4.29-4.24 (m, 2H), 3.89-3.56 (m, 8H), 3.52-3.49 (m, 1H), 3.08-3.04 (m, 1H), 2.49-2.39 (m, 1H), 1.96-1.88 (m, 1H), 1.09 (d, J=6.8 Hz, 1H); LCMS 2.12 min, 444 (M+H)

IRAK4 IC50 is 23 nM for Example 47.

Example 48

5-(Benzo[d]thiazol-2-yl)-2-(cyclobutylamino)-6-((1R,2S,3R)-2,3-dihydroxycyclopentylamino)pyrimidin-4(3H)-one.HCl Prepared as in Scheme 1, except (3a'S,4'R,6a'R)-tetrahydro-3a'H-spiro[cyclohexane-1,2'-cyclopenta[d][1,3]dioxol]-4'-amine (synthesized according to Arasappan, A.; et. al in WO2010022121) was used in place of (1R,2S,3R,5R)-3-amino-5-(hydroxymethyl)cyclopentane-1,2-diol hydrochloride for Step 3.

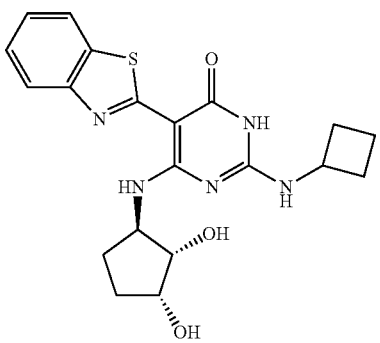 [SMILES: O=c1[nH]c(NC2CCC2)nc(N[C@@H]2CC[C@@H](O)[C@H]2O)c1-c1nc2ccccc2s1]

¹H NMR (DMSO) δ 10.94 (br s, 1H), 10.25 (br s, 1H), 7.89 (d, J=8 Hz, 1H), 7.73 (d, J=8 Hz, 1H), 7.36 (t, J=8.4 Hz, 1H), 7.21 (t, J=8.4 Hz, 1H), 4.36-4.33 (m, 2H), 3.99-3.96 (m, 1H), 3.87-3.84 (m, 1H), 2.31-2.30 (m, 3H), 2.00-2.19 (m, 3H), 1.73-1.57 (m, 3H), 1.39-1.38 (m, 1H); LCMS 1.99 min, 414 (M+H)

IRAK4 IC50 is 2261 nM for Example 48.

Example 49

(S)-5-(Benzo[d]thiazol-2-yl)-2-(cyclobutylamino)-6-(2,3-dihydroxypropylamino)pyrimidin-4(3H)-one.HCl Prepared as in Scheme 1, except (S)-3-aminopropane-1,2-diol was used in place of (1R,2S,3R,5R)-3-amino-5-(hydroxymethyl)cyclopentane-1,2-diol hydrochloride for Step 3.

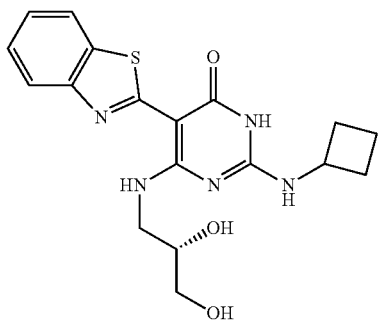 [SMILES: O=c1[nH]c(NC2CCC2)nc(NC[C@H](O)CO)c1-c1nc2ccccc2s1]

$^{1}$H NMR (DMSO) δ 10.89 (br s, 1H), 10.28 (br s, 1H), 7.88 (d, J=8 Hz, 1H), 7.69 (d, J=8 Hz, 1H), 7.37 (t, J=8.4 Hz, 1H), 7.20 (t, J=8.4 Hz, 1H), 7.04 (br s, 1H), 4.35-4.33 (m, 1H), 3.82-3.71 (m, 3H), 3.48-3.38 (m, 3H), 2.30-2.28 (m, 3H), 1.98-1.93 (m, 2H), 1.68 (m, 2H), 1.15-0.83 (m, 3H); LCMS 1.78 min, 388 (M+H)

IRAK4 IC50 is 5327 nM for Example 49.

Example 50

5-(Benzo[d]thiazol-2-yl)-6-(((1R,2S,3R,4R)-2,3-dihydroxy-4-(hydroxymethyl)cyclopentyl)amino)-2-((2,6-dimethylpyridin-4-yl)amino)pyrimidin-4(3H)-one.HCl

SCHEME 2

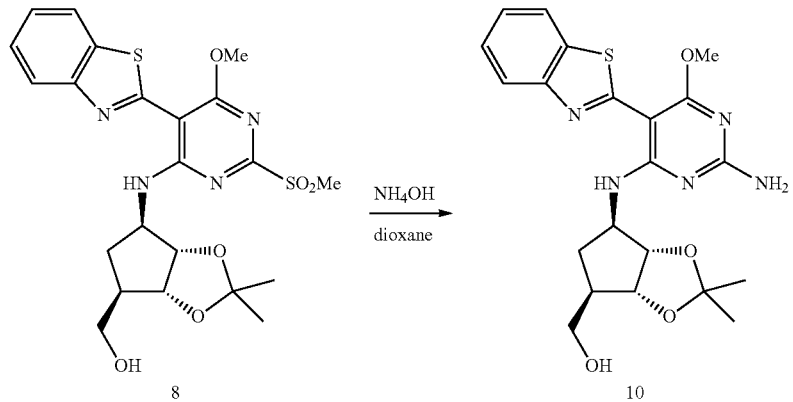

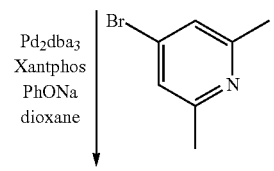

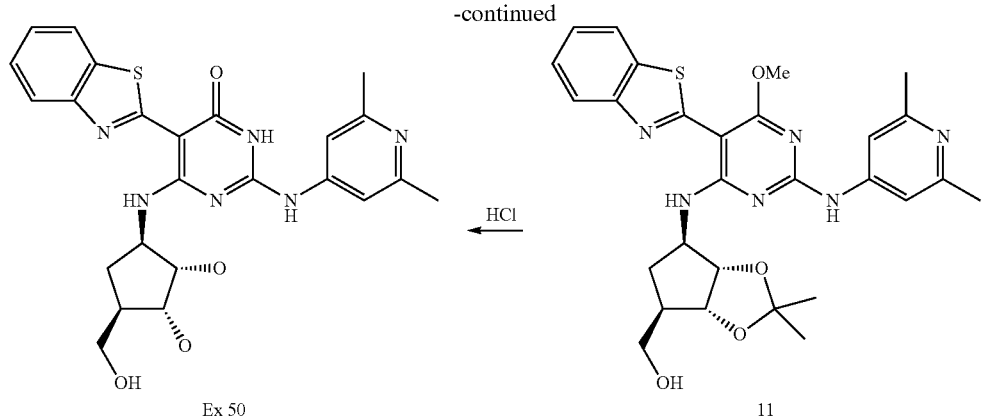

Ex 50

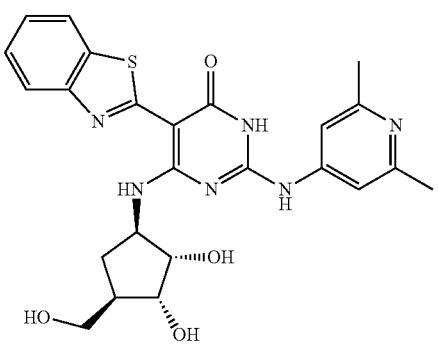 [SMILES: Cc1cc(Nc2nc(N[C@@H]3C[C@H](CO)[C@@H](O)[C@H]3O)c(-c3nc4ccccc4s3)c(=O)[nH]2)cc(C)n1]

11

Step 1: ((3aR,4R,6R,6aS)-6-(2-Amino-5-(benzo[d]thiazol-2-yl)-6-methoxypyrimidin-4-ylamino)-2,2-dimethyltetrahydro-3aH-cyclopenta[d][1,3]dioxol-4-yl)methanol (Compound 10)

A mixture of Compound 8 (1.36 g, 2.458 mmol) and ammonium hydroxide (25 ml, 180 mmol) in 1,4-dioxane (25 ml) was heated in a sealed tube at 80° C. for a period of 1 hr. The solution was cooled to room temperature, and water was added. The aqueous layer was extracted twice by dichloromethane and the combined organic extracts were dried ($Na_2SO_4$), filtered and concentrated under vacuum. The residue was then purified by column chromatrography on silica gel (EtOAc/hexanes) to give the title compound. $^1$H NMR ($CDCl_3$) δ 10.65-10.64 (m, 1H), 7.89-7.43 (m, 2H), 7.43-7.39 (m, 1H), 7.30-7.26 (m, 1H), 4.99 (s, 2H), 4.71-4.69 (m, 1H), 4.63-4.58 (m, 2H), 4.08 (s, 3H), 3.90-3.86 (m, 2H), 2.59-2.54 (m, 1H), 2.47-2.46 (m, 1H), 2.17 (s, 1H), 1.84-1.76 (m, 2H), 1.54 (s, 3H), 1.27 (s, 3H); LCMS 2.01 min, 444 (M+H)

Step 2: ((3aR,4R,6R,6aS)-6-(5-(Benzo[d]thiazol-2-yl)-2-(2,6-dimethylpyridin-4-ylamino)-6-methoxy-pyrimidin-4-ylamino)-2,2-dimethyltetrahydro-3aH-cyclopenta[d][1,3]dioxol-4-yl)methanol (Compound 11)

A mixture of Compound 10 (0.10 g, 0.225 mmol), 4-bromo-2,6-dimethylpyridine (0.108 g, 0.676 mmol), Xantphos (0.078 g, 0.135 mmol), sodium phenoxide (0.044 g, 0.383 mmol) and $Pd_2(dba)_3$ (0.041 g, 0.045 mmol) in dioxane (3.0 ml) were degassed and heated under nitrogen to reflux for 18 h. The reaction was cooled to room temperature and concentrated. The residue was then purified by column chromatography on silica gel (MeOH/DCM) to give the title compound. LCMS 1.86 min, 549 (M+H)

Step 3: 5-(Benzo[d]thiazol-2-yl)-6-(((1R,2S,3R,4R)-2,3-dihydroxy-4-(hydroxymethyl)cyclopentyl)amino)-2-((2,6-dimethylpyridin-4-yl)amino)pyrimidin-4(3H)-one.HCl (Example 50)

Compound 11 (87 mg, 0.167 mmol) in hydrochloric Acid, 37% (10 ml) was heated at reflux for 2 h and concentrated. The residue was tritrated with methanol and filtered to collect the product of Example 50.

$^1$H NMR (DMSO) δ 11.40 (m, 1H), 11.15 (d, J=6.8 Hz, 1H), 11.00 (s, 1H), 7.98 (d, J=7.6 Hz, 1H), 7.89-7.50 (m, 3H), 7.42 (t, J=8 Hz, 1H), 7.30 (t, J=8 Hz, 1H), 5.00-4.60 (m, 3H), 4.44 (m, 1H), 3.90-3.70 (m, 2H), 3.60-3.40 (m, 2H), 2.62 (S, 6H), 2.40 (m, 1H), 2.05 (m, 1H), 1.44 (m, 1H); LCMS: 1.91 min., 495 (M+H IRAK4 IC50 is 73 nM for Example 50.

Using a similar synthetic scheme as described for Example 50, Examples 51-54 were prepared, as described in more detail below.

Example 51

5-(Benzo[d]thiazol-2-yl)-6-(((1R,2S,3R,4R)-2,3-dihydroxy-4-(hydroxymethyl)cyclopentyl)amino)-2-(pyrimidin-5-ylamino)pyrimidin-4(3H)-one.HCl Prepared as in Scheme 2, except 4-bromopyrimidine was used in Step 2 in place of 4-bromo-2,6-dimethylpyridine.

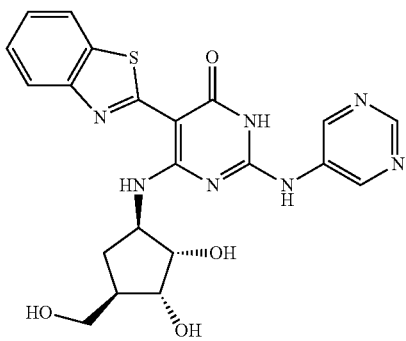 [SMILES: O=c1[nH]c(Nc2cncnc2)nc(N[C@@H]2C[C@H](CO)[C@@H](O)[C@H]2O)c1-c1nc2ccccc2s1]

¹H NMR (DMSO) δ 11.12 (d, J=7.2 Hz, 1H), 11.03 (s, 1H), 9.35 (s, 1H), 9.10 (s, 2H), 8.91 (s, 1H), 7.95 (d, J=7.2 Hz, 1H), 7.81 (d, J=8 Hz, 1H), 7.41 (t, J=7.8 Hz, 1H), 7.27 (t, J=8 Hz, 1H), 4.80-4.40 (m, 3H), 4.33 (m, 1H), 3.84-3.79 (m, 2H), 3.50-3.40 (m, 2H), 2.29 (m, 1H), 1.99 (m, 1H), 1.30 (m, 1H); LCMS: 1.92 min., 468.2 (M+H)

IRAK4 IC50 is 345 nM for Example 51.

Example 52

5-(Benzo[d]thiazol-2-yl)-6-((1R,2S,3R,4R)-2,3-dihydroxy-4-(hydroxymethyl)cyclopentylamino)-2-(4-fluorophenylamino)pyrimidin-4(3H)-one.HCl Prepared as in Scheme 2, except 4-fluoro-bromobenzene was used in Step 2 in place of 4-bromo-2,6-dimethylpyridine.

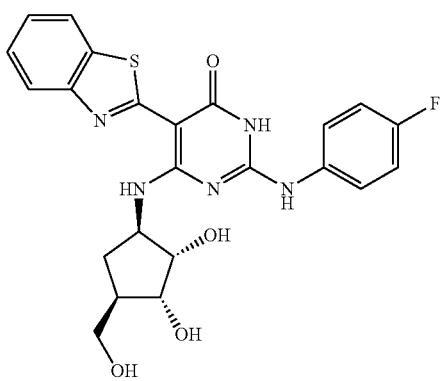 [SMILES: O=c1[nH]c(Nc2ccc(F)cc2)nc(N[C@@H]2C[C@H](CO)[C@@H](O)[C@H]2O)c1-c1nc2ccccc2s1]

¹H NMR (DMSO) δ 9.31 (s, 1H), 7.95-7.55 (m, 5H), 7.24-7.06 (m, 5H), 4.38-4.36 (m, 1H), 3.65-3.45 (m, 2H), 3.09-3.04 (m, 1H), 2.39-2.31 (m, 1H), 2.05-2.01 (m, 1H), 1.34-1.31 (m, 1H), 1.79-1.14 (m, 1H); LCMS 2.01 min, 484 (M+H)

IRAK4 IC50 is 284 nM for Example 52.

Example 53

5-(Benzo[d]thiazol-2-yl)-6-((1R,2S,3R,4R)-2,3-dihydroxy-4-(hydroxymethyl)cyclopentylamino)-2-(phenylamino)pyrimidin-4(3H)-one.HCl Prepared as in Scheme 2, except bromobenzene was used in Step 2 in place of 4-bromo-2,6-dimethylpyridine.

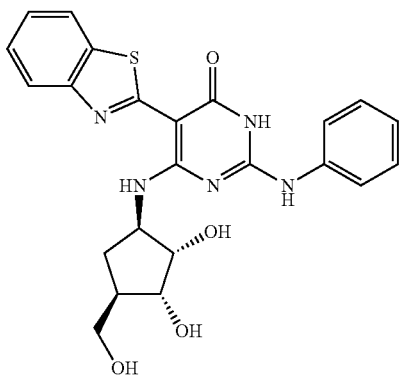 [SMILES: O=c1[nH]c(Nc2ccccc2)nc(N[C@@H]2C[C@H](CO)[C@@H](O)[C@H]2O)c1-c1nc2ccccc2s1]

¹H NMR (DMSO) δ 11.01 (br s, 1H), 10.4 (br s, 1H), 9.04 (br s, 1H), 7.93-7.69 (m, 4H), 7.34-7.08 (m, 5H), 4.73-4.58 (m, 3H), 4.38 (m, 1H), 3.84-3.81 (m, 2H), 3.50-3.48 (m, 2H), 2.37-2.30 (m, 1H), 2.02 (s, 1H), 1.34-1.30 (m, 1H); LCMS 2.02 min, 466 (M+H)

IRAK4 IC50 is 327 nM for Example 53.

Example 54

5-(Benzo[d]thiazol-2-yl)-6-((1R,2S,3R,4R)-2,3-dihydroxy-4-(hydroxymethyl)cyclopentylamino)-2-(pyridin-4-ylamino)pyrimidin-4(3H)-one.HCl Prepared as in Scheme 1, except 4-bromopyridine was used in Step 2 in place of 4-bromo-2,6-dimethylpyridine.

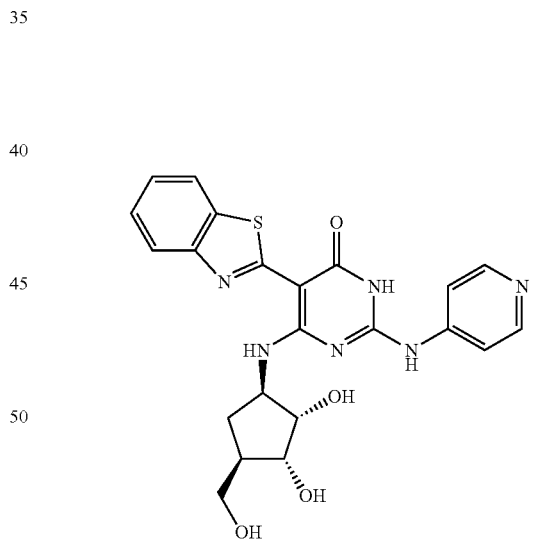

¹H NMR (DMSO) δ 11.67 (d, J=6.8 1H), 11.07 (s, 1H) 10.96 (s, 1H), 8.67 (d, J=7.2 1H), 8.27 (d, J=7.2 1H), 8.09-7.89 (m, 6H), 7.45-7.24 (m, 3H), 6.77 (d, J=7.6 2H), 4.46-4.34 (m, 1H), 4.18-4.15 (m, 1H), 3.87-3.76 (m, 2H), 3.56-3.49 (m, 1H) 2.38-2.29 (m, 1H), 2.07-2.00 (m, 1H), 1.49-1.36 (m, 1H); LCMS 1.51 min, 467 (M+H)

IRAK4 IC50 is 654 nM for Example 54.

Example 55

2-(Cyclobutylamino)-6-(((1R,2S,3R,4R)-2,3-dihydroxy-4-(hydroxymethyl)cyclopentylamino)-5-(thiazolo[4,5-c]pyridin-2-yl)pyrimidin-4(3H)-one.HCl

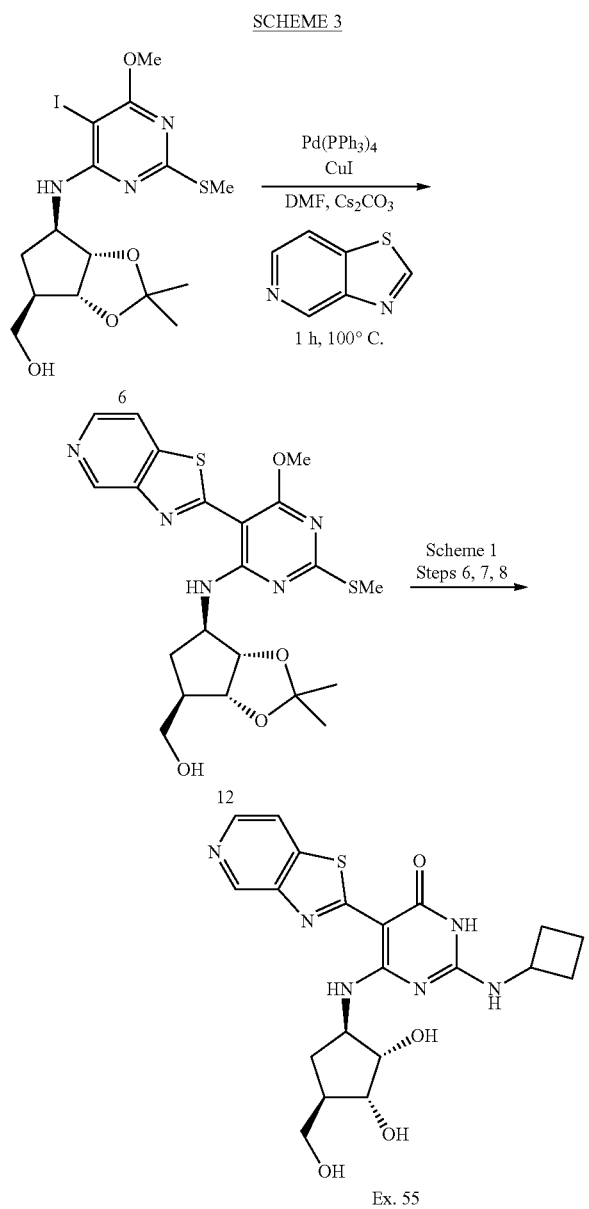

Step 1: ((3aR,4R,6R,6aS)-6-(6-Methoxy-2-(methylthio)-5-(thiazolo[4,5-c]pyridin-2-yl)pyrimidin-4-ylamino)-2,2-dimethyltetrahydro-3aH-cyclopenta[d][1,3]dioxol-4-yl)methanol (Compound 12)

Compound 6 (467 mg, 1.00 mmol), thiazolo[4,5-c]pyridine (272 mg, 2.00 mmol), CuI (67.0 mg, 0.350 mmol), cesium carbonate (1.95 mg, 6.00 mmol) and Pd(Ph$_3$P)$_4$ (231 mg, 0.200 mmol) were combined and suspended in DMF (10 mL). The reaction was degassed and heated to 100° C. for a 1 h. The reaction mixture was cooled to room temperature, extracted twice with ethyl acetate. The combined organics were washed with water, brine, dried (MgSO$_4$), filtered and concentrated. The residue was then purified by column chromatography on silica gel (MeOH/DCM) to give the title compound. LCMS 1.90 min, 476 (M+H)

Using Steps 6-8 of Scheme 1, Example 55 was prepared.

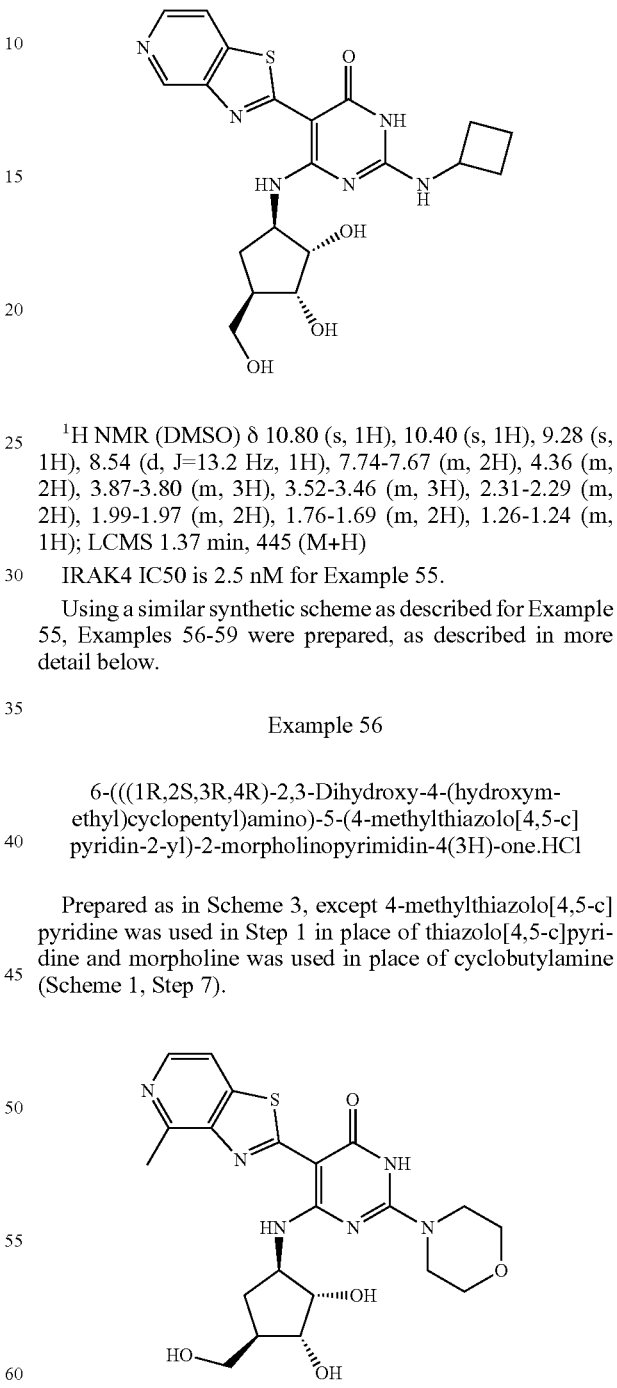

$^1$H NMR (DMSO) δ 10.80 (s, 1H), 10.40 (s, 1H), 9.28 (s, 1H), 8.54 (d, J=13.2 Hz, 1H), 7.74-7.67 (m, 2H), 4.36 (m, 2H), 3.87-3.80 (m, 3H), 3.52-3.46 (m, 3H), 2.31-2.29 (m, 2H), 1.99-1.97 (m, 2H), 1.76-1.69 (m, 2H), 1.26-1.24 (m, 1H); LCMS 1.37 min, 445 (M+H)

IRAK4 IC50 is 2.5 nM for Example 55.

Using a similar synthetic scheme as described for Example 55, Examples 56-59 were prepared, as described in more detail below.

Example 56

6-(((1R,2S,3R,4R)-2,3-Dihydroxy-4-(hydroxymethyl)cyclopentyl)amino)-5-(4-methylthiazolo[4,5-c]pyridin-2-yl)-2-morpholinopyrimidin-4(3H)-one.HCl Prepared as in Scheme 3, except 4-methylthiazolo[4,5-c]pyridine was used in Step 1 in place of thiazolo[4,5-c]pyridine and morpholine was used in place of cyclobutylamine (Scheme 1, Step 7).

$^1$H NMR (DMSO) δ 11.28 (s, 1H), 10.35 (d, J=6.4 Hz, 1H), 8.45-8.40 (m, 2H), 4.28 (m, 1H), 3.84-3.30 (m, 13H), 2.99 (s, 3H), 2.40 (m, 1H), 2.00 (m, 1H), 1.21 (m, 1H); LCMS: 1.44 min., 475.2 (M+H)

IRAK4 IC50 is 8.4 nM for Example 56.

Example 57

6-(((1R,2S,3R,4R)-2,3-Dihydroxy-4-(hydroxymethyl)cyclopentyl)amino)-5-(4,6-dimethylthiazolo[4,5-c]pyridin-2-yl)-2-morpholinopyrimidin-4(3H)-one.HCl Prepared as in Scheme 3, except 4,6-dimethylthiazolo[4,5-c]pyridine was used in Step 1 in place of thiazolo[4,5-c]pyridine and morpholine was used in place of cyclobutylamine (Scheme 1, Step 7).

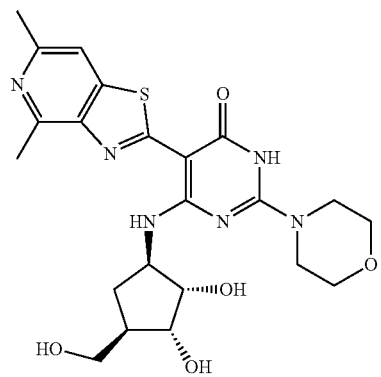 [SMILES: Cc1cc2sc(-c3c(N[C@@H]4C[C@H](CO)[C@@H](O)[C@H]4O)nc(N4CCOCC4)[nH]c3=O)nc2c(C)n1]

$^1$H NMR (DMSO) δ 11.25 (s, 1H), 10.32 (d, J=6 Hz, 1H), 8.00 (s, 1H), 4.28 (m, 1H), 3.85-3.60 (m, 8H), 3.55-3.20 (m, 4H), 2.96 (s, 3H), 2.69 (s, 3H), 2.38 (m, 1H), 2.00(m, 1H), 1.21 (m, 1H); LCMS: 1.68 min., 489.2 (M+H)

IRAK4 IC50 is 923 nM for Example 57.

Example 58

6-(((1R,2S,3R,4R)-2,3-Dihydroxy-4-(hydroxymethyl)cyclopentyl)amino)-5-(4-(4-fluorophenyl)thiazol-2-yl)-2-morpholinopyrimidin-4(3H)-one.HCl Prepared as in Scheme 3, except 4-(4-fluorophenyl)thiazole was used in Step 1 in place of thiazolo[4,5-c]pyridine and morpholine was used in place of cyclobutylamine (Scheme 1, Step 7).

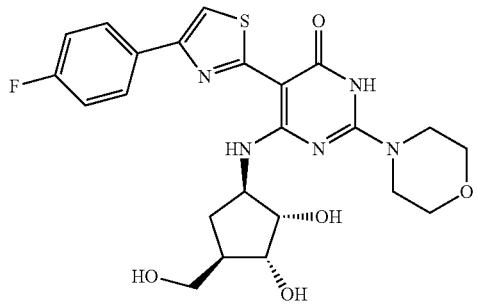 [SMILES: O=c1[nH]c(N2CCOCC2)nc(N[C@@H]2C[C@H](CO)[C@@H](O)[C@H]2O)c1-c1nc(-c2ccc(F)cc2)cs1]

$^1$H NMR (DMSO) δ 10.93 (s, 1H), 10.60 (d, J=6.4 Hz, 1H), 7.97 (dd, J=8.8, 5.4 Hz, 2H), 7.95 (s, 1H), 7.25 (t, J=8.8 Hz, 1H), 4.28 (m, 1H), 3.90-3.27 (m, 12H), 2.33 (m, 1H), 1.99 (m, 1H), 1.22 (m, 1H); LCMS: 1.93 min., 504.2 (M+H)

IRAK4 IC50 is 5.6 nM for Example 58.

Example 59

6-(((1R,2S,3R,4R)-2,3-Dihydroxy-4-(hydroxymethyl)cyclopentyl)amino)-5-(4-(4-fluorophenyl)thiazol-2-yl)-2-(piperidin-1-yl)pyrimidin-4(3H)-one HCl Prepared as in Scheme 3, except 4-(4-fluorophenyl)thiazole was used in Step 1 in place of thiazolo[4,5-c]pyridine and piperidine was used in place of cyclobutylamine (Scheme 1, Step 7).

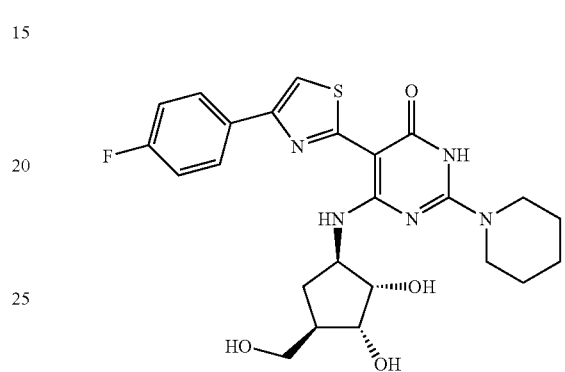

$^1$H NMR (DMSO) δ 10.79 (s, 1H), 10.55 (d, J=6.8 Hz, 1H), 7.96 (dd, J=8.8, 5.6 Hz, 2H), 7.57 (s, 1H), 7.25 (t, J=8.8 Hz, 1H), 4.27 (m, 1H), 4.10-3.30 (m, 8H), 2.34 (m, 1H), 1.99 (m, 1H), 1.62-1.50 (m, 6H), 1.21 (m, 1H); LCMS: 1.39 min., 502.2 (M+H)

IRAK4 IC50 is 22.5 nM for Example 59.

Example 60

5-(Benzo[d]thiazol-2-yl)-6-((1R,2S,3R,4R)-2,3-dihydroxy-4-(hydroxymethyl)cyclopentylamino)-2-(methylthio)pyrimidin-4(3H)-one.HCl

SCHEME 4

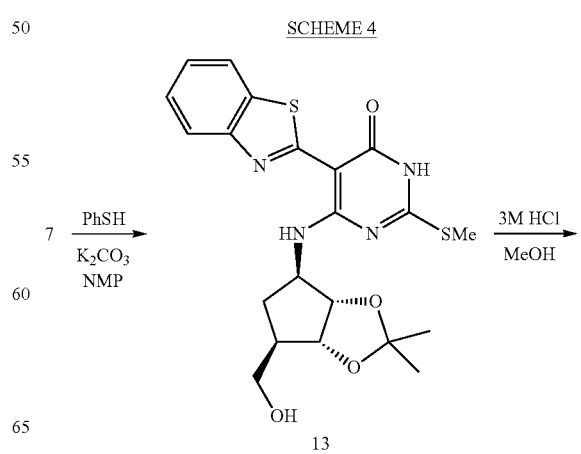

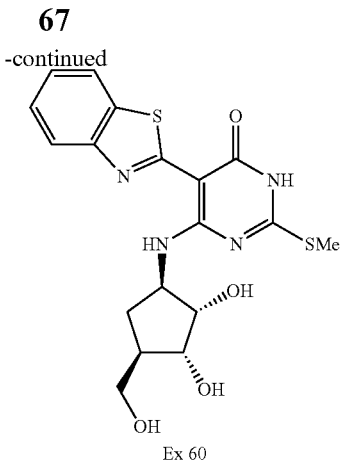

Ex 60

¹H NMR (DMSO) δ 11.05 (d, J=6.4, 1H), 7.99 (d, J=8 Hz, 1H), 7.86 (d, J=8 Hz, 1H), 7.43 (t, J=5 Hz, 1H), 7.29 (t, J=5 Hz, 1H), 4.48-4.42 (m, 1H), 3.83-3.78 (m, 2H), 2.57 (s, 3H), 2.47-2.31 (m, 1H), 2.01-2.00 (m, 1H), 1.35-1.21 (m, 2H); LCMS 1.62 min, 421 (M+H)

IRAK4 IC50 is 352 nM for Example 60.

Example 61

5-(Benzo[d]thiazol-2-yl)-6-((1R,2S,3R,4R)-2,3-dihydroxy-4-(hydroxymethyl)cyclopentylamino)-2-ethylpyrimidin-4(3H)-one.HCl

SCHEME 5

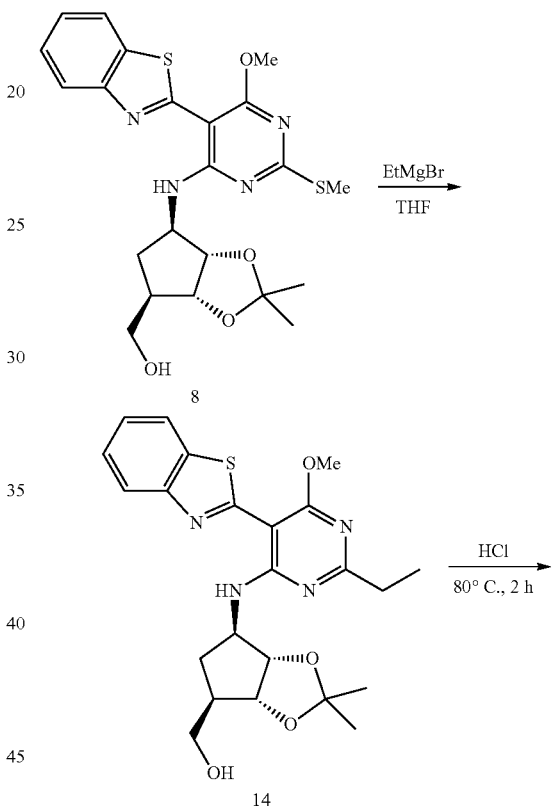

Step 1: 5-(Benzo[d]thiazol-2-yl)-6-((3aS,4R,6R,6aR)-6-(hydroxymethyl)-2,2-dimethyltetrahydro-3aH-cyclopenta[d][1,3]dioxol-4-ylamino)-2-(methylthio)pyrimidin-4(3H)-one (Compound 13)

Compound 7 (800 mg, 1.686 mmol) and potassium carbonate (46.6 mg, 0.337 mmol) were suspended in NMP (843 µl) and thiophenol (208 µl, 2.023 mmol) was added. The reaction was sealed and heated to 190° C. for 20 min to consume all SM. The reaction was diluted with EtOAc, washed with water, brine, dried (MgSO₄), filtered and concentrated. The residue was purified by column chromatography on silica gel, eluting with CH₂C2/MeOH to give the title compound as a white solid. ¹H NMR (CD₃OD) δ 7.80-7.77 (m, 2H), 7.35-7.31 (m, 1H), 7.23-7.19 (m, 1H), 4.61-4.56 (m, 2H), 4.43-4.04 (m, 1H), 3.76-3.74 (m, 2H), 2.54 (s, 3H), 2.57-2.46 (m, 1H), 2.35-2.31 (m, 1H), 1.82-1.77 (m, 1H), 1.44 (s, 3H), 1.27 (s, 3H); LCMS 2.29 min, 461 (M+H)

Step 2: 5-(Benzo[d]thiazol-2-yl)-6-((1R,2S,3R,4R)-2,3-dihydroxy-4-(hydroxymethyl)cyclopentylamino)-2-(methylthio)pyrimidin-4(3H)-one (Example 60)

Compound 13 (15 mg, 0.033 mmol) was dissolved in MeOH (1 ml) and 3 M HCl (1 ml) and stirred at room temperature for 18 h. The solvents were evaporated to give the title compound as a white solid.

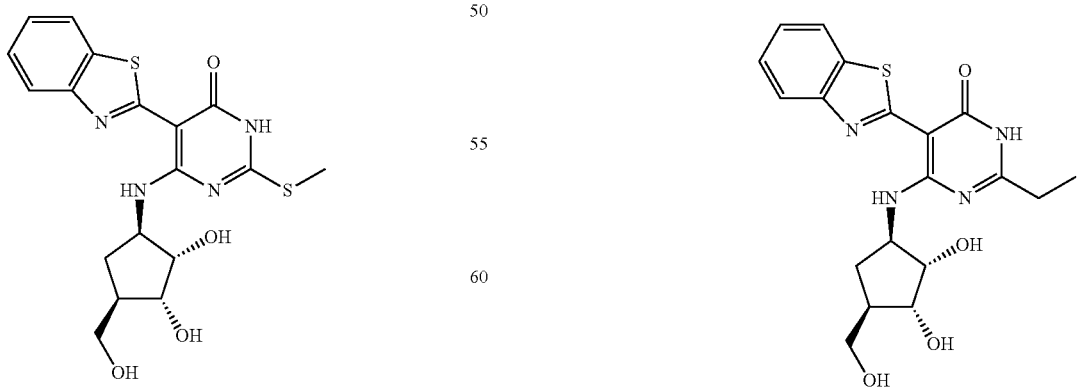

Ex 61

Step 1: ((3aR,4R,6R,6aS)-6-(5-(Benzo[d]thiazol-2-yl)-2-ethyl-6-methoxypyrimidin-4-ylamino)-2,2-dimethyltetrahydro-3aH-cyclopenta[d][1,3]dioxol-4-yl)methanol (14)

Compound 8 (100 mg, 0.197 mmol) was dissolved in THF (2 ml) and cooled to 0° C. EtMgBr (0.592 ml, 0.592 mmol, 1.0 M in THF) was added dropwise and stirred at 0° C. The reaction was quenched at 0° C. with sat. NH₄Cl, diluted with water and EtOAc. The aqueous layer was extracted with EtOAc three times, dried (MgSO₄), filtered and evaporated to dryness. The residue was purified by column chromatography on silica gel, eluting with CH₂C2/MeOH to give the title compound as a colorless solid. ¹H NMR (CDCl₃) δ 10.58 (d, J=6.0 Hz, 1H), 7.96 (d, J=7.6 Hz, 1H), 7.88 (d, J=7.6 Hz, 1H), 7.46 (t, J=6.8 Hz, 1H), 7.33 (t, J=6.8 Hz, 1H), 4.75-4.69 (m, 2H), 4.63-4.61 (m, 1H), 4.16 (s, 3H), 3.84 (d, J=6.8 Hz, 1H), 2.76 (q, J=6.8, 1.2 Hz, 2H), 2.61-2.53 (m, 1H), 2.45-2.41 (m, 1H), 1.81-1.75 (m, 1H), 1.75 (s, 3H), 1.34 (s, 3H), 1.33 (t, J=6.8 Hz, 3H); LCMS 2.61 min, 457 (M+H)

Step 2: 5-(Benzo[d]thiazol-2-yl)-6-((1R,2S,3R,4R)-2,3-dihydroxy-4-(hydroxymethyl)cyclopentylamino)-2-ethylpyrimidin-4(3H)-one (Example 61)

Compound 14 (48 mg, 0.108 mmol) was suspended in MeOH (3 ml) and 3 M HCl (3) was added. The mixture was stirred at room temperature for 18 h. The mixture was evaporated to dryness to give the title compound as a white solid.

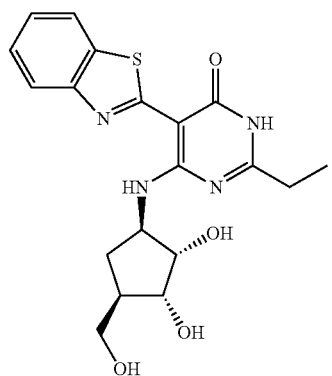 [SMILES: CCc1nc(N[C@@H]2C[C@H](CO)[C@@H](O)[C@H]2O)c(-c2nc3ccccc3s2)c(=O)[nH]1]

¹H NMR (DMSO) δ 12.19 (s, 1H), 11.01 (d, J=7.2 Hz, 1H), 7.98 (d, J=8 Hz, 1H), 7.87 (d, J=8 Hz, 1H), 7.44 (t, J=5 Hz, 1H), 7.30 (t, J=5 Hz, 1H), 3.84-3.79 (m, 2H), 3.48-3.43 (m, 2H), 2.59-2.53 (m, 2H), 2.38-2.30 (m, 1H), 1.99 (br s, 1H), 1.31-1.20 (m, 4H); LCMS 1.59 min, 403 (M+H)

IRAK4 IC50 is 1162 nM for Example 61.

Example 62

5-(Benzo[d]thiazol-2-yl)-6-((1R,2S,3R,4R)-2,3-dihydroxy-4-(hydroxymethyl)cyclopentylamino)-2-methylpyrimidin-4(3H)-one.HCl Prepared in a similar manner to Example 61 except MeMgBr was used in place of EtMgBr in Step 1.

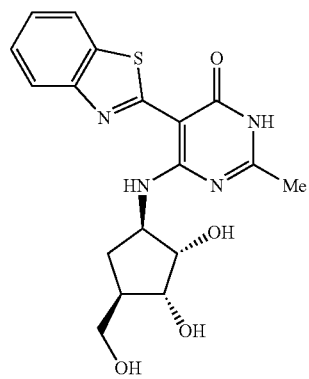 [SMILES: Cc1nc(N[C@@H]2C[C@H](CO)[C@@H](O)[C@H]2O)c(-c2nc3ccccc3s2)c(=O)[nH]1]

¹H NMR (DMSO) δ 12.21 (br s, 1H), 11.03 (d, J=7.6 Hz, 1H), 7.97 (d, J=8 Hz, 1H), 7.87 (d, J=8 Hz, 1H), 7.43 (t, J=5 Hz, 1H), 7.30 (t, J=5 Hz, 1H), 4.50-4.48 (m, 1H), 3.80-3.77 (m, 2H), 3.49-3.46 (m, 2H), 2.31-2.29 (m, 1H), 2.30 (s, 3H), 2.00-1.98 (m, 1H), 1.25-1.20 (m 1H); LCMS 1.53 min, 389 (M+H)

IRAK4 IC50 is 635 nM for Example 62.

Using Scheme 6, Examples 63 to 82 were prepared as described in more detail below.

SCHEME 6

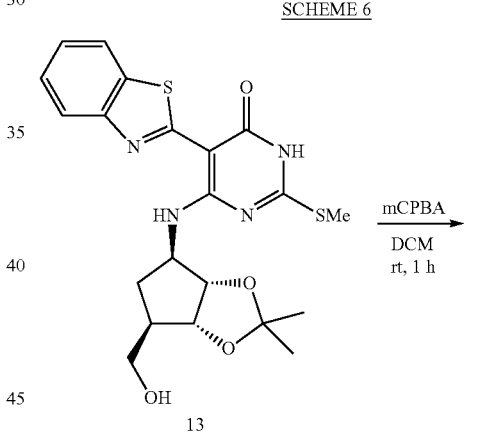

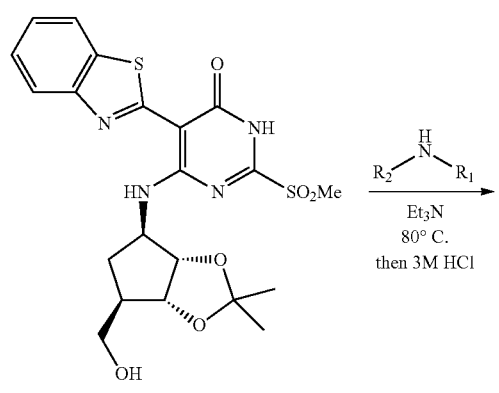

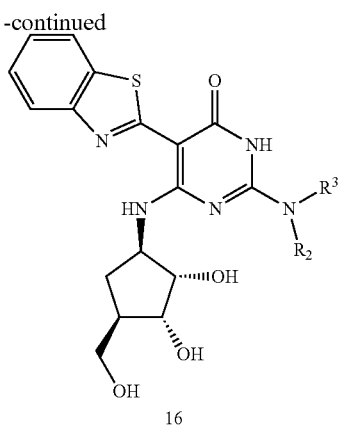

16

Step 1: 5-(Benzo[d]thiazol-2-yl)-6-((3aS,4R,6R, 6aR)-6-(hydroxymethyl)-2,2-dimethyltetrahydro-3aH-cyclopenta[d][1,3]dioxol-4-ylamino)-2-(methylsulfonyl)pyrimidin-4(3H)-one (Compound 15)

Compound 13 (305 mg, 0.662 mmol) was dissovled in DCM (10 mL) and mCPBA (286 mg, 1.656 mmol) was added. The reaction was stirred at room temperature for 2 h. The reaction was washed with sat. $NaHCO_3$, ×2, dried, filtered and concentrated to give the title compound as a yellow solid. LCMS 2.32 min, 493 (M+H).

Step 2: Library Synthesis

A solution of Compound 15 (11 mg, 0.022 mmol) and triethylamine (19 μL) in 1.05 mL of anhydrous acetonitrile was added into a vial containing a secondary amine (3.5 eq.). The mixture was heated at 80° C. for 3 h. After cooling to rt, the solvent was removed in a GeneVac. To the residue was added 1 mL of MeOH and 3 mL of 3M HCl After the solution was shaken at rt for 24 h, the solvent was removed in a GeneVac. The resulting residue was dissolved in 1 mL of DMSO and purified by semi-preparative HPLC.

Analytical HPLC conditions: The mobile phase ($H_2O$/acetonitrile) contains 0.1% $NH_3$ and the gradients run from 5% to 100% acetonitrile, hold for 0.4 min, then go back to initial condition of 5% acetonitrile. Total run time is 2 min for each sample.

| Time (min) | Flow (ml/min) | $H_2O$ % | Acetonitrile % |
|---|---|---|---|
| 0 | 1 | 95 | 5 |
| 1.4 | 1 | 0 | 100 |
| 1.8 | 1 | 0 | 100 |
| 2.0 | 1 | 95 | 5 |

The following compounds were prepared according to the procedure described above:

Structure 16

| Exple | $R^2$, $R^3$ | Name | LCMS Mass (Ret. time, min.) | IRAK4 $IC_{50}$ |
|---|---|---|---|---|
| 63 | piperazine with pyridin-3-yl | 5-(benzo[d]thiazol-2-yl)-6-((1R,2S,3R,4R)-2,3-dihydroxy-4-(hydroxymethyl)cyclopentylamino)-2-(4-(pyridin-3-yl)piperazin-1-yl)pyrimidin-4(3H)-one | 535.20 (0.63) | 3.7 |
| 64 | piperidine with pyrimidin-5-yl | 5-(benzo[d]thiazol-2-yl)-6-((1R,2S,3R,4R)-2,3-dihydroxy-4-(hydroxymethyl)cyclopentylamino)-2-(4-(pyrimidin-5-yl)piperidin-1-yl)pyrimidin-4(3H)-one | 535.20 (0.63) | 6.2 |

-continued

Structure 16

| Exple | [R² / R³ group structure] | Name | LCMS Mass (Ret. time, min.) | IRAK4 IC₅₀ |
|---|---|---|---|---|
| 65 | 3,4-dihydro-2,7-naphthyridin-2(1H)-yl | 5-(benzo[d]thiazol-2-yl)-2-(3,4-dihydro-2,7-naphthyridin-2(1H)-yl)-6-((1R,2S,3R,4R)-2,3-dihydroxy-4-(hydroxymethyl)cyclopentylamino)pyrimidin-4(3H)-one | 506.17 (0.62) | 7.2 |
| 66 | 2-methyl-1-oxo-2,8-diazaspiro[4.5]decan-8-yl | 8-(5-(benzo[d]thiazol-2-yl)-4-((1R,2S,3R,4R)-2,3-dihydroxy-4-(hydroxymethyl)cyclopentylamino)-6-oxo-1,6-dihydropyrimidin-2-yl)-2-methyl-2,8-diazaspiro[4.5]decan-1-one | 540.22 (0.63) | 8.8 |
| 67 | 4-(1H-1,2,3-triazol-1-yl)piperidin-1-yl | 2-(4-(1H-1,2,3-triazol-1-yl)piperidin-1-yl)-5-(benzo[d]thiazol-2-yl)-6-((1R,2S,3R,4R)-2,3-dihydroxy-4-(hydroxymethyl)cyclopentylamino)pyrimidin-4(3H)-one | 524.20 (0.59) | 11.8 |
| 68 | 4-(pyridin-2-yl)piperazin-1-yl | 5-(benzo[d]thiazol-2-yl)-6-((1R,2S,3R,4R)-2,3-dihydroxy-4-(hydroxymethyl)cyclopentylamino)-2-(4-(pyridin-2-yl)piperazin-1-yl)pyrimidin-4(3H)-one | 535.20 (0.70) | 12.1 |
| 69 | 4-(pyrazin-2-yl)piperidin-1-yl | 5-(benzo[d]thiazol-2-yl)-6-((1R,2S,3R,4R)-2,3-dihydroxy-4-(hydroxymethyl)cyclopentylamino)-2-(4-(pyrazin-2-yl)piperidin-1-yl)pyrimidin-4(3H)-one | 535.20 (0.66) | 12.5 |

-continued

Structure 16

| Exple | R2/R3 group | Name | LCMS Mass (Ret. time, min.) | IRAK4 IC$_{50}$ |
|---|---|---|---|---|
| 70 | 4-(pyridin-3-yl)piperidin-1-yl | 5-(benzo[d]thiazol-2-yl)-6-((1R,2S,3R,4R)-2,3-dihydroxy-4-(hydroxymethyl)cyclopentylamino)-2-(4-(pyridin-3-yl)piperidin-1-yl)pyrimidin-4(3H)-one | 534.21 (0.70) | 13.3 |
| 71 | 3-(methylsulfonyl)azetidin-1-yl | 5-(benzo[d]thiazol-2-yl)-6-((1R,2S,3R,4R)-2,3-dihydroxy-4-(hydroxymethyl)cyclopentylamino)-2-(3-(methylsulfonyl)azetidin-1-yl)pyrimidin-4(3H)-one | 507.13 (0.50) | 17.9 |
| 72 | 4-(pyridin-4-yl)piperidin-1-yl | 5-(benzo[d]thiazol-2-yl)-6-((1R,2S,3R,4R)-2,3-dihydroxy-4-(hydroxymethyl)cyclopentylamino)-2-(4-(pyridin-4-yl)piperidin-1-yl)pyrimidin-4(3H)-one | 534.21 (0.69) | 19.0 |
| 73 | 4-(1-methyl-1H-1,2,3-triazol-4-yl)piperidin-1-yl | 5-(benzo[d]thiazol-2-yl)-6-((1R,2S,3R,4R)-2,3-dihydroxy-4-(hydroxymethyl)cyclopentylamino)-2-(4-(1-methyl-1H-1,2,3-triazol-4-yl)piperidin-1-yl)pyrimidin-4(3H)-one | 538.21 (0.64) | 19.4 |
| 74 | 3,4-dihydro-2,6-naphthyridin-2(1H)-yl | 5-(benzo[d]thiazol-2-yl)-2-(3,4-dihydro-2,6-naphthyridin-2(1H)-yl)-6-((1R,2S,3R,4R)-2,3-dihydroxy-4-(hydroxymethyl)cyclopentylamino)pyrimidin-4(3H)-one | 506.17 (0.61) | 26.4 |

-continued

Structure 16

| Exple | (structure) | Name | LCMS Mass (Ret. time, min.) | IRAK4 IC$_{50}$ |
|---|---|---|---|---|
| 75 | 1,4-diazepane with thiazol-2-ylmethyl substituent | 5-(benzo[d]thiazol-2-yl)-6-((1R,2S,3R,4R)-2,3-dihydroxy-4-(hydroxymethyl)cyclopentylamino)-2-(4-(thiazol-2-ylmethyl)-1,4-diazepan-1-yl)pyrimidin-4(3H)-one | 569.19 (0.72) | 226 |
| 76 | 3-(pyridin-4-yl)pyrrolidine | 5-(benzo[d]thiazol-2-yl)-6-((1R,2S,3R,4R)-2,3-dihydroxy-4-(hydroxymethyl)cyclopentylamino)-2-(3-(pyridin-4-yl)pyrrolidin-1-yl)pyrimidin-4(3H)-one | 520.19 (0.68) | 30.9 |
| 77 | 4-(methylsulfonyl)-1,4-diazepane | 5-(benzo[d]thiazol-2-yl)-6-((1R,2S,3R,4R)-2,3-dihydroxy-4-(hydroxymethyl)cyclopentylamino)-2-(4-(methylsulfonyl)-1,4-diazepan-1-yl)pyrimidin-4(3H)-one | 550.17 (0.62) | 225 |
| 78 | 4-(pyridin-2-yl)piperidine | 5-(benzo[d]thiazol-2-yl)-6-((1R,2S,3R,4R)-2,3-dihydroxy-4-(hydroxymethyl)cyclopentylamino)-2-(4-(pyridin-2-yl)piperidin-1-yl)pyrimidin-4(3H)-one | 534.21 (0.73) | 36 |
| 79 | 4-(acetamidomethyl)piperidine | N-((1-(5-(benzo[d]thiazol-2-yl)-4-((1R,2S,3R,4R)-2,3-dihydroxy-4-(hydroxymethyl)cyclopentylamino)-6-oxo-1,6-dihydropyrimidin-2-yl)piperidin-4-yl)methyl)acetamide | 528.22 (0.63) | 36.7 |

Structure 16

| Exple | R², R³ group | Name | LCMS Mass (Ret. time, min.) | IRAK4 IC₅₀ |
|---|---|---|---|---|
| 80 | 4-((1H-pyrazol-1-yl)methyl)piperidin-1-yl | 2-(4-((1H-pyrazol-1-yl)methyl)piperidin-1-yl)-5-(benzo[d]thiazol-2-yl)-6-(((1R,2S,3R,4R)-2,3-dihydroxy-4-(hydroxymethyl)cyclopentylamino)pyrimidin-4(3H)-one | 537.22 (0.71) | 119 |
| 81 | 3-oxa-1,8-diazaspiro[4.5]decan-2-one-8-yl | 8-(5-(benzo[d]thiazol-2-yl)-4-((1R,2S,3R,4R)-2,3-dihydroxy-4-(hydroxymethyl)cyclopentylamino)-6-oxo-1,6-dihydropyrimidin-2-yl)-3-oxa-1,8-diazaspiro[4.5]decan-2-one | 528.18 (0.56) | 196 |
| 82 | 3-(pyridin-2-yl)pyrrolidin-1-yl | 5-(benzo[d]thiazol-2-yl)-6-((1R,2S,3R,4R)-2,3-dihydroxy-4-(hydroxymethyl)cyclopentylamino)-2-(3-(pyridin-2-yl)pyrrolidin-1-yl)pyrimidin-4(3H)-one | 520.19 (0.72) | 197 |

Example 83

(R)-5-(Benzo[d]thiazol-2-yl)-2-morpholino-6-(piperidin-3-ylamino)pyrimidin-4(3H)-one

SCHEME 7

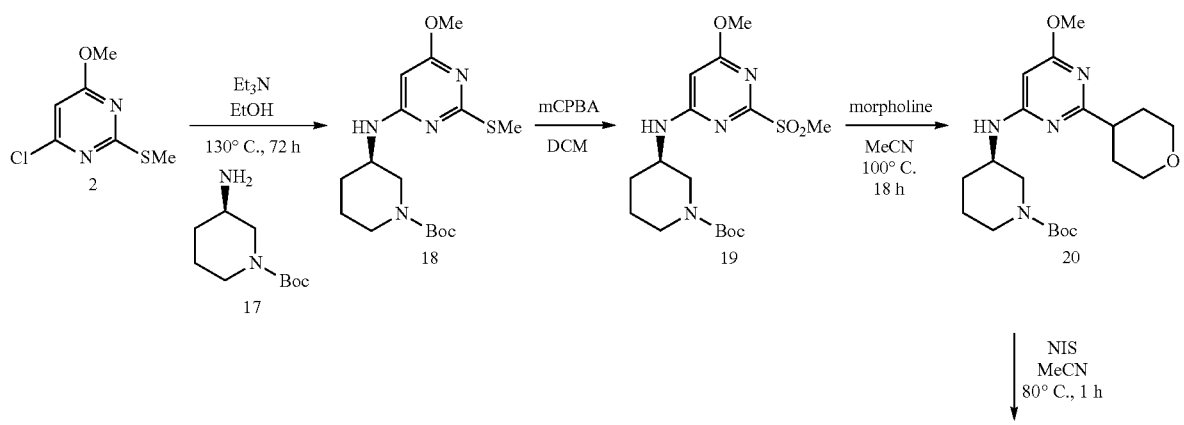

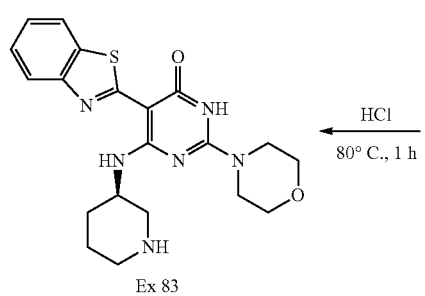 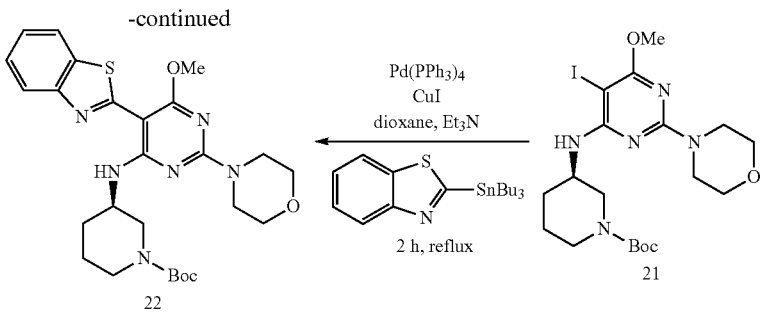

Step 1: (R)-Tert-butyl 3-(6-methoxy-2-(methylthio) pyrimidin-4-ylamino)piperidine-1-carboxylate (Compound 18)

Compound 2 (3.6 g, 18.9 mmol) and (R)-1-Boc-3-aminopiperidine (9.45 g, 47.2 mmol) were dissolved in ethanol (50 mL) and TEA (10.5 mL, 76 mmol) was added. The reaction was sealed and heated to 130° C. for 72 h. The orange solution was concentrated and the residue was purified by column chromatography on silica gel, eluting with EtOAc/hexane to give the title compound as a white foam. $^1$H NMR (CDCl$_3$) δ 5.40 (s, 1H), 4.78 (br s, 1H), 3.88 (s, 3H), 3.84-3.81 (m, 1H), 3.58-3.56 (m, 2H), 3.17-3.05 (m, 2H), 2.49 (s, 3H), 2.04-1.91 (m, 1H), 1.75-1.67 (m, 1H), 1.57-1.51 (m, 2H), 1.44 (s, 9H); LCMS 2.30 min, 355 (M+H).

Step 2: (R)-Tert-butyl 3-(6-methoxy-2-(methylsulfonyl)pyrimidin-4-ylamino)piperidine-1-carboxylate (Compound 19)

Compound 18 (526 mg, 1.48 mmol) was dissolved in DCM (20 mL) and cooled to 0° C. mCPBA (640 mg, 3.71 mmol) was added in one portion and the reaction mixture was stirred at room temperature for 1 h. Sat. NaHCO$_3$ was added and the mixture stirred for 10 min. The layers were separated, the organic was dried (MgSO$_4$), filtered, and concentrated to give the title compound as a yellow foam. Used without further purification. LCMS 2.42 min, 371 (M+H).

Step 3: (R)-Tert-butyl 3-(6-methoxy-2-morpholinopyrimidin-4-ylamino)piperidine-1-carboxylate (Compound 20)

Compound 19 (150 mg, 0.405 mmol) was dissolved in acetonitrile (2 mL) and morpholine (0.282 mL, 3.24 mmol) was added. The solution was sealed and heated to 100° C. for 18 h. The solution was concentrated and the residue was purified by column chromatography on silica gel, eluting with EtOAc/hexane to give the title compound as a colorless oil. $^1$H NMR (CDCl$_3$) δ 5.13 (s, 1H), 4.52-4.51 (m, 1H), 3.82 (s, 3H), 3.72 (s, 8H), 3.62-3.59 (m, 2H), 3.14-3.10 (m, 2H), 1.94 (m, 1H), 1.72-1.70 (m, 1H), 1.55-1.53 (m, 2H), 1.43 (s, 9H); LCMS 2.02 min, 394 (M+H).

Step 4: (R)-Tert-butyl 3-(5-iodo-6-methoxy-2-morpholinopyrimidin-4-ylamino)piperidine-1-carboxylate (Compound 21)

Compound 20 (113 mg, 0.287 mmol) was dissolved in acetonitrile (3 mL) and NIS (129 mg, 0.574 mmol) was added. The solution was heated to reflux for 1 h. The solvent was evaporated and the residue dissolved in EtOAc, washed with sat. NaHCO$_3$, NaS$_2$O$_3$, water, and brine. The organics were dried (MgSO$_4$), filtered and concentrated. The residue was purified by column chromatography on silica gel, eluting with EtOAc/hexane to give the title compound as a colorless foam. $^1$H NMR (CDCl$_3$) δ 5.07 (d, J=6.8 Hz, 1H), 3.99 (br s, 1H), 3.88 (s, 3H), 3.86-3.73 (m, 8H), 3.43 (br s, 3H), 1.90-1.86 (m, 1H), 1.70-1.63 (m, 2H), 1.56-1.55 (m, 1H), 1.42 (s, 9H); LCMS 2.95 min, 520 (M+H).

Step 5: (R)-Tert-butyl 3-(5-(benzo[d]thiazol-2-yl)-6-methoxy-2-morpholinopyrimidin-4-ylamino)piperidine-1-carboxylate (Compound 22)

2-Tributylstannylbenzothiazole (221 mg, 0.520 mmol), Compound 21 (150 mg, 0.289 mmol), Tetrakis(triphenylphosphine)palladium (67 mg, 0.0578 mmol), and CuI (11 mg, 0.0578 mmol) were combined. Dioxane (4 mL) was added followed by Et$_3$N (161 μL, 1.16 mmol) and the mixture was degassed and heated to reflux for 2 h. The solution was cooled to room temperature and an aqueous 10% KF solution was added and the mixture was stirred for 30 min. The mixture was diluted with EtOAc and washed with water, brine, dried (MgSO$_4$), filtered and evaporated to dryness. The residue was purified by column chromatography on silica gel, eluting with EtOAc/hexane to give the title compound as a yellow solid. $^1$H NMR (CDCl$_3$) δ 10.74 (br s, 1H), 7.86-7.82 (m, 2H), 7.41 (t, J=7.2 Hz, 1H), 7.27 (t, J=7.2 Hz, 1H), 4.25 (br s, 1H), 4.09 (s, 3H), 3.87 (br s, 4H), 3.78-3.76 (m, 4H), 3.52 (br s, 4H), 2.03 (br s, 1H), 1.90 (br s, 1H), 1.76-1.73 (m, 1H), 1.66-1.64 (m, 1H), 1.33 (s, 9H); LCMS 3.28 min, 527 (M+H).

Step 6: (R)-5-(Benzo[d]thiazol-2-yl)-2-morpholino-6-(piperidin-3-ylamino)pyrimidin-4(3H)-one (Example 83)

Compound 15 (260 mg, 0.494 mmol) was dissolved in concentrated HCl (7 ml) and heated to 80° C. for 1 h. The solution was evaporated to approximately 1 mL. The residue was basified with 1M NaOH and diluted with water, filtered and the solid washed with water. The white solid was dried to give the title compound as a white solid.

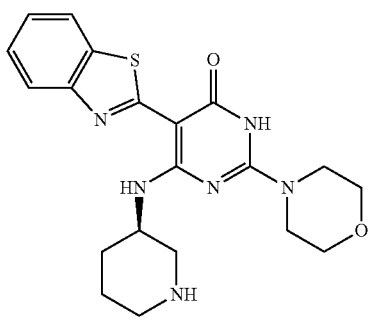

¹H NMR (DMSO) δ 10.86 (d, J=7.2 Hz, 1H), 7.92 (d, J=8 Hz, 1H), 7.72 (d, J=8 Hz, 1H), 7.38 (t, J=8.4 Hz, 1H), 7.22 (t, J=8.4 Hz, 1H), 4.18-4.16 (m, 1H), 3.67 (m, 8H), 3.15-3.12 (m, 1H), 2.87-2.83 (m, 1H), 2.74-2.64 (m, 2H), 1.95 (m, 1H), 1.75-1.45 (m, 4H); LCMS 1.49 min, 413 (M+H)

IRAK4 IC50 is 19 nM for Example 83.

Example 84

(S)-5-(Benzo[d]thiazol-2-yl)-2-morpholino-6-(piperidin-3-ylamino)pyrimidin-4(3H)-one.HCl Prepared according to Scheme 7 except (S)-tert-butyl 3-aminopiperidine-1-carboxylate was used in place of (R)-tert-butyl 3-aminopiperidine-1-carboxylate in Step 1.

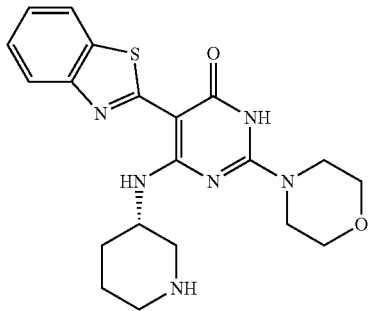

¹H NMR (DMSO) δ 10.87 (d, J=7.2 Hz, 1H), 7.92 (d, J=8 Hz, 1H), 7.72 (d, J=8 Hz, 1H), 7.38 (t, J=8.4 Hz, 1H), 7.22 (t, J=8.4 Hz, 1H), 4.17-4.15 (m, 1H), 3.67 (m, 8H), 3.15-3.12 (m, 1H), 2.87-2.83 (m, 1H), 2.74-2.64 (m, 2H), 1.94-1.93 (m, 1H), 1.75-1.53 (m, 4H); LCMS 1.52 min, 413 (M+H)

IRAK4 IC50 is 255 nM for Example 84.

Example 85

5-(Benzo[d]thiazol-2-yl)-2-morpholino-6-(pyrrolidin-3-ylamino)pyrimidin-4(3H)-one.HCl Prepared according to Scheme 7 except tert-butyl 3-aminopyrrolidine-1-carboxylate was used in place of (R)-tert-butyl 3-aminopiperidine-1-carboxylate in Step 1.

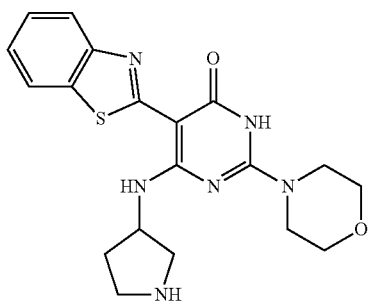 [SMILES: O=c1[nH]c(N2CCOCC2)nc(NC2CCNC2)c1-c1nc2ccccc2s1]

¹H NMR (DMSO) δ 10.77 (d, J=6.4 Hz, 1H), 7.74 (d, J=8 Hz, 1H), 7.53 (d, J=8 Hz, 1H), 7.23 (t, J=8.4 Hz, 1H), 7.05 (t, J=8.4 Hz, 1H), 4.52 (t, J=6.8 Hz, 1H), 3.60-3.42 (m, 8H), 3.42-3.06 (m, 5H), 2.14-2.10 (m, 1H), 1.77-1.74 (m, 1H); LCMS 1.81 min, 399 (M+H)

IRAK4 IC50 is 177 nM for Example 85.

Example 86

(S)-5-(Benzo[d]thiazol-2-yl)-2-morpholino-6-(pyrrolidin-3-ylamino)pyrimidin-4(3H)-one.HCl Prepared according to Scheme 7 except (S)-tert-butyl 3-aminopyrrolidine-1-carboxylate was used in place of (R)-tert-butyl 3-aminopiperidine-1-carboxylate in Step 1.

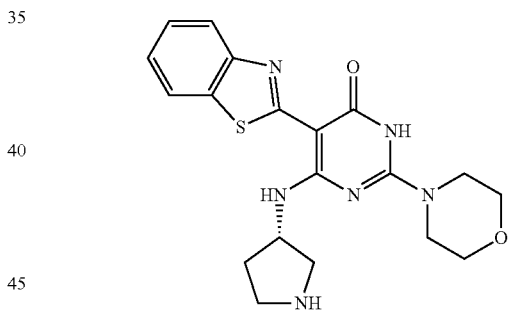

¹H NMR (DMSO) δ 10.77 (d, J=6.4 Hz, 1H), 7.73 (d, J=8 Hz, 1H), 7.53 (d, J=8 Hz, 1H), 7.23 (t, J=8.4 Hz, 1H), 7.05 (t, J=8.4 Hz, 1H), 4.49 (m, 1H), 3.60-3.42 (m, 8 H), 3.42-3.06 (m, 5H), 2.13-2.10 (m, 1H), 1.77-1.74 (m, 1H); LCMS 1.72 min, 399 (M+H)

IRAK4 IC50 is 620 nM for Example 86.

Example 87

(R)-5-(Benzo[d]thiazol-2-yl)-2-morpholino-6-(pyrrolidin-3-ylamino)pyrimidin-4(3H)-one.HCl Prepared according to Scheme 7 except (R)-tert-butyl 3-aminopyrrolidine-1-carboxylate was used in place of (R)-tert-butyl 3-aminopiperidine-1-carboxylate in Step 1

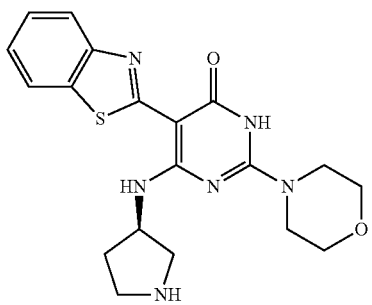

¹H NMR (DMSO) δ 10.78 (d, J=6.4 Hz, 1H), 7.73 (d, J=8 Hz, 1H), 7.53 (d, J=8 Hz, 1H), 7.26 (t, J=8.4 Hz, 1H), 7.04 (t, J=8.4 Hz, 1H), 4.52 (m, 1H), 3.60-3.42 (m, 8 H), 3.42-3.06 (m, 5H), 2.13-2.11 (m, 1H), 1.77-1.72 (m, 1H); LCMS 1.76 min, 399 (M+H)

IRAK4 IC50 is 36 nM for Example 87.

Example 88

5-(Benzo[d]thiazol-2-yl)-2-morpholino-6-(piperidin-4-ylamino)pyrimidin-4(3H)-one HCl Prepared according to Scheme 7 except tert-butyl 4-aminopiperidine-1-carboxylate was used in place of (R)-tert-butyl 3-aminopiperidine-1-carboxylate in Step 1.

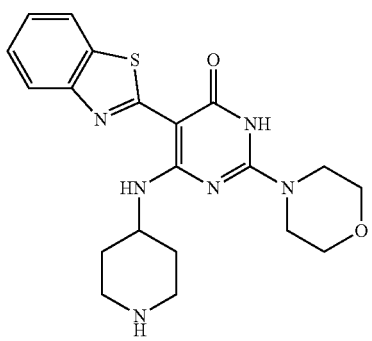 [SMILES: O=c1[nH]c(N2CCOCC2)nc(NC2CCNCC2)c1-c1nc2ccccc2s1]

¹H NMR (DMSO) δ 10.82 (d, J=7.2 Hz, 1H), 7.91 (d, J=8 Hz, 1H), 7.72 (d, J=8 Hz, 1H), 7.36 (t, J=8.4 Hz, 1H), 7.25 (t, J=8.4 Hz, 1H), 4.21 (m, 1H), 3.66 (m, 8H), 3.30 (s, 3H), 3.07-3.03 (m, 2H), 2.80-2.65 (m, 2H), 2.01-1.99 (m, 2H), 1.61-1.53 (m, 2H); LCMS 1.74 min, 413 (M+H)

IRAK4 IC50 is 121 nM for Example 88.

Example 89

(R)-5-(Benzo[d]thiazol-2-yl)-2-morpholino-6-(6-oxopiperidin-3-ylamino)pyrimidin-4(3H)-one.HCl Prepared according to Scheme 7 except (R)-tert-butyl 5-amino-2-oxopiperidine-1-carboxylate was used in place of (R)-tert-butyl 3-aminopiperidine-1-carboxylate in Step 1.

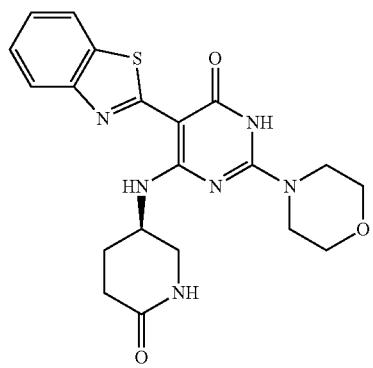 [SMILES: O=C1CC[C@@H](Nc2nc(N3CCOCC3)[nH]c(=O)c2-c2nc3ccccc3s2)CN1]

¹H NMR (DMSO) δ 11.15 (d, J=7.6 Hz, 1H), 7.93 (d, J=8 Hz, 1H), 7.70 (d, J=8 Hz, 1H), 7.58 (s, 1H), 7.38 (t, J=8.4 Hz, 1H), 7.23 (t, J=8.4 Hz, 1H), 4.54-4.51, (m, 1H), 3.68 (m, 8H), 3.52-3.49 (m, 1H), 3.32-3.20 (m, 1H), 2.49-2.48 (m, 2H), 2.47-2.36 (m, 2H), 2.09-1.97 (m, 2H); LCMS 1.94 min, 427 (M+H)

IRAK4 IC50 is 450 nM for Example 89.

Example 90

6-(3-Aminocyclohexylamino)-5-(benzo[d]thiazol-2-yl)-2-morpholinopyrimidin-4(3H)-one.HCl Prepared according to Scheme 7 except cyclohexane-1,3-diamine was used in place of (R)-tert-butyl 3-aminopiperidine-1-carboxylate in Step 1.

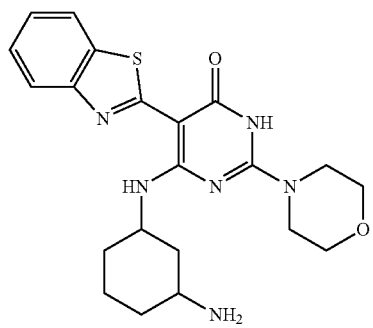 [SMILES: NC1CCCC(Nc2nc(N3CCOCC3)[nH]c(=O)c2-c2nc3ccccc3s2)C1]

¹H NMR (major) (DMSO) δ 11.06 (br s, 1H), 10.70 (d, J=7.2 Hz, 1H), 8.23 (br s, 2H), 7.94 (d, J=8 Hz, 1H), 7.76 (d, J=8 Hz, 1H), 7.38 (t, J=8.4 Hz, 1H), 7.23 (t, J=8.4 Hz, 1H), 5.96 (br s, 2H), 4.08-4.04, (m, 1H), 3.68 (m, 8H), 3.20-3.15 (m, 1H), 2.06-1.74 (m, 3H), 1.49-1.30 (m, 3H); LCMS 1.87 min, 427 (M+H)

IRAK4 IC50 is 258 nM for Example 90.

Example 91

(R)-3-(5-(Benzo[d]thiazol-2-yl)-2-morpholino-6-oxo-1,6-dihydropyrimidin-4-ylamino)azepan-2-one-.HCl Prepared according to Scheme 7 except (R)-3-aminoazepan-2-one was used in place of (R)-tert-butyl 3-aminopiperidine-1-carboxylate in Step 1.

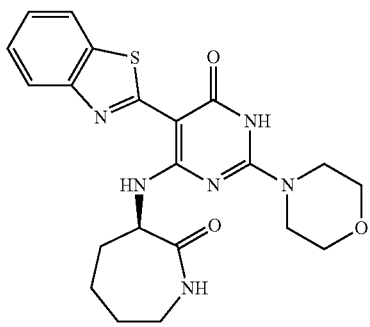 [SMILES: O=C1NCCCC[C@H]1Nc1nc(N2CCOCC2)[nH]c(=O)c1-c1nc2ccccc2s1]

$^1$H NMR (DMSO) δ 11.10 (br s, 1H), 10.71 (d, J=6.8 Hz, 1H), 9.40 (br s, 1H), 9.02 (br s, 1H), 7.90 (d, J=8 Hz, 1H), 7.71 (d, J=8 Hz, 1H), 7.31 (t, J=8.4 Hz, 1H), 7.25 (t, J=8.4 Hz, 1H), 5.12 (br s, 1H), 4.49, (m, 1H), 3.70-3.61 (m, 8H), 3.40-3.21 (m, 2H), 3.01 (m, 2H), 2.01-1.85 (m, 1H), 1.90-1.83 (m, 3H), 1.78-1.71 (m, 1H); LCMS 2.12 min, 441 (M+H)

IRAK4 IC50 is 2429 nM for Example 91.

Example 92

6-(Azepan-3-ylamino)-5-(benzo[d]thiazol-2-yl)-2-morpholinopyrimidin-4(3H)-one.HCl Prepared according to Scheme 7 except azepan-3-amine was used in place of (R)-tert-butyl 3-aminopiperidine-1-carboxylate in Step 1.

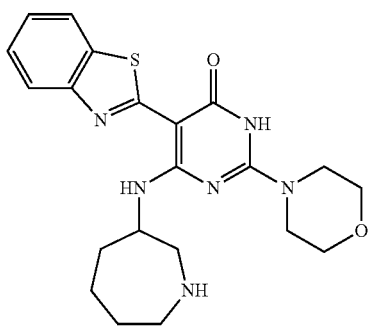 [SMILES: O=c1[nH]c(N2CCOCC2)nc(NC2CCCCNC2)c1-c1nc2ccccc2s1]

$^1$H NMR (DMSO) δ 11.14 (br s, 1H), 10.70 (d, J=6.8 Hz, 1H), 9.39 (br s, 1H), 9.13 (br s, 1H), 7.95 (d, J=8 Hz, 1H), 7.75 (d, J=8 Hz, 1H), 7.40 (t, J=8.4 Hz, 1H), 7.26 (t, J=8.4 Hz, 1H), 4.99 (br s, 3H), 4.58, (m, 1H), 3.76-3.65 (m, 8H), 3.41-3.29 (m, 2H), 3.15 (m, 2H), 2.12-1.95 (m, 1H), 1.95-1.89 (m, 3H), 1.80-1.76 (m, 1H); LCMS 1.89 min, 427 (M+H)

IRAK4 IC50 is 27 nM for Example 92.

Example 93

(R)-2-Morpholino-6-(piperidin-3-ylamino)-5-(quinolin-2-yl)pyrimidin-4(3H)-one.HCl Prepared according to Scheme 7 except 2-(tributylstannyl) quinoline was used in place of 2-(tributylstannyl)benzo[d]thiazole in Step 5.

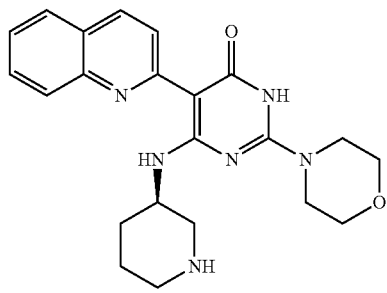 [SMILES: O=c1[nH]c(N2CCOCC2)nc(N[C@@H]2CCCNC2)c1-c1ccc2ccccc2n1]

$^1$H NMR (DMSO) δ 11.10 (br s, 1H), 9.68 (d, J=8.4 Hz, 1H), 9.25 (br s, 1H), 8.49 (m, 2H), 8.09-8.01 (m, 2H), 7.84 (t, J=7.6 Hz, 1H), 7.63 (t, J=7.6 Hz, 1H), 4.44 (m, 1H), 3.87-3.54 (m, 8H), 3.48-3.38 (m, 1H), 3.18 (m, 1H), 2.83-2.81 (m, 2H), 2.03-1.97 (m, 1H), 1.90-1.69 (m, 3H); LCMS 1.73 min, 407 (M+H)

IRAK4 IC50 is 26 nM for Example 93.

Example 94

(R)-5-(4-Methylthiazol-2-yl)-2-morpholino-6-(piperidin-3-ylamino)pyrimidin-4(3H)-one.HCl Prepared according to Scheme 7 except 4-methyl-2-(tributylstannyl)thiazole was used in place of 2-(tributylstannyl)benzo[d]thiazole in Step 5.

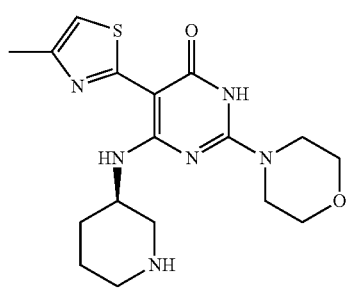 [SMILES: Cc1csc(-c2c(N[C@@H]3CCCNC3)nc(N3CCOCC3)[nH]c2=O)n1]

$^1$H NMR (DMSO) δ 10.96 (br s, 1H), 10.51 (d, J=6.4 Hz, 1H), 9.64 (d, J=9.6 Hz, 1H), 9.00 (d, J=9.2 Hz, 1H), 6.82 (s, 1H), 4.03 (m, 1H), 3.73-3.64 (m, 8H), 3.48-3.40 (m, 1H), 3.19-3.16 (m, 1H), 2.89-2.86 (m, 1H), 2.80-2.69 (m, 1H), 2.33 (s, 3H), 2.05-2.02 (m, 1H), 1.89-1.82 (m, 2H), 1.70-1.61 (m, 1H); LCMS 1.85 min, 378 (M+H)

IRAK4 IC50 is 554 nM for Example 94.

Example 95

(R)-5-(Benzo[d]thiazol-2-yl)-6-(1-methylpiperidin-3-ylamino)-2-morpholinopyrimidin-4(3H)-one.HCl Prepared according to Scheme 5 except (R)-1-methylpiperidin-3-amine was used in place of (R)-tert-butyl 3-aminopiperidine-1-carboxylate in Step 1.

89

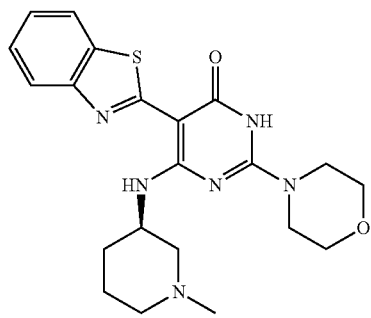 [SMILES: CN1CCC[C@@H](Nc2nc(N3CCOCC3)[nH]c(=O)c2-c2nc3ccccc3s2)C1]

$^1$H NMR (DMSO) δ 11.28 (br s, 1H), 11.12 (s, 1H), 10.66 (d, J=7.2 Hz, 1H), 7.95-7.93 (m, 1H), 7.77-7.73 (m, 1H), 7.43-7.34 (m, 1H), 7.28-7.21 (m, 1H), 4.61-4.59 (m, 1H), 3.77-3.66 (m, 8H), 3.49-3.37 (m, 2H), 3.06 (m, 1H), 2.88-2.80 (m, 2H), 2.75 (s, 3H), 2.13-2.10 (m, 1H), 1.95 (br s, 1H), 1.71-1.64 (m, 1H); LCMS 1.86 min, 427 (M+H)

IRAK4 IC50 is 354 nM for Example 95.

Example 96

5-(Benzo[d]thiazol-2-yl)-6-(3-hydroxycyclohexy-lamino)-2-morpholinopyrimidin-4(3H)-one.HCl Prepared according to Scheme 5 except 3-aminocyclohexanol was used in place of (R)-tert-butyl 3-aminopiperidine-1-carboxylate in Step 1.

90

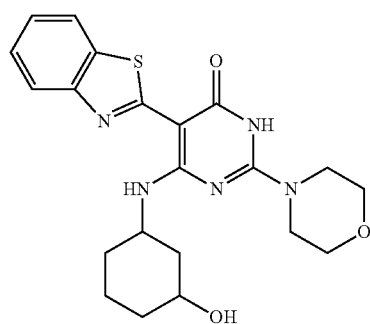 [SMILES: O=c1[nH]c(N2CCOCC2)nc(NC2CCCC(O)C2)c1-c1nc2ccccc2s1]

$^1$H NMR (major) (DMSO) δ 10.98 (s, 1H), 10.75 (d, J=7.2 Hz, 1H), 7.92 (d, J=7.2 Hz, 1H), 7.74 (d, J=7.2 Hz, 1H), 7.34 (t, J=8.4 Hz, 1H), 7.20 (t, J=8.4 Hz, 1H), 4.71 (br s, 2H), 4.06-4.02 (m, 1H), 3.66 (m, 8H), 3.57-3.51 (m, 1H), 2.20-2.10 (m, 1H), 1.97-1.95 (m, 1H), 1.81-1.68 (M, 2H), 1.58-1.55 (m, 1H), 1.38-1.1.14 (m, 3H); LCMS 2.23 min (major) 2.27 (minor), 428 (M+H)

IRAK4 IC50 is 1803 nM for Example 96.

Example 97

(R)-5-(5-Fluorobenzo[d]thiazol-2-yl)-2-morpholino-6-(piperidin-3-ylamino)pyrimidin-4(3H)-one.HCl

SCHEME 8

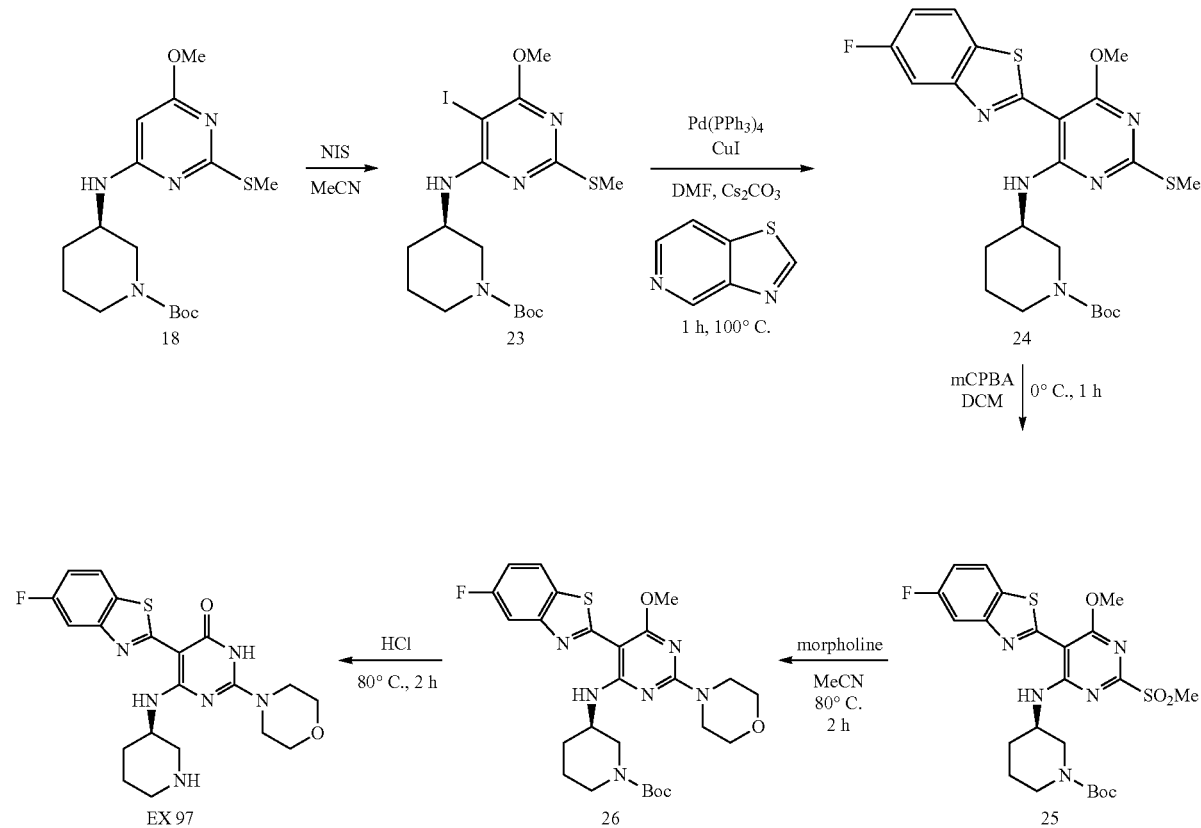

Step 1: (R)-Tert-butyl 3-(5-iodo-6-methoxy-2-(methylthio)pyrimidin-4-ylamino)piperidine-1-carboxylate (Compound 23)

Compound 18 (1.00 g, 2.82 mmol) was dissolved in MeCN (50 mL) and NIS (952 mg, 4.23 mmol) was added and the reaction was heated to reflux for 1 h. The solution was concentrated and the residue was dissolved in EtOAc, wash with a saturated aqueous solution of NaHCO$_3$ and a saturated aqueous solution of NaS$_2$O$_3$, dried (MgSO$_4$), filtered and concentrated to give the title compound as a light yellow solid. LCMS 2.06 min, 481 (M+H)

Step 2 (R)-Tert-butyl 3-(5-(5-fluorobenzo[d]thiazol-2-yl)-6-methoxy-2-(methylthio)pyrimidin-4-ylamino)piperidine-1-carboxylate (24)

DMF (4.3 mL) was added to a 125 mL round-bottom flask containing 5-fluorobenzo[d]thiazole (268 mg, 1.749 mmol). Compound 23 (420 mg, 0.874 mmol), Pd(Ph$_3$P)$_4$ (202 mg, 0.175 mmol), Cs$_2$CO$_3$ (1709 mg, 5.25 mmol) and CuI (33.3 mg, 0.175 mmol) were then added. The mixture was degassed placed in an oil bath that was preheated to 100° C. for 1 h. The reaction mixture was cooled to room temperature, diluted with water and ethyl acetate and filtered through celite. The organics were then separated and the water layer was washed with ethyl acetate. The organics were combined, washed with brine (×3), dried over sodium sulfate, filtered, and concentrated. The residue was purified by column chromatography on silica gel, eluting with EtOAc/hexane to give the title compound as a white solid. $^1$H NMR (CDCl$_3$) δ 10.81-10.78 (m, 1H), 7.79-7.75 (m, 1H), 7.62-7.59 (m, 1H), 7.11-7.07 (m, 1H), 4.41-4.89 (m, 1H), 4.16-4.14 (m, 2H), 3.69-3.44 (m, 2H), 2.00-1.25 (m, 13H), LCMS 3.30 min, 506 (M+H)

Step 3 and 4: (R)-Tert-butyl3-((5-(5-fluorobenzo[d]thiazol-2-yl)-6-methoxy-2-morpholinopyrimidin-4-yl)amino)piperidine-1-carboxylate (Compound 26)

Compound 24 (352 mg, 0.697 mmol) was dissolved in CH$_2$Cl$_2$ (3.5 mL) in a 250 mL round-bottom flask and cooled to 0° C. mCPBA (240 mg, 1.39 mmol) was added portion wise. This was then allowed at to stir at 0° C. for approx 1 h. The reaction was then diluted with aqueous sodium bicarbonate and extracted with dichloromethane. The aqueous layer was then washed with dichloromethane and the organics were combined. The organics were then dried over sodium sulfate, filtered, and then concentrated to give Compound 25 as a yellow foam. LCMS 2.54 min, 544 (M+Na)

To a solution of Compound 25 (326 mg, 0.626 mmol) in acetonitrile (3.1 mL) was added morpholine (0.436 mL, 5.01 mmol). The reaction was heated to 80° C. for 1 h. The reaction mixture was concentrated under reduced pressure. The residue was purified by column chromatography on silica gel, eluting with EtOAc/hexane to give the title compound as a white solid. $^1$H NMR (CDCl$_3$) δ 7.727-7.69 (m, 1H), 7.533-7.50 (m, 1H), 7.04-7.03 (m, 1H), 4.27-4.24 (m, 1H), 4.08 (s, 2H), 3.88-3.77 (m, 6H), 3.51-3.45 (m, 2H), 2.02-1.5 (m, 12H), 1.40-1.25 (m, 6H); LCMS 3.30 min, 506 (M+H)

Step 5 (R)-5-(5-Fluorobenzo[d]thiazol-2-yl)-2-morpholino-6-(piperidin-3-ylamino)pyrimidin-4(3H)-one hydrochloride (Example 97)

To a 250 mL flask containing Compound 26 (255 mg, 0.469 mmol), hydrochloric acid, (37%, 7 ml) was added. This was then heated and stirred at 80° C. for approx 1 h. The reaction mixture was then concentrated to dryness to obtain the title compound.

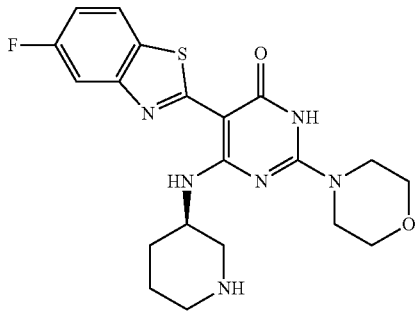 [SMILES: O=c1[nH]c(N2CCOCC2)nc(N[C@@H]2CCCNC2)c1-c1nc2cc(F)ccc2s1]

$^1$H NMR (DMSO) δ 11.14 (s, 1H), 10.62-10.60 (m, 1H), 9.58-9.56 (m, 1H), 9-8.97 (m, 1H), 7.97-7.927 (m, 1H), 7.59-7.56 (m, 1H), 7.12-7.09 (m, 1H), 4.56 (s, 1H), 3.76-3.64 (m, 5H), 3.45-3.41 (m, 1H), 3.23-3.2 (m, 1H), 2.89-2.85 (m, 2H), 2.08-2.06 (m, 1H), 1.93-1.77 (m, 3H) LCMS 1.89 min, 431 (M+H)

IRAK4 IC50 is 8.4 nM for Example 97.

Example 98

(R)-5-(4-(4-Fluorophenyl)thiazol-2-yl)-2-morpholino-6-(piperidin-3-ylamino)pyrimidin-4(3H)-one.HCl Prepared according to Scheme 8 except 4-(4-fluorophenyl)thiazole was used in place of 5-fluorobenzo[d]thiazole in Step 2.

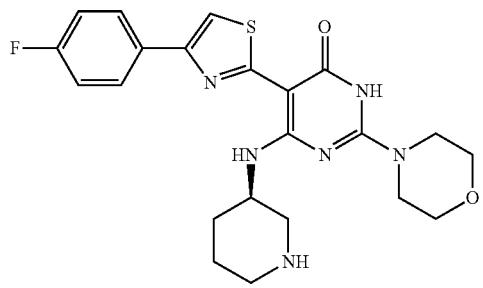 [SMILES: O=c1[nH]c(N2CCOCC2)nc(N[C@@H]2CCCNC2)c1-c1nc(-c2ccc(F)cc2)cs1]

$^1$H NMR (DMSO) δ 11.06 (br s, 1H), 10.42 (d, J=6.4 Hz, 1H), 9.30 (s, 1H), 8.87 (m, 1H), 7.94-7.90 (m, 2H), 7.71 (s, 1H), 7.30-7.26 (m, 2H), 4.36-4.35 (m, 1H), 3.71-3.66 (m, 8H), 3.50-3.48 (m, 1H), 3.23-3.20 (m, 1H), 2.94-2.84 (m, 2H), 2.15-2.12 (m, 1H), 1.95-1.76 (m, 3H); LCMS 1.96 min, 457 (M+H)

IRAK4 IC50 is 24 nM for Example 98.

Example 99

(R)-5-(4-Methylthiazolo[4,5-c]pyridin-2-yl)-2-morpholino-6-(piperidin-3-ylamino)pyrimidin-4(3H)-one.HCl Prepared according to Scheme 8 except 4-methylthiazolo[4,5-c]pyridine was used in place of 5-fluorobenzo[d]thiazole in Step 2.

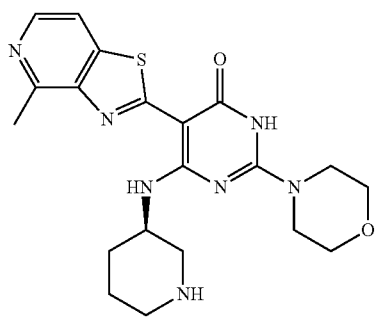

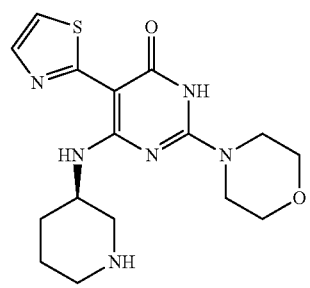

¹H NMR (DMSO) δ 11.27 (s, 1H), 10.15-10.3 (m, 1H), 9.46-9.43 (m, 1H), 9-8.96 (m, 1H), 8.44 (s, 1H), 4.47-4.4 (m, 1H), 3.78 (s, 1H), 3.69-3.66 (m, 2H), 3.01 (s, 2H), 2.92-2.88 (m, 2H), 2.15-2.11 (m, 1H), 1.95-1.78 (m, 3H) LCMS 1.28 min, 428 (M+H)

IRAK4 IC50 is 5.7 nM for Example 99.

Example 100

(R)-5-(4-cyclopropylthiazol-2-yl)-2-morpholino-6-(piperidin-3-ylamino)pyrimidin-4(3H)-one.HCl The title compound was prepared using a route similar to that shown in Scheme 8.

¹H NMR (DMSO) δ 10.99 (s, 1H), 10.36 (d, J=7.2 Hz, 1H), 9.19 (m, 1H), 8.79 (s, 1H), 7.67 (d, J=3.6 Hz, 1H), 7.30 (d, J=3.6 Hz, 1H), 4.38-4.35 (m, 1H), 3.69-3.65 (m, 5H), 3.45 (m, 8H), 3.22-3.19 (m, 1H), 2.88-2.80 (m, 1H), 2.04-1.65 (m, 2H); LCMS 1.74 min, 363 (M+H)

IRAK4 IC50 is 1830 nM for Example 101.

Example 102

(R)-5-(5-methylthiazol-2-yl)-2-morpholino-6-(piperidin-3-ylamino)pyrimidin-4(3H)-one.HCl The title compound was prepared using a route similar to that shown in Scheme 7.

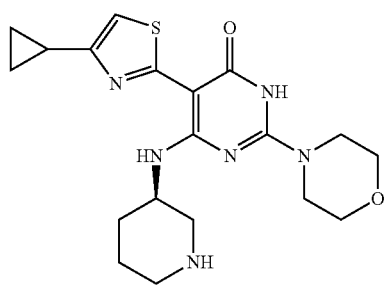 [SMILES: O=c1[nH]c(N2CCOCC2)nc(N[C@@H]2CCCNC2)c1-c1nc(C2CC2)cs1]

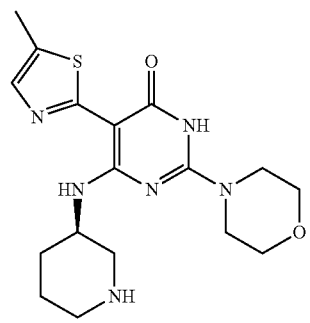 [SMILES: Cc1cnc(-c2c(N[C@@H]3CCCNC3)nc(N3CCOCC3)[nH]c2=O)s1]

¹H NMR (DMSO) δ 10.38 (d, J=7.2 Hz, 1H), 8.25 (s, 1H), 6.84 (s, 1H), 4.12-4.11 (m, 1H), 3.63 (m, 8H) 3.20-3.17 (m, 1H), 2.90-2.87 (m, 1H), 2.71-2.68 (m, 1H), 2.05-1.94 (m, 2H), 1.74 (m, 1H), 1.58-1.47 (m, 2H), 0.96-0.81 (m, 4H); LCMS 1.73 min, 403 (M+H)

IRAK4 IC50 is 433 nM for Example 100.

Example 101

(R)-2-morpholino-6-(piperidin-3-ylamino)-5-(thiazol-2-yl)pyrimidin-4(3H)-one.HCl The title compound was prepared using a route similar to that shown in Scheme 7.

¹H NMR (DMSO) δ 10.98 (s, 1H), 10.25 (d, J=7.2 Hz, 1H), 9.02 (m, 1H), 8.74 (m, 1H), 7.63-7.53 (m, 1H), 7.32 (s, 1H), 4.35-4.32 (m, 1H), 3.66 (m, 8H), 3.55-3.41 (m, 1H), 3.22-3.15 (m, 1H), 2.88-2.79 (m, 2H). 2.36 (s, 3H), 1.99-1.62 (m, 4H); LCMS 1.66 min, 377 (M+H)

IRAK4 IC50 is 1271 nM for Example 102.

Example 103

(R)-2-morpholino-6-(piperidin-3-ylamino)-5-(4-(4-(trifluoromethoxy)phenyl)thiazol-2-yl)pyrimidin-4(3H)-one.HCl The title compound was prepared using a route similar to that shown in Scheme 8.

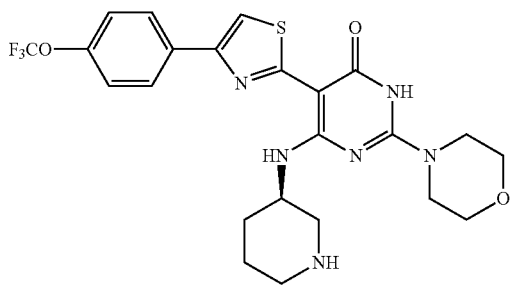 [SMILES: O=c1[nH]c(N2CCOCC2)nc(N[C@@H]2CCCNC2)c1-c1nc(-c2ccc(OC(F)(F)F)cc2)cs1]

¹H NMR (DMSO) δ 11.05 (s, 1H), 10.35 (d, J=7.2 Hz, 1H), 9.61 (m, 1H), 9.03 (m, 1H), 8.00 (d, J=8.8 Hz, 2H), 7.80 (s, 1H), 7.44 (d, J=8.8 Hz, 2H), 4.42-4.40 (m, 1H), 3.73 (m, 4H), 3.69-3.65 (m, 3H), 3.55-3.48 (m, 3H), 3.23-3.20 (m, 1H), 2.94-2.81 (m, 2H), 2.16-2.13 (m, 1H), 1.98-1.74 (m, 3H); LCMS 2.09 min, 523 (M+H)

IRAK4 IC50 is 2246 nM for Example 103.

Example 104

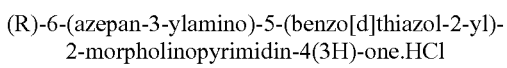

(R)-6-(azepan-3-ylamino)-5-(benzo[d]thiazol-2-yl)-2-morpholinopyrimidin-4(3H)-one.HCl The title compound was prepared using a route similar to that shown in Scheme 7.

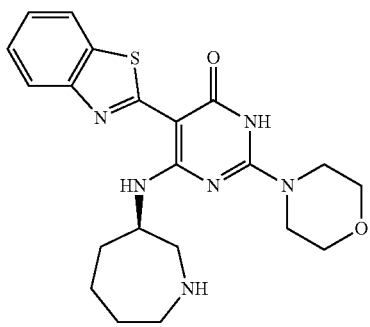 [SMILES: O=c1[nH]c(N2CCOCC2)nc(N[C@@H]2CCCCNC2)c1-c1nc2ccccc2s1]

¹H NMR (DMSO) δ 11.11 (d, J=7.6 Hz, 1H), 10.96 (d, J=7.6 Hz, 1H), 8.20 (s, 1H), 7.92-7.90 (m, 1H), 7.74-7.69 (m, 1H), 7.39-7.36 (m, 1H), 7.39-7.20 (m, 1H), 4.37-4.34 (m, 1H), 3.49 (m, 8H), 3.11-2.52 (m, 4H); 1.93-1.49 (m, 5H); LCMS 2.05 min, 427 (M+H)

IRAK4 IC50 is 79 nM for Example 104.

Example 105

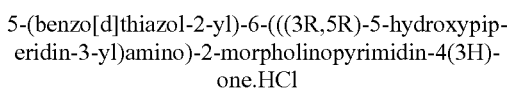

5-(benzo[d]thiazol-2-yl)-6-(((3R,5R)-5-hydroxypiperidin-3-yl)amino)-2-morpholinopyrimidin-4(3H)-one.HCl The title compound was prepared using a route similar to that shown in Scheme 7. (3R,5R)-tert-butyl 3-amino-5-hydroxypiperidine-1-carboxylate was prepared according to the procedure outlined in Erlanson, Daniel A.; et al. WO 2011029046.

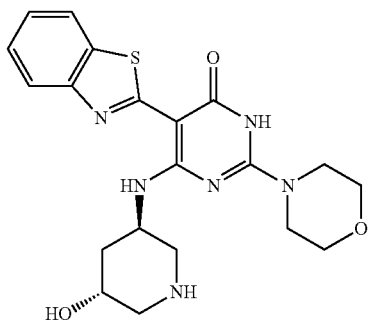 [SMILES: O=c1[nH]c(N2CCOCC2)nc(N[C@H]2CNC[C@H](O)C2)c1-c1nc2ccccc2s1]

¹H NMR (DMSO) δ 11.11 (s, 1H), 10.72 (d, J=7.6 Hz, 1H), 9.36-9.34 (m, 1H), 9.01 (m, 1H), 7.93 (d, J=7.6 Hz, 1H), 7.76 (d, J=7.6 Hz, 1H), 7.40 (t, J=7.2 Hz, 1H), 7.24 (t, J=7.2 Hz, 1H), 4.64-4.62 (m, 1H), 4.31 (s, 1H), 3.74-3.68 (m, 8H), 3.45-3.38 (m, 1H), 3.06 (s, 2H), 2.93-2.85 (m, 1H), 2.14-2.11 (m, 1H), 1.99-1.93 (m, 1H), 1.21 (s, 1H); LCMS 1.69 min, 429 (M+H)

IRAK4 IC50 is 85 nM for Example 105.

Example 106

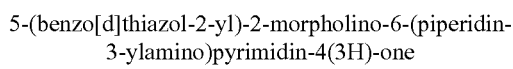

5-(benzo[d]thiazol-2-yl)-2-morpholino-6-(piperidin-3-ylamino)pyrimidin-4(3H)-one The title compound was prepared using a route similar to that shown in Scheme 7.

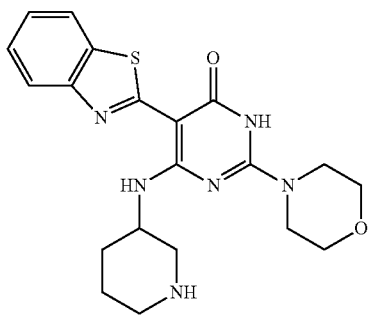 [SMILES: O=c1[nH]c(N2CCOCC2)nc(NC2CCCNC2)c1-c1nc2ccccc2s1]

¹H NMR (DMSO) δ 10.87 (d, J=7.2 Hz, 1H), 7.92 (d, J=8 Hz, 1H), 7.72 (d, J=8 Hz, 1H), 7.38 (t, J=8.4 Hz, 1H), 7.22 (t, J=8.4 Hz, 1H), 4.17-4.15 (m, 1H), 3.67 (m, 8H), 3.15-3.12 (m, 1H), 2.87-2.83 (m, 1H), 2.74-2.64 (m, 2H), 1.94-1.93 (m, 1H), 1.75-1.53 (m, 4H); LCMS 1.78 min, 413 (M+H)

IRAK4 IC50 is 244 nM for Example 106.

Example 107

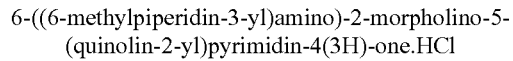

6-((6-methylpiperidin-3-yl)amino)-2-morpholino-5-(quinolin-2-yl)pyrimidin-4(3H)-one.HCl The title compound was prepared using a route similar to that shown in Scheme 7. 6-Methylpiperidin-3-amine was prepared according to the procedure of Ninkovic, Sasha; et al. WO 2010016005.

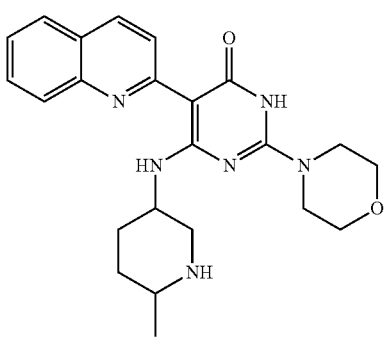 [SMILES: CC1CCC(Nc2nc(N3CCOCC3)[nH]c(=O)c2-c2ccc3ccccc3n2)CN1]

LCMS 1.67 min, 421 (M+H)
IRAK4 IC50 is 91 nM for Example 107.

Example 108

5-(benzo[d]thiazol-2-yl)-6-(((1R,3R)-3-hydroxycyclohexyl)amino)-2-morpholinopyrimidin-4(3H)-one.HCl The title compound was prepared using a route similar to Scheme 7.

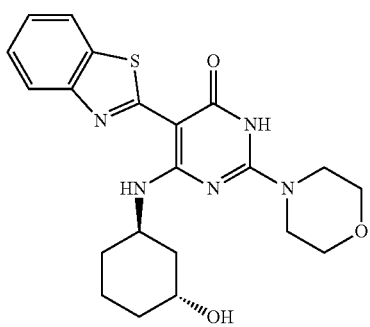 [SMILES: O=c1[nH]c(N2CCOCC2)nc(N[C@@H]2CCC[C@@H](O)C2)c1-c1nc2ccccc2s1]

LCMS 2.04 min, 428 (M+H)
IRAK4 IC50 is 454 nM for Example 108.

Example 109

(R)-5-(6-methylpyridin-2-yl)-2-morpholino-6-(piperidin-3-ylamino)pyrimidin-4(3H)-one The title compound was prepared using a route similar to Scheme 7.

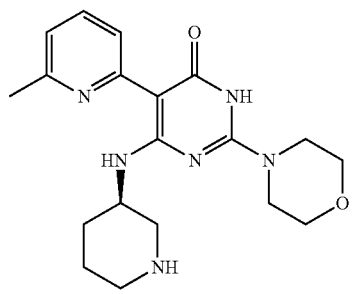 [SMILES: Cc1cccc(-c2c(N[C@@H]3CCCNC3)nc(N3CCOCC3)[nH]c2=O)n1]

$^1$H NMR (CD$_3$OD) δ 8.37 (d, 1H), 7.60 (m, 2H), 6.90 (d, 1H), 4.11 (m, 1H), 3.78-3.47 (m, 8H), 3.33 (m, 2H), 2.98 (m, 1H), 2.67-2.49 (m, 5H), 2.10 (m, 1H), 1.88 (m, 1H), 1.70-1.44 (m, 2H), LCMS 0.98 min, 371 (M+H)
IRAK4 IC50 is 1474 nM for Example 109.

Example 110

(R)-5-(5-methylpyridin-2-yl)-2-morpholino-6-(piperidin-3-ylamino)pyrimidin-4(3H)-one The title compound was prepared using a route similar to Scheme 7.

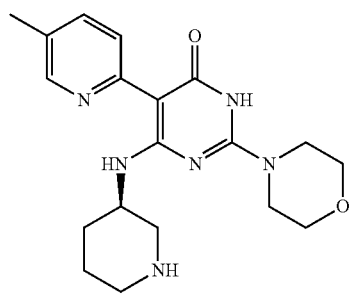 [SMILES: Cc1ccc(-c2c(N[C@@H]3CCCNC3)nc(N3CCOCC3)[nH]c2=O)nc1]

$^1$H NMR (CD$_3$OD) δ 8.40 (d, 1H), 8.26 (s, 1H), 7.56 (d, 1H), 4.12 (m, 1H), 3.87-3.47 (m, 7H), 3.75 (m, 2H), 3.12 (m, 1H), 2.94 (m, 1H), 2.68 (m, 1H), 2.56 (m, 1H), 2.27 (s, 3H), 2.12 (m, 1H), 1.85 (m, 1H), 1.79-1.44 (m, 2H), LCMS 1.22 min, 371 (M+H)
IRAK4 IC50 is 872 nM for Example 110.

Example 111

(R)-5-(4-cyclopropylthiazolo[4,5-c]pyridin-2-yl)-2-morpholino-6-(piperidin-3-ylamino)pyrimidin-4(3H)-one.HCl The title compound was prepared using a route similar to Scheme 8.

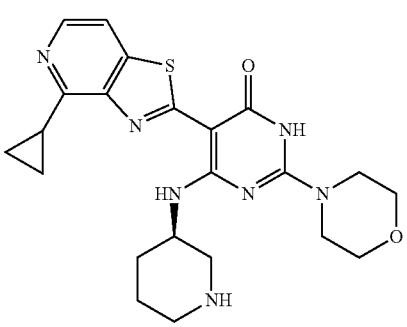 [SMILES: O=c1[nH]c(N2CCOCC2)nc(N[C@@H]2CCCNC2)c1-c1nc2c(C3CC3)nccc2s1]

$^1$H NMR (DMSO) δ 11.34-11.37 (m, 1H), 9.34-9.33 (m, 1H), 8.90-8.88 (m, 1H), 8.28-8.26 (m, 1H), 3.77 (b, 4H), 3.69-3.67 (m, 4H), 2.91-2.81 (m, 4H), 2.15-2.12 (m, 2H), 1.98-1.92 (m, 2H), 1.88-1.71 (m, 4H), 1.62-1.49 (m, 3H), 1.36 (b, 2H); LCMS 1.69 min, 454 (M+H)
IRAK4 IC50 is 9 nM for Example 111.

Example 112

(R)-5-(6-fluorobenzo[d]thiazol-2-yl)-2-morpholino-6-(piperidin-3-ylamino)pyrimidin-4(3H)-one.HCl The title compound was prepared using a route similar to Scheme 8.

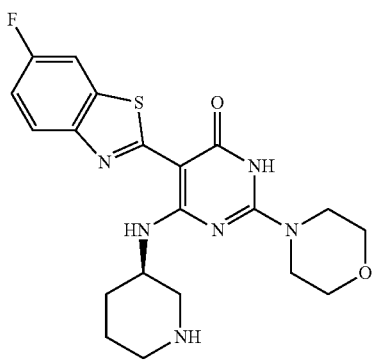 [SMILES: O=c1[nH]c(N2CCOCC2)nc(N[C@@H]2CCCNC2)c1-c1nc2ccc(F)cc2s1]

¹H NMR (DMSO) δ 11.13 (s, 1H), 10.59 (m, 1H), 9.21-9.18 (m, 1H), 7.84-7.74 (m, 1H), 7.27-7.22 (m, 1H) 4.40 (b, 1H), 3.72-3.66 (m, 5H), 2.90-2.87 (m, 1H), 2.08 (b, 1H), 1.99-1.94 (m, 1H), 1.82-1.79 (m, 1H); LCMS 1.93 min, 431 (M+H)

IRAK4 IC50 is 46 nM for Example 112.

Example 113

(R)-2-morpholino-6-(piperidin-3-ylamino)-5-(thiazolo[4,5-c]pyridin-2-yl)pyrimidin-4(3H)-one.HCl The title compound was prepared using a route similar to Scheme 8.

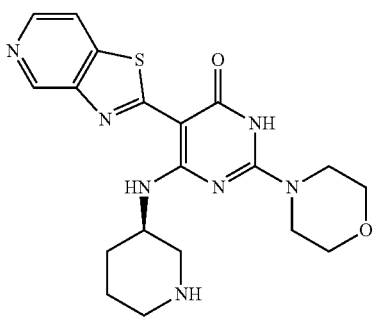 [SMILES: O=c1[nH]c(N2CCOCC2)nc(N[C@@H]2CCCNC2)c1-c1nc2cnccc2s1]

¹H NMR (DMSO) δ 8.46 (s, 1H), 7.76-7.66 (m, 2H), 4.17-4.16 (b, 2H), 2.86-2.82 (m, 4H), 2.36-2.39 (m, 1H) 1.44-1.38 (m, 2H), 1.20-1.17 (m, 2H), 0.473 (b, 3H); LCMS 1.63 min, 414 (M+H)

IRAK4 IC50 is 12 nM for Example 113.

Example 114

(R)-6-(piperidin-3-ylamino)-2-(pyrrolidin-1-yl)-5-(quinolin-2-yl)pyrimidin-4(3H)-one.HCl The title compound was prepared using a route similar to Scheme 7.

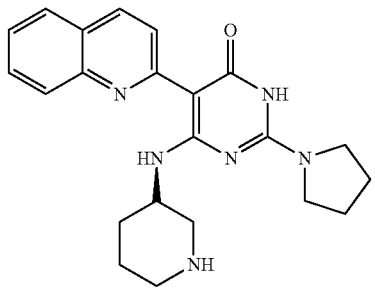

¹H NMR (DMSO) δ 10.94 (s, 1H), 9.30-9.22 (m, 2H), 8.46 (s, 2H) 8.07-8.00 (m, 2H), 7.85-7.81 (m, 1H), 8.63-7.60 (m, 1H) 4.38 (b, 2H), 3.92-3.47 (m, 5H) 3.15 (b, 1H), 2.91-2.84 (m, 2H), 2.01-1.67 (m, 8H); LCMS 0.59 min, 391 (M+H)

IRAK4 IC50 is 24 nM for Example 114.

Example 115

(R)-2-(piperidin-1-yl)-6-(piperidin-3-ylamino)-5-(quinolin-2-yl)pyrimidin-4(3H)-one.HCl The title compound was prepared using a route similar to Scheme 7.

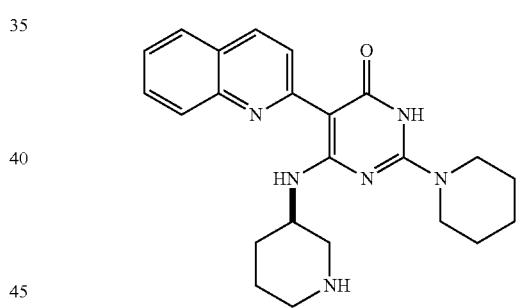

¹H NMR (DMSO) δ 10.93 (b, 1H), 9.33 (b, 1H), 9.13 (b, 1H), 8.51-8.43 (m, 2H) 8.03-7.98 (m, 2H), 7.82-7.79 (m, 1H), 7.61-7.57 (m, 1H) 4.39 (b, 1H), 3.43-3.41 (m, 2H) 3.15-2.89 (m, 1H), 2.88-2.86 (m, 2H), 2.03-1.5 (m, 9h); LCMS 0.63 min, 405 (M+H)

IRAK4 IC50 is 54 nM for Example 115.

Example 116

(R)-2-(4-methylpiperazin-1-yl)-6-(piperidin-3-ylamino)-5-(quinolin-2-yl)pyrimidin-4(3H)-one.HCl The title compound was prepared using a route similar to Scheme 7.

101

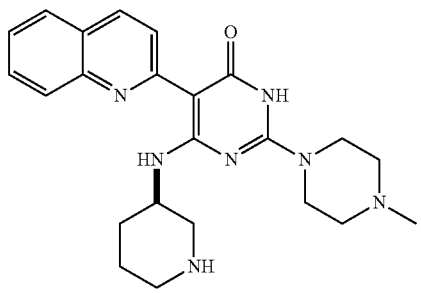

¹H NMR (DMSO) δ 11.04-11.02 (b, 2H), 9.91 (b, 1H), 8.95 (b, 1H), 8.69 (b, 1H), 8.36 (b, 1H), 7.98-7.93 (m, 2H), 7.78-7.75 (m, 1H), 7.57-7.555 (m, 1H) 4.69-4.51 (m, 2H), 3.63-3.11 (m, 8H) 2.83-2.774 (m, 5H), 2.05-1.77 (m, 5H); LCMS 0.47 min, 420 (M+H)

IRAK4 IC50 is 97 nM for Example 116.

Example 117

(R)-5-(4-cyclopropylthiazolo[4,5-c]pyridin-2-yl)-2-(piperidin-1-yl)-6-(piperidin-3-ylamino)pyrimidin-4(3H)-one.HCl The title compound was prepared using a route similar to Scheme 8

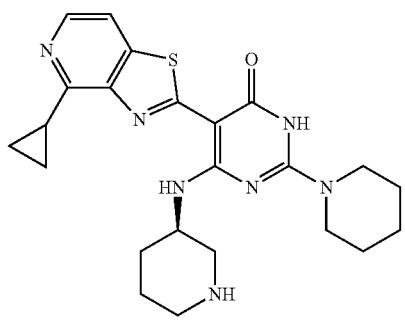 [SMILES: O=c1[nH]c(N2CCCCC2)nc(N[C@@H]2CCCNC2)c1-c1nc2c(C3CC3)nccc2s1]

¹H NMR (DMSO) δ 11.21 (b, 1H), 9.82 (b, 1H), 9.40 (b, 1H), 9.18 (b, 1H), 8.33-8.27 (m, 2H), 4.43 (b, 1H), 3.48 (b, 2H), 3.24-3.20 (m, 2H), 2.86-2.83 (m, 3H), 2.15-1.25 (m, 13H); LCMS 1.78 min, 452 (M+H)

IRAK4 IC50 is 8.6 nM for Example 117.

Example 118

(R)-5-(4-cyclopropylthiazolo[4,5-c]pyridin-2-yl)-6-(piperidin-3-ylamino)-2-(pyrrolidin-1-yl)pyrimidin-4(3H)-one.HCl The title compound was prepared using a route similar to Scheme 8.

102

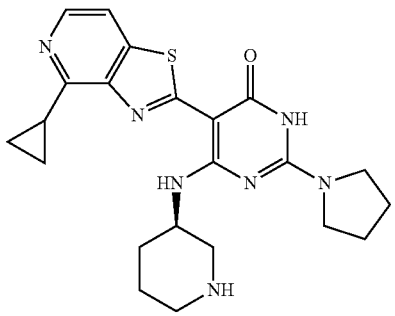 [SMILES: O=c1[nH]c(N2CCCC2)nc(N[C@@H]2CCCNC2)c1-c1nc2c(C3CC3)nccc2s1]

¹H NMR (DMSO) δ 11.56 (b, 1H), 9.15 (b, 1H), 9.29 (b, 1H), 9.26 (b, 1H), 7.76-7.52 (m, 1H), 4.03 (b, 1H), 3.74 (b, 2H), 2.87-2.85 (m, 1H), 2.12-1.21 (m, 7H); LCMS 1.75 min, 438 (M+H)

IRAK4 IC50 is 14 nM for Example 118.

Example 119

(R)-5-(4-cyclopropylthiazolo[4,5-c]pyridin-2-yl)-2-(4-(methylsulfonyl)piperazin-1-yl)-6-(piperidin-3-ylamino)pyrimidin-4(3H)-one.HCl The title compound was prepared using a route similar to Scheme 8

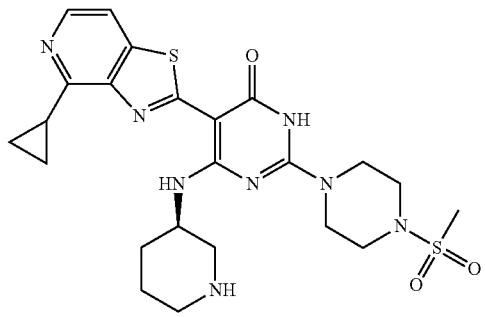 [SMILES: CS(=O)(=O)N1CCN(c2nc(N[C@@H]3CCCNC3)c(-c3nc4c(C5CC5)nccc4s3)c(=O)[nH]2)CC1]

¹H NMR (DMSO) δ 11.48 (b, 1H), 9.19 (b, 1H), 9.03 (b, 1H), 9.26 (b, 1H), 8.29-8.27 (m, 2H), 4.25 (b, 1H), 3.94 (b, 2H), 3.21 (b, 3H), 2.90-2.81 (m, 4H), 2.14-1.38 (m, 7H); LCMS 1.70 min, 538 (M+H)

IRAK4 IC50 is 6.9 nM for Example 119.

Example 120

(R)-5-(4-cyclopropylthiazolo[4,5-c]pyridin-2-yl)-2-(4-methylpiperazin-1-yl)-6-(piperidin-3-ylamino)pyrimidin-4(3H)-one.HCl The title compound was prepared using a route similar to Scheme 8.

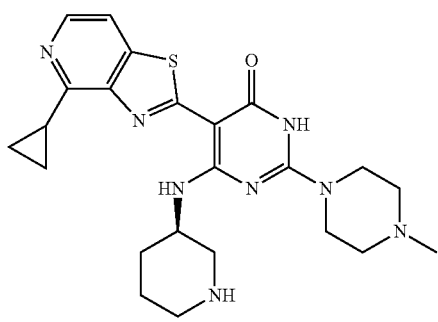 [SMILES: CN1CCN(c2nc(N[C@@H]3CCCNC3)c(-c3nc4c(C5CC5)nccc4s3)c(=O)[nH]2)CC1]

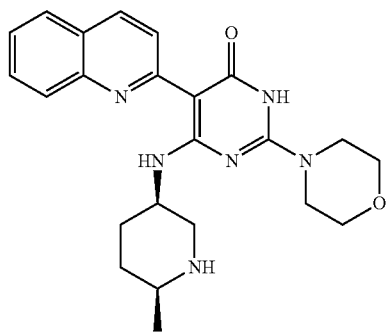

¹H NMR (DMSO) δ 11.54 (b, 1H), 11.00 (b, 1H), 10.09 (b, 1H), 8.95 (b, 1H), 8.27 (b, 1H), 4.57 (b, 1H), 3.23-3.84 (m, 4H), 2.82-2.79 (b, 5H), 2.3-1.5 (m, 7H); LCMS 1.56 min, 467 (M+H)

IRAK4 IC50 is 30 nM for Example 120.

Example 121

6-(methylpiperidin-3-yl)amino-2-morpholino-5-(quinolin-2-yl)pyrimidin-4(3H)-one.HCl The title compound was prepared using a route similar to Scheme 7.

¹H NMR (DMSO) (cis, racemic) δ 11.13 (br s, 1H), 9.43 (m, 1H), 8.87-8.80 (m, 2H), 8.09-8.02 (m, 3H), 7.84 (m 1H), 7.62 (m, 1H), 7.31-7.06 (m, 1H), 4.36 (m, 1H), 3.69-3.66 (m, 8H), 3.43 (m, 1H), 3.27-3.10 (m, 2H), 1.93-1.64 (m, 4H), 1.26 (d. J=6.4 Hz 3H); LCMS 1.57 min, 421 (M+H)

IRAK4 IC50 is 541 nM for Example 122.

Example 123

5-(benzo[d]thiazol-2-yl)-6((6-methylpiperidin-3-yl)amino)-2-morpholinopyrimidin-4(3H)-one.HCl The title compound was prepared using a route similar to Scheme 7.

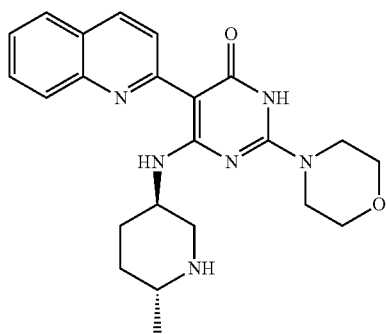 [SMILES: C[C@@H]1CC[C@@H](Nc2nc(N3CCOCC3)[nH]c(=O)c2-c2ccc3ccccc3n2)CN1]

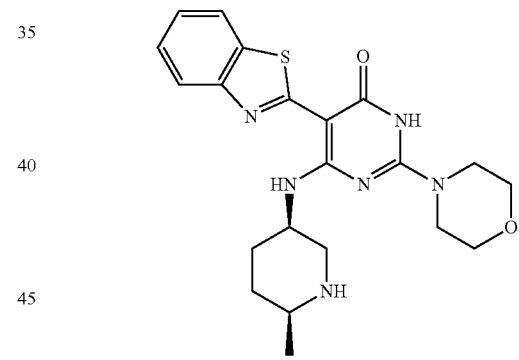

¹H NMR (DMSO) (trans, racemic) δ 11.11 (br s, 1H), 9.43 (m, 1H), 8.87-8.80 (m, 2H), 8.09-8.02 (m, 3H), 7.84 (m 1H), 7.62 (m, 1H), 7.31-7.06 (m, 1H), 4.39 (m, 1H), 3.73-3.68 (m, 8H), 3.53 (m, 1H), 2.10 (m, 2H), 1.95-1.92 (m, 2H), 1.80-1.64 (m, 2H), 1.26 (d. J=6.4 Hz 3H); LCMS 1.55 min, 421 (M+H)

IRAK4 IC50 is 38 nM for Example 121.

Example 122

6-(methylpiperidin-3-yl)amino-2-morpholino-5-(quinolin-2-yl)pyrimidin-4(3H)-one.HCl The title compound was prepared using a route similar to Scheme 7.

¹H NMR (DMSO) (cis, racemic) δ 11.11 (br s, 1H), 11.00 (d, J=6.4 Hz, 1H), 9.73 (m, 1H), 8.32 (m, 1H), 7.94 (d, J=6.4 Hz, 1H), 7.74 (d, J=6.4 Hz, 1H), 7.42 (t, J=7.2 Hz, 1H), 7.27 (t, J=7.2 Hz, 1H), 4.42 (s, 1H), 3.71-3.66 (m, 8H), 3.32 (m, 2H), 3.18-3.14 (m, 1H), 2.05-1.98 (m, 3H), 1.83-1.80 (m, 1H), 1.28 (d, J=6.4 Hz, 3H); LCMS 1.81 min, 427 (M+H)

IRAK4 IC50 is 847 nM for Example 123.

Example 124

5-(benzo[d]thiazol-2-yl)-6((6-methylpiperidin-3-yl)amino)-2-morpholinopyrimidin-4(3H)-one.HCl The title compound was prepared using a route similar to Scheme 7.

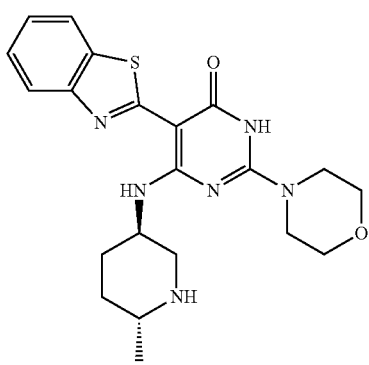 [SMILES: C[C@@H]1CC[C@@H](Nc2nc(N3CCOCC3)[nH]c(=O)c2-c2nc3ccccc3s2)CN1]

¹H NMR (DMSO) (trans, racemic) δ 11.10 (br s, 1H), 10.65 (d, J=6.4 Hz, 1H), 9.42 (m, 1H), 9.14 (m, 1H), 7.94 (d, J=6.4 Hz, 1H), 7.75 (d, J=6.4 Hz, 1H), 7.40 (t, J=7.2 Hz, 1H), 7.25 (t, J=7.2 Hz, 1H), 4.45 (s, 1H), 3.75-3.65 (m, 8H), 3.53-3.51 (m, 1H), 3.20 (m, 1H), 2.84-2.81 (m, 1H), 2.13-2.10 (m, 1H), 1.97-1.94 (m, 1H), 1.83-1.80 (m, 1H), 1.68-1.65 (m, 1H), 1.28 (d, J=6.4 Hz, 3H); LCMS 1.80 min, 427 (M+H)

IRAK4 IC50 is 114 nM for Example 124.

The reaction was degassed and heated to reflux for 18 h. The reaction was cooled to rt, diluted with EtOAc and 10% KF was added. The mixture was stirred for 15 min. The layers were separated and the organics were washed with water and brine, dried (MgSO₄), filtered and concentrated. The residue was purified by column chromatography on silica gel, eluting with EtOAc/hexane to give the title compound as a yellow oil. LCMS 2.70 min, 488 (M+H).

Step 2: (R)-tert-butyl 3-((5-(benzo[d]thiazol-2-yl)-6-methoxy-2-(methylsulfonyl)pyrimidin-4-yl)amino) piperidine-1-carboxylate (Compound 28)

Compound 27 (417 mg, 0.855 mmol) was dissolved in DCM (20 mL) and cooled to 0° C. mCPBA (369 mg, 2.138 mmol) was added in one portion and the reaction stirred at room temperature for 1 h. The solution was washed with sat. NaHCO₃, dried (MgSO₄), filtered and concentrated to give the title compound as a yellow solid. Product was used without any further purification.

Step 3: Library Synthesis

A solution of Compound 28 (11 mg, 0.022 mmol) and triethylamine (19 µL) in 1.05 mL of anhydrous acetonitrile

SCHEME 9

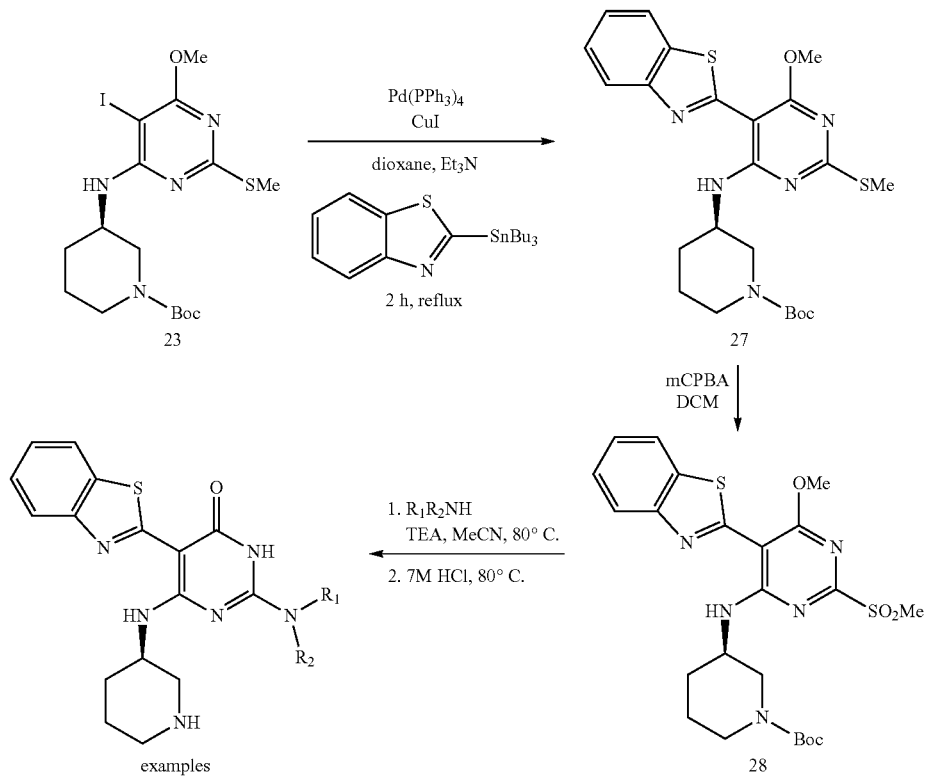

Step 1: (R)-tert-butyl 3-((5-(benzo[d]thiazol-2-yl)-6-methoxy-2-(methylthio)pyrimidin-4-yl)amino)piperidine-1-carboxylate (Compound 27)

2-Tributylstannylbenzothiazole (655 mg, 1.544 mmol), compound 23 (412 mg, 0.858 mmol), Pd(PPh₄)₄(198 mg, 0.172 mmol) and CuI (32.7 mg, 0.172 mmol) were dissolved in dioxane (18 mL) and TEA (359 µl, 2.57 mmol) was added.

was added into a vial containing the amine (3.5 eq.). The mixture was heated at 80° C. for 3 h. After cooling to rt, the solvent was removed in a GeneVac. To the residue was added 1 mL of 7 M HCl After the solution was heated at 80° C. for 24 h, the solvent was removed in a GeneVac. The resulting residue was dissolved in 1 mL of DMSO and purified by HPLC.

HPLC conditions: The mobile phase (H2O/Acetonitrile) contains 0.1% NH$_3$ and the gradients run from 5% to 100% acetonitrile, hold for 0.4 min, then go back to initial condition of 5% acetonitrile. Total run time is 2 min for each sample.

| Time (min) | Flow (ml/min) | H$_2$O % | Acetonitrile % |
|---|---|---|---|
| 0 | 1 | 95 | 5 |
| 1.4 | 1 | 0 | 100 |
| 1.8 | 1 | 0 | 100 |
| 2.0 | 1 | 95 | 5 |

The following compounds were prepared according to the procedure described above:

| Example | Structure | IRAK4 IC$_{50}$ (nM) | LCMS Mass Found (retention time, min) |
|---|---|---|---|
| 125 | 5-(benzo[d]thiazol-2-yl)-2-(3-(hydroxymethyl)morpholino)-6-((R)-piperidin-3-ylamino)pyrimidin-4(3H)-one | 864 | 442.18 (0.82) |
| 126 | 5-(benzo[d]thiazol-2-yl)-2-(2-methylmorpholino)-6-((R)-piperidin-3-ylamino)pyrimidin-4(3H)-one | 97 | 426.18 (0.96) |
| 127 | 5-(benzo[d]thiazol-2-yl)-2-((R)-3-methylmorpholino)-6-((R-piperidin-3-ylamino)pyrimidin-4(3H)-one | 1691 | 426.18 (0.97) |

| Example | Structure | IRAK4 IC$_{50}$ (nM) | LCMS Mass Found (retention time, min) |
|---|---|---|---|
| 128 | 5-(benzo[d]thiazol-2-yl)-2-((S)-3-methylmorpholino)-6-((R-piperidin-3-ylamino)pyrimidin-4(3H)-one | 431 | 426.18 (0.97) |
| 129 | 5-(benzo[d]thiazol-2-yl)-2-(2-(2-hydroxyethyl)morpholino)-6-((R)-piperidin-3-ylamino)pyrimidin-4(3H)-one | 57 | 456.19 (0.85) |
| 130 | 5-(benzo[d]thiazol-2-yl)-6-((R)-piperidin-3-ylamino)-2-(2-(trifluoromethyl)morpholino)pyrimidin-4(3H)-one | 201 | 480.16 (0.95) |

-continued

| Example | Structure | IRAK4 IC$_{50}$ (nM) | LCMS Mass Found (retention time, min) |
|---|---|---|---|
| 131 | (R)-5-(benzo[d]thiazol-2-yl)-2-(2,2-dimethylmorpholino)-6-(piperidin-3-ylamino)pyrimidin-4(3H)-one | 145 | 440.20 (1.00) |
| 132 | (R)-5-(benzo[d]thiazol-2-yl)-6-(piperidin-3-ylamino)-2-(4-(pyridin-2-yl)piperazin-1-yl)pyrimidin-4(3H)-one | 8 | 488.21 (1.04) |
| 133 | (R)-5-(benzo[d]thiazol-2-yl)-2-(4-(3-chloro-5-(trifluoromethyl)pyridin-2-yl)piperazin-1-yl)-6-(piperidin-3-ylamino)pyrimidin-4(3H)-one | 17 | 590.16 (1.31) |

| Example | Structure | IRAK4 IC$_{50}$ (nM) | LCMS Mass Found (retention time, min) |
|---|---|---|---|
| 134 | (R)-5-(benzo[d]thiazol-2-yl)-6-(piperidin-3-ylamino)-2-(4-(pyrazin-2-yl)piperazin-1-yl)pyrimidin-4(3H)-one | 8 | 489.21 (0.93) |
| 135 | (R)-5-(benzo[d]thiazol-2-yl)-6-(piperidin-3-ylamino)-2-(4-(5-(trifluoromethyl)pyridin-2-yl)piperazin-1-yl)pyrimidin-4(3H)-one | 11 | 556.20 (1.20) |
| 136 | (R)-5-(benzo[d]thiazol-2-yl)-6-(piperidin-3-ylamino)-2-(4-(pyrimidin-2-yl)piperazin-1-yl)pyrimidin-4(3H)-one | 10 | 489.21 (1.00) |

-continued

| Example | Structure | IRAK4 IC$_{50}$ (nM) | LCMS Mass Found (retention time, min) |
|---------|-----------|----------------------|---------------------------------------|
| 137 | (R)-5-(benzo[d]thiazol-2-yl)-2-(4-(6-chloropyridin-2-yl)piperazin-1-yl)-6-(piperidin-3-ylamino)pyrimidin-4(3H)-one | 25 | 522.17 (1.20) |
| 138 | (R)-5-(benzo[d]thiazol-2-yl)-6-(piperidin-3-ylamino)-2-(4-(pyridin-3-yl)piperazin-1-yl)pyrimidin-4(3H)-one | 6 | 488.21 (0.93) |
| 139 | (R)-5-(benzo[d]thiazol-2-yl)-2-(4-(4-methyl-1,2,5-oxadiazol-3-yl)piperazin-1-yl)-6-(piperidin-3-ylamino)pyrimidin-4(3H)-one | 15 | 493.20 (1.00) |

| Example | Structure | IRAK4 IC$_{50}$ (nM) | LCMS Mass Found (retention time, min) |
|---|---|---|---|
| 140 | (R)-5-(benzo[d]thiazol-2-yl)-6-(piperidin-3-ylamino)-2-(2-(trifluoromethyl)-5,6-dihydroimidazo[1,2-a]pyrazin-7(8H)-yl)pyrimidin-4(3H)-one | 113 | 516.17 (0.83) |
| 141 | (R)-5-(benzo[d]thiazol-2-yl)-2-(4-(5-methoxypyridin-2-yl)piperazin-1-yl)-6-(piperidin-3-ylamino)pyrimidin-4(3H)-one | 5 | 518.22 (1.06) |
| 142 | (R)-5-(benzo[d]thiazol-2-yl)-2-(4-(4-methoxypyridin-2-yl)piperazin-1-yl)-6-(piperidin-3-ylamino)pyrimidin-4(3H)-one | 6 | 518.22 (1.04) |

-continued

| Example | Structure | IRAK4 IC$_{50}$ (nM) | LCMS Mass Found (retention time, min) |
|---|---|---|---|
| 143 | (R)-5-(benzo[d]thiazol-2-yl)-2-(4-(6-methoxypyridin-2-yl)piperazin-1-yl)-6-(piperidin-3-ylamino)pyrimidin-4(3H)-one | 10 | 518.22 (1.18) |
| 144 | (R)-5-(benzo[d]thiazol-2-yl)-2-(4-(5-chloropyridin-2-yl)piperazin-1-yl)-6-(piperidin-3-ylamino)pyrimidin-4(3H)-one | 8 | 524.05 (1.09) |
| 145 | (R)-5-(benzo[d]thiazol-2-yl)-2-(4-(4-chloropyridin-2-yl)piperazin-1-yl)-6-(piperidin-3-ylamino)pyrimidin-4(3H)-one | 9 | 524.05 (1.09) |

| Example | Structure | IRAK4 IC$_{50}$ (nM) | LCMS Mass Found (retention time, min) |
|---|---|---|---|
| 146 | (R)-5-(benzo[d]thiazol-2-yl)-2-(4-(2-fluorophenyl)piperazin-1-yl)-6-(piperidin-3-ylamino)pyrimidin-4(3H)-one | 16 | 505.21 (1.23) |
| 147 | (R)-5-(benzo[d]thiazol-2-yl)-2-(4-(2-chloro-4-(methylsulfonyl)phenyl)piperazin-1-yl)-6-(piperidin-3-ylamino)pyrimidin-4(3H)-one | 11 | 599.15 (1.11) |
| 148 | (R)-5-(benzo[d]thiazol-2-yl)-6-(piperidin-3-ylamino)-2-(4-(2-(trifluoromethyl)phenyl)piperazin-1-yl)pyrimidin-4(3H)-one | 45 | 555.20 (1.35) |

| Example | Structure | IRAK4 IC$_{50}$ (nM) | LCMS Mass Found (retention time, min) |
|---|---|---|---|
| 149 | (R)-5-(benzo[d]thiazol-2-yl)-6-(piperidin-3-ylamino)-2-(4-(thiazol-2-yl)piperazin-1-yl)pyrimidin-4(3H)-one | 12 | 494.17 (1.03) |
| 150 | (R)-5-(benzo[d]thiazol-2-yl)-2-(4-(4-fluoro-2-(methylsulfonyl)phenyl)piperazin-1-yl)-6-(piperidin-3-ylamino)pyrimidin-4(3H)-one | 14 | 583.18 (1.12) |
| 151 | (R)-5-(benzo[d]thiazol-2-yl)-2-(4-(2-chlorophenyl)piperazin-1-yl)-6-(piperidin-3-ylamino)pyrimidin-4(3H)-one | 27 | 521.18 (1.31) |

| Example | Structure | IRAK4 IC$_{50}$ (nM) | LCMS Mass Found (retention time, min) |
|---|---|---|---|
| 152 | (R)-5-(benzo[d]thiazol-2-yl)-6-(piperidin-3-ylamino)-2-(4-(3-(trifluoromethyl)phenyl)piperazin-1-yl)pyrimidin-4(3H)-one | 42 | 555.20 (1.32) |
| 153 | (R)-5-(benzo[d]thiazol-2-yl)-2-(4-(3,4-dichlorophenyl)piperazin-1-yl)-6-(piperidin-3-ylamino)pyrimidin-4(3H)-one | 57 | 555.14 (1.37) |
| 154 | (R)-5-(benzo[d]thiazol-2-yl)-2-(4-(4-methoxyphenyl)piperazin-1-yl)-6-(piperidin-3-ylamino)pyrimidin-4(3H)-one | 10 | 517.23 (1.15) |

| Example | Structure | IRAK4 IC$_{50}$ (nM) | LCMS Mass Found (retention time, min) |
|---------|-----------|----------------------|----------------------------------------|
| 155 | (R)-2-(4-(benzo[d][1,3]dioxol-5-yl)piperazin-1-yl)-5-(benzo[d]thiazol-2-yl)-6-(piperidin-3-ylamino)pyrimidin-4(3H)-one | 11 | 531.21 (1.14) |
| 156 | (R)-5-(benzo[d]thiazol-2-yl)-2-(4-(2-(methylsulfonyl)phenyl)piperazin-1-yl)-6-(piperidin-3-ylamino)pyrimidin-4(3H)-one | 9 | 565.19 (1.08) |
| 157 | (R)-5-(benzo[d]thiazol-2-yl)-2-(4-(3-methylisothiazol-5-yl)piperazin-1-yl)-6-(piperidin-3-ylamino)pyrimidin-4(3H)-one | 8 | 508.18 (1.00) |

-continued

| Example | Structure | IRAK4 IC$_{50}$ (nM) | LCMS Mass Found (retention time, min) |
|---|---|---|---|
| 158 | (R)-5-(benzo[d]thiazol-2-yl)-2-(4-(3-methylpyridin-4-yl)piperazin-1-yl)-6-(piperidin-3-ylamino)pyrimidin-4(3H)-one | 8 | 502.23 (1.01) |
| 159 | (R)-5-(benzo[d]thiazol-2-yl)-2-(4-(1-methyl-1H-pyrazol-4-yl)piperazin-1-yl)-6-(piperidin-3-ylamino)pyrimidin-4(3H)-one | 20 | 491.22 (0.93) |
| 160 | (R)-5-(benzo[d]thiazol-2-yl)-2-(4-(3,6-dimethylpyrazin-2-yl)piperazin-1-yl)-6-(piperidin-3-ylamino)pyrimidin-4(3H)-one | 22 | 517.24 (1.13) |

-continued

| Example | Structure | IRAK4 IC$_{50}$ (nM) | LCMS Mass Found (retention time, min) |
|---|---|---|---|
| 161 | (R)-5-(benzo[d]thiazol-2-yl)-2-(4-(2,5-dimethoxyphenyl)piperazin-1-yl)-6-(piperidin-3-ylamino)pyrimidin-4(3H)-one | 14 | 547.24 (1.21) |
| 162 | (R)-5-(benzo[d]thiazol-2-yl)-2-(4-(5-cyclopropyl-1,3,4-oxadiazol-2-yl)piperazin-1-yl)-6-(piperidin-3-ylamino)pyrimidin-4(3H)-one | 27 | 519.22 (0.94) |
| 163 | (R)-2-(4-(1,3,4-thiadiazol-2-yl)piperazin-1-yl)-5-(benzo[d]thiazol-2-yl)-6-(piperidin-3-ylamino)pyrimidin-4(3H)-one | 20 | 495.16 (0.88) |

The following compounds were synthesized in similar manner to that shown in Scheme 9 except that 2-tributylstannyl-benzothiazole was replaced by 2-(tributylstannyl)quinoline in Step 1:

| Example | Structure | IRAK4 IC$_{50}$ (nM) | LCMS Mass Found (retention time, min) |
|---|---|---|---|
| 164 | 2-((R)-3-(dimethylamino)pyrrolidin-1-yl)-6-((R)-piperidin-3-ylamino)-5-(quinolin-2-yl)pyrimidin-4(3H)-one | 62 | 433.24 (1.00) |
| 165 | N-(1-(6-oxo-4-((R)-piperidin-3-ylamino)-5-(quinolin-2-yl)-1,6-dihydropyrimidin-2-yl)pyrrolidin-3-yl)acetamide | 54 | 447.23 (0.87) |
| 166 | 2-((S)-3-(dimethylamino)pyrrolidin-1-yl)-6-((R)-piperidin-3-ylamino)-5-(quinolin-2-yl)pyrimidin-4(3H)-one | 158 | 433.24 (1.00) |
| 167 | 2-(3-hydroxypyrrolidin-1-yl)-6-((R)-piperidin-3-ylamino)-5-(quinolin-2-yl)pyrimidin-4(3H)-one | 20 | 406.21 (0.89) |

-continued

| Example | Structure | IRAK4 IC$_{50}$ (nM) | LCMS Mass Found (retention time, min) |
|---|---|---|---|
| 168 | 2-(3-azabicyclo[3.1.0]hexan-3-yl)-6-((R)-piperidin-3-ylamino)-5-(quinolin-2-yl)pyrimidin-4(3H)-one | 34 | 402.22 (1.09) |
| 169 | (R)-2-(3-(methylsulfonyl)azetidin-1-yl)-6-(piperidin-3-ylamino)-5-(quinolin-2-yl)pyrimidin-4(3H)-one | 32 | 454.16 (0.86) |
| 170 | (R)-2-(3-hydroxy-3-(trifluoromethyl)azetidin-1-yl)-6-(piperidin-3-ylamino)-5-(quinolin-2-yl)pyrimidin-4(3H)-one | 18 | 460.18 (0.97) |
| 171 | (R)-2-(3-hydroxy-3-methylazetidin-1-yl)-6-(piperidin-3-ylamino)-5-(quinolin-2-yl)pyrimidin-4(3H)-one | 3147 | 406.21 (0.95) |

| Example | Structure | IRAK4 IC$_{50}$ (nM) | LCMS Mass Found (retention time, min) |
|---|---|---|---|
| 172 | (R)-2-(3-(2-hydroxypropan-2-yl)azetidin-1-yl)-6-(piperidin-3-ylamino)-5-(quinolin-2-yl)pyrimidin-4(3H)-one | 42 | 434.22 (0.95) |
| 173 | 2-((3S,4S)-3-hydroxy-4-methoxypyrrolidin-1-yl)-6-((R)-piperidin-3-ylamino)-5-(quinolin-2-yl)pyrimidin-4(3H)-one | 40 | 436.23 (0.90) |
| 174 | 2-(3,3-dioxido-3-thia-6-azabicyclo[3.2.1]octan-6-yl)-6-((R)-piperidin-3-ylamino)-5-(quinolin-2-yl)pyrimidin-4(3H)-one | 139 | 480.19 (0.87) |
| 175 | 2-((3S,4S)-3,4-difluoropyrrolidin-1-yl)-6-((R)-piperidin-3-ylamino)-5-(quinolin-2-yl)pyrimidin-4(3H)-one | 17 | 426.19 (1.01) |

| Example | Structure | IRAK4 IC$_{50}$ (nM) | LCMS Mass Found (retention time, min) |
|---|---|---|---|
| 176 | (R)-2-(3-methoxy-3-methylazetidin-1-yl)-6-(piperidin-3-ylamino)-5-(quinolin-2-yl)pyrimidin-4(3H)-one | 22 | 420.23 (1.01) |
| 177 | 2-((S)-3-fluoropyrrolidin-1-yl)-6-((R)-piperidin-3-ylamino)-5-(quinolin-2-yl)pyrimidin-4(3H)-one | 13 | 408.20 (1.01) |
| 178 | 2-((S)-3-methoxypyrrolidin-1-yl)-6-((R)-piperidin-3-ylamino)-5-(quinolin-2-yl)pyrimidin-4(3H)-one | 35 | 420.22 (1.00) |
| 179 | 2-((R)-3-(hydroxymethyl)pyrrolidin-1-yl)-6-((R)-piperidin-3-ylamino)-5-(quinolin-2-yl)pyrimidin-4(3H)-one | 13 | 420.22 (0.92) |

-continued

| Example | Structure | IRAK4 IC$_{50}$ (nM) | LCMS Mass Found (retention time, min) |
|---|---|---|---|
| 180 | 2-((S)-3-(hydroxymethyl)pyrrolidin-1-yl)-6-((R)-piperidin-3-ylamino)-5-(quinolin-2-yl)pyrimidin-4(3H)-one | 15 | 420.23 (0.92) |
| 181 | 2-(3-hydroxy-3-methylpyrrolidin-1-yl)-6-((R)-piperidin-3-ylamino)-5-(quinolin-2-yl)pyrimidin-4(3H)-one | 31 | 420.23 (0.93) |
| 182 | 6-((R)-piperidin-3-ylamino)-2-(2-(pyridin-4-yl)pyrrolidin-1-yl)-5-(quinolin-2-yl)pyrimidin-4(3H)-one | 3180 | 467.24 (0.90) |
| 183 | 2-((S)-2-(fluoromethyl)pyrrolidin-1-yl)-6-((R)-piperidin-3-ylamino)-5-(quinolin-2-yl)pyrimidin-4(3H)-one | 85 | 422.22 (1.07) |

| Example | Structure | IRAK4 IC$_{50}$ (nM) | LCMS Mass Found (retention time, min) |
|---|---|---|---|
| 184 | 2-(3-(2-hydroxypropan-2-yl)pyrrolidin-1-yl)-6-((R)-piperidin-3-ylamino)-5-(quinolin-2-yl)pyrimidin-4(3H)-one | 42 | 448.26 (1.01) |
| 185 | 2-(6-methyloctahydro-1H-pyrrolo[2,3-c]pyridin-1-yl)-6-((R)-piperidin-3-ylamino)-5-(quinolin-2-yl)pyrimidin-4(3H)-one | 851 | 459.27 (1.12) |
| 186 | 2-(3-methoxypyrrolidin-1-yl)-6-((R)-piperidin-3-ylamino)-5-(quinolin-2-yl)pyrimidin-4(3H)-one | 26 | 420.23 (1.00) |
| 187 | (R)-2-(4-phenylpiperidin-1-yl)-6-(piperidin-3-ylamino)-5-(quinolin-2-yl)pyrimidin-4(3H)-one | 16 | 480.26 (1.34) |

-continued

| Example | Structure | IRAK4 IC$_{50}$ (nM) | LCMS Mass Found (retention time, min) |
|---|---|---|---|
| 188 | (R)-6-(piperidin-3-ylamino)-5-(quinolin-2-yl)-2-(4-(o-tolyl)piperidin-1-yl)pyrimidin-4(3H)-one | 17 | 494.28 (1.41) |
| 189 | (R)-2-(4-(2-methoxyphenyl)piperidin-1-yl)-6-(piperidin-3-ylamino)-5-(quinolin-2-yl)pyrimidin-4(3H)-one | 13 | 510.27 (1.37) |
| 190 | (R)-6-(piperidin-3-ylamino)-5-(quinolin-2-yl)-2-(4-(2-(trifluoromethyl)phenyl)piperidin-1-yl)pyrimidin-4(3H)-one | 32 | 548.25 (1.43) |

| Example | Structure | IRAK4 IC$_{50}$ (nM) | LCMS Mass Found (retention time, min) |
|---------|-----------|----------------------|----------------------------------------|
| 191 | (R)-2-(4-(3-methyl-1,2,4-thiadiazol-5-yl)piperidin-1-yl)-6-(piperidin-3-ylamino)-5-(quinolin-2-yl)pyrimidin-4(3H)-one | 138 | 502.23 (1.08) |
| 192 | (R)-2-(4-(3-methyl-1H-pyrazol-5-yl)piperidin-1-yl)-6-(piperidin-3-ylamino)-5-(quinolin-2-yl)pyrimidin-4(3H)-one | 66 | 484.27 (1.03) |
| 193 | (R)-2-(4-(6-fluoropyridin-2-yl)piperidin-1-yl)-6-(piperidin-3-ylamino)-5-(quinolin-2-yl)pyrimidin-4(3H)-one | 45 | 499.25 (1.18) |

| Example | Structure | IRAK4 IC$_{50}$ (nM) | LCMS Mass Found (retention time, min) |
|---|---|---|---|
| 194 | 2-(2,5-diazabicyclo[2.2.1]heptan-2-yl)-6-((R)-piperidin-3-ylamino)-5-(quinolin-2-yl)pyrimidin-4(3H)-one | 169 | 417.23 (0.98) |
| 195 | 2-(5-(4-methoxyphenyl)-2,5-diazabicyclo[2.2.1]heptan-2-yl)-6-((R)-piperidin-3-ylamino)-5-(quinolin-2-yl)pyrimidin-4(3H)-one | 757 | 523.27 (1.18) |

SCHEME 10

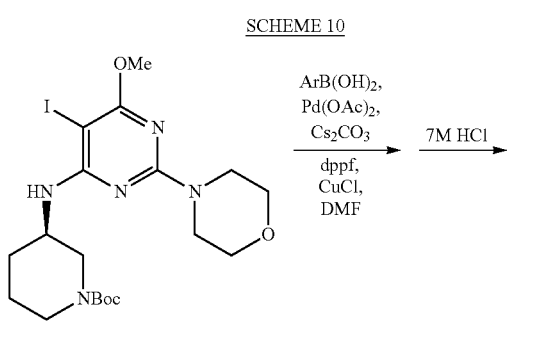

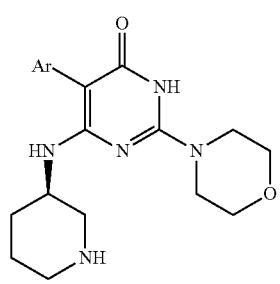

Library Synthesis

A solution of compound 21 (30 mg, 0.058 mmol) in DMF (1.5 mL) was added ArB(OH)$_2$ (0.07 mmol), Cs$_2$CO$_3$ (75 mg, 0.231 mmol), Pd(OAc)$_2$ (1.3 mg, 0.006 mmol), dppf (6.4 mg, 0.012 mmol) and CuCl (5.72 mg, 0.058 mmol) under a N$_2$ atmosphere and agitated for 16 h at 95° C. After the solvent was removed in a GeneVac, 2 mL of 7N HCl was added to the residue. The mixture was agitated for 2 hours at 65° C. The solvent was removed in a GeneVac and 1 mL DMSO was added to residue. The mixture was filtered and purified by HPLC to yield products.

HPLC conditions: The mobile phase (H2O/Acetonitrile) contains 0.1% NH$_3$ and the gradients run from 5% to 100% acetonitrile, hold for 0.4 min, then go back to initial condition of 5% acetonitrile. Total run time is 2 min for each sample.

| Time (min) | Flow (ml/min) | H$_2$O % | Acetonitrile % |
|---|---|---|---|
| 0 | 1 | 95 | 5 |
| 1.4 | 1 | 0 | 100 |
| 1.8 | 1 | 0 | 100 |
| 2.0 | 1 | 95 | 5 |

The following compounds were prepared according to the procedure described above:

| Example | Structure | IRAK4 IC$_{50}$ (nM) | LCMS Mass Found (retention time, min) |
|---|---|---|---|
| 196 | (R)-5-(benzo[d]oxazol-2-yl)-2-morpholino-6-(piperidin-3-ylamino)pyrimidin-4(3H)-one | 1802 | 397.30 (0.60) |
| 197 | (R)-5-(6-(tert-butyl)pyridin-2-yl)-2-morpholino-6-(piperidin-3-ylamino)pyrimidin-4(3H)-one | 537 | 412.26 (1.01) |
| 198 | (R)-5-(6-(1H-pyrrol-1-yl)pyrazin-2-yl)-2-morpholino-6-(piperidin-3-ylamino)pyrimidin-4(3H)-one | 3457 | 422.22 (0.80) |
| 199 | (R)-2-morpholino-6-(piperidin-3-ylamino)-5-(pyridin-2-yl)pyrimidin-4(3H)-one | 4759 | 356.20 (0.74) |
SCHEME 11
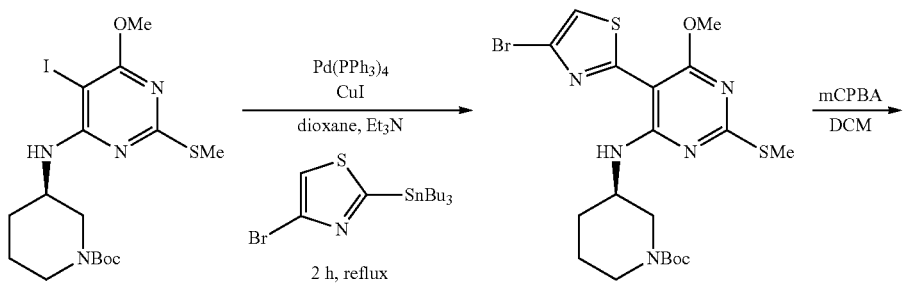

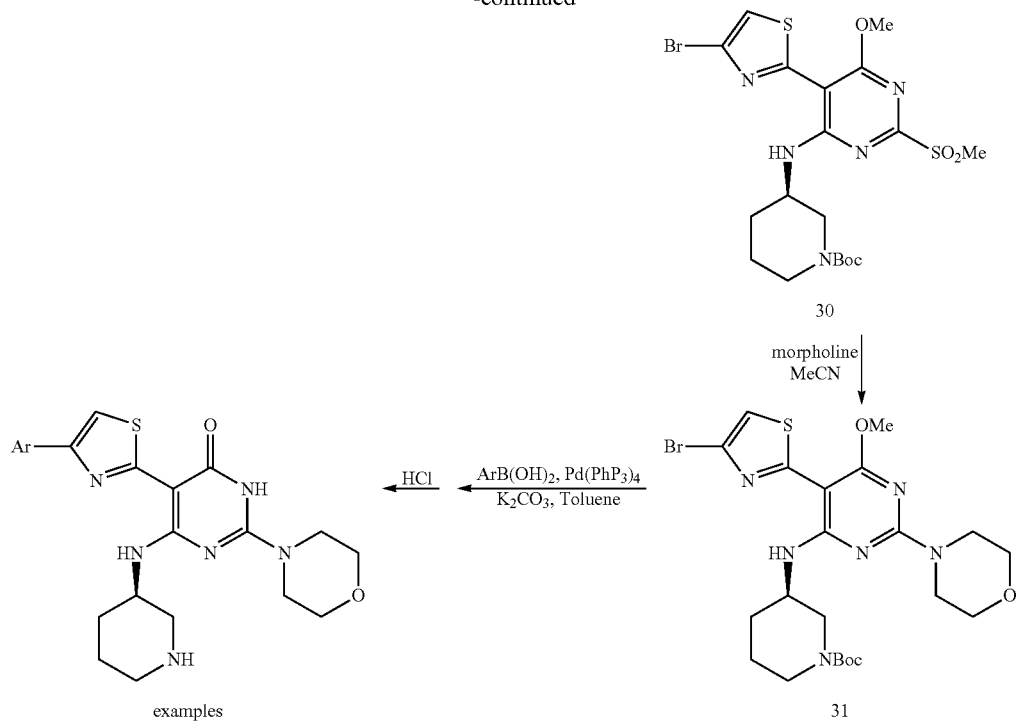

Step 1: (R)-tert-butyl 3-((5-(4-bromothiazol-2-yl)-6-methoxy-2-(methylthio)pyrimidin-4-yl)amino)piperidine-1-carboxylate (Compound 29)

4-Bromo-2-(tributylstannyl)thiazole (1.99 g, 4.38 mmol), compound 21 (1.17 g, 2.436 mmol), Pd(PPh₃)₄ (0.563 g, 0.487 mmol), and CuI (0.093 g, 0.487 mmol) were dissolved in dioxane (48.7 ml) and TEA (1.02 ml, 7.31 mmol) was added. The reaction was degassed and heated to 90° C. for 5 h to consume all SM. 10% KF was added and the mixture was stirred for 30 min. The mixture was diluted with EtOAc, and washed with water and brine, dried (MgSO₄), filtered and concentrated. The residue was purified by column chromatography on silica gel, eluting with EtOAc/hexane to give the title compound as a yellow solid. LCMS 2.84 min, 517 (M+H).

Step 2: (R)-tert-butyl 3-((5-(4-bromothiazol-2-yl)-6-methoxy-2-(methylsulfonyl)pyrimidin-4-yl)amino)piperidine-1-carboxylate (Compound 30)

Compound 29 (697 mg, 1.350 mmol) was dissolved in DCM (15 ml) and cooled to 0° C. mCPBA (582 mg, 3.37 mmol) was added and the reaction stirred at 0° C. for 1 h. A saturated aqueous solution of NaHCO₃ was added and the layers were separated. The organics were washed with a saturated aqueous solution of NaHCO₃, dried (MgSO₄), filtered and concentrated to give the title compound as a yellow foam. The product was used without any further purification.

Step 3: (R)-tert-butyl 3-((5-(4-bromothiazol-2-yl)-6-methoxy-2-morholinopyrimidin-4-yl)amino)piperidine-1-carboxylate (Compound 31)

Compound 31 (740 mg, 1.35 mmol) was dissolved in acetonitrile (20 ml) and morpholine (0.940 ml, 10.8 mmol) was added. The reaction was heated to 80° C. for 1 h. The solvent was evaporated and the residue was purified by column chromatography on silica gel, eluting with EtOAc/hexane to give the title compound as a white solid. LCMS 3.25 min, 556 (M+H).

Step 4: Library Synthesis

To a solution of compound 31 (30 mg, 0.04 mmol) in toluene (1.5 mL) was added ArB(OH)₂ (0.12 mmol), 1N K₂CO₃ (0.1 mL), Pd(PhP₃)₄ (9.15 mg, 0.008 mmol) under N₂ atmosphere and the solution was agitated for 16 hours at 105° C. The solvent was removed in a GeneVac. 2 mL of a 7N HCl solution was added to the residue and the mixture was agitated for 2 hours at 65° C. The solvent was removed in a GeneVac. To the residue was added 1 mL of DMSO, followed by filtration and HPLC purification to yield the products.

HPLC conditions: The mobile phase (H2O/Acetonitrile) contains 0.1% NH₃ and the gradients run from 5% to 100% acetonitrile, hold for 0.4 min, then go back to initial condition of 5% acetonitrile. Total run time is 2 min for each sample.

| Time (min) | Flow (ml/min) | H₂O % | Acetonitrile % |
|---|---|---|---|
| 0 | 1 | 95 | 5 |
| 1.4 | 1 | 0 | 100 |
| 1.8 | 1 | 0 | 100 |
| 2.0 | 1 | 95 | 5 |

The following compounds were prepared according to the procedure described above:

| Example | Structure | IRAK4 IC$_{50}$ (nM) | LCMS Mass Found (retention time, min) |
|---|---|---|---|
| 200 | (R)-2-morpholino-6-(piperidin-3-ylamino)-5-(4-(3-(trifluoromethyl)phenyl)thiazol-2-yl)pyrimidin-4(3H)-one | 141 | 506.17 (1.13) |
| 201 | (R)-5-(4-(2-fluorophenyl)thiazol-2-yl)-2-morpholino-6-(piperidin-3-ylamino)pyrimidin-4(3H)-one | 60 | 456.17 (1.02) |
| 202 | (R)-5-(4-(4-chlorophenyl)thiazol-2-yl)-2-morpholino-6-(piperidin-3-ylamino)pyrimidin-4(3H)-one | 153 | 472.14 (1.12) |

| Example | Structure | IRAK4 IC$_{50}$ (nM) | LCMS Mass Found (retention time, min) |
|---------|-----------|----------------------|---------------------------------------|
| 203 | (R)-5-(4-(3,5-difluorophenyl)thiazol-2-yl)-2-morpholino-6-(piperidin-3-ylamino)pyrimidin-4(3H)-one | 99 | 474.17 (1.10) |
| 204 | (R)-5-(4-(3-fluorophenyl)thiazol-2-yl)-2-morpholino-6-(piperidin-3-ylamino)pyrimidin-4(3H)-one | 40 | 456.17 (1.03) |
| 205 | (R)-5-(4-(2,5-difluorophenyl)thiazol-2-yl)-2-morpholino-6-(piperidin-3-ylamino)pyrimidin-4(3H)-one | 90 | 474.17 (1.09) |

-continued

| Example | Structure | IRAK4 IC$_{50}$ (nM) | LCMS Mass Found (retention time, min) |
|---|---|---|---|
| 206 | (R)-2-morpholino-6-(piperidin-3-ylamino)-5-(4-(5-(trifluoromethyl)pyridin-2-yl)thiazol-2-yl)pyrimidin-4(3H)-one | 2403 | 507.17 (1.00) |
| 207 | (R)-2-morpholino-6-(piperidin-3-ylamino)-5-(4-(pyridin-2-yl)thiazol-2-yl)pyrimidin-4(3H)-one | 21 | 439.18 (0.73) |

The following compounds were prepared according to the procedure described in Scheme 1.

| Example | Structure | Name | IC$_{50}$ (nM) | MS (m/z) | NMR |
|---|---|---|---|---|---|
| 208 | 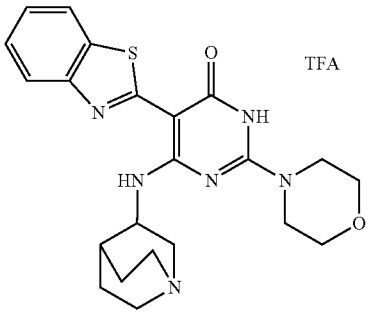 TFA | 5-(benzo[d]thiazol-2-yl)-2-morpholino-6-(quinolidin-3-ylamino)pyrimidin-4(3H)-one | 50 | 439 M + H | $^1$H NMR δ (ppm) (DMSO-d$_6$): 2.00-1.94 (3 H, m), 2.20 (1 H, br s), 2.34-2.32 (1 H, m), 3.67-3.65 (7 H, m), 3.79 (6 H, br t, J = 1.95 Hz), 4.44 (1 H, d, J = 7.45 Hz), 7.23-7.22 (1 H, m), 7.38-7.37 (1 H, m), 7.76 (1 H, d, J = 8.08 Hz), 7.93 (1 H, d, J = 7.85 Hz), 9.68 (1 H, s), 11.12 (1 H, s), 11.25 (1 H, d, J = 5.96 Hz). |

| Example | Structure | Name | IC$_{50}$ (nM) | MS (m/z) | NMR |
|---------|-----------|------|----------------|----------|-----|
| 209 | TFA | 5-(benzo[d]thiazol-2-yl)-6-(((3R,5S)-5-methylpyrrolidin-3-yl)amino)-2-morpholinopyrimidin-4(3H)-one | 359 | 413 M + H | $^1$H NMR δ (ppm) (DMSO-d$_6$): 1.36 (1 H, d, J = 6.55 Hz), 1.42 (4 H, d, J = 6.53 Hz), 2.57 (1 H, s), 2.67-2.66 (2 H, m), 3.68-3.64 (7 H, m), 4.74 (1 H, d, J = 2.00 Hz), 7.23 (2 H, t, J = 7.53 Hz), 7.39 (2 H, t, J = 7.64 Hz), 7.79 (1 H, d, J = 8.10 Hz), 7.92 (1 H, d, J = 7.85 Hz), 10.86 (1 H, d, J = 5.76 Hz), 11.14 (1 H, s). |
| 210 | TFA | 5-(benzo[d]thiazol-2-yl)-6-(((3R,5R)-5-methylpyrrolidin-3-yl)amino)-2-morpholinopyrimidin-4(3H)-one | 150 | 413 M + H | $^1$H NMR δ (ppm) (DMSO-d$_6$): 1.36 (3 H, d, J = 6.56 Hz), 2.06 (1 H, dt, J = 13.78, 8.26 Hz), 2.28 (1 H, ddd, J = 13.58, 6.84, 3.90 Hz), 2.46-2.45 (4 H, m), 3.68-3.66 (5 H, m), 3.88 (1 H, br s), 4.77 (1 H, t, J = 6.11 Hz), 7.23-7.22 (1 H, m), 7.38-7.37 (1 H, m), 7.84 (1 H, d, J = 8.08 Hz), 7.92 (1 H, d, J = 7.84 Hz), 8.69 (1 H, s), 9.17 (1 H, br s), 10.93 (1 H, d, J = 5.82 Hz), 11.14 (1 H, s) |
| 211 | TFA | 6-((1S,4R,6R)-2-azabicyclo[2.2.1]heptan-6-ylamino)-5-(benzo[d]thiazol-2-yl)-2-morpholinopyrimidin-4(3H)-one | 191 | 425 M + H | $^1$H NMR δ (ppm) (DMSO-d$_6$): 1.44 (1 H, d, J = 13.28 Hz), 1.72 (1 H, d, J = 11.16 Hz), 1.95 (1 H, d, J = 11.13 Hz), 2.40 (1 H, s), 2.67 (1 H, s), 3.06 (1 H, s), 3.17 (1 H, s), 3.68-3.65 (7 H, m), 4.25 (1 H, s), 4.37 (1 H, d, J = 4.62 Hz), 4.39 (1 H, s), 7.24 (1 H, t, J = 7.50 Hz), 7.38-7.37 (1 H, m), 7.87 (1 H, d, J = 8.08 Hz), 7.93 (1 H, d, J = 7.83 Hz), 9.07 (1 H, s), 10.89 (1 H, d, J = 4.25 Hz), 11.16 (1 H, s). |
| 212 | TFA | (R)-5-(benzo[d]thiazol-2-yl)-6-((5,5-difluoropiperidin-3-yl)amino)-2-morpholinopyrimidin-4(3H)-one | 792 | 449 M + H | $^1$H NMR δ (ppm) (DMSO-d$_6$): 3.47 (1 H, s), 3.58 (2 H, s), 3.68 (13 H, m), 7.24 (1 H, t, J = 7.48 Hz), 7.39 (1 H,d, J = 7.58 Hz), 7.75 (1 H, d, J = 8.10 Hz), 7.93 (1 H, d, J = 7.80 Hz), 10.95 (1 H, d, J = 6.91 Hz), 11.18 (1 H, s). |

| Example | Structure | Name | IC$_{50}$ (nM) | MS (m/z) | NMR |
|---|---|---|---|---|---|
| 213 | 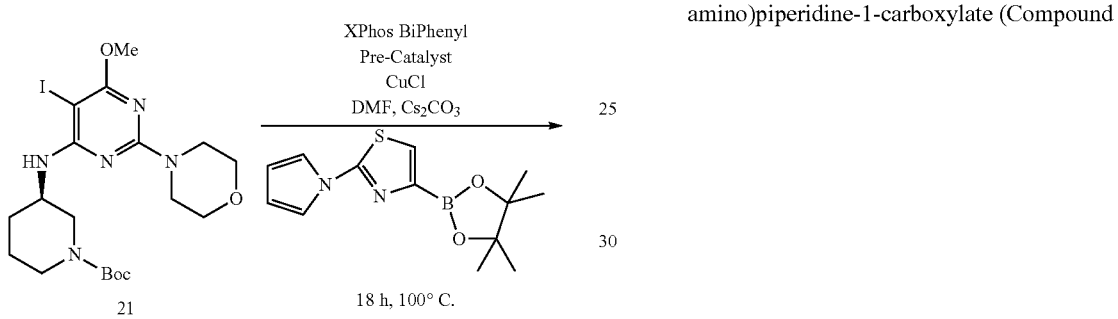 TFA | 5-(benzo[d]thiazol-2-yl)-6-(((3S,4S)-4-fluoropiperidin-3-yl)amino)-2-morpholinopyrimidin-4(3H)-one | 14 | 431 M + H | $^1$H NMR δ (ppm) (DMSO-d$_6$): 2.37 (1 H, s), 3.06-3.02 (2 H, m), 3.43 (1 H, s), 3.53 (1 H, s), 3.54 (1 H, s), 3.66 (5 H, d, J = 4.85 Hz), 3.71 (5 H, s), 4.62 (1 H, s), 6.54 (1 H, s), 7.24 (1 H, t, J = 7.52 Hz), 7.40 (1 H, t, J = 7.70 Hz), 7.79 (1 H, d, J = 8.09 Hz), 7.94 (1 H, d, J = 7.85 Hz), 10.96 (1 H, d, J = 7.22 Hz). |

Scheme 12

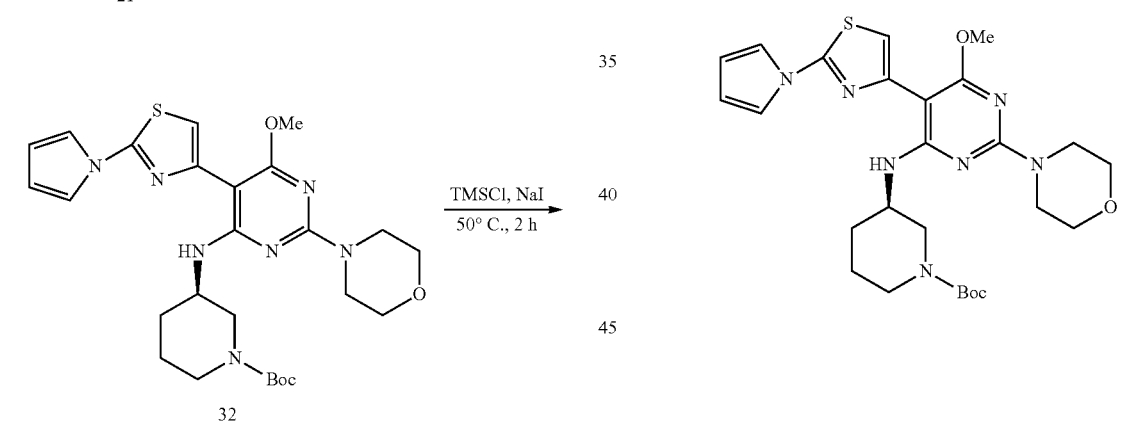

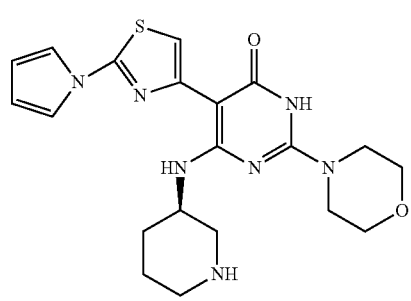

Example 214

Step 1: (R)-tert-butyl 3-((5-(2-(1H-pyrrol-1-yl)thiazol-4-yl)-6-methoxy-2-morpholinopyrimidin-4-yl)amino)piperidine-1-carboxylate (Compound 32)

In a 40 mL vial chloro(2-dicyclohexylphosphino-2',4',6'-triisopropyl-1,1'-biphenyl)[2-(2-aminoethyl)phenyl)]-palladium(II) (0.023 g, 0.029 mmol), tert-butyl 3-((5-iodo-6-methoxy-2-morpholinopyrimidin-4-yl)amino)piperidine-1-carboxylate (Compound (21) (0.15 g, 0.289 mmol), 2-(1H-pyrrol-1-yl)-4-(4,4,5,5-tetramethyl-1,3,2-dioxaborolan-2-yl)thiazole (0.088 g, 0.318 mmol) and CuCl (0.031 g, 0.318 mmol) were combined. This mixture was then evacuated and backfilled with argon. Then DMF (2.89 ml) and Cs$_2$CO$_3$ (0.376 g, 1.16 mmol) were added to this flask all under argon. This mixture was then heated at 100° C. for 18 h. The mixture was cooled, filtered, diluted with ethyl acetate (mL), washed with water, then dried (Na$_2$SO$_4$), filtered and the solvent was evaporated under reduced pressure. The residue was purified via column chromatography. (0-50% EtOAc/hexane) to give the title compound as a white solid. MS (m/z)=542 (M+H).

Step 2: (R)-5-(2-(1H-pyrrol-1-yl)thiazol-4-yl)-2-morpholino-6-(piperidin-3-ylamino)pyrimidin-4(3H)-one (Example 214)

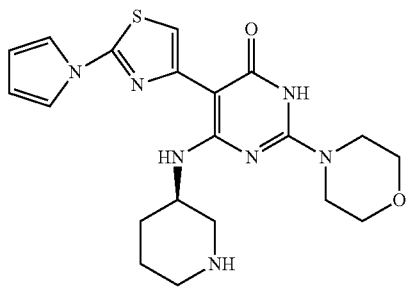 [SMILES: O=c1[nH]c(N2CCOCC2)nc(N[C@@H]2CCCNC2)c1-c1csc(-n2cccc2)n1]

To (R)-tert-butyl 3-((5-(2-(1H-pyrrol-1-yl)thiazol-4-yl)-6-methoxy-2-morpholinopyrimidin-4-yl)amino)piperidine-1-carboxylate (xx) (0.08 g, 0.148 mmol) in MeCN (2.95 ml) was added NaI (0.033 g, 0.222 mmol) followed by TMS-Cl (0.028 ml, 0.222 mmol) under argon. The reaction was stirred at room temperature for 15 min., then heated to 50° C. for 2 h until the reaction was complete, monitored by LCMS. The solvent was removed and the reaction material was purified by preparative HPLC to give the title compound. MS (m/z) =428 (M+H). IRAK4 IC50=12 nM The following compounds were prepared according to Scheme 12:

| Exple | Structure | Name | IC$_{50}$ (nM) | MS (m/z) | NMR |
|---|---|---|---|---|---|
| 215 | 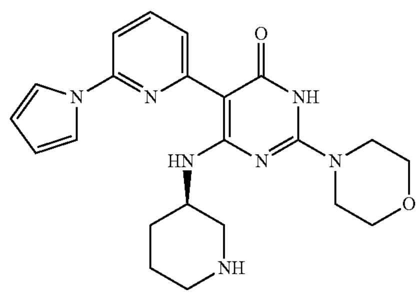 [SMILES: O=c1[nH]c(N2CCOCC2)nc(N[C@@H]2CCCNC2)c1-c1cccc(-n2cccc2)n1] | (R)-5-(6-(1H-pyrrol-1-yl)pyridin-2-yl)-2-morpholino-6-(piperidin-3-ylamino)pyrimidin-4(3H)-one | 185 | 422 M + H | 500 MHz (DMSO-d6) 10.70 (br s, 1 H); 10.20 (br s, 1 H); 9.18 (br s, 1 H); 8.74 (s, 1 H); 8.53 (s, 1 H); 7.77 (t, J = 8.1 Hz, 1 H); 7.51 (t, J = 2.2 Hz, 2 H); 7.27 (d, J = 7.9 Hz, 1 H); 6.30 (t, J = 2.2 Hz, 2 H); 4.30 (br s, 1 H); 3.64-3.66 (m, 8 H); 3.45 (d, J = 11.4 Hz, 1 H); 3.17 (s, 1 H); 2.77-2.81 (m, 1 H); 2.69-2.71 (m, 1 H); 2.08 (m, 1 H); 1.84 (m, 1 H); 1.73 (m, 1 H); 1.56-1.58 (m, 1 H) |
| 216 | 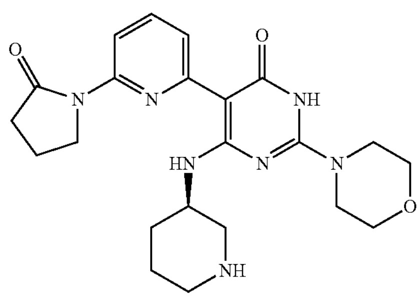 [SMILES: O=C1CCCN1c1cccc(-c2c(N[C@@H]3CCCNC3)nc(N3CCOCC3)[nH]c2=O)n1] | (R)-2-morpholino-5-(6-(2-oxopyrrolidin-1-yl)pyridin-2-yl)-6-(piperidin-3-ylamino)pyrimidin-4(3H)-one | 258 | 440 M + H | 500 MHz (DMSO-d6) 10.65 (br s, 1 H); 9.98 (br s, 1 H); 9.33 (d, J = 12.0 Hz, 1 H); 8.92 (d, J = 10.9 Hz, 1 H); 8.38 (s, 1 H); 7.64-7.65 (m, 2 H); 4.68 (br, s 1 H); 4.41 (br s, 1 H); 3.93-3.94 (m, 2 H); 3.63 (m, 8 H); 3.38 (d, J = 12 Hz, 1 H); 3.20 (d, J = 12.3 Hz, 1 H); 2.71 (dd, J = 22.0, 11.2 Hz, 2 H); 2.55 (t, J = 8.0 Hz, 2 H); 2.06 (m, 2 H); 1.96 (m, 1 H); 1.85 (m, 1 H); 1.76 (m 1 H); 1.60 (m, 1 H) |
| 217 | 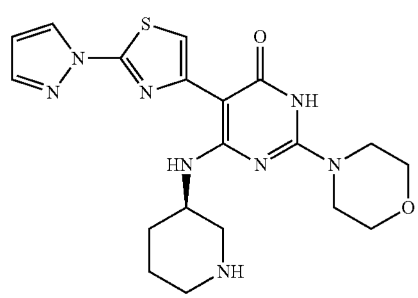 [SMILES: O=c1[nH]c(N2CCOCC2)nc(N[C@@H]2CCCNC2)c1-c1csc(-n2cccn2)n1] | (R)-5-(2-(1H-pyrazol-1-yl)thiazol-4-yl)-2-morpholino-6-(piperidin-3-ylamino)pyrimidin-4(3H)-one | 82 | 429 M + H | 500 MHz (DMSO-d6) 10.77 (br s, 1 H); 8.95 (br s, 1 H); 8.41 (s, 1 H); 8.08 (br s, 1 H); 7.86 (d, J = 1.6 Hz, 1 H); 6.67 (t, J = 2.1 Hz, 1 H); 4.22 (m, 1 H); 3.53-3.61 (m, 10 H); 3.19-3.21 (m, 1 H); 2.86 (br m, 2 H); 2.05 (m, 1 H); 1.90 (m, 1 H); 1.73 (m, 2 H) |

-continued
| Exple | Structure | Name | IC$_{50}$ (nM) | MS (m/z) | NMR |
|---|---|---|---|---|---|
| 218 | 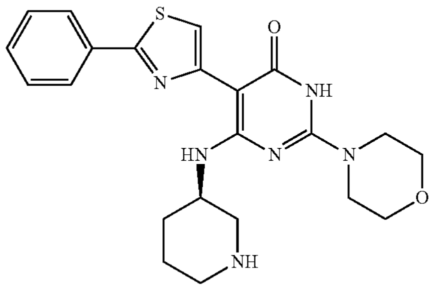 [SMILES: O=c1[nH]c(N2CCOCC2)nc(N[C@@H]2CCCNC2)c1-c1csc(-c2ccccc2)n1] | (R)-2-morpholino-5-(2-phenylthiazol-4-yl)-6-(piperidin-3-ylamino)pyrimidin-4(3H)-one | 7 | 439 M + H | 500 MHz (DMSO-d6) 10.75 (s, 1 H); 9.70 (br s, 1 H); 9.24 (br s, 1 H); 8.81 (br s, 1H); 8.36 (s, 1 H); 7.89 (d, J = 7.6 Hz, 2 H); 7.48-7.49 (m, 3 H); 4.28 (m, 1 H); 3.64 (s, 8 H); 3.40 (br s, 1 H); 3.19 (m, 1 H); 2.88-2.92 (m, 1 H); 2.80 (q, J = 10.5 Hz, 1 H); 2.11 (m, 1 H); 1.93 (m, 1 H); 1.74-1.80 (m, 2 H) |
| 219 | 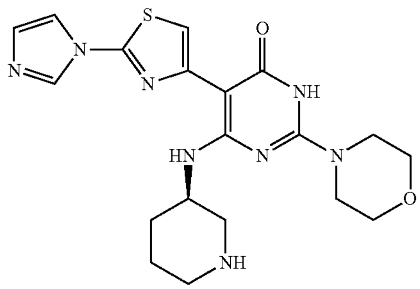 [SMILES: O=c1[nH]c(N2CCOCC2)nc(N[C@@H]2CCCNC2)c1-c1csc(-n2ccnc2)n1] | (R)-5-(2-(1H-imidazol-1-yl)thiazol-4-yl)-2-morpholino-6-(piperidin-3-ylamino)pyrimidin-4(3H)-one | 4 | 429 M + H | 500 MHz (DMSO-d6) 10.79 (br s, 1 H); 9.31 (br s, 1 H); 8.77 (br s, 1 H); 8.21 (s, 1 H); 8.02 (br s, 1 H); 7.40 (br s, 1 H); 4.24 (br, s, 1 H); 3.63 (m, 8 H); 3.39 (m, 1 H); 3.18 (m, 1 H); 2.84 (m, 2 H); 2.02 (m, 2 H); 1.87 (m, 1 H); 1.71 (s, 1 H); 1.62-1.68 (m, 2 H) |
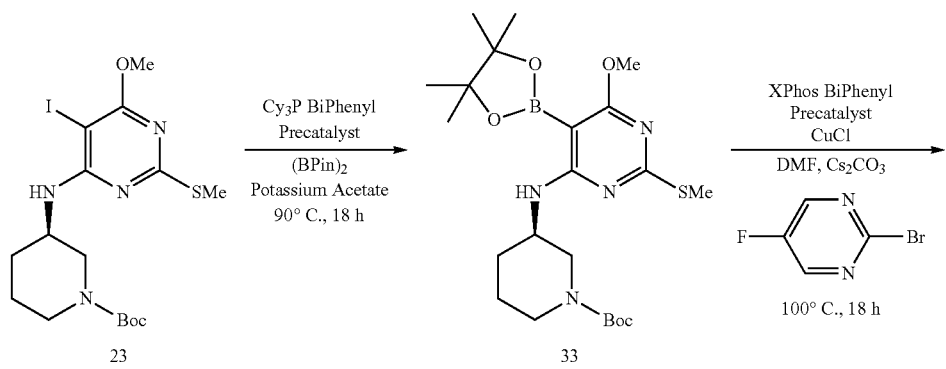
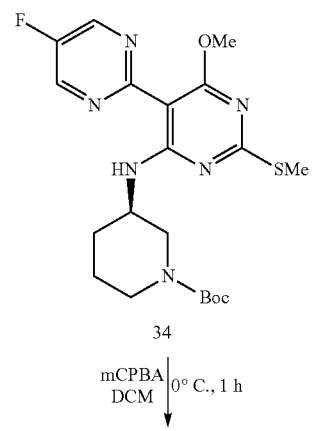

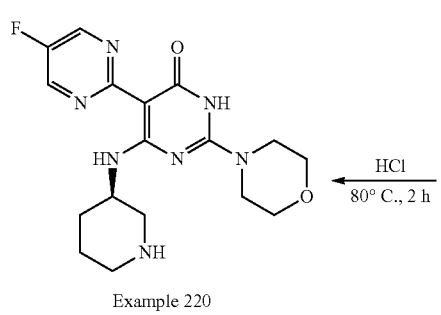

Example 220

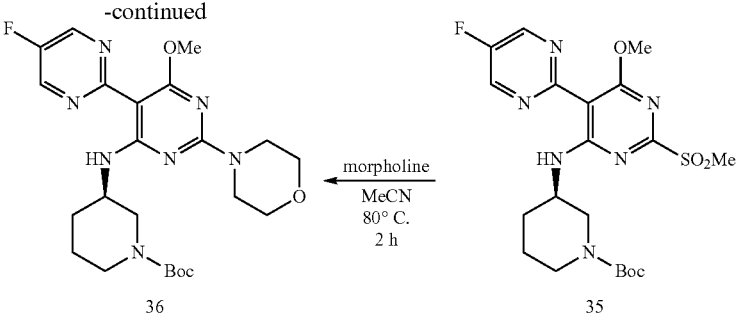

36    35

Step 1: (R)-tert-butyl 3-((6-methoxy-2-(methylthio)-5-(4,4,5,5-tetramethyl-1,3,2-dioxaborolan-2-yl)pyrimidin-4-yl)amino)piperidine-1-carboxylate (Compound 33)

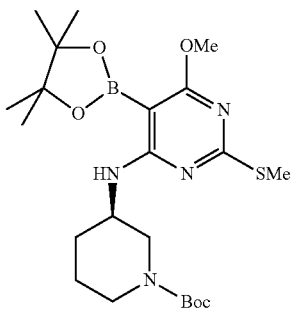 [SMILES: COc1nc(SC)nc(N[C@@H]2CCCN(C(=O)OC(C)(C)C)C2)c1B1OC(C)(C)C(C)(C)O1]

To tert-butyl 3-((5-iodo-6-methoxy-2-(methylthio)pyrimidin-4-yl)amino)piperidine-1-carboxylate (23) (6.9 g, 14.4 mmol), 4,4,4',4',5,5,5',5'-octamethyl-2,2'-bi(1,3,2-dioxaborolane) (7.30 g, 28.7 mmol), chloro(2-dicyclohexylphosphino-2',4',6'-triisopropyl-1,1'-biphenyl)[2-(2-aminoethyl)phenyl)]palladium(II) (0.848 g, 1.44 mmol), and KOAc (4.23 g, 43.1 mmol) in a sealed flask purged with argon was added anhydrous DMA (70 mL). The reaction was heated to 90° C. for 18 h. The reaction was cooled to room temperature and water was added. The mixture was extracted with EtOAc. The organic layer was washed with water and brine. The combined organic layers were filtered through celite then dried, filtered and the solvent was reduced to dryness. The material was purified by column chromatography on silica gel (0-25% EtOAc in Hexanes) to afford the desired product as a white solid. MS (m/z)=481 (M+H).

Step 2: (R)-tert-butyl 3-((5-fluoro-6'-methoxy-2'-(methylthio)-[2,5'-bipyrimidin]-4'-yl)amino)piperidine-1-carboxylate (Compound 34)

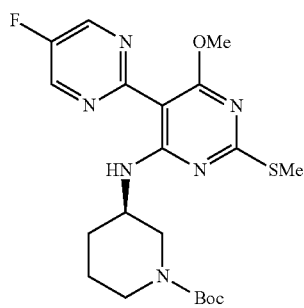 [SMILES: COc1nc(SC)nc(N[C@@H]2CCCN(C(=O)OC(C)(C)C)C2)c1-c1ncc(F)cn1]

In a 40 mL vial, chloro(2-dicyclohexylphosphino-2',4',6'-triisopropyl-1,1'-biphenyl)[2-(2-aminoethyl)phenyl)]palladium(II) (0.025 g, 0.031 mmol), tert-butyl 3-((6-methoxy-2-(methylthio)-5-(4,4,5,5-tetramethyl-1,3,2-dioxaborolan-2-yl)pyrimidin-4-yl)amino)piperidine-1-carboxylate (0.15 g, 0.312 mmol), 2-bromo-5-fluoropyrimidine (0.083 g, 0.468 mmol) and CuCl (0.031 g, 0.312 mmol) were combined, then purged with argon. Then degassed DMF (3 mL) followed by Cs₂CO₃ (0.407 g, 1.249 mmol) were added to the vial. The reaction was then heated at 100° C. for 18 h. The mixture was cooled, diluted with ethyl acetate, washed with water, dried (Na₂SO₄), filtered and the solvent was evaporated under reduced pressure. The material was purified by column chromatography on silica gel (0-100% EtOAc in hexanes) to afford the desired product. MS (m/z)=451 (M+H).

Step 3: (R)-tert-butyl 3-((5-fluoro-6'-methoxy-2'-(methylsulfonyl)-[2,5'-bipyrimidin]-4'-yl)amino)piperidine-1-carboxylate (Compound 35)

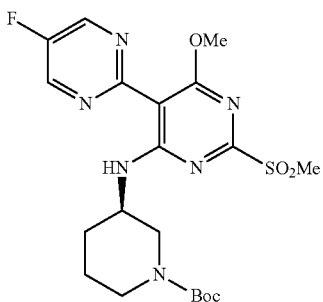 [SMILES: COc1nc(S(C)(=O)=O)nc(N[C@@H]2CCCN(C(=O)OC(C)(C)C)C2)c1-c1ncc(F)cn1]

(S)-tert-butyl 3-((5-fluoro-6'-methoxy-2'-(methylthio)-[2,5'-bipyrimidin]-4'-yl)amino)piperidine-1-carboxylate (0.08 g, 0.178 mmol) in DCM (2 mL) was cooled to 0° C. then mCPBA (0.092 g, 0.533 mmol) was added and the ice bath was removed. The reaction was stirred at room temperature for 90 min. The reaction was quenched with saturated aqueous sodium bicarbonate and let stir for 10 min. The mixture was extracted with DCM (2×), dried with sodium sulfate, concentrated and the yellow solid was taken to the next step without further purification. MS (m/z)=483 (M+H).

Step 4: (R)-tert-butyl 3-((5-fluoro-6'-methoxy-2'-morpholino-[2,5'-bipyrimidin]-4'-yl)amino)piperidine-1-carboxylate (Compound 36)

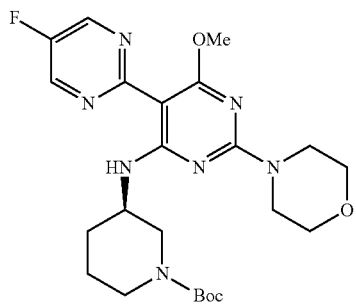 [SMILES: COc1nc(N2CCOCC2)nc(N[C@@H]2CCCN(C(=O)OC(C)(C)C)C2)c1-c1ncc(F)cn1]

To (S)-tert-butyl 3-((5-fluoro-6'-methoxy-2'-(methylsulfonyl)-[2,5'-bipyrimidin]-4'-yl)amino)piperidine-1-carboxylate (0.05 g, 0.104 mmol) in MeCN (3.5 mL) was added morpholine (0.027 ml, 0.311 mmol) in a pressure tube. The reaction was heated to 100° C. for 18 h. Upon completion of the reaction, the solvent was removed and reaction was purified via column chromatography (0-50% EtOAc/Hex) to afford the desired product as a white solid. MS (m/z)=490 (M+H).

Step 5: (R)-5-fluoro-2'-morpholino-6'-(piperidin-3-ylamino)-[2,5'-bipyrimidin]-4'(3'H)-one (Example 220)

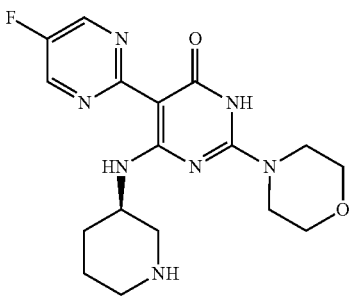 [SMILES: O=c1[nH]c(N2CCOCC2)nc(N[C@@H]2CCCNC2)c1-c1ncc(F)cn1]

To (R)-tert-butyl 3-((5-fluoro-6'-methoxy-2'-morpholino-[2,5'-bipyrimidin]-4'-yl)amino)piperidine-1-carboxylate (0.025 g, 0.051 mmol) in MeCN (1 mL) was added NaI (0.011 g, 0.077 mmol) followed by TMS-Cl (9.79 µl, 0.077 mmol). The reaction was stirred at room temperature for 15 min. then heated to 50° C. for 3 h. The solvent was removed in vacuo and the residue was purified via semi-preparative HPLC to afford the desired product as a white solid. MS (m/z)=376 (M+H). IRAK4 $IC_{50}$=220 nM The following compounds were prepared according to Scheme 13:

| Exple | Structure | Name | IC₅₀ (nM) | MS (m/z) | NMR |
|---|---|---|---|---|---|
| 221 | 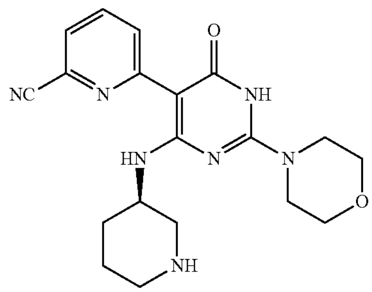 [SMILES: N#Cc1cccc(-c2c(N[C@@H]3CCCNC3)nc(N3CCOCC3)[nH]c2=O)n1] | (R)-6-(2-morpholino-6-oxo-4-(piperidin-3-ylamino)-1,6-dihydropyrimidin-5-yl)picolinonitrile | 167 | 382 M + H | 500 MHz (DMSO-d6) 10.77 (br s, 1 H); 10.47 (s, 1 H); 9.08 (br s, 1 H); 7.86 (s, 1 H); 7.62 (d, J = 7.4 Hz, 1 H); 4.27 (m, 1 H); 3.62-3.65 (m, 8 H); 3.39 (d, J = 12.0 Hz, 1 H); 3.15 (d, J = 12.4 Hz, 1 H); 2.92 (t, J = 11.5 Hz, 1 H); 2.83 (t, J = 10.5 Hz, 1 H); 2.03 (br s, 1 H); 1.91-1.96 (m, 1 H); 1.74-1.79 (m, 1 H); 1.63 (m, 1 H) |
| 222 | 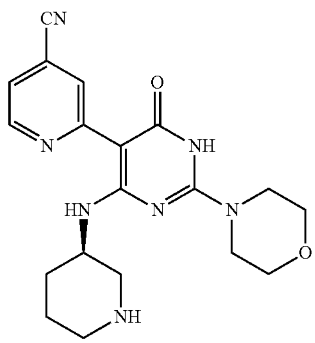 [SMILES: N#Cc1ccnc(-c2c(N[C@@H]3CCCNC3)nc(N3CCOCC3)[nH]c2=O)c1] | (R)-2-(2-morpholino-6-oxo-4-(piperidin-3-ylamino)-1,6-dihydropyrimidin-5-yl)isonicotinonitrile | 5621 | 382 M + H | 500 MHz (DMSO-d6) 10.96 (s, 1 H); 10.78 (s, 1 H); 8.73 (br s, 1 H); 8.57-8.58 (br s, 1 H); 7.37 (d, J = 5.2 Hz, 1 H); 4.33 (br s, 2 H); 3.64 (m, 8 H); 3.39 (s, 1 H); 3.17 (s, 1 H); 2.77-2.80 (m, 2 H); 1.97 (s, 1 H); 1.86 (d, J = 14.0 Hz, 1 H); 1.74 (s, 1 H); 1.64 (d, J = 12.0 Hz, 1 H) |
| 223 | 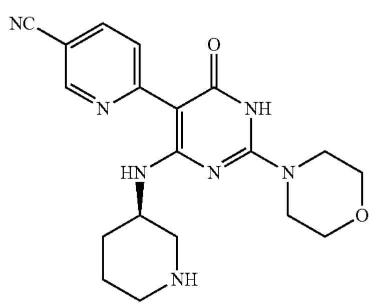 [SMILES: N#Cc1ccc(-c2c(N[C@@H]3CCCNC3)nc(N3CCOCC3)[nH]c2=O)nc1] | (R)-6-(2-morpholino-6-oxo-4-(piperidin-3-ylamino)-1,6-dihydropyrimidin-5-yl)nicotinonitrile | 81 | 382 M + H | 500 MHz (DMSO-d6) 11.09 (br s, 1 H); 10.79 (br s, 1 H); 8.96 (d, J = 9.0 Hz, 1 H); 8.77 (s, 1 H); 8.02 (d, J = 9.0 Hz, 1 H); 4.30 (s, 1 H); 3.63-3.66 (m, 9 H); 3.20 (s, 1 H); 2.82 (m, 2 H); 1.99 (s, 1 H); 1.87 (s, 1 H); 1.74 (s, 1 H); 1.65 (s, 1 H) |
| 224 | 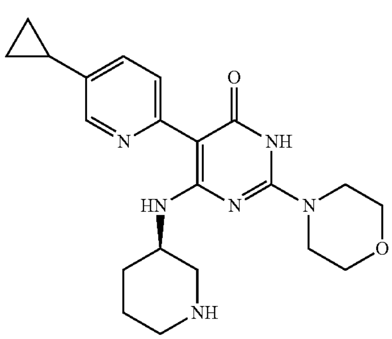 [SMILES: O=c1[nH]c(N2CCOCC2)nc(N[C@@H]2CCCNC2)c1-c1ccc(C2CC2)cn1] | (R)-5-(5-cyclopropylpyridin-2-yl)-2-morpholino-6-(piperidin-3-ylamino)pyrimidin-4(3H)-one | 512 | 397 M + H | 500 MHz (DMSO-d6) 10.89-10.90 (br s, 1 H); 9.10 (br s, 1 H); 8.82 (br s, 1 H); 8.35 (s, 1 H); 8.19-8.19 (br s, 1 H); 7.69-7.69 (br s, 1 H); 4.28 (br s, 1 H); 3.64 (m, 9 H); 3.32 (d, J = 11.8 Hz, 1 H); 3.16 (d, J = 12.1 Hz, 1 H); 2.74-2.78 (m, 2 H); 1.99-2.05 (m, 1 H); 1.91 (m, 1 H); 1.83 (m, 1 H); 1.69-1.73 (m, 1 H); 1.55 (m, 1 H); 1.02 (m, 2 H); 7.75 (m, 2 H) |

-continued
| Exple | Structure | Name | IC$_{50}$ (nM) | MS (m/z) | NMR |
|---|---|---|---|---|---|
| 225 | 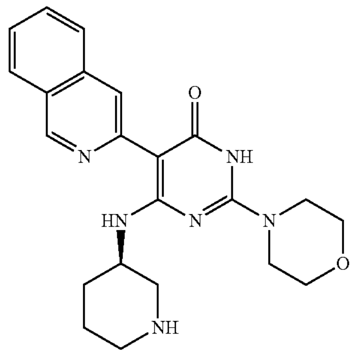 [SMILES: O=c1[nH]c(N2CCOCC2)nc(N[C@@H]2CCCNC2)c1-c1cc2ccccc2cn1] | (R)-5-(isoquinolin-3-yl)-2-morpholino-6-(piperidin-3-ylamino)pyrimidin-4(3H)-one | 466 | 407 M + H | 500 MHz (DMSO-d6) 10.84 (br s, 1 H); 9.47 (br s, 1 H); 9.12 (br, s, 1 H); 8.87 (br s, 1 H); 8.74 (br s, 1 H); 8.22 (br s, 1 H); 8.01 (br s, 1 H); 7.87 (br s, 1 H); 7.69 (br s, 1 H); 4.30 (m, 1 H); 3.65 (m, 8 H); 3.33 (m, 1 H); 3.14 (m, 1 H); 2.78 (m, 2 H); 1.93 (br s, 1 H); 1.83 (br s, 1 H); 1.72 (m, 1 H); 1.56 (m, 1 H) |
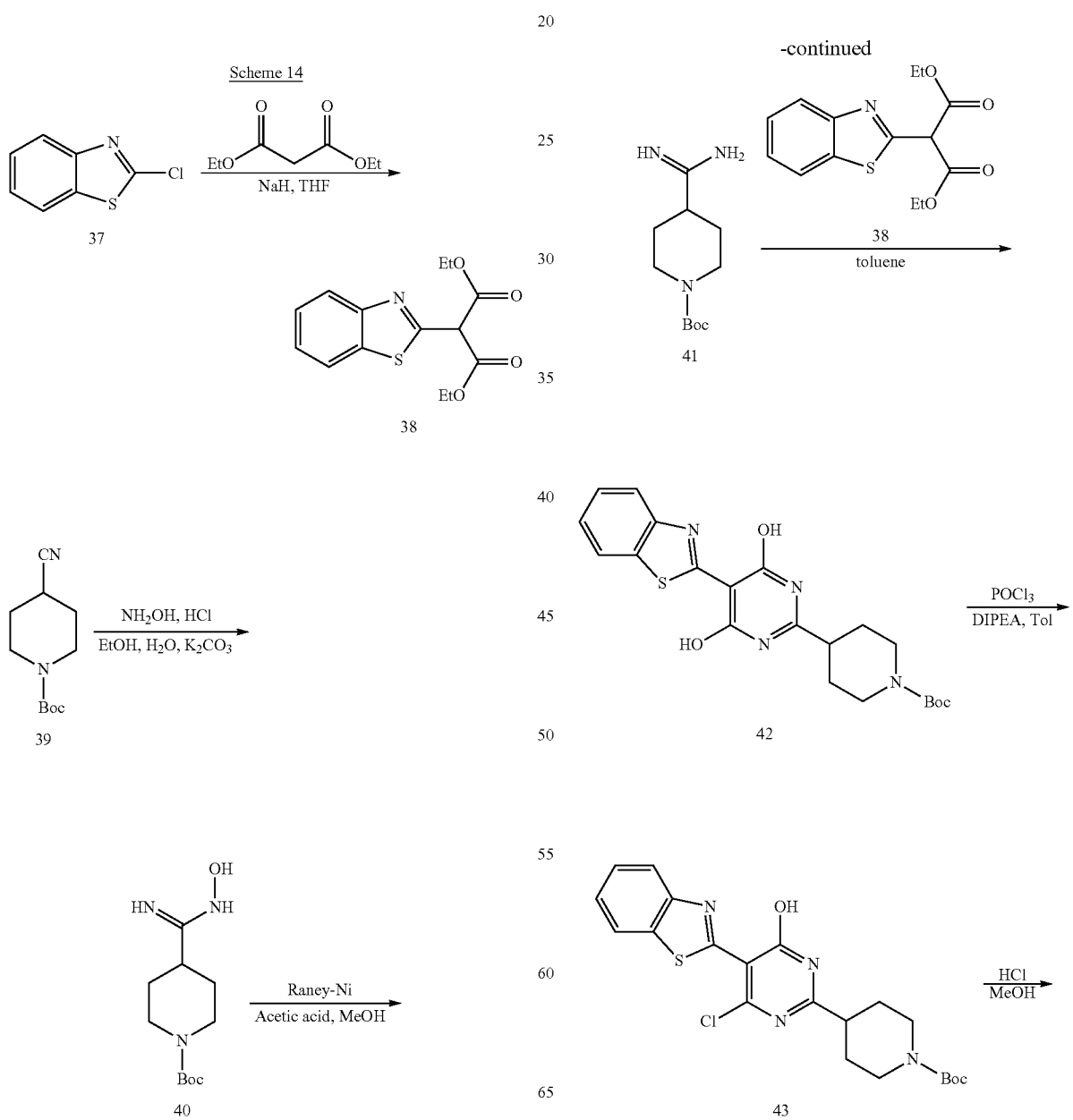

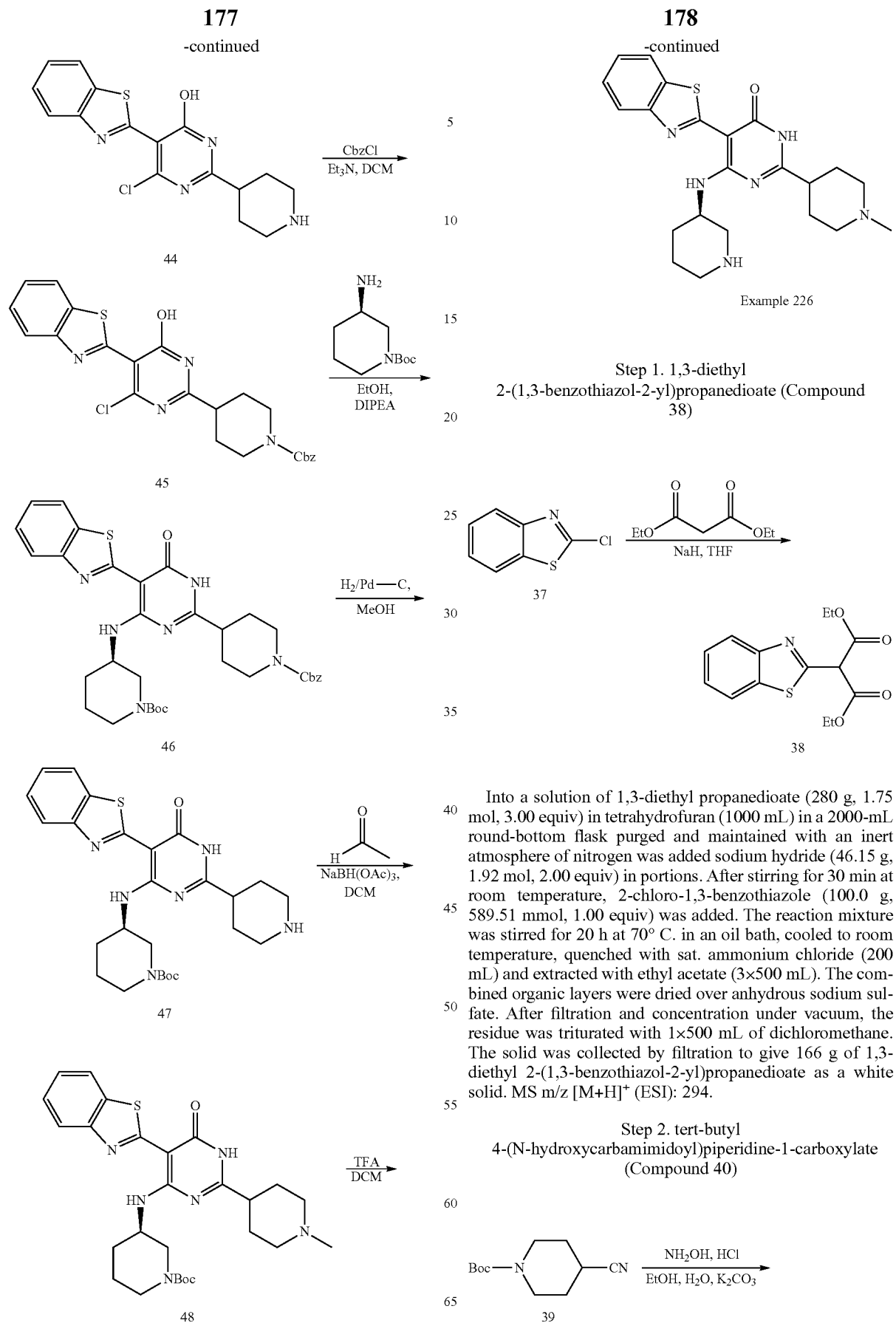

Example 226

Step 1. 1,3-diethyl 2-(1,3-benzothiazol-2-yl)propanedioate (Compound 38)

Into a solution of 1,3-diethyl propanedioate (280 g, 1.75 mol, 3.00 equiv) in tetrahydrofuran (1000 mL) in a 2000-mL round-bottom flask purged and maintained with an inert atmosphere of nitrogen was added sodium hydride (46.15 g, 1.92 mol, 2.00 equiv) in portions. After stirring for 30 min at room temperature, 2-chloro-1,3-benzothiazole (100.0 g, 589.51 mmol, 1.00 equiv) was added. The reaction mixture was stirred for 20 h at 70° C. in an oil bath, cooled to room temperature, quenched with sat. ammonium chloride (200 mL) and extracted with ethyl acetate (3×500 mL). The combined organic layers were dried over anhydrous sodium sulfate. After filtration and concentration under vacuum, the residue was triturated with 1×500 mL of dichloromethane. The solid was collected by filtration to give 166 g of 1,3-diethyl 2-(1,3-benzothiazol-2-yl)propanedioate as a white solid. MS m/z [M+H]$^+$ (ESI): 294.

Step 2. tert-butyl 4-(N-hydroxycarbamimidoyl)piperidine-1-carboxylate (Compound 40)

-continued

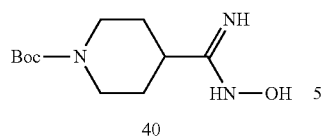
40

Into a mixture of hydroxylamine hydrochloride (52 g, 748.30 mmol, 3.00 equiv) and potassium carbonate (55.5 g, 402.47 mmol, 1.60 equiv) in water (125 mL) was added a solution of tert-butyl 4-cyanopiperidine-1-carboxylate (52.5 g, 249.68 mmol, 1.00 equiv) in ethyl alcohol (625 mL) dropwise with stirring. The resulting mixture was stirred overnight at 90° C. in an oil bath, cooled down to room temperature, filtered and concentrated under reducing pressure. The residue was diluted with 2000 mL of ethyl acetate, washed with 1×800 mL of water and dried over anhydrous sodium sulfate. Filtration and concentration under reducing pressure gave 60 g of tert-butyl 4-(N-hydroxycarbamimidoyl)piperidine-1-carboxylate as a white solid, which was used directly for next step without further purification. MS m/z [M+H]$^+$ (ESI): 245.

Step 3. tert-butyl 4-carbamimidoylpiperidine-1-carboxylate (Compound 41)

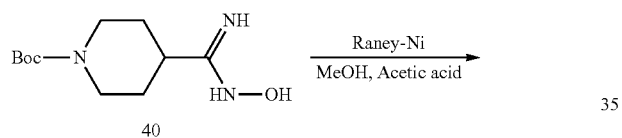

Into a 2-L round-bottom flask purged and maintained with an inert atmosphere of argon, was placed tert-butyl 4-(N-hydroxycarbamimidoyl)piperidine-1-carboxylate (46.5 g, 181.56 mmol, 1.00 equiv, 95%), methanol (1500 mL), acetic acid (20 mL), and Raney-Ni (13 g). The reaction system was bubbled for 5 times with hydrogen. The resulting mixture was stirred for 3 h at 50° C. in an oil bath. The solids were filtered out. The resulting solution was concentrated under vacuum to afford 40 g of tert-butyl 4-carbamimidoylpiperidine-1-carboxylate as yellow green crude oil, which was used directly for next step without further purification. MS m/z [M+H]$^+$ (ESI): 278.

Step 4. tert-butyl 4-[5-(1,3-benzothiazol-2-yl)-4,6-dihydroxypyrimidin-2-yl]piperidine-1-carboxylate (Compound 42)

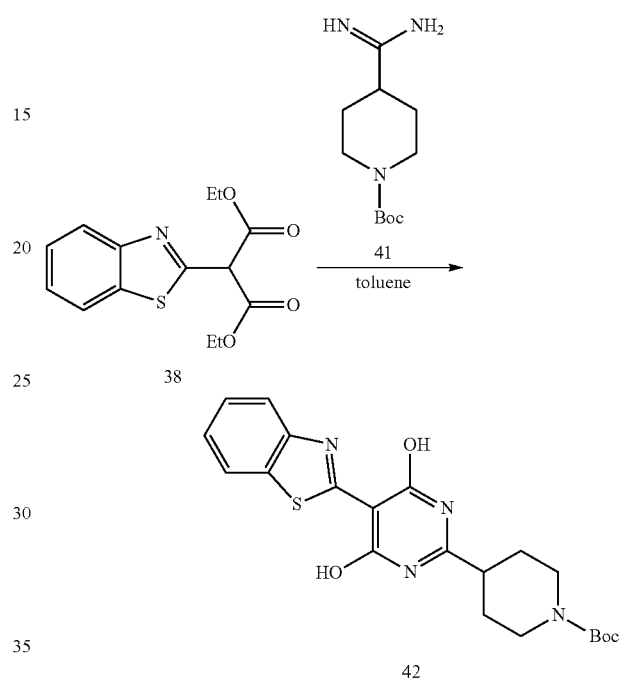

A mixture of tert-butyl 4-carbamimidoylpiperidine-1-carboxylate (35 g, 153.98 mmol, 1.00 equiv) and 1,3-diethyl 2-(1,3-benzothiazol-2-yl)propanedioate (49.7 g, 169.43 mmol, 1.10 equiv) in toluene (500 ml) was heated overnight at 120° C. in an oil bath under nitrogen. After cooled to room temperature, the solid was collected by filtration. 45 g of tert-butyl 4-[5-(1,3-benzothiazol-2-yl)-4,6-dihydroxypyrimidin-2-yl]piperidine-1-carboxylate was obtained as a light yellow solid. MS m/z [M+H]$^+$ (ESI): 429.

Step 5. tert-butyl 4-[5-(1,3-benzothiazol-2-yl)-4-chloro-6-hydroxypyrimidin-2-yl]piperidine-1-carboxylate (Compound 43)

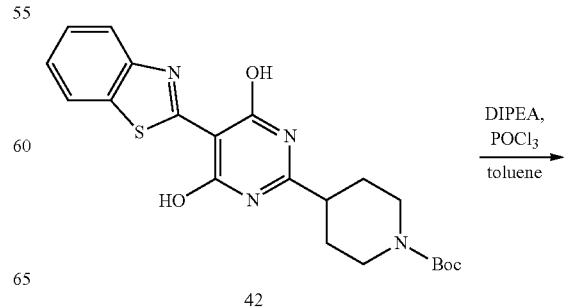

-continued

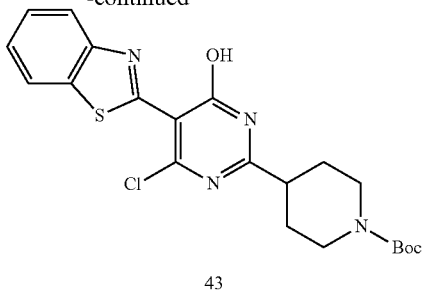
43

Into a solution of tert-butyl 4-[5-(1,3-benzothiazol-2-yl)-4,6-dihydroxypyrimidin-2-yl]piperidine-1-carboxylate (45 g, 105.02 mmol, 1.00 equiv) in toluene (500 ml) was added phosphoryl trichloride (16.1 g, 105.00 mmol, 1.00 equiv) and N,N-Diisopropylethylamine (27 g, 209.30 mmol, 1.99 equiv). The resulting solution was stirred for 20 mins at 120° C. Upon concentrated under vacuum, the residue was purified by flash chromatography on a silica gel column eluting with ethyl acetate/petroleum ether (1:10) to give 30 g of tert-butyl 4-[5-(1,3-benzothiazol-2-yl)-4-chloro-6-hydroxypyrimidin-2-yl]piperidine-1-carboxylate as a light yellow solid. MS m/z [M+H]$^+$ (ESI): 447.

Step 6. 5-(1,3-benzothiazol-2-yl)-6-chloro-2-(piperidin-4-yl)pyrimidin-4-ol (Compound 44)

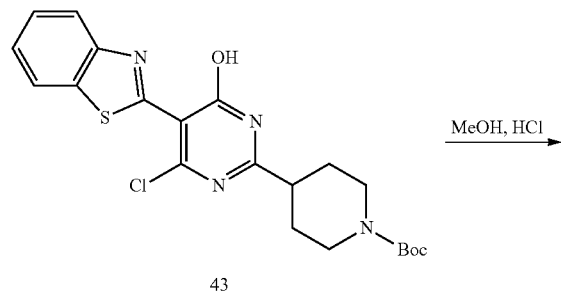
43

Into a solution of tert-butyl 4-[5-(1,3-benzothiazol-2-yl)-4-chloro-6-hydroxypyrimidin-2-yl]piperidine-1-carboxylate (44.7 g, 100.01 mmol, 1.00 equiv) in methanol (50 ml) was added concentrated hydrochloric acid (50 mL, 12 M). The resulting solution was stirred for 30 min at room temperature. Concentration under vacuum gave 34 g of 5-(1,3-benzothiazol-2-yl)-6-chloro-2-(piperidin-4-yl)pyrimidin-4-ol as a yellow solid, which was used directly for next step without further purification. MS m/z [M+H](ESI): 347.

Step 7. benzyl 4-[5-(1,3-benzothiazol-2-yl)-4-chloro-6-hydroxypyrimidin-2-yl]piperidine-1-carboxylate (Compound 45)

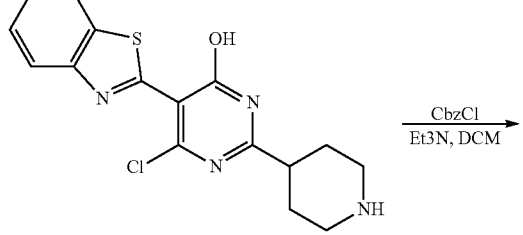

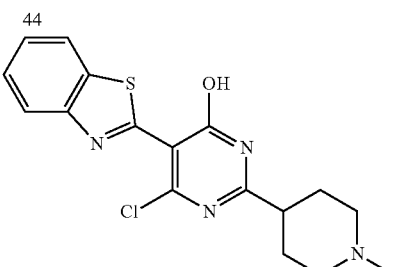
45

Into a mixture of 5-(1,3-benzothiazol-2-yl)-6-chloro-2-(piperidin-4-yl)pyrimidin-4-ol (50 g, 144.16 mmol, 1.00 equiv) and triethylamine (36.5 g, 361.39 mmol, 2.51 equiv) in dichloromethane (300 ml) was added benzyl chloroformate (29.5 g, 172.93 mmol, 1.20 equiv) dropwise. The resulting solution was stirred overnight at room temperature. Upon concentrated under vacuum, the residue was purified by flash chromatography on a silica gel column eluting with petroleum ether/ethyl acetate (2:1) to give 3 g of benzyl 4-[5-(1,3-benzothiazol-2-yl)-4-chloro-6-hydroxypyrimidin-2-yl]piperidine-1-carboxylate as yellow solid. MS m/z [M+H]$^+$ (ESI): 481.

Step 8. benzyl 4-[5-(1,3-benzothiazol-2-yl)-4-[[(3R)-1-[(tert-butoxy)carbonyl]piperidin-3-yl]amino]-6-oxo-1,6-dihydropyrimidin-2-yl]piperidine-1-carboxylate (Compound 46)

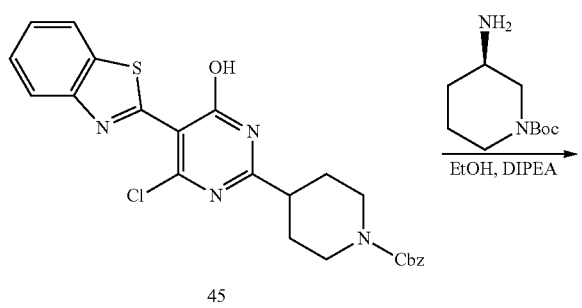
45

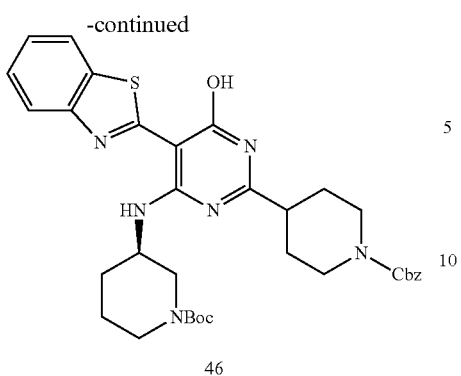

46

A mixture of benzyl 4-[5-(1,3-benzothiazol-2-yl)-4-chloro-6-hydroxypyrimidin-2-yl]piperidine-1-carboxylate (48.1 mg, 0.10 mmol, 1.00 equiv), tert-butyl (3R)-3-aminopiperidine-1-carboxylate (20.1 mg, 0.10 mmol, 1.00 equiv), and N-ethyl-N-isopropylpropan-2-amine (25.4 mg, 0.20 mmol, 1.97 equiv) in ethanol (3 ml) was heated overnight at 90° C. in an oil bath. Upon concentrated under vacuum, the residue was purified by flash chromatography on a silica gel column eluting with petroleum ether/ethyl acetate (1:1) to afford the title compound. as a yellow solid. MS m/z [M+H]$^+$ (ESI): 645.

Step 9. tert-butyl (3R)-3-[[5-(1,3-benzothiazol-2-yl)-6-oxo-2-(piperidin-4-yl)-1,6-dihydropyrimidin-4-yl]amino]piperidine-1-carboxylate (Compound 47)

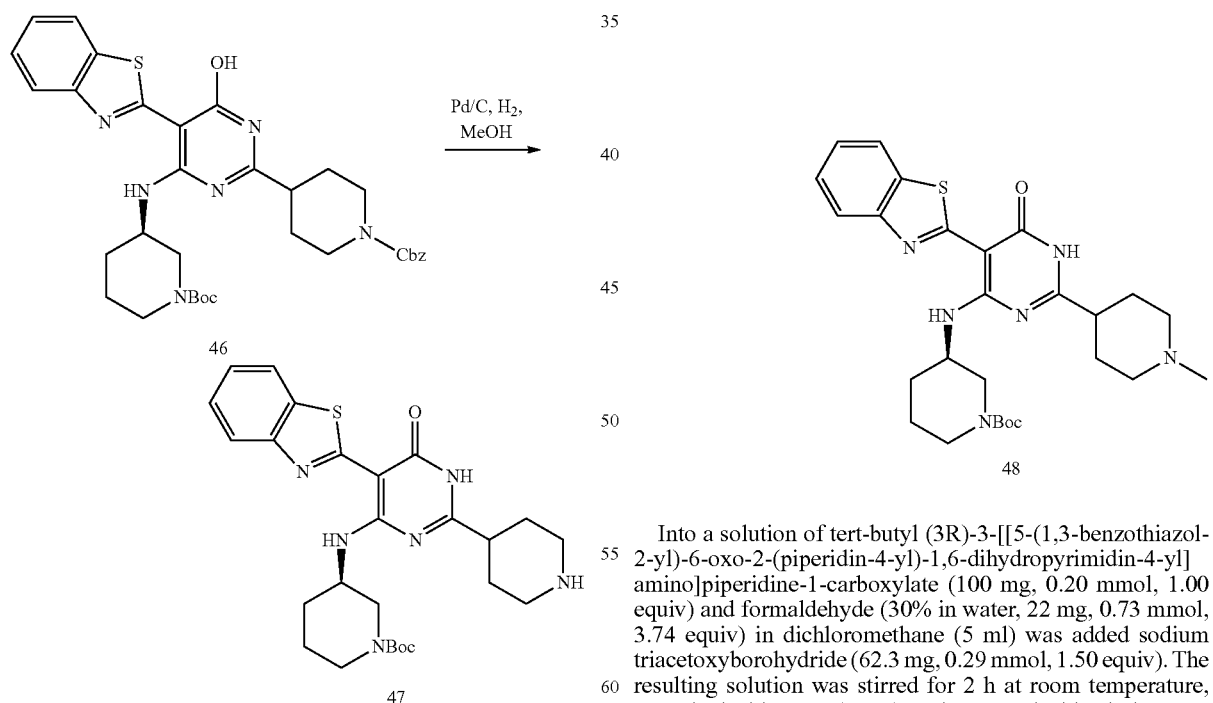

Into a 10-mL round-bottom flask purged and maintained with an atmosphere of hydrogen, was placed a solution of benzyl 4-[5-(1,3-benzothiazol-2-yl)-4-[[(3R)-1-[(tert-butoxy)carbonyl]piperidin-3-yl]amino]-6-oxo-1,6-dihydropyrimidin-2-yl]piperidine-1-carboxylate (644 mg, 1.00 mmol, 1.00 equiv), Palladium carbon (64.4 mg) and methanol (20 mL). The resulting mixture was stirred overnight at room temperature. Filtration and evaporation gave 480 mg (94%) of the title compound as a light yellow solid, which was used directly for next step without further purification. MS m/z [M+H]$^+$ (ESI): 511.

Step 10. tert-butyl (3R)-3-[[5-(1,3-benzothiazol-2-yl)-2-(1-methylpiperidin-4-yl)-6-oxo-1,6-dihydropyrimidin-4-yl]amino]piperidine-1-carboxylate (Compound 48)

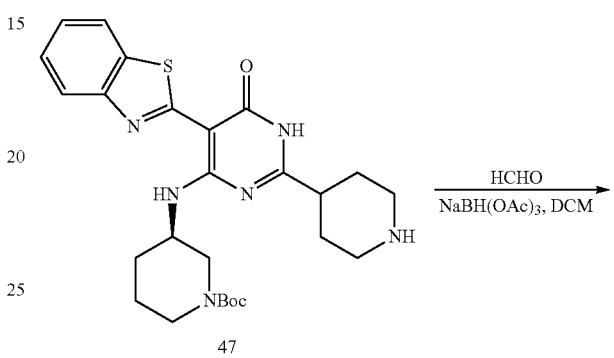

Into a solution of tert-butyl (3R)-3-[[5-(1,3-benzothiazol-2-yl)-6-oxo-2-(piperidin-4-yl)-1,6-dihydropyrimidin-4-yl]amino]piperidine-1-carboxylate (100 mg, 0.20 mmol, 1.00 equiv) and formaldehyde (30% in water, 22 mg, 0.73 mmol, 3.74 equiv) in dichloromethane (5 ml) was added sodium triacetoxyborohydride (62.3 mg, 0.29 mmol, 1.50 equiv). The resulting solution was stirred for 2 h at room temperature, quenched with water (5 mL), and extracted with ethyl acetate (2×5 mL). The combined organic phases were washed with brine (10 mL) and dried over anhydrous sodium sulfate. After filtration and concentration under vacuum, 100 mg of the title compound was obtained as a solid, which was used directly for next step without further purification. MS m/z [M+H]$^+$ (ESI): 525.

185

Step 11. (R)-5-(1,3-benzothiazol-2-yl)-2-(1-methylpiperidin-4-yl)-6-[[(3R)-piperidin-3-yl]amino]-3,4-dihydropyrimidin-4-one (Example 226)

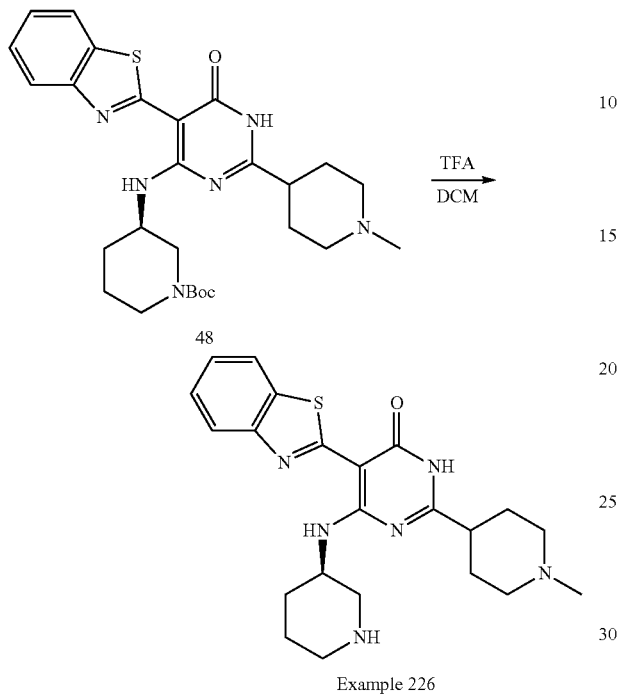

Example 226

186

Into a solution of tert-butyl (3R)-3-[[5-(1,3-benzothiazol-2-yl)-2-(1-methylpiperidin-4-yl)-6-oxo-1,6-dihydropyrimidin-4-yl]amino]piperidine-1-carboxylate (100 mg, 0.19 mmol, 1.00 equiv in dichloromethane (5 ml) was added trifluoroacetic acid (1 mL). The resulting solution was stirred for 1 h at room temperature. After concentrated under reducing pressure, the crude product was purified by Prep-HPLC with the following conditions (1#-Pre-HPLC-001(SHIMADZU)): Column, SunFire Prep C18 OBD Column, 5 um, 19*150 mm; mobile phase, WATER WITH 0.05% TFA and CH3CN (17% CH$_3$CN up to 28% in 7 min, up to 100% in 4 min, down to 17% in 1 min); Detector, Waters 2489 254&220 nm to afford the title compound as the corresponding TFA salt. as a white solid. $^1$H-NMR (400 MHz, DMSO-d$_6$): δ ppm 1.87-2.19(m, 8H), 2.33-2.36(m, 1H), 2.82-2.88(m, 4H), 3.06-3.26(m, 5H), 3.36-3.55(m, 3H), 4.47(s, 1H), 7.35-7.39(m, 1H), 7.48-7.52 (m, 1H), 7.91(d, J=8.0 Hz, 1H), 8.04(d, J=7.6 Hz, 1H), 8.87(s, 1H), 9.03(s, 1H), 9.75(s, 1H), 11.02(d, J=6.0 Hz, 1H), 12.53 (s, 1H); MS m/z [M+H]$^+$ (ESI): 425. IRAK4 IC$_{50}$=690 nM The following examples were synthesized according to Scheme 14.

| Exple | Structure | Name | IC$_{50}$ (nM) | MS (m/z) | NMR |
|---|---|---|---|---|---|
| 227 | 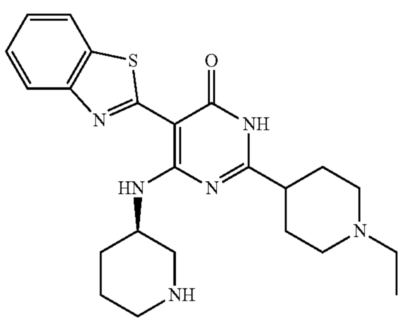 [SMILES: CCN1CCC(c2nc(N[C@@H]3CCCNC3)c(-c3nc4ccccc4s3)c(=O)[nH]2)CC1] | (R)-N-[1-(2,4-difluorophenyl)-3-[4-(methylsulfamoyl)phenyl]-1H-pyrazol-5-yl]pyrazolo[1,5-a]pyrimidine-3-carboxamide | 1,400 | 439 M + H | $^1$H-NMR (400 MHz, DMSO-d$_6$): δ ppm 1.21-1.27 (m, 3H), 1.87-2.33 (m, 8H), 2.77-3.61 (m, 12H), 4.49 (s, 1H), 7.31-7.39 (m, 1H), 7.48-7.52 (m, 1H), 7.91 (d, J = 8.0 Hz, 1H), 8.46 (d, J = 7.6 Hz, 1H), 8.81 (s, 1H), 9.00 (s, 1H), 9.41 (s, 1H), 11.00 (d, J = 6.8 Hz, 1H), 12.54 (s, 1H) |
| 228 | 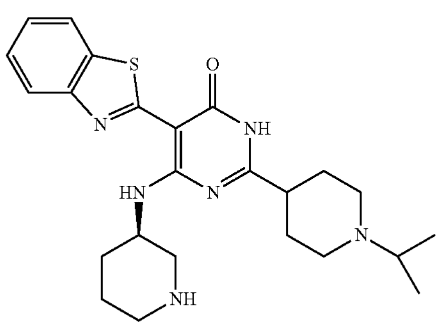 [SMILES: CC(C)N1CCC(c2nc(N[C@@H]3CCCNC3)c(-c3nc4ccccc4s3)c(=O)[nH]2)CC1] | (R)-5-(1,3-benzothiazol-2-yl)-6-[[(3R)-piperidin-3-yl]amino]-2-[1-(propan-2-yl)piperidin-4-yl]-3,4-dihydropyrimidin-4-one | 660 | 453 M + H | $^1$H-NMR (400 MHz, DMSO-d$_6$): δ ppm 1.25-1.30 (m, 6H), 1.86-2.33 (m, 8H), 2.78-3.33 (m, 7H), 3.43-3.51 (m, 4H), 4.49 (s, 1H), 7.35-7.39 (m, 1H), 7.48-7.52 (m, 1H), 7.91 (d, J = 8.0 Hz, 1H), 8.04 (d, J = 7.6 Hz, 1H), 8.85 (s, 1H), 9.05 (s, 1H), 9.34 (s, 1H), 11.02 (s, 1H), 12.56 (s, 1H) |

| Exple | Structure | Name | IC$_{50}$ (nM) | MS (m/z) | NMR |
|---|---|---|---|---|---|
| 229 | 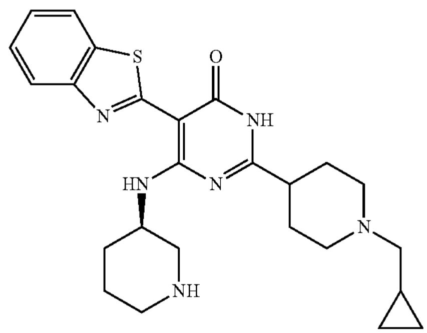 [SMILES: O=c1[nH]c(C2CCN(CC3CC3)CC2)nc(N[C@@H]2CCCNC2)c1-c1nc2ccccc2s1] | 5-(1,3-benzothiazol-2-yl)-2-[1-(cyclopropylmethyl)piperidin-4-yl]-6-[[(3R)-piperidin-3-yl]amino]-3,4-dihydropyrimidin-4-one | 340 | 465 M + H | $^1$H-NMR (400 MHz, CD$_3$OD): δ ppm 0.48-0.52 (m, 2H), 0.79-0.84 (m, 2H), 1.18-1.20 (m, 1H), 2.04-2.09 (m, 2H), 2.26-2.37 (m, 6H), 2.91-2.93 (m, 1H), 3.10-3.41 (m, 7H), 3.62-3.66 (m, 1H), 3.81-3.86 (m, 2H), 4.66-4.68 (m, 1H), 7.38 (t, J = 7.2 Hz, 1H), 7.50 (t, J = 7.5 Hz, 1H), 7.93-7.98 (m, 2H) |
| 230 | 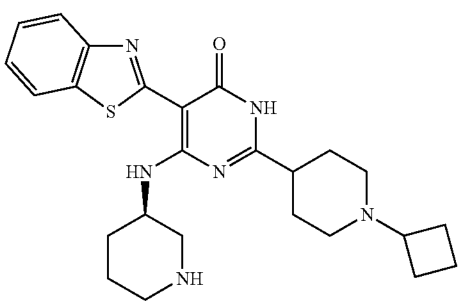 [SMILES: O=c1[nH]c(C2CCN(C3CCC3)CC2)nc(N[C@@H]2CCCNC2)c1-c1nc2ccccc2s1] | (R)-5-(1,3-benzothiazol-2-yl)-2-[1-cyclobutylpiperidin-4-yl]-6-[(piperidin-3-yl)amino]-3,4-dihydropyrimidin-4-one | 730 | 465 M + H | $^1$H-NMR (400 MHz, D$_2$O): δ ppm 1.67 (m, 4H), 1.89-1.97 (m, 4H), 2.01-2.16 (m, 4H), 2.24-2.35 (m, 3H), 2.71-2.80 (m, 2H), 3.20-3.26 (m, 3H), 3.36-3.40 (m, 1H), 3.46-3.49 (m, 1H), 3.54-3.62 (m, 1H), 4.10 (s, 1H), 7.18-7.25 (m, 1H), 7.31-7.37 (m, 1H), 7.67-7.75 (m, 1H), 7.77-7.81 (m, 1H) |
| 231 | 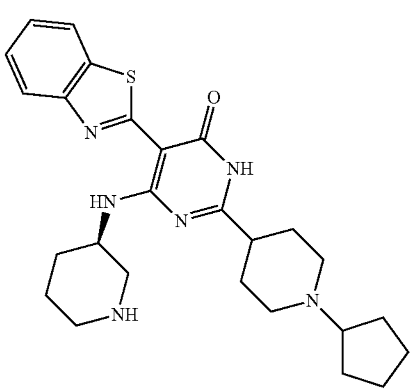 [SMILES: O=c1[nH]c(C2CCN(C3CCCC3)CC2)nc(N[C@@H]2CCCNC2)c1-c1nc2ccccc2s1] | 5-(1,3-benzothiazol-2-yl)-2-(1-cyclopentylpiperidin-4-yl)-6-[[(3R)-piperidin-3-yl]amino]-3,4-dihydropyrimidin-4-one | 620 | 479 M + H | $^1$H-NMR (400 MHz, D$_2$O): δ ppm 1.54-1.82 (m, 8H), 1.90-2.11 (m, 8H), 2.31 (t, J = 12.0 Hz, 1H), 2.88 (s, J = 13.0 Hz, 2H), 3.16-3.48 (m, 5H), 3.59 (d, J = 10.4 Hz, 1H), 4.10 (s, 1H), 7.19 (t, J = 7.8 Hz, 1H), 7.28 (t, J = 8.0 Hz, 1H), 7.67 (d, J = 8.0 Hz, 1H), 7.75 (d, J = 8.0 Hz, 1H) |

-continued

| Exple | Structure | Name | IC$_{50}$ (nM) | MS (m/z) | NMR |
|---|---|---|---|---|---|
| 232 | 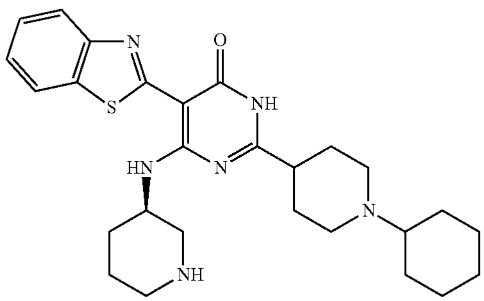 [SMILES: O=c1[nH]c(C2CCN(C3CCCCC3)CC2)nc(N[C@@H]2CCCNC2)c1-c1nc2ccccc2s1] | (R)-5-(1,3-benzothiazol-2-yl)-2-(1-cyclohexylpiperidin-4-yl)-6-[(piperidin-3-yl)amino]-3,4-dihydropyrimidin-4-one | 450 | 493 M + H | $^1$H-NMR (400 MHz, D$_2$O): δ ppm 1.07-1.13 (m, 1H), 1.22-1.37 (m, 2H), 1.40-1.46 (m, 2H), 1.59-1.62 (m, 2H), 1.78-1.85 (m, 4H), 1.94-2.00 (m, 6H), 2.10-2.12 (m, 2H), 2.33-2.39 (m, 1H), 2.96-3.02 (m, 2H), 3.10-3.26 (m, 4H), 3.38-3.42 (m, 1H), 3.48-3.50 (m, 2H), 4.15 (s, 1H), 7.21-7.28 (m, 1H), 7.33-7.37 (m, 1H), 7.70-7.78 (m, 1H), 7.80-7.84 (m, 1H) |
| 233 | 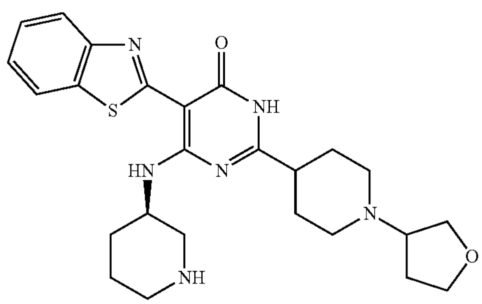 [SMILES: O=c1[nH]c(C2CCN(C3CCOC3)CC2)nc(N[C@@H]2CCCNC2)c1-c1nc2ccccc2s1] | 5-(1,3-benzothiazol-2-yl)-2-[1-(oxolan-3-yl)piperidin-4-yl]-6-[[(3R)-piperidin-3-yl]amino]pyrimidin-4-ol | 180 | 481 M + H | $^1$H-NMR (400 MHz, DMSO-d$_6$): δ ppm 1.88-2.33 (m, 10H), 2.90-2.93 (m, 1H), 3.07-3.23 (m, 5H), 3.42-3.55 (m, 4H), 3.64-3.68 (m, 1H), 3.70-3.81 (m, 1H), 3.92-4.08 (m, 3H), 4.50 (m, 1H), 7.36-7.40 (t, J = 7.6 Hz, 1H), 7.49-7.52 (t, J = 7.6 Hz, 1H), 7.91-7.93 (d, J = 8.0 Hz, 1H), 8.05-8.07 (d, J = 8.0 Hz, 1H), 8.82-9.02 (m, 2H), 9.70-10.10 (m, 1H), 11.05 (s, 1H), 12.56 (s, 1H) |
| 234 | 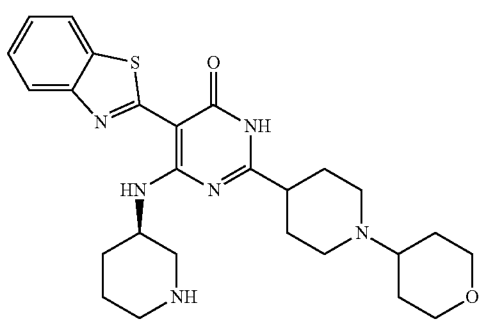 [SMILES: O=c1[nH]c(C2CCN(C3CCOCC3)CC2)nc(N[C@@H]2CCCNC2)c1-c1nc2ccccc2s1] | (R)-5-(benzo[d]thiazol-2-yl)-6-(piperidin-3-ylamino)-2-(1-(tetrahydro-2H-pyran-4-yl)piperidin-4-yl)pyrimidin-4(3H)-one | 440 | 495 M + H | $^1$H-NMR (300 MHz, CD$_3$OD): δ ppm 1.80~2.08 (m, 6H), 2.24~2.38 (m, 6H), 2.67 (s, 1H), 2.85~2.87 (m, 1H), 3.07~3.29 (m, 4H), 3.34~3.62 (m, 5H), 3.69-3.74 (m, 2H), 4.05~4.09 (m, 2H), 4.62~4.63 (m, 1H), 7.31~7.36 (m, 1H), 7.42~7.47 (m, 1H), 7.87~7.91 (m, 2H) |

Scheme 15

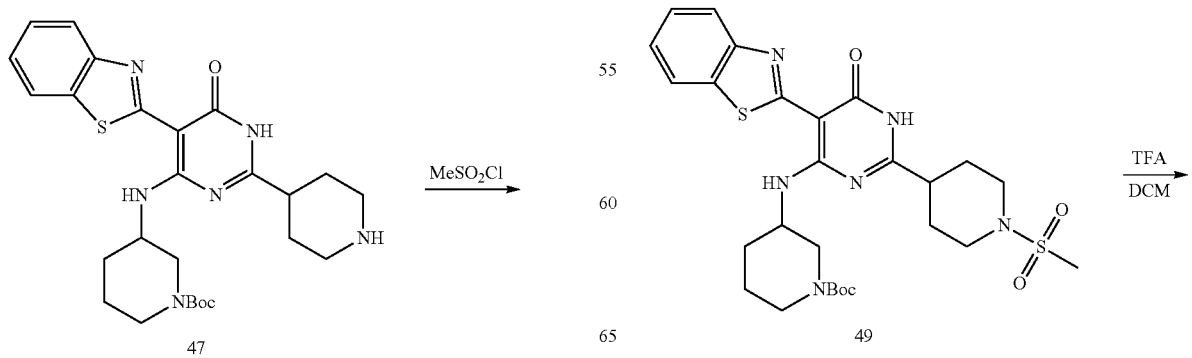

-continued

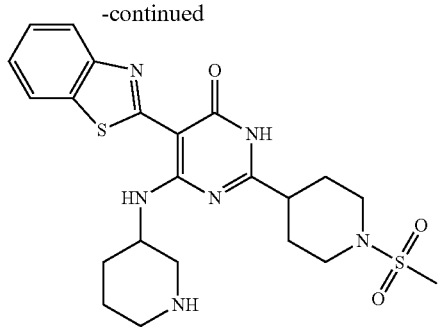

Example 235

Step 1. tert-butyl (3R)-3-[[5-benzothiazol-2-yl)-2-(1-methanesulfonylpiperidin-4-yl)-6-oxo-1,6-dihydro-pyrimidin-4-yl]amino]piperidine-1-carboxylate (Compound 49)

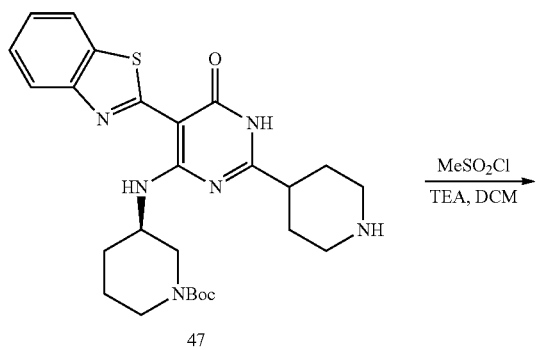

47

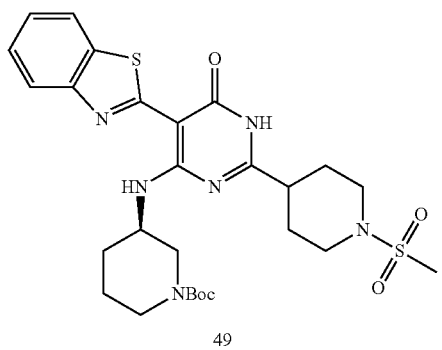

49

Into a solution of tert-butyl (3R)-3-[[5-(1,3-benzothiazol-2-yl)-6-oxo-2-(piperidin-4-yl)-1,6-dihydropyrimidin-4-yl]amino]piperidine-1-carboxylate (100 mg, 0.20 mmol, 1.00 equiv) and triethylamine (79 mg, 0.78 mmol, 3.99 equiv) in dichloromethane (5 ml) was added methanesulfonyl chloride (0.39 mmol, 2.00 equiv). The resulting mixture was stirred for 2 h at room temperature. Concentration under vacuum gave 100 mg of the title compound as a solid, which was used directly for next step without further purification. MS m/z [M+H]$^+$ (ESI): 589.

Step 2. (R) 5-(1,3-benzothiazol-2-yl)-2-(1-methane-sulfonylpieridin-4-yl)-6-[[(3R)-piperidin-3-yl]amino]-3,4-dihydropyrimidin-4-one (Example 235)

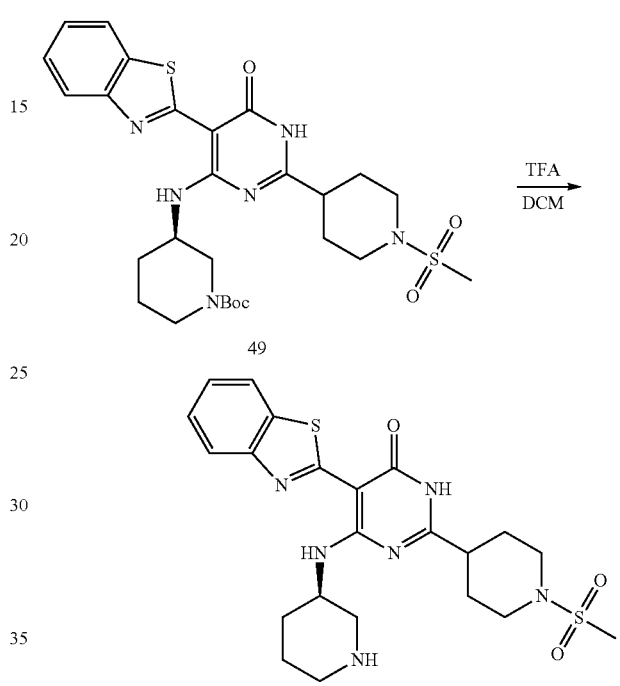

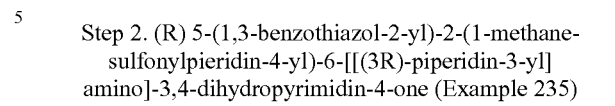

Into a 10-mL round-bottom flask, was placed a solution of tert-butyl (3R)-3-[[5-(1,3-benzothiazol-2-yl)-2-(1-methane-sulfonylpiperidin-4-yl)-6-oxo-1,6-dihydropyrimidin-4-yl]amino]piperidine-1-carboxylate (100 mg, 0.17 mmol, 1.00 equiv), trifluoroacetic acid (1 mL) in dichloromethane (5 ml). The resulting mixture was stirred for 1 h at room temperature. Upon concentrated under reducing pressure, the residue was purified by flash chromatography on a silica gel column eluting with dichloromethane/methanol (10:1) and then by Prep-HPLC with the following conditions (1#-Pre-HPLC-001 (SHIMADZU)): Column, SunFire Prep C18 OBD Column, 5 um, 19*150 mm; mobile phase, water with 0.05% TFA and CH$_3$CN (26% CH$_3$CN up to 38% in 6 min, up to 100% in 3 min, down to 26% in 1 min); Detector, Waters 2489 254&220 nm to afford the title compound as the corresponding TFA salt. as a white solid. $^1$H-NMR (400 MHz, DMSO-d$_6$): δ ppm 1.89-1.93(m, 4H), 2.02(d, J=10.8 Hz, 3H), 2.15(d, J=2.4 Hz, 1H), 2.68-2.83(m, 3H), 2.92(s, 3H), 2.96-3.06(m, 2H), 3.26 (d, J=11.2 Hz, 1H), 3.54 (d, J=10.8 Hz, 2H), 3.66(d, J=12.0 Hz, 2H), 4.48(d, J=6.0 Hz, 6H), 7.34-7.48(m, 1H), 7.47-7.49 (m, 1H), 7.90(d, J=8.0 Hz, 1H), 8.03(d, J=8.0 Hz, 1H), 8.74(s, 1H), 8.84(s, 1H), 10.93(d, J=6.8 Hz, 1H), 12.51(s, 1H); $^{19}$F-NMR (400 MHz, DMSO-d$_6$): δ ppm −73.559; MS m/z [M+H]$^+$ (ESI): 489. IRAK4 IC$_{50}$=380

The following examples were synthesized according to Scheme 15.

| Exple | Structure | Name | IC$_{50}$ (nM) | MS (m/z) | NMR |
|---|---|---|---|---|---|
| 236 | 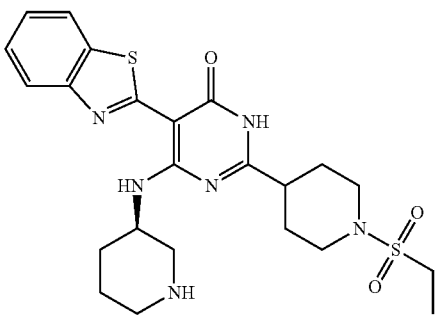 [SMILES: CCS(=O)(=O)N1CCC(c2nc(N[C@@H]3CCCNC3)c(-c3nc4ccccc4s3)c(=O)[nH]2)CC1] | 5-(1,3-benzothiazol 2-yl)-2-[1-(ethanesulfonyl) piperidin-4-yl]-6-[[(3R)-piperidin-3-yl]amino-3,4-dihydropyrimidin-4-one | 550 | 503 M + H | $^1$H-NMR (400 MHz, CD$_3$OD): δ ppm 1.34-1.38 (m, 3H), 1.95-2.07 (m, 6H), 2.21 (s, 1H), 2.31 (s, 1H), 2.70-2.80 (m, 1H), 2.91-3.00 (m, 2H), 3.06-3.25 (m, 4H), 3.32-3.40 (m, 2H), 3.67 (d, J = 3.6 Hz, 1H), 3.90 (d, J = 12.4 Hz, 2H), 4.60 (s, 1H), 7.35-7.37 (m, 1H), 7.47-7.49 (m, 1H), 7.91-7.98 (m, 2H) |
| 237 | 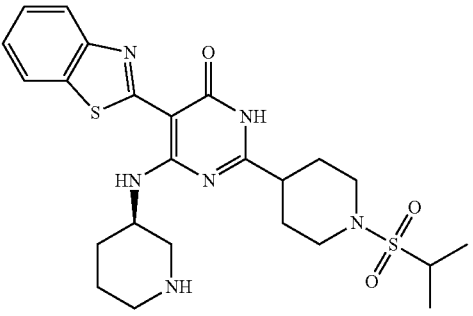 [SMILES: CC(C)S(=O)(=O)N1CCC(c2nc(N[C@@H]3CCCNC3)c(-c3nc4ccccc4s3)c(=O)[nH]2)CC1] | 5-(1,3-benzothiazol-2-yl)-6-[[(3R)-piperidin-3-yl]amino]-2-[1-(propane-2-sulfonyl)piperidin-4-yl]-3,4-dihydropyrimidin-4-one | 210 | 517 M + H | $^1$H-NMR (400 MHz, DMSO-d$_6$): δ ppm 1.22-1.27 (m, 6H), 1.70-1.95 (m, 3H), 1.95-2.05 (m, 3H), 2.10-2.20 (m, 1H), 2.74-2.80 (m, 1H), 2.95-3.15 (m, 3H), 3.25-3.60 (m, 5H), 3.77-3.81 (d, J = 12.8 Hz, 2H), 4.40-4.55 (m, 1H), 7.35-7.39 (t, J = 7.2 Hz, 1H), 7.47-7.51 (t, J = 7.2 Hz, 1H), 7.90-7.92 (d, J = 8.4 Hz, 1H), 8.04-8.06 (d, J = 7.6 Hz, 1H), 8.67 (br, 1H), 8.79 (br, 1H), 10.96-10.98 (d, J = 6.8 Hz, 1H) |
| 238 | 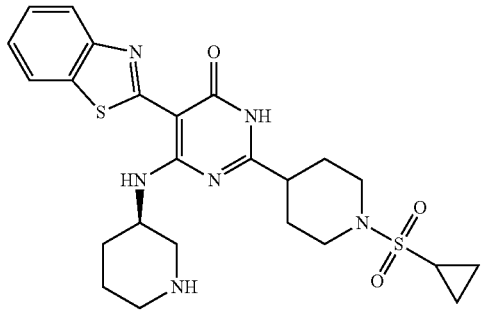 [SMILES: O=c1[nH]c(C2CCN(S(=O)(=O)C3CC3)CC2)nc(N[C@@H]2CCCNC2)c1-c1nc2ccccc2s1] | (R)-5-(1,3-benzothiazol-2-yl) 2-[1-(cyclopropane-sulfonyl)piperidin-4-yl]-6-[(piperidin-3-yl)amino]-3,4-dihydropyrimidin-4-one | 170 | 515 M + H | $^1$H-NMR (400 MHz, DMSO-d$_6$): δ ppm 0.95-1.03 (m, 4H), 1.85-1.91 (m, 4H), 2.02-2.05 (m, 3H), 2.16-2.17 (m, 1H), 2.64-2.68 (m, 2H), 2.71-3.07 (m, 4H), 3.26-3.28 (m, 1H), 3.53-3.54 (m, 1H), 3.71-7.74 (m, 2H), 4.49 (s, 1H), 7.35-7.39 (m, 1H), 7.48-7.52 (m, 1H), 7.90-7.92 (d, J = 8.4 Hz, 1H), 8.04-8.06 (d, J = 7.6 Hz, 1H), 8.66 (s, 1H), 8.81 (s, 1H), 10.93-10.95 (m, 1H), 12.51 (s, 1H) |

Scheme 16

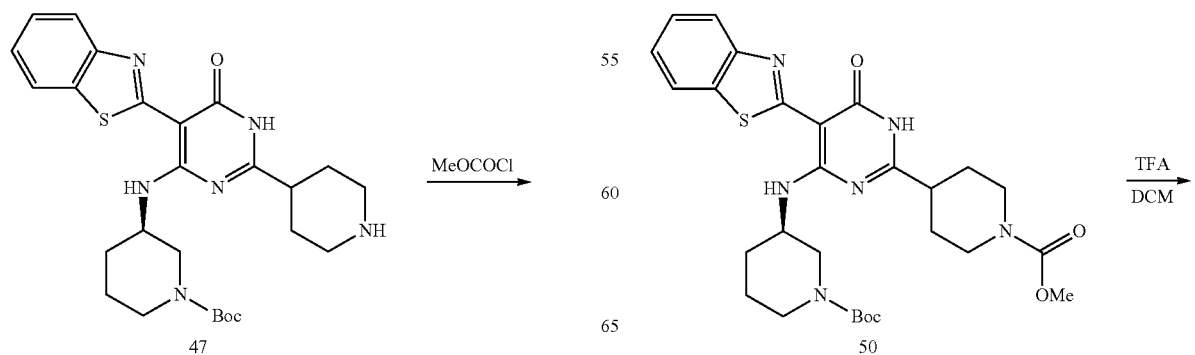

-continued

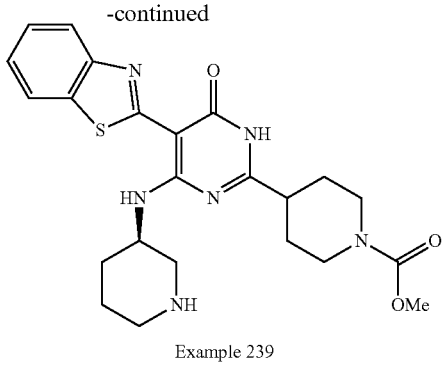

Example 239

Step 1. methyl 4-[5-(1,3-benzothiazol-2-yl)-4-[[(3R)-1-[(tert-butoxy)carbonyl]piperidin-3-yl]amino]-6-oxo-1,6-dihydropyrimidin-2-yl]piperidine-1-carboxylate (Compound 50)

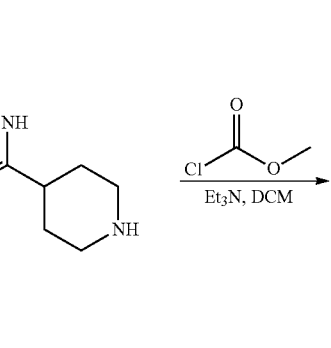

47

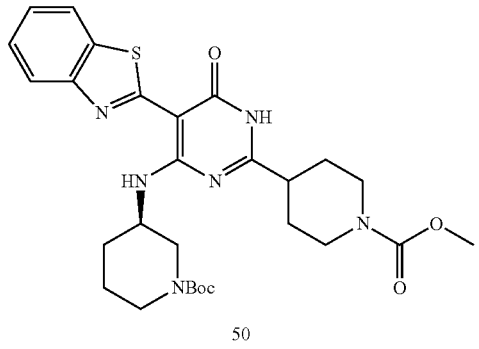

50

Into a solution of tert-butyl (3R)-3-[[5-(1,3-benzothiazol-2-yl)-6-oxo-2-(piperidin-4-yl)-1,6-dihydropyrimidin-4-yl]amino]piperidine-1-carboxylate (100 mg, 0.20 mmol, 1.00 equiv) and triethylamine (29.7 mg, 0.29 mmol, 1.50 equiv) in dichloromethane (5 ml) was added methyl chloroformate (14.8 mg, 0.16 mmol, 0.80 equiv). The resulting mixture was stirred for 2 h at room temperature. Concentration under reducing pressure gave 100 mg of the title compound as a crude product, which was used directly for next step without further purification. MS m/z [M+H]$^+$ (ESI): 569.

Step 2. methyl 4-[(R)-5-(1,3-benzothiazol-2-yl)-6-oxo-4-[[(3R)-piperidin-3-yl]amino]-1,6-dihydropyrimidin-2-yl]piperidine-1-carboxylate (Example 239)

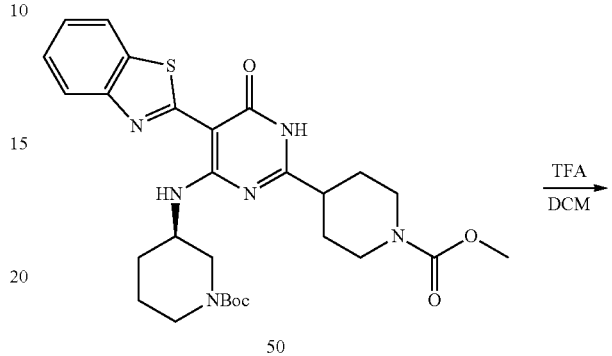

Example 239

Following the same procedure as in step 2 of Example 10 using methyl 4-[5-(1,3-benzothiazol-2-yl)-4-[[(3R)-1-[(tert-butoxy)carbonyl]piperidin-3-yl]amino]-6-oxo-1,6-dihydropyrimidin-2-yl]piperidine-1-carboxylate (100 mg, 0.18 mmol, 1.00 equiv) and trifluoroacetic acid (0.5 mL) in dichloromethane (5 ml). The crude product (100 mg) was purified by Prep-HPLC with the following conditions (1#-Pre-HPLC-001(SHIMADZU)): Column, SunFire Prep C18 OBD Column, 5 um, 19*150 mm; mobile phase, water with 0.05% TFA and CH$_3$CN (26% CH$_3$CN up to 38% in 6 min, up to 100% in 3 min, down to 26% in 1 min); Detector, Waters 2489 254&220 nm to afford the title compound as the corresponding TFA salt. as a white solid. $^1$H-NMR (400 MHz, DMSO-d$_6$): δ ppm 1.63-2.00(m, 7H), 2.14(s, 1H), 2.75-3.06(m, 5H), 3.23(d, J=12.4 Hz, 1H), 3.48(d, J=10.0 Hz, 2H), 4.08(s, 2H), 4.45(s, 1H), 7.33-7.37(m, 1H), 7.46-7.50(m, 1H), 7.89(d, J=8.0 Hz, 1H), 8.03(d, J=7.6 Hz, 1H), 8.64-8.76(m, 2H), 10.92(d, J=7.2 Hz, 1H), 12.43(s, 1H); $^{19}$F-NMR (400 MHz, DMSO-d$_6$): δ ppm −73.640; MS m/z [M+H]$^+$ (ESI): 469. IRAK4 IC$_{50}$=270 nM The following examples were synthesized according to Scheme 16.

| Exple | Structure | Name | IC$_{50}$ (nM) | MS (m/z) | NMR |
|---|---|---|---|---|---|
| 240 | 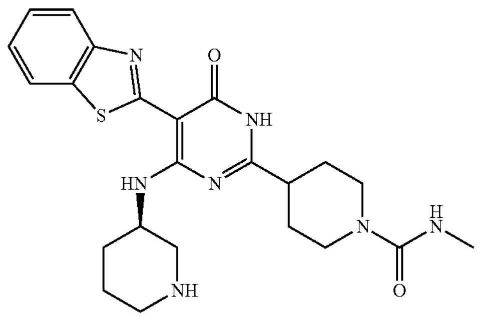 [SMILES: CNC(=O)N1CCC(c2nc(N[C@@H]3CCCNC3)c(-c3nc4ccccc4s3)c(=O)[nH]2)CC1] | (R)-4-[5-(1,3-benzo-thiazol-2-yl)-6-oxo-4-[[(3R)-piperidin-3-yl]amino]-1,6-dihydro-pyrimidin-2-yl]-N-methyl-piperidine-1-carboxamide | 200 | 468 M + H | $^1$H-NMR (300 MHz, DMSO-d$_6$ + D$_2$O): δ ppm 1.66-2.03 (m, 8H), 2.70-2.78 (m, 2H), 2.92-3.02 (m, 2H), 3.15-3.18 (m, 1H), 3.40-3.45 (m, 1H), 3.90-4.00 (m, 2H), 4.42-4.44 (m, 1H), 7.33-7.38 (t, J = 8.1 Hz, 1H), 7.46-7.51 (t, J = 8.1 Hz, 1H), 7.89-7.92 (d, J = 7.8 Hz, 1H), 8.00-8.02 (d, J = 7.8 Hz, 1H), 10.96-10.98 (s, 0.5H) |
| 241 | 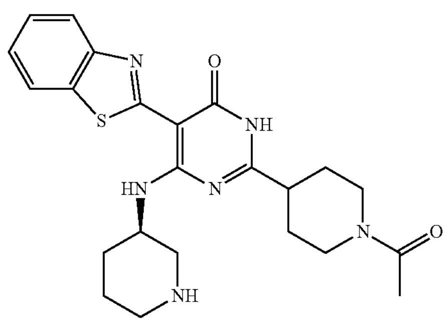 [SMILES: CC(=O)N1CCC(c2nc(N[C@@H]3CCCNC3)c(-c3nc4ccccc4s3)c(=O)[nH]2)CC1] | 2-(1-acetyl-piperidin-4-yl)-5-(1,3-benzothiazol-2-yl)-6-[[(3R)-piperidin-3-yl]amino]-4,5-dihydro-pyrimidin-4-one | 450 | 453 M + H | $^1$H-NMR (400 MHz, DMSO-d$_6$): δ ppm 1.61-2.20 (m, 11H), 2.55-2.68 (m, 1H), 2.80-3.28 (m, 5H), 3.48 (d, J = 12 Hz, 1H), 3.93 (d, J = 13.6 Hz, 2H), 4.48 (d, J = 10.8 Hz, 2H), 7.34-7.38 (t, J = 7.6 Hz, 1H), 7.47-7.51 (t, J = 7.2 Hz, 1H), 7.90-7.92 (d, J = 8.0 Hz, 1H), 8.03-8.05 (d, J = 7.6 Hz, 1H), 9.0 (br, 1H), 10.93 (d, J = 6.4 Hz, 1H), 12.4 (br, 1H) |

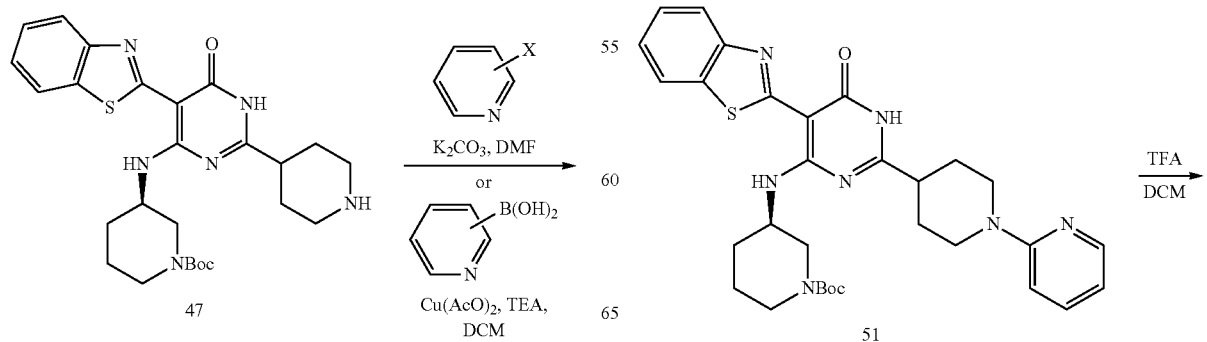

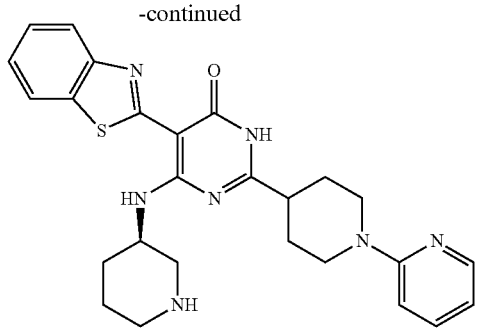

Example 242

Step 1: (R)-tert-butyl 3-(5-(benzo[d]thiazol-2-yl)-6-oxo-2-(1-(pyridin-2-yl)piperidin-4-yl)-1,6-dihydro-pyrimidin-4-ylamino)piperidine-1-carboxylate (Compound 51)

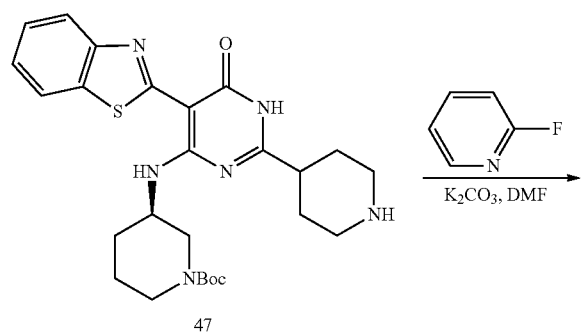

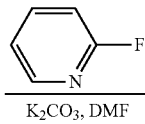

47

51

Into a 25-mL round-bottom flask, was placed a solution of tert-butyl (3R)-3-[[5-(1,3-benzothiazol-2-yl)-6-oxo-2-(piperidin-4-yl)-1,6-dihydropyrimidin-4-yl]amino]piperidine-1-carboxylate (150 mg, 0.29 mmol, 1.00 equiv) in N,N-dimethylformamide (5 mL) and 2-fluoropyridine (114 mg, 1.17 mmol, 4.00 equiv). This was followed by the addition of potassium carbonate (81 mg, 0.59 mmol, 2.00 equiv). The resulting solution was stirred for 24 h at 100° C. The solids were filtered out. The resulting mixture was concentrated under reduced pressure. The residue was purified through a silica gel column with dichloromethane/methanol (50:1-20:1) to afford 70 mg of tert-butyl (3R)-3-[[5-(1,3-benzothiazol-2-yl)-6-oxo-2-[1-(pyridin-2-yl)piperidin-4-yl]-1,6-dihydropyrimidin-4-yl]amino]piperidine-1-carboxylate as a light yellow solid.

Step 2: (R)-5-(benzo[d]thiazol-2-yl)-6-(piperidin-3-ylamino)-2-(1-(pyridin-2-yl)piperidin-4-yl)pyrimidin-4(3H)-one (Example 242)

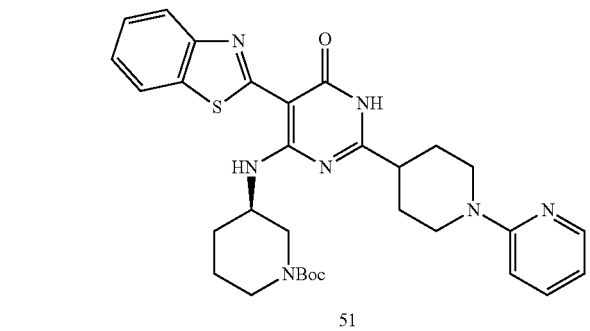

51

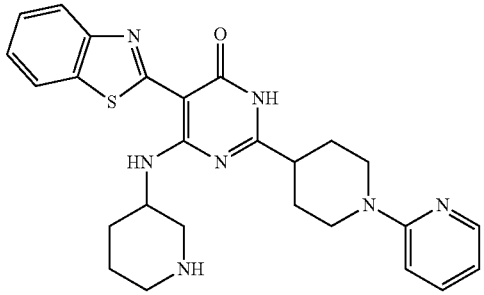

Example 242

Trifluoroacetic acid (0.2 mL) was added into a solution of tert-butyl (3R)-3-[[5-(1,3-benzothiazol-2-yl)-6-oxo-2-[1-(pyridin-2-yl)piperidin-4-yl]-1,6-dihydropyrimidin-4-yl]amino]piperidine-1-carboxylate (60 mg, 0.10 mmol, 1.00 equiv) in dichloromethane (2 mL). The resulting solution was stirred for 1 h at room temperature. After concentrated under vacuum, the crude product was purified by Prep-HPLC with the following conditions (1#-Pre-HPLC-001(SHIMADZU)): Column, SunFire Prep C18 OBD Column, 5 um, 19*150 mm,; mobile phase, water with 0.05% TFA and CH$_3$CN (17.0% CH$_3$CN up to 29.0% in 7 min, up to 100.0% in 4 min, down to 17.0% in 1 min); Detector, Waters 2489 254&220 nm to afford the title compound as the corresponding TFA salt. (white solid). $^1$H-NMR (400 MHz, DMSO-d6): δ ppm δ 1.67-1.70 (m, 2H), 1.93 (s, 4H), 2.11-2.16 (m, 2H), 2.52-2.59 (m, 1H), 3.01-3.30 (m, 5H), 3.37-3.44 (m, 1H), 4.00-4.16 (m, 3H), 6.86-6.90 (t, J=6.8 Hz, 1H), 7.20-7.24 (m, 2H), 7.35-7.39 (t, J=7.6 Hz, 1H), 7.74-7.81 (m, 3H), 7.88-7.99 (m, 1H). MS m/z [M+H]$^+$ (ESI): 488. IRAK4 IC$_{50}$=180 nM The following examples were synthesized according to Scheme 17.

| Exple | Structure | Name | IC$_{50}$ (nM) | MS (m/z) | NMR |
|---|---|---|---|---|---|
| 243 | 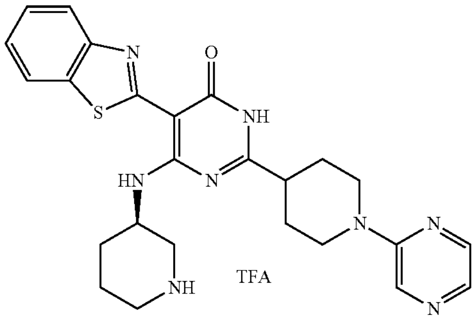 [SMILES: O=c1[nH]c(C2CCN(c3cnccn3)CC2)nc(N[C@@H]2CCCNC2)c1-c1nc2ccccc2s1] | (R)-5-(benzo[d]thiazol-2-yl)-6-(piperidin-3-ylamino)-2-(1-(pyrazin-2-yl)piperidin-4-yl)pyrimidin-4(3H)-one | 180 | 489 M + H | $^1$H-NMR (400 MHz, DMSO-d$_6$): δ ppm 1.82-1.85 (m, 4H), 2.01-2.04 (m, 3H), 2.13 (s, 1H), 2.87-2.99 (m, 5H), 3.05-3.06 (d, J = 7.6 Hz, 1H), 3.22-3.25 (d, J = 13.2 Hz, 1H), 4.47-4.49 (m, 3H), 7.34-7.38 (m, 1H), 7.47-7.49 (m, 1H), 7.83-7.91 (m, 2H), 8.03-8.10 (m, 2H), 8.38 (s, 1H), 8.66-8.72 (br, 2H), 10.94-10.96 (d, J = 7.2 Hz, 1H), 12.46 (s, 1H) |
| 244 | 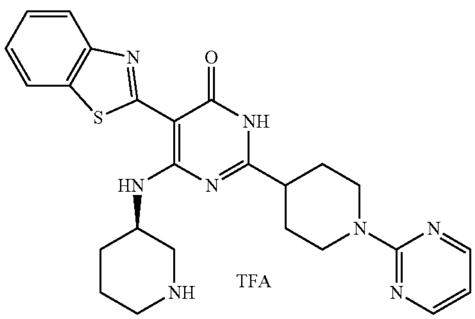 [SMILES: O=c1[nH]c(C2CCN(c3ncccn3)CC2)nc(N[C@@H]2CCCNC2)c1-c1nc2ccccc2s1] | (R)-5-(benzo[d]thiazol-2-yl)-6-(piperidin-3-ylamino)-2-(1-(pyrimidin-2-yl)piperidin-4-yl)pyrimidin-4(3H)-one | 260 | 489 M + H | $^1$H-NMR (400 MHz, DMSO-d$_6$): δ ppm 1.71-1.88 (m, 4H), 1.98-2.02 (m, 3H), 2.13 (s, 1H), 2.89-3.07 (m, 5H), 3.15-3.21 (m, 2H), 4.45 (s, 1H), 4.80-4.84 (d, J = 13.6 Hz, 2H), 6.61-6.64 (t, J = 4.8 Hz, 1H), 7.34-7.38 (m, 1H), 7.47-7.51 (m, 1H), 7.89-7.91 (d, J = 7.6 Hz, 1H), 8.03-8.05 (d, J = 7.6 Hz, 1H), 8.37-8.38 (d, J = 4.8 Hz, 2H), 8.62-8.73 (br, 2H), 10.93-10.95 (d, J = 7.2 Hz, 1H), 12.46 (s, 1H). |
| 245 | 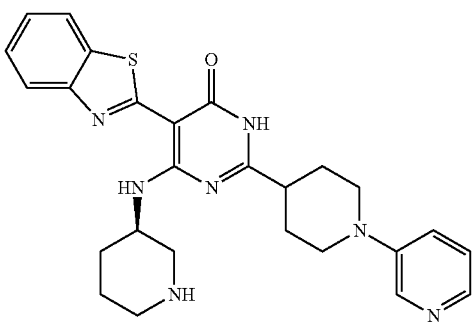 [SMILES: O=c1[nH]c(C2CCN(c3cccnc3)CC2)nc(N[C@@H]2CCCNC2)c1-c1nc2ccccc2s1] | (R)-5-(benzo[d]thiazol-2-yl)-6-(piperidin-3-ylamino)-2-(1-(pyridin-3-yl)piperidin-4-yl)pyrimidin-4(3H)-one | 89 | 488 M + H | $^1$H-NMR (300 MHz, DMSO-d6): δ ppm 1.48-2.03 (m, 9H), 2.62-2.82 (m, 5H), 3.04 (d, J = 11.4 Hz, 1H), 3.84 (d, J = 12.0 Hz, 2H), 4.25 (s, 1H), 7.19 (d, J = 4.5 Hz, 1H), 7.22-7.48 (m, 3H), 7.84 (d, J = 8.4 Hz, 1H), 7.99 (d, J = 7.2 Hz, 2H), 8.34 (s, 1H), 11.10 (d, J = 7.8 Hz, 1H). |

-continued

Scheme 18

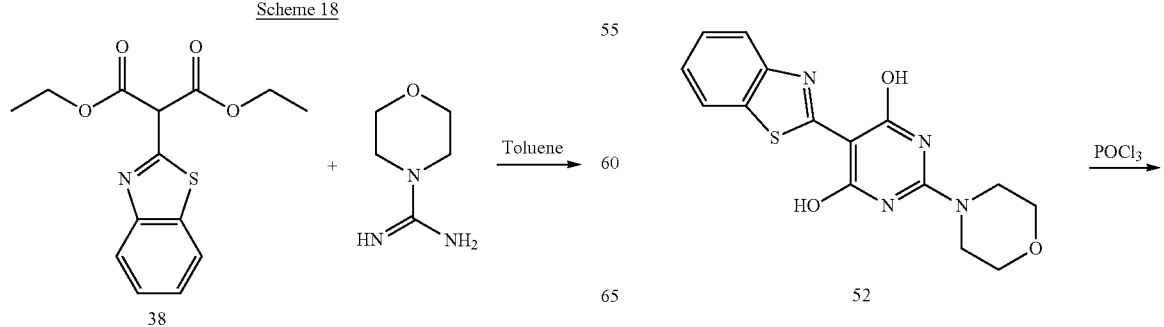

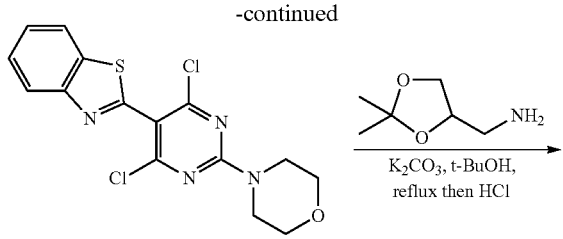

Example 246

Step 1. 5-(1,3-benzothiazol-2-yl)-2-(morpholin-4-yl)pyrimidine-4,6-diol (Compound 52)

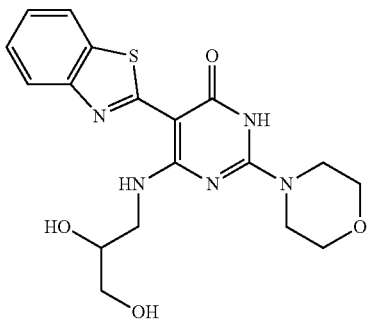

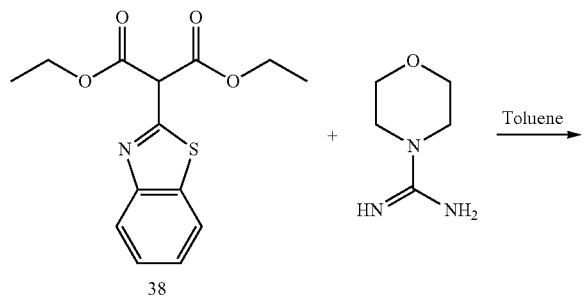

A mixture 1,3-diethyl 2-(1,3-benzothiazol-2-yl)propanedioate (3.00 g, 10.23 mmol, 1.00 equiv), and morpholine-4-carboximidamide (1.33 g, 10.30 mmol, 1.00 equiv) in Toluene (30 mL) was heated for 20 h at 120° C. under an inert atmosphere of nitrogen. After cooling down, the white solid was collected by filtration, washed with a mixture solution of Dichloromethane/Methanol and dried in an IR oven to afford the title compound. as a white solid. MS m/z [M+H]$^+$ (ESI): 331.

Step 2. 2-[4,6-dichloro-2-(morpholin-4-yl)pyrimidin-5-yl]-1,3-benzothiazole (Compound 53)

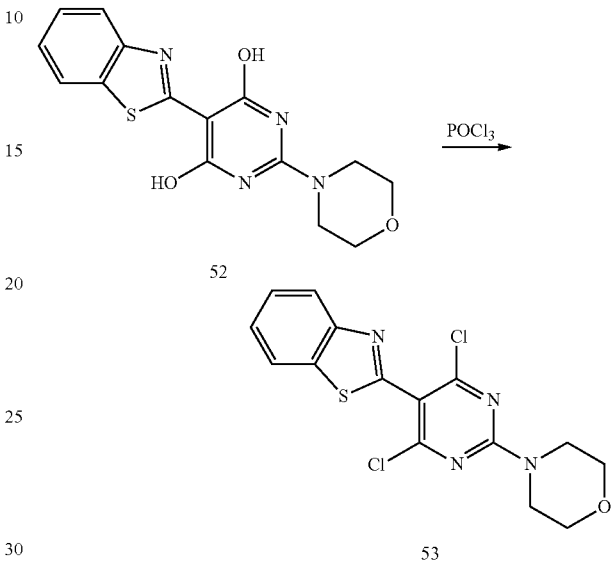

Into a 100-mL round-bottom flask, was placed 5-(1,3-benzothiazol-2-yl)-2-(morpholin-4-yl)pyrimidine-4,6-diol (511.4 mg, 1.55 mmol, 1.00 equiv) and phosphoryl trichloride (50 mL). The resulting solution was stirred overnight at 80° C. Upon concentrated under reducing pressure, the residue was diluted with water and extracted with dichloromethane. The combined organic layers were dried over anhydrous sodium sulfate. Filtration and evaporation gave the title compound, which was used directly for net step without further purification (yellow solid). MS m/z [M+H]$^+$ (ESI): 367.

Step 3. (2,2-dimethyl-1,3-dioxolan-4-yl)methylamine

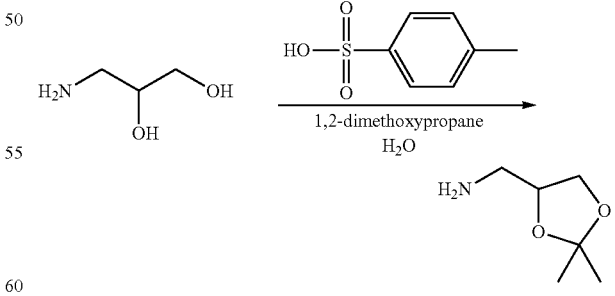

Into a 100-mL round-bottom flask, was placed a solution of 3-aminopropane-1,2-diol (5 g, 54.88 mmol, 1.00 equiv) in water (15 mL). The pH value of the solution was adjusted to 1 with 37% hydrochloric acid. The resulting solution was stirred for 15 min at room temperature. Then the mixture was concentrated to dryness under vacuum. This was followed by the addition of 2,2-dimethoxypropane (32 mL), and 4-methylbenzene-1-sulfonic acid (423 mg, 2.46 mmol, 0.04 equiv). The resulting solution was stirred for 30 min at 85° C. The solid was collected by filtration, washed with acetone and then dissolved in dichloromethane. The PH value of the solution was adjusted to 9 with 2N sodium hydroxide solution. Two phases were separated. The aqueous phase was extracted with dichloromethane. The combined organic phases were dried over anhydrous sodium sulfate. Filtration and concentration under reducing pressure gave the title compound (light yellow oil). $^1$H-NMR (300 MHz, CDCl$_3$): δ ppm 1.24(s, 3H), 1.33(s, 3H), 2.77 (s, 1H), 2.91(s, 1H), 3.67-3.72(m, 1H), 3.96-4.01(m, 1H), 4.20-4.28(m, 1H), 8.15(brs, 3H).

Step 4. 5-(1,3-benzothiazol-2-yl)-6-chloro-N-[(2,2-dimethyl-1,3-dioxolan-4-yl)methyl]-2-(morpholin-4-yl)pyrimidin-4-amine

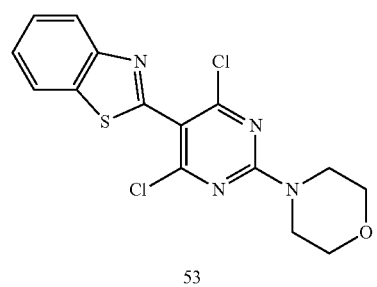

53

+

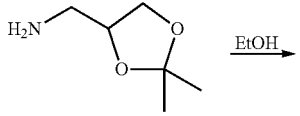 $\xrightarrow{\text{EtOH}}$

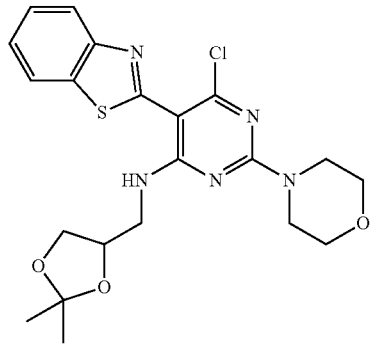

Into a solution of 2-[4,6-dichloro-2-(morpholin-4-yl)pyrimidin-5-yl]-1,3-benzothiazole (200 mg, 0.54 mmol, 1.00 equiv) in ethanol (3 mL) was added (2,2-dimethyl-1,3-dioxolan-4-yl)methylamine (142.9 mg, 1.09 mmol, 2.00 equiv). The resulting solution was stirred for 3 h at 85° C. Removal of the solvent under reducing pressure gave 0.35 g (crude) of the title compound as a yellow solid, which was used for next step without further purification. MS m/z [M+H]$^+$ (ESI): 462.

Step 5. 5-(1,3-benzothiazol-2-yl)-6-[(2,3-dihydroxypropyl)amino]-2-(morpholin-4-yl)-3,4-dihydropyrimidin-4-one (Example 246)

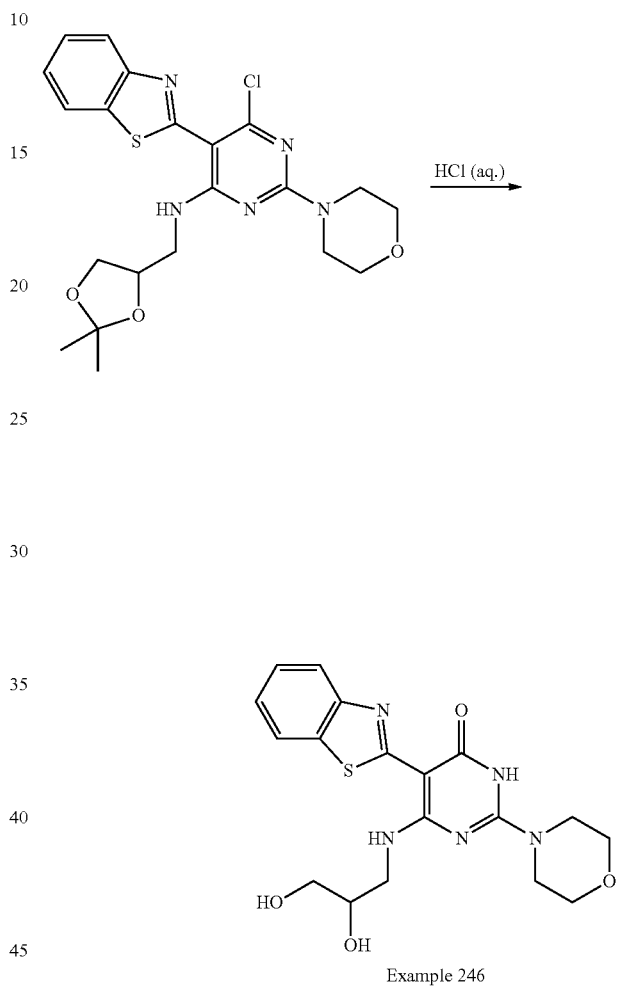

Example 246

Into a 25-mL round-bottom flask, was placed 5-(1,3-benzothiazol-2-yl)-6-chloro-N-[(2,2-dimethyl-1,3-dioxolan-4-yl)methyl]-2-(morpholin-4-yl)pyrimidin-4-amine (350 mg, 0.76 mmol, 1.00 equiv) and concentrated hydrochloric acid (14 mL). The resulting solution was stirred overnight at 85° C. Upon concentrated under vacuum, the crude product was purified by Prep-HPLC with the following conditions (1#-Pre-HPLC-001(SHIMADZU)): Column; mobile phase, water with 0.03% NH$_3$H$_2$O and CH$_3$CN (8% CH$_3$CN up to 20% in 7 min, up to 32% in 3 min, up to 100% in 4 min, down to 8% in 1 min); Detector, Waters 2489 254&220 nm to afford the title compound as a light yellow solid. $^1$H-NMR (300 MHz, CDCl$_3$): δ ppm 3.06-3.13(m, 1H), 3.22-3.27(m, 1H), 3.62-3.96(m, 8H), 4.32-4.64(m, 3H), 7.37-7.42(m, 1H), 7.48-7.53(m, 1H), 7.70-7.77(m, 1H), 7.80-8.00(m, 1H); MS m/z [M+H]$^+$ (ESI): 403.8. IRAK4 IC$_{50}$=8100 nM The following examples were synthesized according to Scheme 18.

| Exple | Structure | Name | IC$_{50}$ (nM) | MS (m/z) | NMR |
|---|---|---|---|---|---|
| 247 | 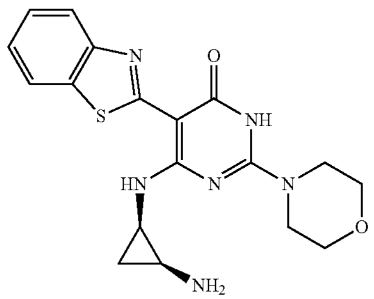 [SMILES: N[C@H]1C[C@H]1Nc1nc(N2CCOCC2)[nH]c(=O)c1-c1nc2ccccc2s1] | 6-[[(1R,2S)-2-amino-cyclopropyl]amino]-5-(1,3-benzothiazol-2-yl)-2-(morpholin-4-yl)-3,4-dihydropyrimidin-4-one | 3,000 | 385 M + H | $^1$H-NMR (400 MHz, DMSO + D$_2$O): δ ppm 1.11-1.17 (m, 1H), 1.36-1.43 (m, 1H), 2.74-2.77 (m, 1H), 2.83-2.90 (m, 1H), 3.10-3.17 (m, 1H), 3.65-3.83 (m, 8H), 7.26-7.31 (m, 1H), 7.41-7.46 (m, 1H), 7.87 (d, J = 8.1 Hz, 1H), 7.95 (m, J = 7.8 Hz, 1H) |
| 248 | 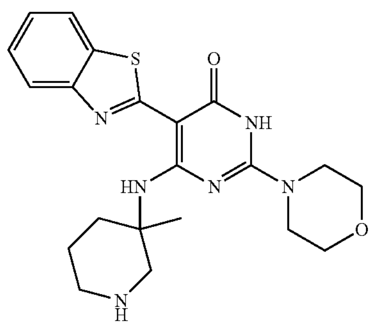 [SMILES: CC1(Nc2nc(N3CCOCC3)[nH]c(=O)c2-c2nc3ccccc3s2)CCCNC1] | 5-(1,3-benzothiazol-2-yl)-6-[(3-methylpiperidin-3-yl)amino]-2-(morpholin-4-yl)-3,4-dihydro-pyrimidin-4-one | 150 | 427 M + H | $^1$H-NMR (300 MHz, CD$_3$OD): δ ppm 1.26-1.31 (d, J = 14.4 Hz, 1H), 1.61 (s, 3H), 1.85-1.94 (m, 1H), 2.09-2.16 (m, 1H), 2.27-2.31 (d, J = 12.6 Hz, 1H), 2.49-2.59 (m, 1H), 3.05-3.20 (m, 2H), 3.42-3.51 (m, 4H), 3.63-3.72 (m, 4H), 4.56-4.61 (m, 1H), 7.27~7.33 (m, 1H), 7.40-7.45 (m, 1H), 7.76-7.81 (m, 1H), 7.87-7.90 (d, J = 7.2 Hz, 1H), 11.46 (s, 1H) |
| 249 | 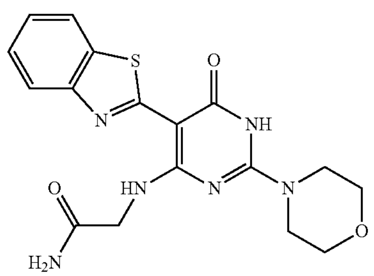 [SMILES: NC(=O)CNc1nc(N2CCOCC2)[nH]c(=O)c1-c1nc2ccccc2s1] | 2-[[5-(1,3-benzothiazol-2-yl)-2-(morpholin-4-yl)-6-oxo-1,6-dihydropyrimidin-4-yl]amino]acetamide | 3,900 | 387 M + H | $^1$H-NMR (300 MHz, DMSO-d$_6$): δ ppm 3.679 (s, 8H), 4.152-4.247 (s, 2H), 7.076 (s, 1H), 7.266 (d, J = 6.6 Hz, 1H), 7.322-7.487 (m, 2H), 7.776 (d, J = 7.2 Hz, 1H), 7.879 (d, J = 8.1 Hz, 1H), 10.826 (s, 1H), 11.046 (s, 1H) |
| 250 | 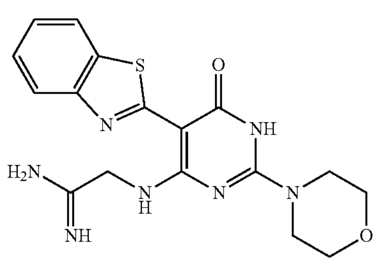 [SMILES: N=C(N)CNc1nc(N2CCOCC2)[nH]c(=O)c1-c1nc2ccccc2s1] | 2-[[5-(1,3-benzothiazol-2-yl)-2-(morpholin-4-yl)-6-oxo-1,6-dihydropyrimidin-4-yl]amino]ethanimidamide | 300 | 386 M + H | $^1$H-NMR (300 MHz, DMSO-d$_6$): δ ppm 3.67 (s, 8H), 4.48-4.49 (d, J = 4.8 Hz, 1H), 7.25-7.30 (t, J = 8.1 Hz, 1H), 7.41-7.46 (t, J = 8.1 Hz, 1H), 7.82-7.85 (d, J = 8.1 Hz, 1H), 7.97-7.99 (d, J = 7.8 Hz, 1H), 8.68 (s, 1H), 8.89 (s, 1H), 10.78 (s, 1H), 11.27 (s, 1H) |
| 251 | 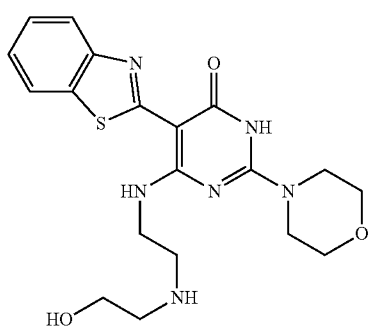 [SMILES: O=c1[nH]c(N2CCOCC2)nc(NCCNCCO)c1-c1nc2ccccc2s1] | 5-(benzo[d]thiazol-2-yl)-6-(2-(2-hydroxyethyl-amino)ethylamino)-2-morpholino-pyrimidin-4(3H)-one | 640 | 417 M + H | $^1$H-NMR (300 MHz, DMSO-d$_6$): δ ppm 2.93-2.96 (m, 2H), 3.12-3.14 (d, J = 5.4 Hz, 2H), 3.58-3.67 (m, 1H), 3.80-3.82 (d, J = 6 Hz, 2H), 7.19-7.24 (m, 1H), 7.34-7.39 (m, 1H), 7.75-7.78 (d, 1H), 7.89-7.92 (d, J = 8.1 Hz, 1H), 8.10 (s, 1H), 10.70 (s, 1H) |

| Exple | Structure | Name | IC$_{50}$ (nM) | MS (m/z) | NMR |
|---|---|---|---|---|---|
| 252 | 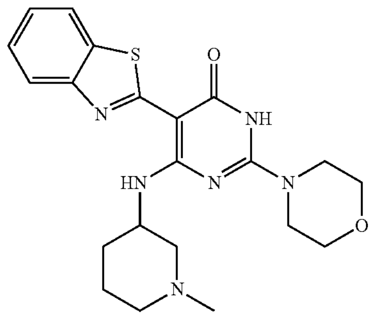 [SMILES: CN1CCCC(Nc2nc(N3CCOCC3)[nH]c(=O)c2-c2nc3ccccc3s2)C1] | 5-(1,3-benzothiazol-2-yl)-6-[(1-methylpiperidin-3-yl)amino]-2-(morpholin-4-yl)-3,4-dihydro-pyrimidin-4-one | 1,200 | 427 M + H | $^1$H-NMR (300 MHz, CDCl$_3$): δ ppm 1.50-1.68 (m, 2H), 1.70-1.84 (m, 2H), 2.25 (s, 6H), 2.50-2.51 (m, 1H), 3.68 (s, 8H), 4.25-4.38 (m, 1H), 7.17-7.32 (m, 1H), 7.36-7.49 (m, 1H), 7.67-7.78 (m, 1H), 7.89-8.04 (m, 1H), 10.88-11.11 (m, 2H) |
| 253 | 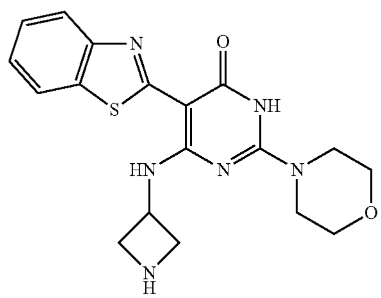 [SMILES: O=c1[nH]c(N2CCOCC2)nc(NC2CNC2)c1-c1nc2ccccc2s1] | 6-[(azetidin-3-yl)amino]-5-(1,3-benzothiazol-2-yl)-2-(morpholin-4-yl)-3,4-dihydro-pyrimidin-4-one | 300 | 385 M + H | $^1$H-NMR (400 MHz, DMSO-d$_6$): δ ppm 3.69 (m, 8H), 4.13 (m, 2H), 4.35 (m, 2H), 4.90 (m, 1H), 7.28-7.31 (t, J = 6.9, 1.2 Hz, 1H), 7.44 (m, 1H), 7.90-7.92 (d, J = 7.8 Hz, 1H), 7.96-7.99 (d, J = 7.5 Hz, 1H), 8.70 (s, 1H), 11.04-11.06 (m, 1H), 11.20 (s, 1H); $^1$H-NMR (400 MHz, DMSO-d$_6$) + D$_2$O): δ ppm 3.69 (m, 8H), 4.09-4.15 (m, 2H), 4.32-4.38 (m, 2H), 4.96 (m, 1H), 7.30-7.33 (d, J = 7.8 Hz, 1H), 7.43-7.48 (m, 1H), 7.92-7.99 (m, 2H) |
| 254 | 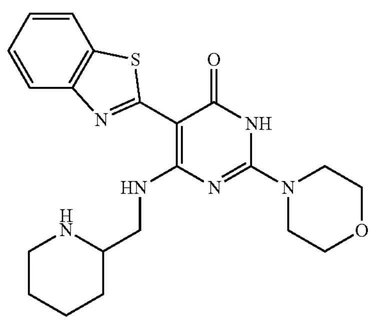 [SMILES: O=c1[nH]c(N2CCOCC2)nc(NCC2CCCCN2)c1-c1nc2ccccc2s1] | 5-(1,3-benzothiazol-2-yl)-2-(morpholin-4-yl)-6-[(piperidin-2-ylmethyl)amino]-3,4-dihydro-pyrimidin-4-one | 1,600 | 427 M + H | $^1$H-NMR (400 MHz, DMSO-d$_6$): δ ppm δ: 1.51-1.58 (m, 3H), 1.73-1.76 (m, 2H), 1.82-1.97 (m, 1H), 2.50-2.57 (m, 1H), 2.88-2.91 (m, 1H), 3.21-3.57 (m, 3H), 3.701-3.79 (m, 8H), 3.81-3.96 (m, 2H), 7.25 (t, J = 7.6 Hz, 1H), 7.40 (t, J = 8 Hz, J = 7.2 Hz, 1H), 7.78 (d, J = 8 Hz, 1H), 7.95 (d, J = 7.6 Hz, 1H), 8.40 (d, J = 9.2 Hz, 1H), 8.74 (d, J = 9.6 Hz, 1H), 10.84 (t, J = 5.6 Hz, J = 6 Hz, 1H), 11.14 (s, 1H) |
| 255 | 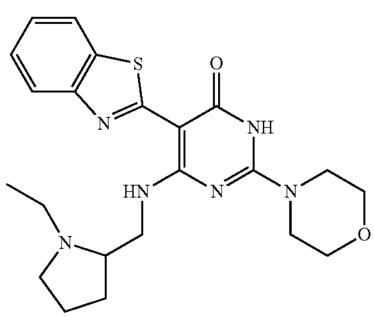 [SMILES: CCN1CCCC1CNc1nc(N2CCOCC2)[nH]c(=O)c1-c1nc2ccccc2s1] | 5-(1,3-benzothiazol-2-yl)-6-[[(1-ethylpyrrolidin-2-yl)methyl]amino]-2-(morpholin-4-yl)-3,4-dihydropyrimidin 4-one | 2,000 | 441 M + H | $^1$H-NMR (400 MHz, DMSO-d$_6$): δ ppm 1.23-1.18 (t, J = 7.2 Hz, 3H), 1.85-2.06 (m, 3H), 2.20-2.31 (m, 1H), 3.08-3.26 (m, 2H), 3.42-3.45 (m, 2H), 3.58-3.78 (m, 4H), 3.90-4.04 (m, 3H), 7.24-7.29 (t, J = 7.2 Hz, 1H), 7.39-7.45 (t, J = 6.9 Hz, 1H), 7.81-7.84 (d, J = 7.8 Hz, 1H), 7.95-7.97 (d, J = 7.8 Hz, 1H), 10.86-10.90 (m, 1H), 11.18 (s, 1H) |
| 256 | 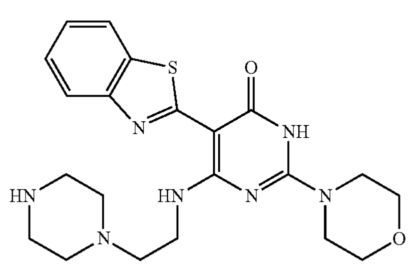 [SMILES: O=c1[nH]c(N2CCOCC2)nc(NCCN2CCNCC2)c1-c1nc2ccccc2s1] | 5-(1,3-benzothiazol-2-yl)-2-(morpholin-4-yl)-6-[[2-(piperazin-1-yl)ethyl]amino]-3,4-dihydropyrimidin-4-one | 55 | 442 M + H | $^1$H-NMR (400 MHz, DMSO-d$_6$): δ ppm 3.17-3.53 (m, 10H), 3.69 (m, 8H), 3.89 (m, 2H), 7.24-7.43 (m, 2H), 7.80-7.97 (m, 2H), 9.18 (s, 2H), 10.74 (m, 1H), 11.12 (s, 1H) |

-continued

| Exple | Structure | Name | IC$_{50}$ (nM) | MS (m/z) | NMR |
|---|---|---|---|---|---|
| 257 | 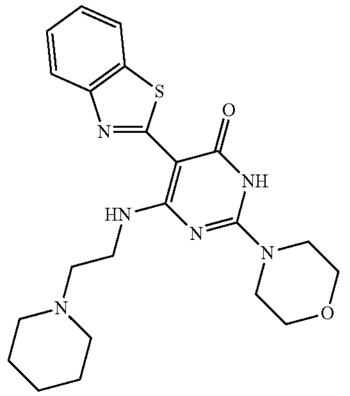 [SMILES: O=c1[nH]c(N2CCOCC2)nc(NCCN2CCCCC2)c1-c1nc2ccccc2s1] | 5-(1,3-benzothiazol-2-yl)-2-(morpholin-4-yl)-6-[[2-(piperidin-1-yl)ethyl]amino]-3,4-dihydropyrimidin-4-one | 2,000 | 441 M + H | $^1$H-NMR (400 MHz, DMSO-d$_6$): δ ppm 1.381-1.444 (m, 1H), 1.609-1.708 (m, 3H), 1.827-1.861 (m, 2H), 2.542-5.556 (m, 1H), 2.961-3.041 (m, 2H), 3.108-3.848 (m, 15H), 3.973-4.018 (m, 2H), 7.255-7.293 (t, J = 7.6 Hz, 1H), 7.411-7.448 (t, J = 7.4 Hz, 1H), 7.820-7.840 (d, J = 8.0 Hz, 1H), 7.956-7.976 (d, J = 8.0 Hz, 1H), 9.278 (s, 1H), 10.799 (s, 1H), 11.170 (s, 1H) |
| 258 | 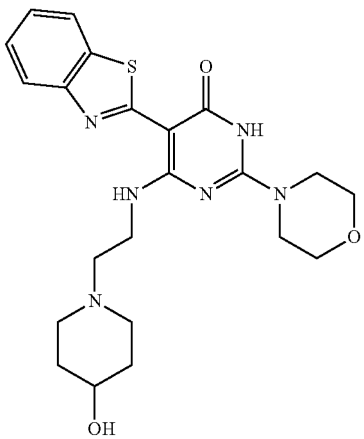 [SMILES: O=c1[nH]c(N2CCOCC2)nc(NCCN2CCC(O)CC2)c1-c1nc2ccccc2s1] | 5-(1,3-benzothiazol-2-yl)-6-[[2-(4-hydroxypiperidin-1-yl)ethyl]amino]-2-(morpholino-4-yl)-3,4-dihydropyrimidin-4-one | 780 | 457 M + H | $^1$H-NMR (400 MHz, DMSO-d$_6$): δ ppm 1.54-1.62 (m, 1H), 1.75 (d, J = 10.5 Hz, 1H), 1.83-1.89 (m, 1H), 1.97 (d, J = 12.8 Hz, 1H), 3.20-3.10 (m, 1H), 3.21-3.44 (m, 5H), 3.58-3.72 (m, 8H), 3.94-4.01 (m, 3H), 5.01 (brs, 1H), 7.25 (t, J = 7.4 Hz, 1H), 7.41 (t, J = 7.6 Hz, 1H), 7.82 (d, J = 8.0 Hz, 1H), 7.95 (d, J = 7.6 Hz, 1H), 9.40 (brs, 1H), 10.78 (s, 1H), 11.16 (s, 1H) |
| 259 | 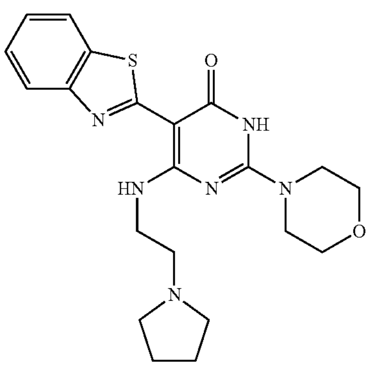 [SMILES: O=c1[nH]c(N2CCOCC2)nc(NCCN2CCCC2)c1-c1nc2ccccc2s1] | 5-(1,3-benzothiazol-2-yl)-2-(morpholin-4-yl)-6-[[2-(pyrrolidin-1-yl)ethyl]amino]-3,4-dihydropyrimidin-4-one | 2,200 | 427 M + H | $^1$H-NMR (400 MHz, DMSO-d$_6$): δ ppm 1.86-1.91 (m, 2H), 1.95-2.03 (m, 2H), 3.02-3.3.12 (m, 2H), 3.40-3.53 (m, 2H), 3.63-3.88 (m, 10H), 3.95 (d, J = 12 Hz, 2H), 7.23 (m, 1H), 7.41 (m, 1H), 7.83 (d, J = 8 Hz, 1H), 7.96 (d, J = 7.6 Hz, 1H), 9.71 (brs, 1H), 10.78 (t, J = 5.6 Hz, 1H), 11.12 (s, 1H) |
| 260 | 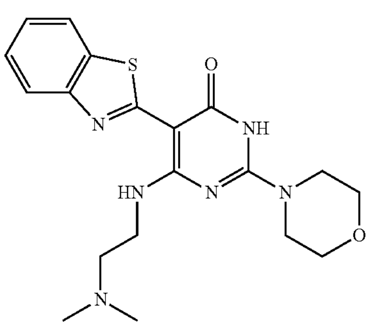 [SMILES: CN(C)CCNc1nc(N2CCOCC2)[nH]c(=O)c1-c1nc2ccccc2s1] | 5-(1,3-benzothiazol-2-yl)-6-[[2-(dimethylamino)ethyl]amino]-2-(morpholin-4-yl)-3,4-dihydropyrimidin-4-one | 1,600 | 401 M + H | $^1$H-NMR (300 MHz, D$_2$O): δ ppm 2.90 (s, 6H), 3.12 (s, 4H), 3.32 (s, 2H), 3.54 (s, 4H), 3.71 (s, 2H), 7.19 (t, J = 6.9 Hz, 1H), 7.27 (t, J = 7.8 Hz, 1H), 7.56 (d, J = 7.2 Hz, 1H), 7.70 (d, J = 6.6 Hz, 1H), 8.35 (s, 1H) |

-continued

| Exple | Structure | Name | IC$_{50}$ (nM) | MS (m/z) | NMR |
|---|---|---|---|---|---|
| 261 | 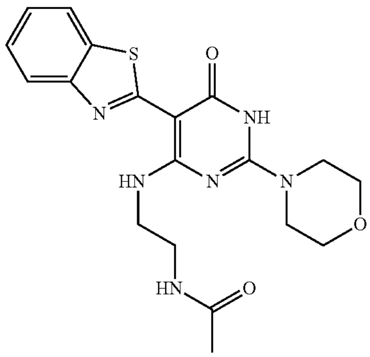 [SMILES: CC(=O)NCCNc1nc(N2CCOCC2)[nH]c(=O)c1-c1nc2ccccc2s1] | N-(2-[[5-(1,3-benzothiazol-2-yl)-2-(morpholin-4-yl)-6-oxo-1,6-dihydropyrimidin-4-yl]amino]ethyl)acetamide | 8,200 | 415 M + H | $^1$H-NMR (400 MHz, DMSO-d$_6$): δ ppm 1.82 (s, 3H), 3.58-3.69 (m, 10H), 7.19-7.24 (t, J = 6.4 Hz, 1H), 7.35-7.40 (t, J = 6.4 Hz, 1H), 7.80-7.83 (d, J = 10.8 Hz, 1H), 7.89-7.92 (d, J = 10.4 Hz, 1H), 10.62-10.65 (m, 2H) |
| 262 | 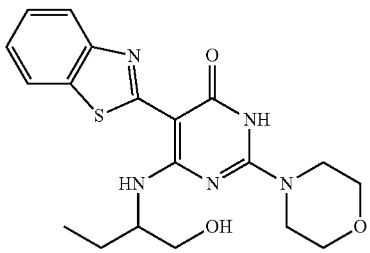 [SMILES: CCC(CO)Nc1nc(N2CCOCC2)[nH]c(=O)c1-c1nc2ccccc2s1] | 5-(benzo[d]thiazol-2-yl)-6-(1-hydroxy-butan-2-ylamino)-2-morpholino-pyrimidin-4(3H)-one | 330 | 402 M + H | $^1$H-NMR (400 MHz, DMSO-d$_6$): δ ppm 1.00 (m, 1H), 1.63-1.82 (m, 2H), 3.49-3.55 (m, 1H), 3.65-3.69 (s, 9H), 4.16-4.17 (m, 1H), 4.85-4.88 (m, 1H), 7.23-7.27 (t, J = 7.6 Hz, 1H), 7.38-7.41 (t, J = 7.2 Hz, 1H), 7.71-7.73 (d, J = 8.0 Hz, 1H), 7.94-7.95 (d, J = 7.6 Hz, 1H), 10.81-10.83 (s, 1H), 10.98 (s, 1H) |
| 263 | 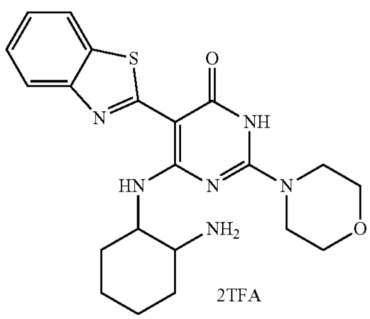 [SMILES: NC1CCCCC1Nc1nc(N2CCOCC2)[nH]c(=O)c1-c1nc2ccccc2s1] | 6-(2-aminocyclohexylamino)-5-(benzo[d]thiazol-2-yl)-2-morpholino-pyrimidin-4(3H)-one | 230 | 427 M + H | $^1$H-NMR (300 MHz, DMSO-d$_6$): δ ppm 1.51~1.79 (m, 2H), 1.84~2.23 (m, 6H), 3.57~3.73 (m, 8H), 4.49 (s, 2H), 7.29~7.42 (m, 1H), 7.43-7.48 (m, 1H), 7.79~7.91 (m, 2H) |
| 264 | 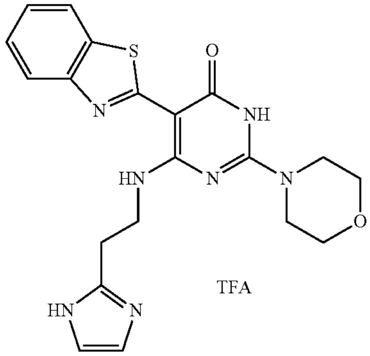 [SMILES: O=c1[nH]c(N2CCOCC2)nc(NCCc2ncc[nH]2)c1-c1nc2ccccc2s1] | 6-(2-(1H-imidazol-2-yl)ethylamino)-5-(benzo[d]thiazol-2-yl)-2-morpholino-pyrimidin-4(3H)-one | 180 | 424 M + H | $^1$H-NMR (400 MHz, DMSO-d6): δ ppm 3.03-3.06 (m, 2H), 3.70 (m, 8H), 3.91-3.95 (m, 2H), 7.24-7.27 (m, 1H), 7.38-7.42 (m, 1H), 7.56 (s, 1H), 7.68-7.72 (m, 1H), 7.93 (d, J = 8.0 Hz, 1H), 8.97 (s, 1H), 10.68-10.70 (m, 1H), 11.06 (s, 1H), 14.19 (d, J = 17.6 Hz, 2H) |

-continued

| Exple | Structure | Name | IC$_{50}$ (nM) | MS (m/z) | NMR |
|---|---|---|---|---|---|
| 265 | 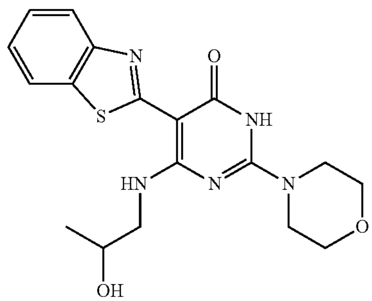 [SMILES: CC(O)CNc1nc(N2CCOCC2)[nH]c(=O)c1-c1nc2ccccc2s1] | 5-(benzo[d]thiazol-2-yl)-6-(2-hydroxypropyl amino)-2-morpholino-pyrimidin-4(3H)-one | 780 | 388 M + H | $^1$H-NMR (400 MHz, DMSO-d6): δ ppm 1.18 (d, J = 6.4 Hz, 3H), 3.40-3.50 (m, 1H), 3.55-3.75 (m, 9H), 3.85-3.92 (m, 1H), 4.92 (d, J = 4.8 Hz, 1H), 7.23-7.27 (t, J = 7.6 Hz, 1H), 7.38-7.42 (t, J = 7.2 Hz, 1H), 7.72-7.74 (d, J = 8.0 Hz, 1H), 7.93-7.95 (d, J = 7.2 Hz, 1H), 10.85-10.87 (d, J = 5.2 Hz, 1H), 10.98 (s, 1H); |
| 266 | 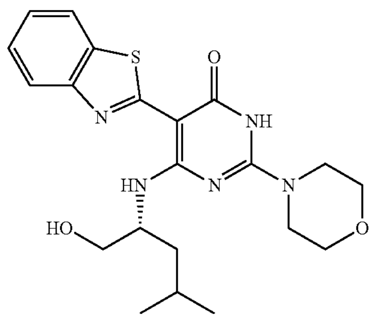 [SMILES: CC(C)C[C@H](CO)Nc1nc(N2CCOCC2)[nH]c(=O)c1-c1nc2ccccc2s1] | (R)-5-(benzo[d]thiazol-2-yl)-6-(1-hydroxy-4-methylpentan-2-ylamino)-2-morpholinopyrimidin-4(3H)-one | 2,500 | 430 M + H | $^1$H-NMR (400 MHz, DMSO-d6): δ ppm 0.94 (d, J = 6.4 Hz, 6H), 1.51-1.63 (m, 2H), 1.67-1.76 (m, 1H), 3.48-3.52 (m, 1H), 3.53-3.63 (m, 1H), 3.64-3.69 (m, 8H), 4.30 (d, J = 4.4 Hz, 1H), 4.85 (t, J = 5.2 Hz, 1H), 7.23 (t, J = 7.6 Hz, 1H), 7.34 (t, J = 8, 7.2 Hz, 1H), 7.71 (d, J = 8 Hz, 1H), 7.93 (d, J = 7.6 Hz, 1H), 10.796 (d, J = 8 Hz, 1H), 10.90 (s, 1H); |
| 267 | 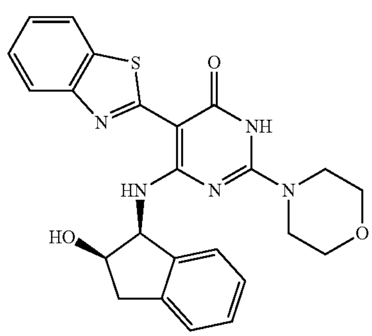 [SMILES: O=c1[nH]c(N2CCOCC2)nc(N[C@H]2c3ccccc3C[C@H]2O)c1-c1nc2ccccc2s1] | 5-(benzo[d]thiazol-2-yl)-6-((1S,2R)-2-hydroxy-2,3-dihydro-1H-inden-1-ylamino)-2-morpholinopyrimidin-4(3H)-one | 8,300 | 462 M + H | $^1$H-NMR (400 MHz, DMSO-d6): δ ppm 2.89 (d, J = 16.0 Hz, 1H), 3.17 (d, J = 16.0 Hz, 1H), 3.66-3.69 (m, 8H), 4.62 (s, 1H), 5.48 (s, 1H), 5.66 (s, 1H), 7.16-7.36 (m, 6H), 7.56 (d, J = 8.0 Hz, 1H), 7.91 (d, J = 8.0 Hz, 1H), 9.81 (brs, 1H), 11.32 (s, 1H); |
| 268 | 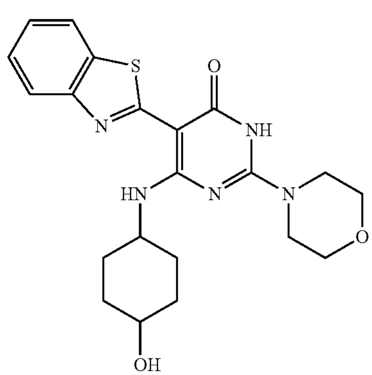 [SMILES: O=c1[nH]c(N2CCOCC2)nc(NC2CCC(O)CC2)c1-c1nc2ccccc2s1] | 5-(benzo[d]thiazol-2-yl)-6-(4-hydroxycyclo-hexylamino)-2-morpholinopyrimidin-4(3H)-one | 620 | 428 M + H | $^1$H-NMR (400 MHz, DMSO-d6): δ ppm δ 1.06-1.49 (m, 4H), 1.88-1.914 (m, 2H), 2.057-2.13 (m, 2H), 3.49-3.69 (m, 9H), 4.01 (d, J = 3.6 Hz, 1H), 4.59 (d, J = 4 Hz, 1H), 7.23 (t, J = 7.2 Hz, 1H), 7.374-7.414 (m, 1H), 7.74 (d, J = 8 Hz, 1H), 7.93 (d, J = 7.6 Hz, 1H), 10.75 (d, J = 7.2 Hz, 1H), 10.99 (s, 1H) |

-continued

| Exple | Structure | Name | IC$_{50}$ (nM) | MS (m/z) | NMR |
|---|---|---|---|---|---|
| 269 | 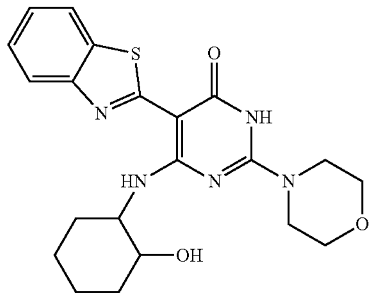 [SMILES: O=c1[nH]c(N2CCOCC2)nc(NC2CCCCC2O)c1-c1nc2ccccc2s1] | 5-(benzo[d]thiazol-2-yl)-6-(2-hydroxycyclohexyl-amino)-2-morpholinopyrimidin-4(3H)-one | 5,600 | 428 M + H | 1H-NMR (300 MHz, DMSO-d6): ppm δ 1.38 (m, 2H), 1.58-1.74 (m, 6H), 3.67 (m, 8H), 3.87 (m, 1H), 4.22 (m, 1H), 4.86-4.88 (d, J = 5.6 Hz, 1H), 7.23-7.29 (t, J = 10.0 Hz, 1H), 7.36-7.42 (t, J = 10.4 Hz, 1H), 7.68-7.72 (d, J = 10.8 Hz, 1H), 7.91-7.94 (d, J = 10.4 Hz, 1H), 10.78-10.99 (br, 1H), 11.01 (s, 1H); |
| 270 | 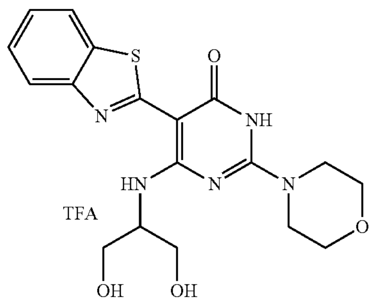 [SMILES: O=c1[nH]c(N2CCOCC2)nc(NC(CO)CO)c1-c1nc2ccccc2s1] | 5-(benzo[d]thiazol-2-yl)-6-(1,3-dihydroxy-propan-2-ylamino)-2-morpholinopyrimidin-4(3H)-one | 110 | 404 M + H | $^1$H-NMR (300 MHz, DMSO-d6): ppm δ 3.56~3.72 (m, 12H), 4.19 (s, 1H), 4.69~4.88 (br, 1H), 7.21-7.26 (m, 1H), 7.36~7.41 (m, 1H), 7.69~7.72 (d, J = 7.8 Hz, 1H), 7.92~7.94 (d, J = 7.5 Hz, 1H), 10.87~10.98 (m, 2H) |
| 271 | 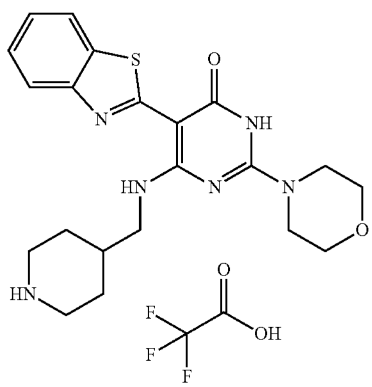 | 5-(1,3-benzothiazol-2-yl)-2-(morpholin-4-yl)-6-[(piperidin-4-ylmethyl)amino]-3,4-dihydropyrimidin-4-one; trifluoroacetic acid | 330 | 427 M + H | $^1$H-NMR (300 MHz, CD$_3$OD-d$_4$): δppm 1.42-1.55 (m, 2H), 1.97 (d, J = 11.1 Hz, 3H), 2.88 (t, J = 12.7 Hz, 2H), 3.32 (d, J = 12.3 Hz, 2H), 3.55-3.68 (m, 10H), 7.13 (t, J = 7.5 Hz, 1H), 7.27 (t, J = 7.6 Hz, 1H), 7.67 (d, J = 7.8 Hz, 1H), 7.75 (d, J = 7.8 Hz, 1H) |

The following examples were synthezized in a sequence similar to Scheme 18, substituting 2-quinoline for benzothiazole.

| Exple | Structure | Name | IC$_{50}$ (nM) | MS (m/z) | NMR |
|---|---|---|---|---|---|
| 272 | 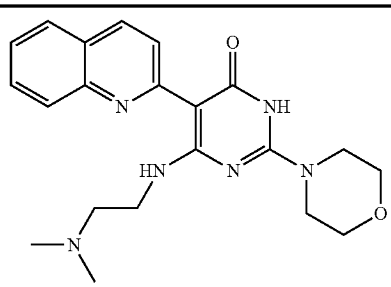 | 6-[[2-(dimethylamino)ethyl]amino]-2-(morpholin-4-yl)-5-(quinolin-2-yl)-3,4-dihydropyrimidin-4-one | 1,600 | 395 M + H | $^1$H-NMR (300 MHz, DMSO-d$_6$): δ ppm 2.27 (s, 6H), 2.50 (s, 2H), 3.62 (s, 10H), 7.34 (t, J = 7.5 Hz 1H), 7.58 (t, J = 7.6 Hz 1H), 7.76 (d, J = 7.8 Hz, 1H), 7.84 (d, J = 8.4 Hz, 1H), 8.05 (d, J = 9.3 Hz, 1H), 8.93 (d, J = 9.0 Hz, 1H), 10.53 (brs, 1H) |

-continued

| Exple | Structure | Name | IC$_{50}$ (nM) | MS (m/z) | NMR |
|---|---|---|---|---|---|
| 273 | 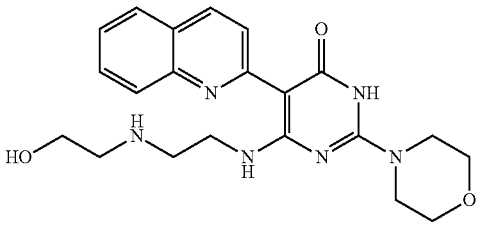 [SMILES: O=c1[nH]c(N2CCOCC2)nc(NCCNCCO)c1-c1ccc2ccccc2n1] | 6-([2-[(2-hydroxyethyl)amino]ethyl]amino)-2-(morpholin-4-yl)-5-(quinolin-2-yl)-3,4-dihydropyrimidin-4-one | 670 | 411 M+H | $^1$H-NMR (300 MHz, DMSO-d$_6$): δ ppm 2.65-2.68 (t, J = 5.7 Hz, 2H), 2.79-2.83 (t, J = 6.0 Hz, 2H), 3.47-3.51 (m, 2H), 3.70-3.81 (m, 1H), 3.56-3.62 (m, 9H), 4.45 (m, 1H), 7.35-7.40 (t, J = 7.2 Hz, 1H), 7.56-7.61 (t, J = 8.1 Hz, 1H), 7.74-7.76 (d, J = 7.8 Hz, 1H), 7.91-7.94 (d, J = 8.4 Hz, 1H), 8.05-8.08 (d, J = 9.0 Hz, 1H), 8.93-8.96 (d, J = 9.0 Hz, 1H), 12.11-12.14 (m, 1H) |
| 274 | 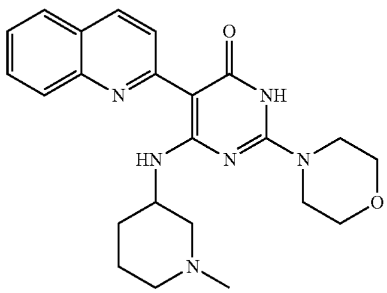 [SMILES: CN1CCCC(Nc2nc(N3CCOCC3)[nH]c(=O)c2-c2ccc3ccccc3n2)C1] | 6-[(1-methylpiperidin-3-yl)amino]-2-(morpholin-4-yl)-5-(quinolin-2-yl)-3,4-dihydropyrimidin-4-one | 720 | 421 M+H | $^1$H-NMR (400 MHz, DMSO-d$_6$): δ ppm 1.66-1.74 (m, 1H), 1.93-2.30 (m, 3H), 2.82-3.06 (m, 5H), 3.50-3.87 (m, 10 H), 4.57-4.76 (m, 1H), 7.63-7.71 (m, 1H), 7.86-8.06 (m, 3H), 8.43 (s, 1H), 8.55 (s, 1H), |
| 275 | 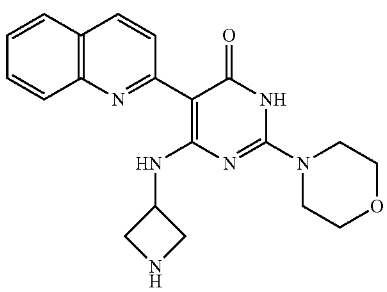 [SMILES: O=c1[nH]c(N2CCOCC2)nc(NC2CNC2)c1-c1ccc2ccccc2n1] | 6-[(azetidin-3-yl)amino]-2-(morpholin-4-yl)-5-(quinolin-2-yl)-3,4-dihydropyrimidin-4-one | 150 | 379 M+H | $^1$H-NMR (400 MHz, DMSO d$_6$): δ ppm 3.60 (m, 4H), 3.74-3.89 (m, 4H), 4.04-4.13 (m, 2H), 4.23-4.34 (m, 2H), 4.86-4.90 (m, 1H), 7.64-7.67 (t, J = 6.4 Hz, J = 7.2 Hz, 1H), 7.82-7.86 (m, 2H), 7.94-7.96 (d, J = 8.4 Hz, 1H), 7.99-8.02 (d, J = 8.0 Hz, 1H), 8.47-8.50 (d, J = 9.2 Hz, 1H) |
| 276 | 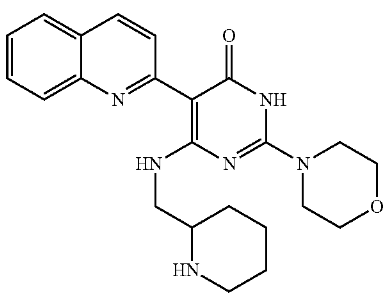 [SMILES: O=c1[nH]c(N2CCOCC2)nc(NCC2CCCCN2)c1-c1ccc2ccccc2n1] | 2-morpholino-6-(piperidin-2-ylmethylamino)-5-(quinolin-2-yl)pyrimidin-4(3H)-one | 340 | 421 M+H | $^1$H-NMR (400 MHz, DMSO-d$_6$): δ ppm 1.325-1.388 (m, 3H), 1.538-1.656 (m, 2H), 1.755 (m, 1H), 2.571-2.639 (m, 3H), 2.730-2.756 (m, 1H), 3.067-3.103 (m, 1H), 3.420-3.499 (m, 2H), 3.616-3.622 (m, 8H), 7.389-7.438 (t, J = 7.5 Hz, J = 7.2 Hz, 1H), 7.622-7.670 (t, J = 7.2 Hz, 1H), 7.784-7.812 (d, J = 8.4 Hz, 1H), 7.947-7.975 (d, J = 8.4 Hz, 1H), 8.099-8.130 (d, J = 9.3 Hz, 1H), 8.994-9.025 (d, J = 9.3 Hz, 1H), 12.257 (s, 1H) |
| 277 | 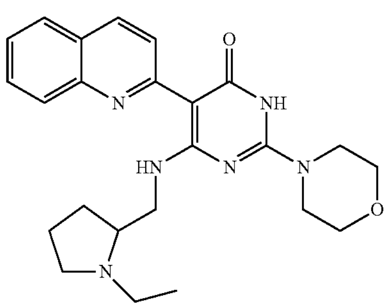 [SMILES: CCN1CCCC1CNc1nc(N2CCOCC2)[nH]c(=O)c1-c1ccc2ccccc2n1] | 6-((1-ethylpyrrolidin-2-yl)methylamino)-2-morpholino-5-(quinolin-2-yl)pyrimidin-4(3H)-one | 1,600 | 434 M+H | $^1$H-NMR (400 MHz, DMSO-d$_6$): δ ppm 1.38 (t, J = 7.2 Hz, 3H), 2.02-2.18 (m, 3H), 2.27-2.40 (m, 1H), 3.17-3.27 (m, 2H), 3.53-3.58 (m, 1H), 3.75-3.88 (m, 10H), 3.90-4.04 (m, 2H), 7.74 (t, J = 7.8 Hz, 1H), 7.93-8.09 (m, 3H), 8.21 (d, J = 9.2 Hz, 1H), 8.62 (d, J = 9.2 Hz, 1H) |

| Exple | Structure | Name | IC$_{50}$ (nM) | MS (m/z) | NMR |
|---|---|---|---|---|---|
| 278 | 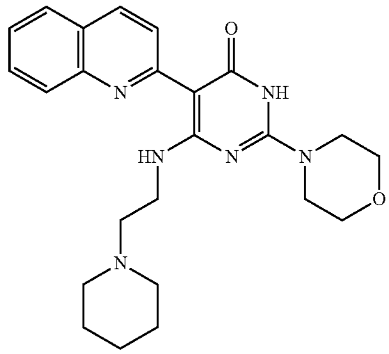 [SMILES: O=c1[nH]c(N2CCOCC2)nc(NCCN2CCCCC2)c1-c1ccc2ccccc2n1] | 2-(morpholin-4-yl)-6-[[2-(piperidin-1-yl)ethyl]amino]-5-(quinolin-2-yl)-3,4-dihydropyrimidin-4-one | 2,800 | 435 M + H | $^1$H-NMR (400 MHz, DMSO-d$_6$): δ ppm 1.430-1.438 (m, 2H), 1.559-1.586 (m, 4H), 2.453 (m, 4H), 2.511 (m, 2H), 3.646-3.671 (m, 10H), 7.410-7.447 (t, J = 7.6 Hz, 1H), 7.625-7.661 (t, J = 14.4 Hz, 1H), 7.799-7.818 (d, J = 1.6 Hz, 1H), 8.015-8.036 (d, J = 6.3 Hz, 1H), 8.110-8.133 (d, J = 9.2 Hz, 1H), 8.968-8.991 (d, J = 9.2 Hz, 1H), 10.577 (s, 1H), 12.019 (s, 1H) |
| 279 | 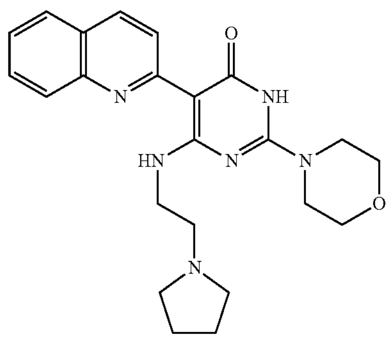 [SMILES: O=c1[nH]c(N2CCOCC2)nc(NCCN2CCCC2)c1-c1ccc2ccccc2n1] | 2-(morpholin-4-yl)-6-[[2-(pyrrolidin-1-yl)ethyl]amino]-5-(quinolin-2-yl)-3,4-dihydropyrimidin-4-one | 4,900 | 421 M + H | $^1$H-NMR (300 MHz, DMSO-d6): δ ppm 1.751 (s, 4H), 2.570 (d, J = 4.2 Hz, 6H), 3.622 (s, 10H), 7.344 (t, J = 7.5 Hz, 1H), 7.567 (t, J = 7.8 Hz, 7.2 Hz, 1H), 7.741 (d, J = 7.5 Hz, 1H), 7.857 (d, J = 8.1 Hz, 1H), 8.054 (d, J = 9.3 Hz, 1H), 8.932 (d, J = 9 Hz, 1H), 10.544 (brs, 1H), 12.171 (s, 1H) |
| 280 | 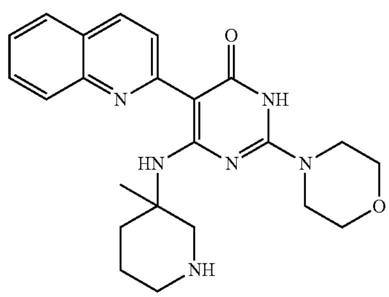 | 6-[(3-methylpiperidin-3-yl)amino]-2-(morpholin-4-yl)-5-(quinolin-2-yl)-3,4-dihydropyrimidin-4-one | 130 | 430 M + H | $^1$H-NMR (300 MHz, CD$_3$OD): δ ppm 1.67 (s, 3H), 1.88~1.93 (m, 1H), 2.04~2.09 (m, 1H), 2.27~2.37 (m, 2H), 3.06~3.13 (m, 2H), 3.68~3.80 (m, 4H), 3.81~3.83 (m, 4H), 4.61~4.65 (d, J = 12.0 Hz, 1H), 7.55~7.60 (m, 1H), 7.75~7.81 (m, 1H), 7.89~7.93 (m, 2H), 8.29~8.33 (d, J = 9.3 Hz, 1H) 8.61~8.64 (d, J = 9.0 Hz, 1H); |
| 281 | 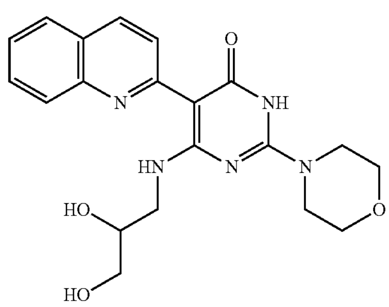 [SMILES: O=c1[nH]c(N2CCOCC2)nc(NCC(O)CO)c1-c1ccc2ccccc2n1] | 6-[(2,3-dihydroxypropyl)amino]-2-(morpholin-4-yl)-5-(quinolin-2-yl)-3,4-dihydropyrimidin-4-one | 1,700 | 398 M + H | $^1$H-NMR (400 MHz, DMSO-d$_6$): δ ppm 3.35-3.46 (m, 3H), 3.55-3.75 (m, 10H), 4.63 (d, J = 15.3 Hz, 1H), 5.03 (s, 1H), 7.35 (t, J = 6.9, 7.2 Hz, 1H), 7.56-7.61 (m, 1H), 7.74 (d, J = 7.5 Hz, 1H), 7.87 (d, J = 8.4 Hz, 1H), 8.06 (d, J = 9.3 Hz, 1H), 8.274 (s, 1H), 8.954 (d, J = 9 Hz, 1H), 10.507 (s, 1H), 12.256 (d, J = 11.4 Hz, 1H) |

| Exple | Structure | Name | IC$_{50}$ (nM) | MS (m/z) | NMR |
|---|---|---|---|---|---|
| 282 | 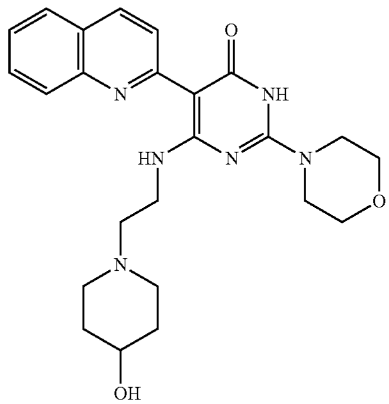 [SMILES: O=c1[nH]c(N2CCOCC2)nc(NCCN2CCC(O)CC2)c1-c1ccc2ccccc2n1] | 6-[[2-(4-hydroxypiperidin-1-yl)ethyl]amino]-2-(morpholin-4-yl)-5-(quinolin-2-yl)-3,4-dihydropyrimidin-4-one | 2,200 | 451 M+H | $^{1}$H-NMR (300 MHz, DMSO-d$_{6}$): δ ppm 1.44-1.94 (m, 4H), 2.89-3.39 (m, 4H), 3.51-3.69 (m, 10H), 3.92 (s, 3H), 7.46 (t, J = 7.2 Hz, 1H), 7.68 (t, J = 7.6 Hz, 1H), 7.85 (d, J = 8.4 Hz, 1H), 8.00 (d, J = 8.4 Hz, 1H), 8.20 (d, J = 9.3 Hz, 1H), 8.91 (s, 1H), 9.29 (brs, 1H), 10.81 (brs, 1H), 11.70 (brs, 1H) |
| 283 | 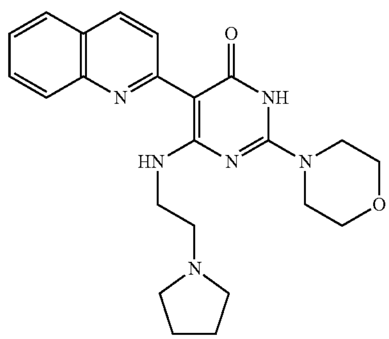 [SMILES: O=c1[nH]c(N2CCOCC2)nc(NCCN2CCCC2)c1-c1ccc2ccccc2n1] | 2-(morpholin-4-yl)-6-[[2-(pyrrolidin-1-yl)ethyl]amino]-5-(quinolin-2-yl)-3,4-dihydropyrimidin-4-one | 4,900 | 421 M+H | $^{1}$H-NMR (400 MHz, DMSO-d$_{6}$): δ ppm 1.751 (s, 4H), 2.570 (d, J = 4.2 Hz, 6H), 3.622 (s, 10H), 7.344 (t, J = 7.5 Hz, 1H), 7.567 (t, J = 7.8 Hz, 7.2 Hz, 1H), 7.741 (d, J = 7.5 Hz, 1H), 7.857 (d, J = 8.1 Hz, 1H), 8.054 (d, J = 9.3 Hz, 1H), 8.932 (d, J = 9 Hz, 1H), 10.544 (brs, 1H), 12.171 (s, 1H) |

Example 284

5-(1,3-benzothiazol-2-yl)-2-(oxan-4-yl)-6-[[(3R)-piperidin-3-yl]amino]-4,5-dihydropyrimidin-4-one

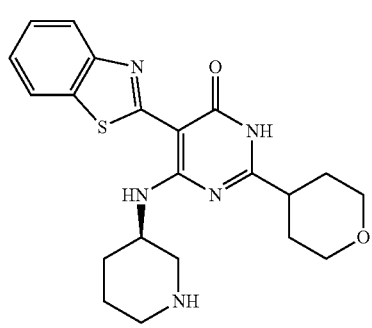 [SMILES: O=c1[nH]c(C2CCOCC2)nc(N[C@@H]2CCCNC2)c1-c1nc2ccccc2s1]

Step 1. Methyl oxane-4-carboxylate (Compound 54)

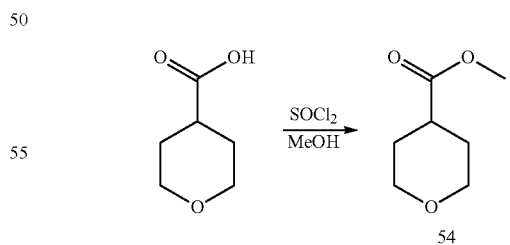

Into a solution of oxane-4-carboxylic acid (50 mg, 0.38 mmol, 1.00 equiv) in methanol (10 mL) was added thionyl chloride (46 mg, 0.39 mmol, 1.01 equiv) dropwise with stirring at room temperature. The resulting solution was stirred for 3 h at room temperature. Concentration under reducing pressure gave the title compound, which was used directly for next step without further purification (brown oil).

Step 2. Oxane-4-carboximidamide (Compound 55)

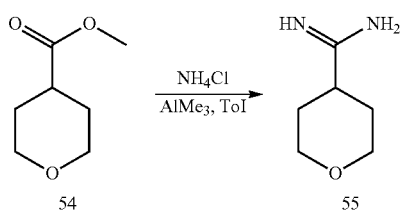

Into a suspension of ammonium chloride (2.65 g, 49.54 mmol, 4.96 equiv) in Toluene (100 mL) was added trimethyl aluminium (50 mL, 1M in hexane) dropwise under nitrogen at 0° C. After stirring for 1 h at 0° C., methyl oxane-4-carboxylate (1.44 g, 9.99 mmol, 1.00 equiv) was added at 0° C. The resulting mixture was stirred overnight at 80° C. in an oil bath, cooled down to room temperature and then quenched by the addition of 100 mL of methanol. Upon filtration, the filtrate was concentrated under reducing pressure. The residue was diluted with 200 mL of ethanol. The pH value of the solution was adjusted to 10 with sodium hydroxide (aq). The resulting mixture was concentrated under reducing pressure and diluted with 200 mL of ethanol. Filtration and concentration under reducing pressure gave 930 mg of the title compound as a white solid, which was used directly for next step without purification.

Step 3. 5-(1,3-benzothiazol-2-yl)-2-(oxan-4-yl)pyrimidine-4,6-diol (Compound 56)

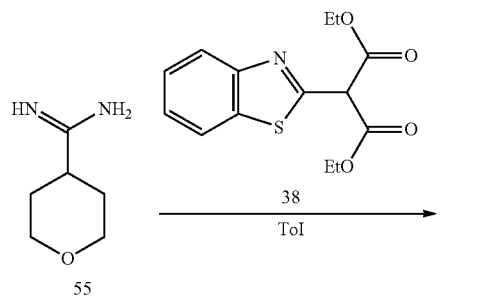

A solution of oxane-4-carboximidamide (160 mg, 1.25 mmol, 1.00 equiv), and 1,3-diethyl 2-(1,3-benzothiazol-2-yl) propanedioate (366 mg, 1.25 mmol, 1.00 equiv) in Toluene (3 mL) was heated for 3 h at 110° C. in an oil bath. After concentrated under reducing pressure, 460 mg (crude) of the title compound was obtained as a white solid, which was used directly for next step without further purification. MS m/z [M+H]+ (ESI): 330.

Step 4. 2-[4,6-dichloro-2-(oxan-4-yl)pyrimidin-5-yl]-1,3-benzothiazole (Compound 57)

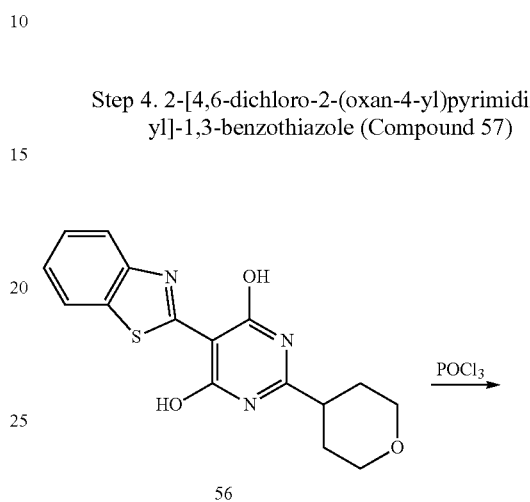

A solution of 5-(1,3-benzothiazol-2-yl)-2-(oxan-4-yl)pyrimidine-4,6-diol (100 mg, 0.30 mmol, 1.00 equiv) in phosphoryl trichloride (2 mL) was heated overnight at 90° C. in an oil bath. Concentration under reducing pressure gave 100 mg of the title compound as a yellow solid, which was used directly for next step without further purification. MS m/z [M+H]+ (ESI): 366.

Step 5. Tert-butyl (3R)-3-[[5-(1,3-benzothiazol-2-yl)-6-chloro-2-(oxan-4-yl)pyrimidin-4-yl]amino]piperidine-1-carboxylate (Compound 58)

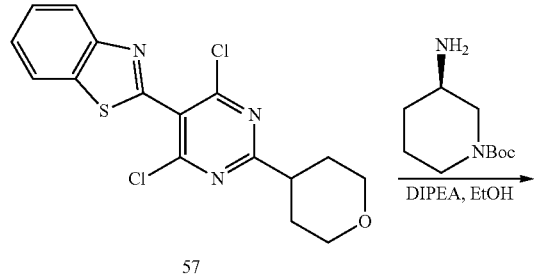

57

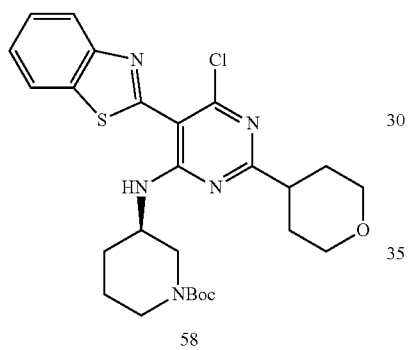

58

Following the same procedure as in step 4 of Example 21 using 2-[4,6-dichloro-2-(oxan-4-yl)pyrimidin-5-yl]-1,3-benzothiazole (90 mg, 0.25 mmol, 1.00 equiv), tert-butyl (3R)-3-aminopiperidine-1-carboxylate (49 mg, 0.24 mmol, 1.00 equiv), and N,N-Diisopropylethylamine (63 mg, 0.49 mmol, 1.98 equiv) in ethanol (2 mL). The reaction mixture was concentrated under reducing pressure to afford 100 mg of the title compound as a yellow solid, which was used directly for next step without further purification. $^1$H-NMR (CDCl$_3$, 400 MHz,): δ ppm 1.29 (s, 9H), 1.73 (s, 1H), 1.90-2.08 (m, 8H), 2.98 (m, 8H), 3.00 (m, 1H), 3.30-4.48 (m, 10H), 7.33-7.50 (m, 2H), 7.46-8.06 (m, 4H), 11.09 (d, J=6.8, 1H).

Step 6. 5-(1,3-benzothiazol-2-yl)-2-(oxan-4-yl)-6-[[(3R)-piperidin-3-yl]amino]-4,5-dihydropyrimidin-4-one (Example 284)

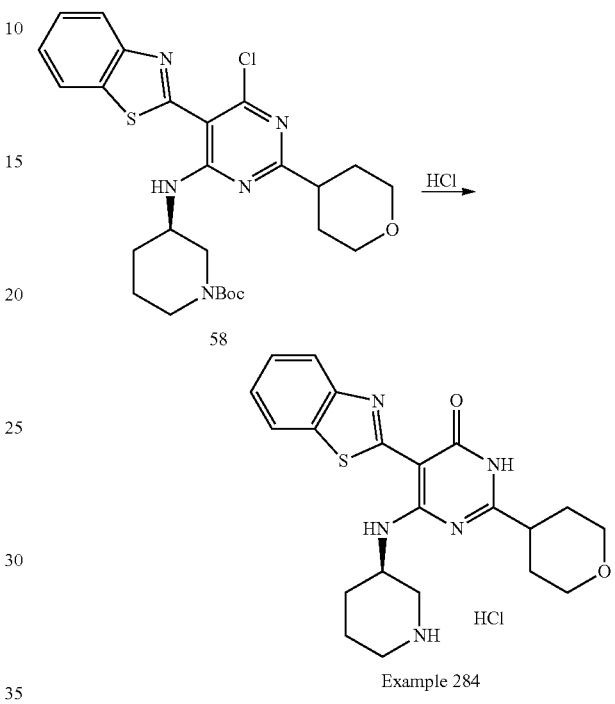

Example 284

Following the same procedure as in step 5 of Example 21 using tert-butyl (3R)-3-[[5-(1,3-benzothiazol-2-yl)-6-chloro-2-(oxan-4-yl)pyrimidin-4-yl]amino]piperidine-1-carboxylate (100 mg, 0.19 mmol, 1.00 equiv) and concentrated hydrochloric acid (3 mL). The crude product was re-crystallized from methanol/Acetonitrile in the ratio of 5:1 to afford the title compound as HCl salt. as an off-white solid. $^1$H-NMR (400 MHz, DMSO-d$_6$): δ ppm 1.80-1.84 (m, 6H), 2.01 (s, 1H), 2.14 (m, 1H), 2.83-3.07 (m, 7H), 3.94 (d, J=10.8 Hz, 2H), 4.48 (s, 1H), 7.33-7.50 (m, 2H), 7.90-8.02 (m, 2H), 10.94 (s, 1H); MS m/z [M+H]+ (ESI): 412. IRAK4 IC$_{50}$=380 nM The following examples were synthesized according to Scheme 9.

| Exple | Structure | Name | IC$_{50}$ (nM) | MS (m/z) |
|---|---|---|---|---|
| 285 | 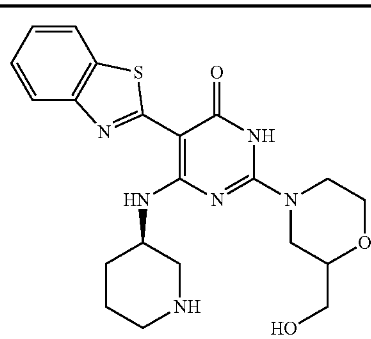 | 5-(1,3-benzothiazol-2-yl)-2-[2-(hydroxymethyl)morpholin-4-yl]-6-[[(3R)-piperidin-3-yl]amino]-3,4-dihydropyrimidin-4-one | 43 | 443 M + H |

-continued

| Exple | Structure | Name | IC$_{50}$ (nM) | MS (m/z) |
|---|---|---|---|---|
| 286 | 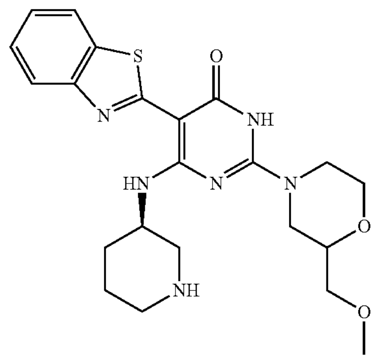 [SMILES: COCC1CN(c2nc(N[C@@H]3CCCNC3)c(-c3nc4ccccc4s3)c(=O)[nH]2)CCO1] | 5-(benzo[d]thiazol-2-yl)-2-(2-(methoxymethyl)morpholino)-6-((R)-piperidin-3-ylamino)pyrimidin-4(3H)-one | 81 | 457 M + H |
| 287 | 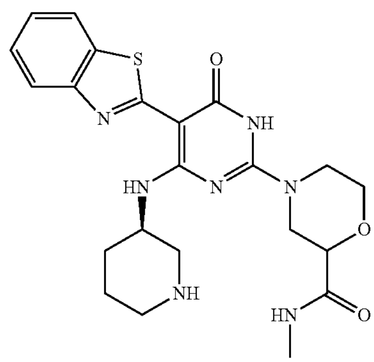 [SMILES: CNC(=O)C1CN(c2nc(N[C@@H]3CCCNC3)c(-c3nc4ccccc4s3)c(=O)[nH]2)CCO1] | 4-(5-(benzo[d]thiazol-2-yl)-6-oxo-4-((R)-piperidin-3-ylamino)-1,6-dihydropyrimidin-2-yl)-N-methylmorpholine-2-carboxamide | 110 | 470 M + H |
| 288 | 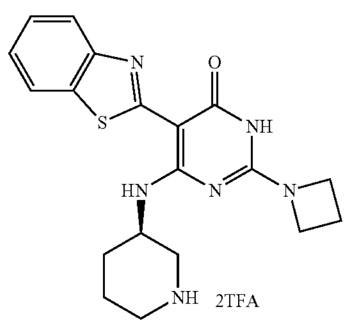 [SMILES: O=c1[nH]c(N2CCC2)nc(N[C@@H]2CCCNC2)c1-c1nc2ccccc2s1] | (R)-2-(azetidin-1-yl)-5-(benzo[d]thiazol-2-yl)-6-(piperidin-3-ylamino)pyrimidin-4(3H)-one | 2,000 | 383 M + H |
| 289 | 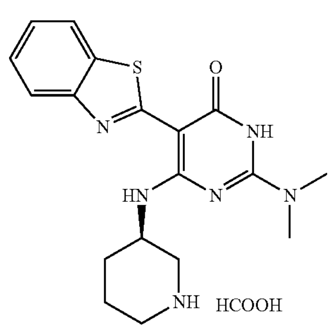 [SMILES: CN(C)c1nc(N[C@@H]2CCCNC2)c(-c2nc3ccccc3s2)c(=O)[nH]1 ; "HCOOH"] | (R)-5-(benzo[d]thiazol-2-yl)-2-(dimethylamino)-6-(piperidin-3-ylamino)pyrimidin-4(3H)-one | 74 | 370.8 M + H |

-continued

| Exple | Structure | Name | IC$_{50}$ (nM) | MS (m/z) |
|---|---|---|---|---|
| 290 | 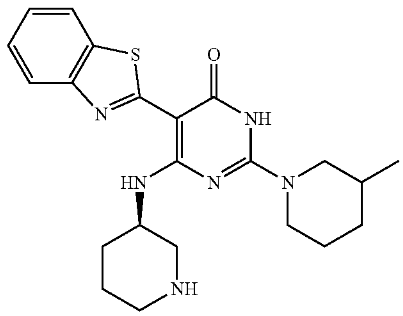 [SMILES: CC1CCCN(c2nc(N[C@@H]3CCCNC3)c(-c3nc4ccccc4s3)c(=O)[nH]2)C1] | 5-(benzo[d]thiazol-2-yl)-2-(3-methylpiperidin-1-yl)-6-((R)-piperidin-3-ylamino)pyrimidin-4(3H)-one | 140 | 425 M + H |
| 291 | 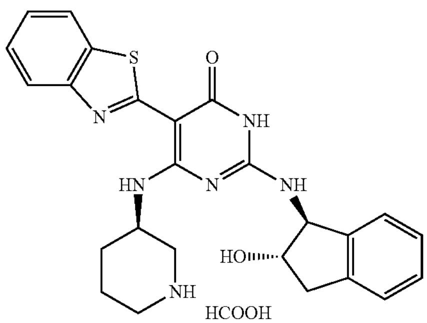 [SMILES: O=c1[nH]c(N[C@H]2c3ccccc3C[C@@H]2O)nc(N[C@@H]2CCCNC2)c1-c1nc2ccccc2s1 ; "HCOOH"] | 5-(benzo[d]thiazol-2-yl)-2-((1S,2S)-2-hydroxy-2,3-dihydro-1H-inden-1-ylamino)-6-((R)-piperidin-3-ylamino)pyrimidin-4(3H)-one | 3,000 | 475 M + H |
| 292 | 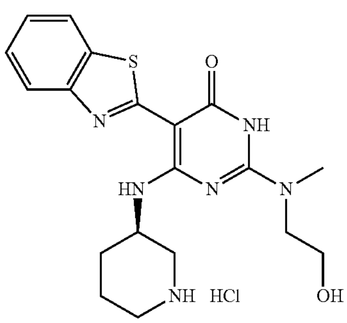 [SMILES: CN(CCO)c1nc(N[C@@H]2CCCNC2)c(-c2nc3ccccc3s2)c(=O)[nH]1 ; Cl] | (R)-5-(benzo[d]thiazol-2-yl)-2-((2-hydroxyethyl)(methyl)amino)-6-(piperidin-3-ylamino)pyrimidin-4(3H)-one | 190 | 401 M + H |
| 293 | 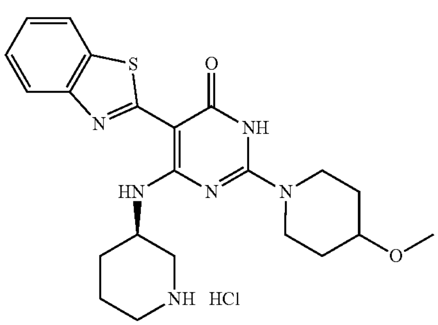 [SMILES: COC1CCN(c2nc(N[C@@H]3CCCNC3)c(-c3nc4ccccc4s3)c(=O)[nH]2)CC1 ; Cl] | (R)-5-(benzo[d]thiazol-2-yl)-2-(4-methoxypiperidin-1-yl)-6-(piperidin-3-ylamino)pyrimidin-4(3H)-one | 63 | 441 M + H |

| Exple | Structure | Name | IC$_{50}$ (nM) | MS (m/z) |
|---|---|---|---|---|
| 294 | 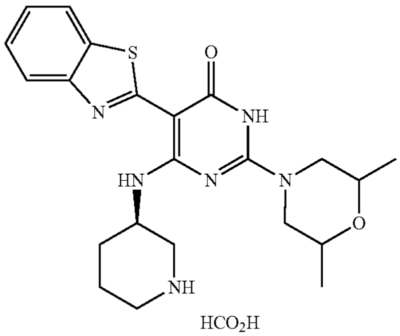 [SMILES: CC1CN(c2nc(N[C@@H]3CCCNC3)c(-c3nc4ccccc4s3)c(=O)[nH]2)CC(C)O1 ; "HCO2H"] | 5-(benzo[d]thiazol-2-yl)-2-(2,6-dimethylmorpholino)-6-((R)-piperidin-3-ylamino)pyrimidin-4(3H)-one | 300 | 441 M + H |
| 295 | 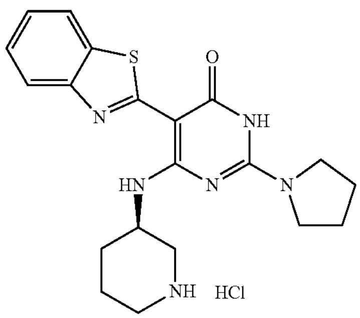 [SMILES: O=c1[nH]c(N2CCCC2)nc(N[C@@H]2CCCNC2)c1-c1nc2ccccc2s1 ; Cl] | 5-(benzo[d]thiazol-2-yl)-2-(2,6-dimethylmorpholino)-6-((R)-piperidin-3-ylamino)pyrimidin-4(3H)-one | 11 | 397 M + H |
| 296 | 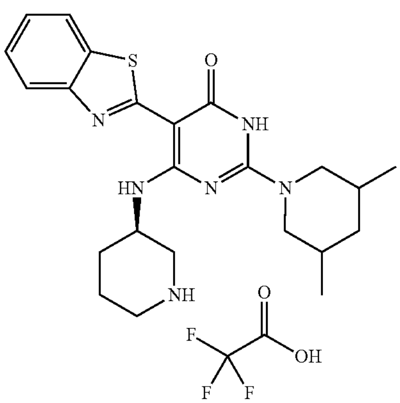 | 5-(1,3-benzothiazol-2-yl)-2-(3,5-dimethylpiperidin-1-yl)-6-[[(3R)-piperidin-3-yl]amino]-3,4-dihydropyrimidin-4-one trifluoroacetic acid | 570 | 439 M + H |
| 297 | 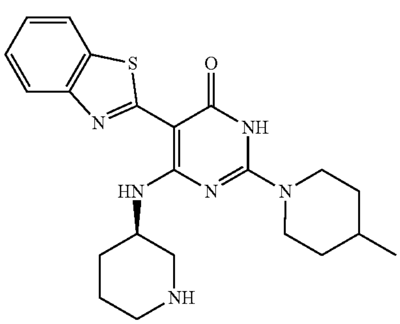 [SMILES: CC1CCN(c2nc(N[C@@H]3CCCNC3)c(-c3nc4ccccc4s3)c(=O)[nH]2)CC1] | 5-(1,3-benzothiazol-2-yl)-2-(4-methylpiperidin-1-yl)-6-[[(3R)-piperidin-3-yl]amino]-3,4-dihydropyrimidin-4-one | 69 | 425 M + H |

-continued

| Exple | Structure | Name | IC₅₀ (nM) | MS (m/z) |
|---|---|---|---|---|
| 298 | 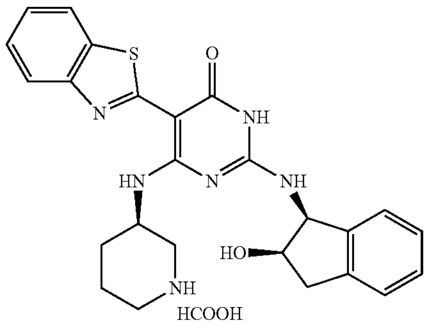 | 5-(1,3-benzothdazol-2-yl)-2-[[(1S,2R)-2-hydroxy-2,3-dihydro-1H-inden-1-yl]amino]-6-[[(3R)-piperidin-3-yl]amino]pyrimidin-4-ol; formic acid | 2,500 | 475 M + H |
| 299 | 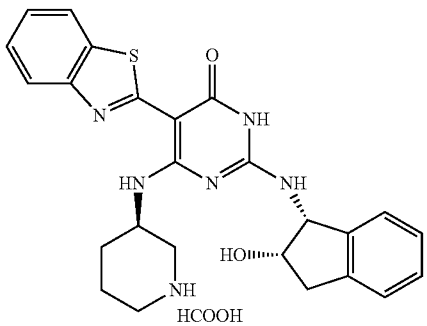 | 5-(1,3-benzothiazol-2-yl)-2-[[(1R,2S)-2-hydroxy-2,3-dihydro-1H-inden-1-yl]amino]-6-[[(3R)-piperidin-3-yl]amino]pyrimidin-4-ol formic acid | 1,200 | 475 M + H |
| 300 | 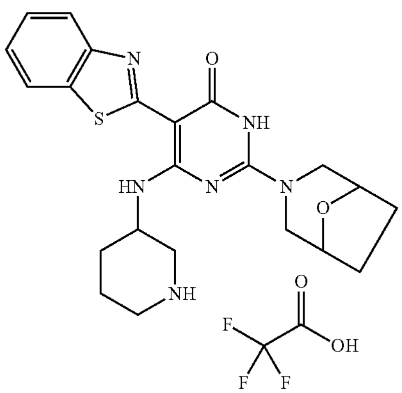 | 5-(1,3-benzothiazol-2-yl)-2-[8-oxa-3-azabicyclo[3.2.1]octan-3-yl]-6-[[(3R)-piperidin-3-yl]amino]-3,4-dihydropyrimidin-4-one; trifluoroacetic acid | 43 | 439 M + H |
| 301 | 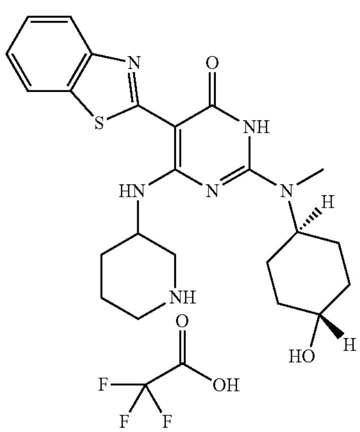 | 5-(1,3-benzothiazol-2-yl)-2-[(4-hydroxycyclohexyl)(methyl)amino]-6-[[(3R)-piperidin-3-yl]amino]-3,4-dihydropyrimidin-4-one; trifluoroacetic acid | 390 | 455 M + H |

-continued

| Exple | Structure | Name | IC₅₀ (nM) | MS (m/z) |
|---|---|---|---|---|
| 302 | 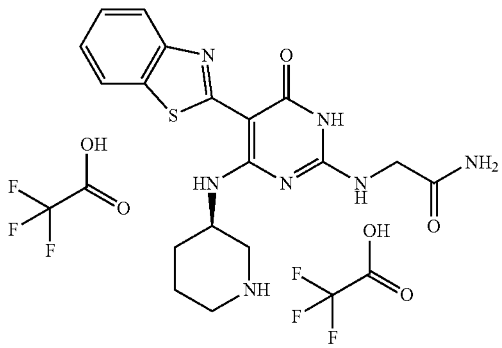 | (R)-2-(5-(benzo[d]thiazol-2-yl)-6-oxo-4-(piperidin-3-ylamino)-1,6-dihydropyrimidin-2-ylamino)acetamide bis(2,2,2-trifluoroacetate) | 2,300 | 400 M + H |
| 303 | 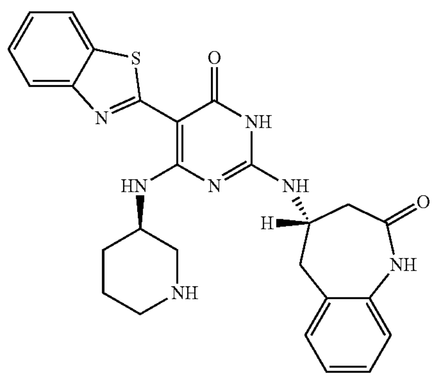 [SMILES: O=C1C[C@@H](Nc2nc(N[C@@H]3CCCNC3)c(-c3nc4ccccc4s3)c(=O)[nH]2)Cc2ccccc2N1] | (S)-4-(5-(benzo[d]thiazol-2-yl)-6-oxo-4-((R)-piperidin-3-ylamino)-1,6-dihydropyrimidin-2-ylamino)-4,5-dihydro-1H-benzo[b]azepin-2(3H)-one | 5,900 | 502 M + H |
| 304 | 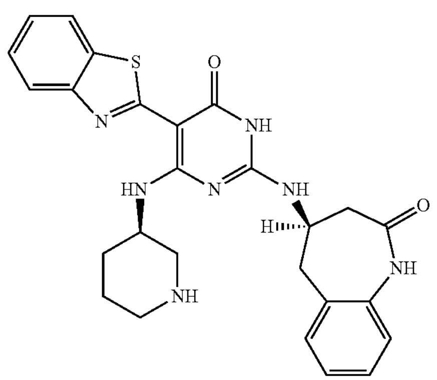 [SMILES: O=C1C[C@H](Nc2nc(N[C@@H]3CCCNC3)c(-c3nc4ccccc4s3)c(=O)[nH]2)Cc2ccccc2N1] | (R)-4-(5-(benzo[d]thiazo]-2-yl)-6-oxo-4-((R)-piperidin-3-ylamino)-1,6-dihydropyrimidin-2-ylamino)-4,5-dihydro-1H-benzo[b]azepin-2(3H)-one | 8,900 | 502 M + H |
| 305 | 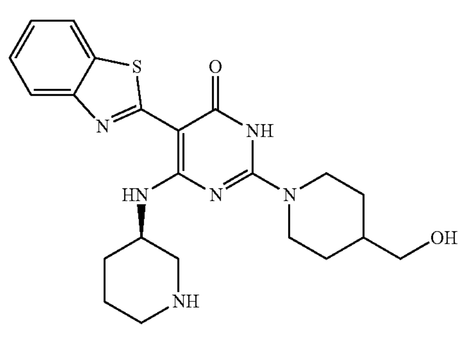 [SMILES: O=c1[nH]c(N2CCC(CO)CC2)nc(N[C@@H]2CCCNC2)c1-c1nc2ccccc2s1] | 5-(1,3-benzothiazol-2-yl)-2-[4-(hydroxymethyl)piperidin-1-yl]-6-[[(3R)-piperidin-3-yl]amino]-3,4-dihydropyrimidin-4-one | 62 | 441 M + H |

-continued

| Exple | Structure | Name | IC₅₀ (nM) | MS (m/z) |
|---|---|---|---|---|
| 306 | 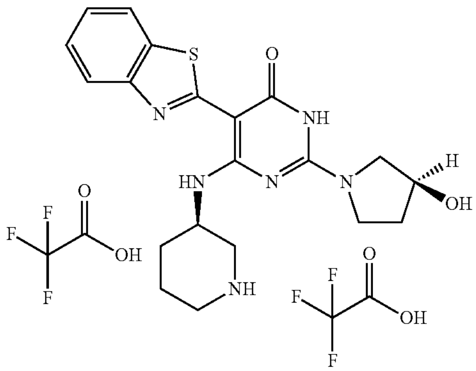 | 5-(benzo[d]thiazol-2-yl)-2-((S)-3-hydroxy-pyrrolidin-1-yl)-6-((R)-piperidin-3-ylamino)pyrimidin-4(3H)-one bis(2,2,2-trifluoro-acetate) | 23 | 413 M + H |
| 307 | 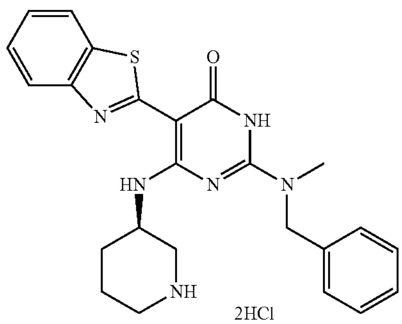 [SMILES: CN(Cc1ccccc1)c1nc(N[C@@H]2CCCNC2)c(-c2nc3ccccc3s2)c(=O)[nH]1] | 5-(1,3-benzothiazol-2-yl)-2-[benzyl(methyl)amino]-6-[[(3R)-piperidin-3-yl]amino]-3,4-dihydropyrimidin-4-one dihydrocbloride | 310 | 447 M + H |
| 308 | 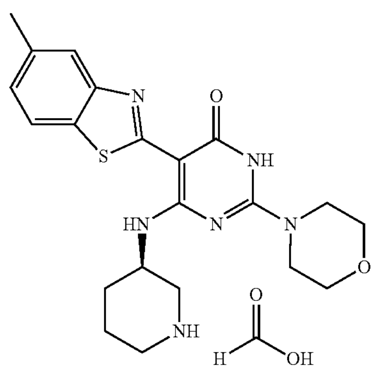 | 5-(5-methyl-1,3-benzothiazol-2-yl)-2-(morpholin-4-yl)-6-[[(3R)-piperidin-3-yl]amino]-3,4-dihydropyrimidin-4-one; formic acid | 120 | 427 M + H |
| 309 | 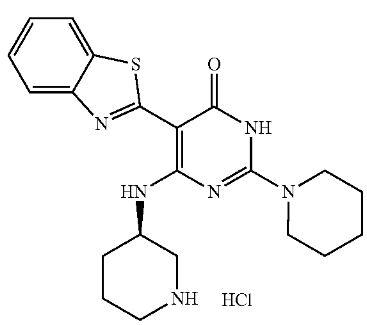 [SMILES: O=c1[nH]c(N2CCCCC2)nc(N[C@@H]2CCCNC2)c1-c1nc2ccccc2s1 ; Cl] | 5-(1,3-benzothiazol-2-yl)-2-(piperidin-1-yl)-6-[[(3R)-piperidin-3-yl]amino]-3,4-dihydropyrimidin-4-one hydrochloride | 71 | 411 M + H |

-continued

| Exple | Structure | Name | IC$_{50}$ (nM) | MS (m/z) |
|---|---|---|---|---|
| 310 | 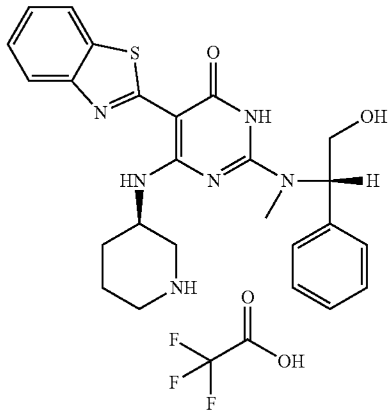 | 5-(1,3-benzothiazol-2-yl)-2-[[(1S)-2-hydroxy-1-phenylethyl](methyl)amino]-6-[[(3R)-piperidin-3-yl]amino]-3,4-dihydropyrimidin-4-one; trifluoroacetic acid | 250 | 477 M + H |
| 311 | 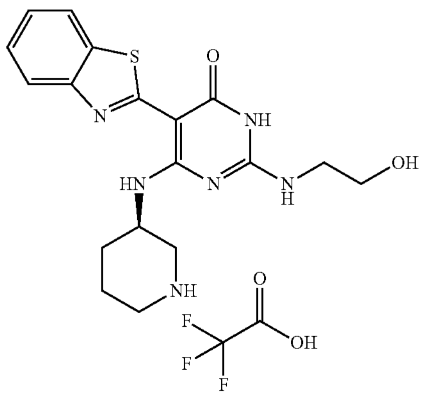 | 5-(1,3-benzothiazol-2-yl)-2-[(2-hydroxyethyl)amino]-6-[[(3R)-piperidin-3-yl]amino]-3,4-dihydropyrimidin-4-one; trifluoroacetic acid | 450 | 387 M + H |
| 312 | 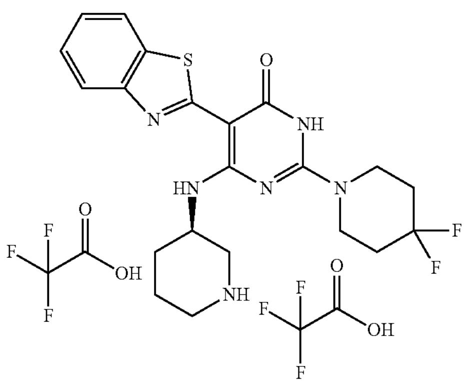 | (R)-5-benzo[d]thiazol-2-yl)-2-(4,4-difluoropiperidin-1-yl)-6-(piperidin-3-ylamino)pyrimidin-4(3H)-one bis(2,2,2-trifluoroacetate) | 78 | 447 M + H |
| 313 | 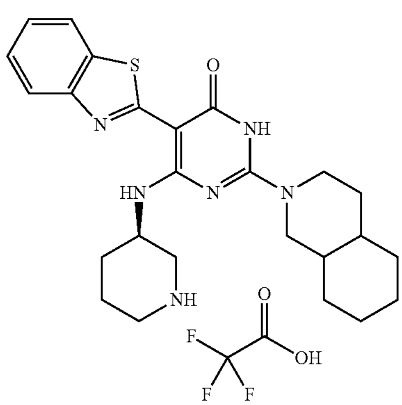 | 5-(1,3-benzothiazol-2-yl)-(decahydroisoquinolin-2-yl)-6-[[(3R)piperidin-3-yl]amino]-3,4-dihydropyrimidin-4-one; trifluoroacetic acid | 330 | 465 M + H |

-continued

| Exple | Structure | Name | IC$_{50}$ (nM) | MS (m/z) |
|---|---|---|---|---|
| 314 | 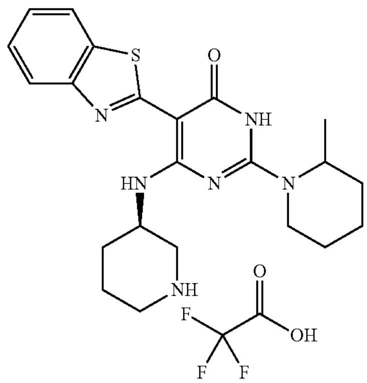 | 5-{1,3-benzothiazol-2-yl)-2-(2-methylpiperidin-1-yl)-6-[[(3R)-piperidin-3-yl]amino]-3,4-dihydropyrimidin-4-one; trifluoroacetic acid | 280 | 425 M + H |
| 315 | 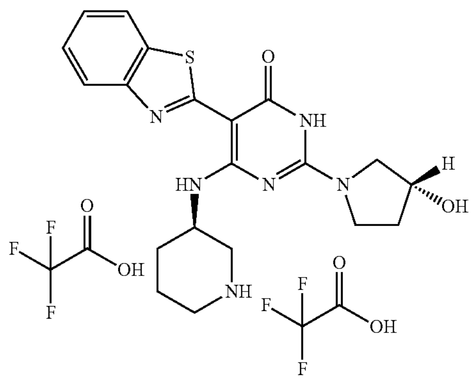 | 5-(1,3-benzothiazol-2-yl)-2-[(3R)-3-hydroxypyrrolidin-1-yl]-6-[[(3R)-piperidin-3-yl]amino]-3,4-dihydropyrimidin-4-one; bis(trifluoroacetic acid | 17 | 413 M + H |
| 316 | 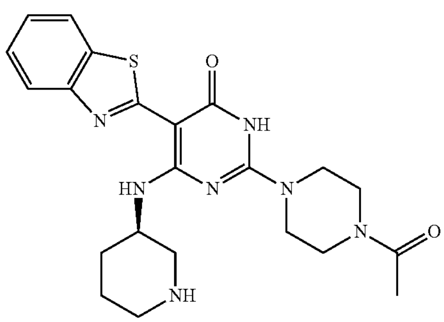 [SMILES: CC(=O)N1CCN(c2nc(N[C@@H]3CCCNC3)c(-c3nc4ccccc4s3)c(=O)[nH]2)CC1] | 2-(4-acetylpiperazin-1-yl)-5-(1,3-benzothiazol-2-yl)-6-[[(3R)-piperidin-3-yl]amino]-3,4-dihydropyrimidin-4-one | 450 | 454 M + H |
| 317 | 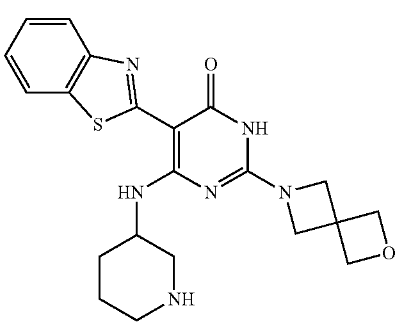 [SMILES: O=c1[nH]c(N2CC3(COC3)C2)nc(NC2CCCNC2)c1-c1nc2ccccc2s1] | 5-(1,3-benzothiazol-2-yl)-2-[2-oxa-6-azaspiro[3.3]heptan-6-yl]-6-[[(3R)-piperidin-3-yl]amino]-3,4-dihydropyrimidin-4-one | 25 | 447 M + H |

| Exple | Structure | Name | IC₅₀ (nM) | MS (m/z) |
|---|---|---|---|---|
| 318 | 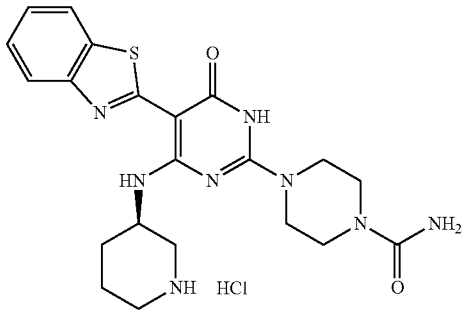 [SMILES: NC(=O)N1CCN(c2nc(N[C@@H]3CCCNC3)c(-c3nc4ccccc4s3)c(=O)[nH]2)CC1 ; Cl] | 1-[5-(1,3-benzothiazol-2-yl)-6-oxo-4-[[(3R)-piperidin-3-yl]amino]-1,6-dihydropyrimidin-2-yl]piperidine-4-carboxamide hydrochloride | 74 | 454 M + H |
| 319 | 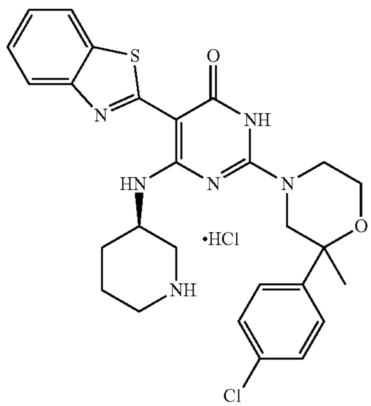 [SMILES: CC1(c2ccc(Cl)cc2)CN(c2nc(N[C@@H]3CCCNC3)c(-c3nc4ccccc4s3)c(=O)[nH]2)CCO1 ; Cl] | 5-(benzo[d]thiazol-2-yl)-2-(2-(4-chlorophenyl)-2-methylmorpholino)-6-((R)-piperidin-3-ylamino)pyrimidin-4(3H)-one hydrochloride | 2,500 | 537 M + H |
| 320 | 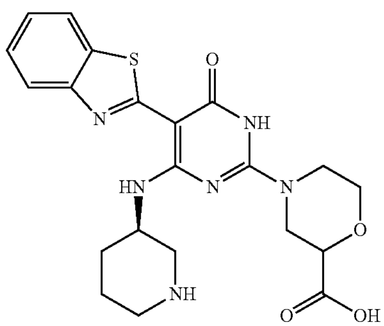 [SMILES: O=C(O)C1CN(c2nc(N[C@@H]3CCCNC3)c(-c3nc4ccccc4s3)c(=O)[nH]2)CCO1] | 4-[5-(1,3-benzothiazol-2-yl)-6-oxo-4-[[(3R)-piperidin-3-yl]amino]-1,6-dihydropyrimidin-2-yl]morpholine-2-carboxylic acid | 250 | 457 M + H |
| 321 | 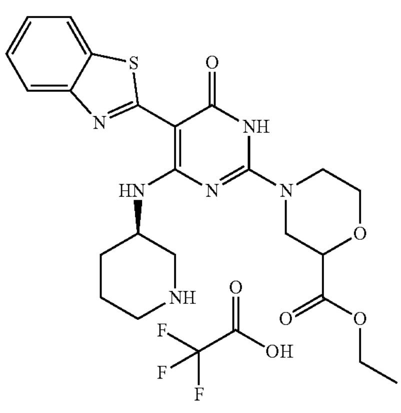 | ethyl 4-[5-(1,3-benzothiazol-2-yl)-6-oxo-4-[[(3R)-piperidin-3-yl]amino]-1,6-dihydropyrimidin-2-yl]morpholine-2-carboxylate; trifluoroacetic acid | 180 | 485 M + H |

| Exple | Structure | Name | IC$_{50}$ (nM) | MS (m/z) |
|---|---|---|---|---|
| 322 | 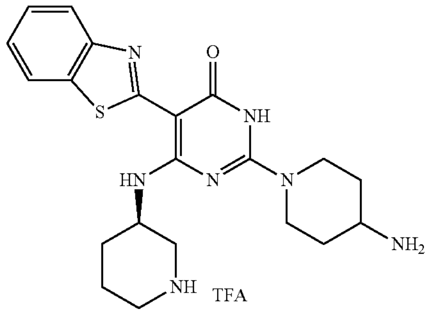 [SMILES: NC1CCN(c2nc(N[C@@H]3CCCNC3)c(-c3nc4ccccc4s3)c(=O)[nH]2)CC1] | 2-(4-aminopiperidin-1-yl)-5-(1,3-benzothiazol-2-yl)-6-[[(3R)-piperidin-3-yl]amino]-3,4-dihydropyrimidin-4-one; trifluoroacetic acid | 240 | 426 M + H |
| 323 | 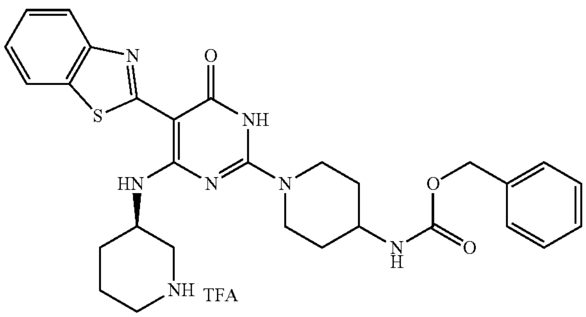 [SMILES: O=C(NC1CCN(c2nc(N[C@@H]3CCCNC3)c(-c3nc4ccccc4s3)c(=O)[nH]2)CC1)OCc1ccccc1] | Benzyl N-[1-[5-(1,3-benzothiazol-2-yl)-6-oxo-4-[[(3R)-piperidin-3-yl]amino]-1,6-dihydropyrimidin-2-yl]piperidin-4-yl]carbamate trifluoroacetic acid | 100 | 560 M + H |
| 324 | 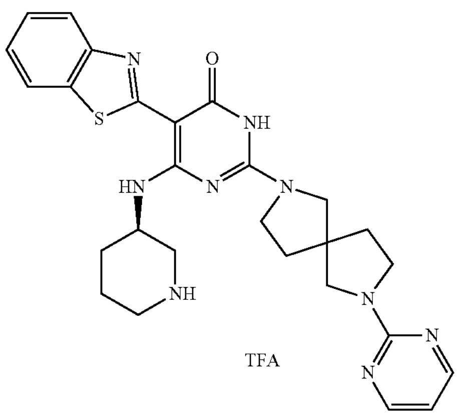 [SMILES: O=c1[nH]c(N2CCC3(CCN(c4ncccn4)C3)C2)nc(N[C@@H]2CCCNC2)c1-c1nc2ccccc2s1] | 5-(1,3-benzothiazol-2-yl)-6-[[(3R)-piperidin-3-yl]amino]-2-[7-(pyrimidin-2-yl)-2,7-diazaspiro[4.4]nonan-2-yl]-3,4-dihydropyrimidin-4-one trifluoroacetic acid | 12 | 530 M + H |
| 325 | 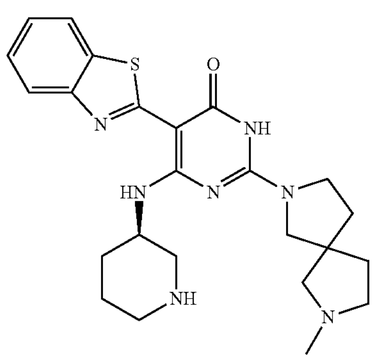 [SMILES: CN1CCC2(CCN(c3nc(N[C@@H]4CCCNC4)c(-c4nc5ccccc5s4)c(=O)[nH]3)C2)C1] | 5-(1,3-benzothiazol-2-yl)-2-[7-methyl-2,7-diazaspiro[4.4]nonan-2-yl]-6-[[(3R)-piperidin-3-yl]amino]-3,4-dihydropyrimidin-4-one | 24 | 466 M + H |

-continued

| Exple | Structure | Name | IC₅₀ (nM) | MS (m/z) |
|---|---|---|---|---|
| 326 | 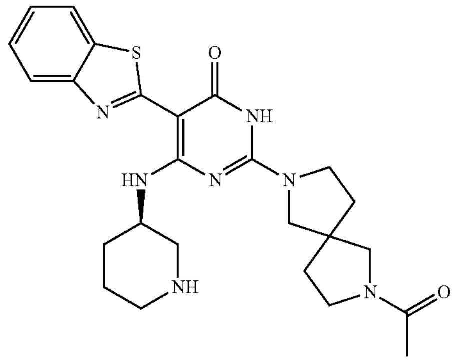 [SMILES: CC(=O)N1CCC2(CCN(c3nc(N[C@@H]4CCCNC4)c(-c4nc5ccccc5s4)c(=O)[nH]3)C2)C1] | 2-[7-acetyl-2,7-diazaspiro[4.4]nonan-2-yl]-5-(1,3-benzothiazol-2-yl)-6-[[(3R)-piperidin-3-yl]amino]-3,4-dihydropyrimidin-4-one | 13 | 494 M + H |
| 327 | 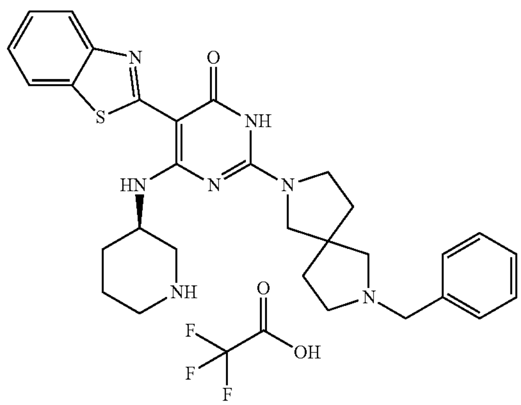 | 5-(1,3-benzothiazol-2-yl)-2-[7-benzyl-2,7-diazaspiro[4.4]nonan-2-yl]-6-[[(3R)-piperidin-3-yl]amino]-3,4-dihydropyrimidin-4-one; trifluoroacetic acid | 27 | 542 M + H |
| 328 | 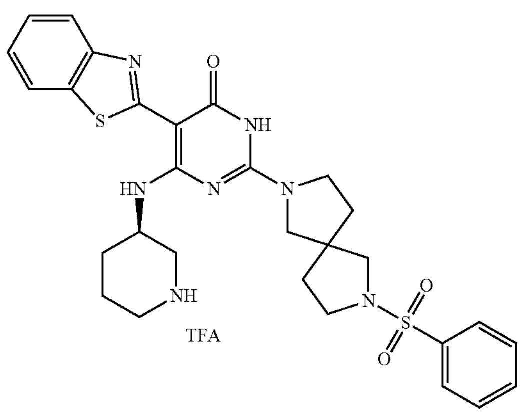 [SMILES: O=c1[nH]c(N2CCC3(CCN(S(=O)(=O)c4ccccc4)C3)C2)nc(N[C@@H]2CCCNC2)c1-c1nc2ccccc2s1] | 6-[4-[7-(benzenesulfony])-2,7-diazaspiro[4.4]nonan-2-yl]piperidin-1-yl]-3-(1,3-benzothiazol-2-yl)-4-[[(3R)-piperidin-3-yl]amino]-1,2-dihydropyridin-2-one trifluoroacetic acid | 23 | 592 M + H |
| 329 | 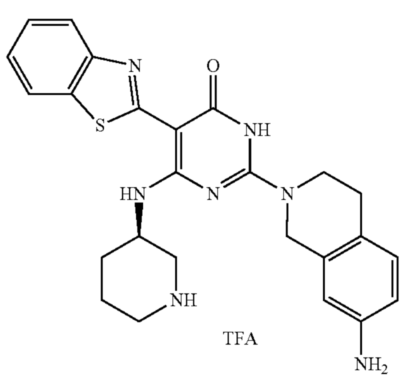 [SMILES: Nc1ccc2c(c1)CN(c1nc(N[C@@H]3CCCNC3)c(-c3nc4ccccc4s3)c(=O)[nH]1)CC2] | 6-(7-amino-1,2,3,4-tetrahydroisoquinolin-2-yl)-3-(1,3-benzothiazol-2-yl)-4-[[(3R)-piperidin-3-yl]amino]-1,2-dihydropyridin-2-one; trifluoroacetic acid | 49 | 474 M + H |

-continued

| Exple | Structure | Name | IC$_{50}$ (nM) | MS (m/z) |
|---|---|---|---|---|
| 330 | 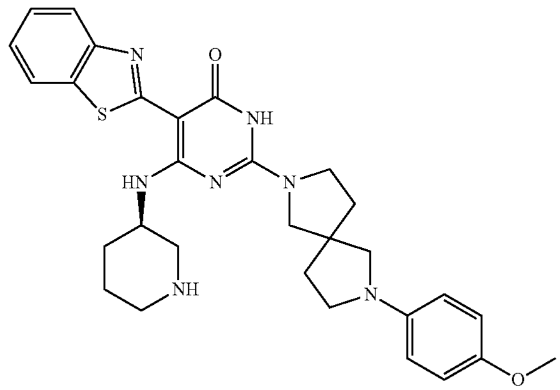 [SMILES: COc1ccc(N2CCC3(CCN(c4nc(N[C@@H]5CCCNC5)c(-c5nc6ccccc6s5)c(=O)[nH]4)C3)C2)cc1] | 5-(1,3-benzothiazol-2-yl)-2-[7-(4-methoxyphenyl)-2,7-diazaspiro[4.4]nonan-2-yl]-6-[[(3R)-piperidin-3-yl]amino]-3,4-dihydropyrimidin-4-one | 21 | 558 M + H |
| 331 | 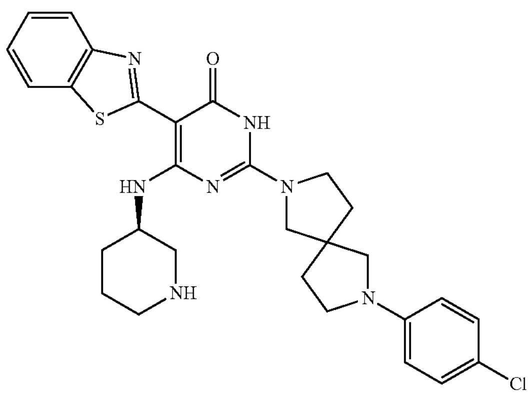 [SMILES: O=c1[nH]c(N2CCC3(CCN(c4ccc(Cl)cc4)C3)C2)nc(N[C@@H]2CCCNC2)c1-c1nc2ccccc2s1] | 5-(1,3-benzothiazol-2-yl)-2-[7-(4-chlorophenyl)-2,7-diazaspiro[4.4]nonan-2-yl]-6-[[(3R)-piperidin-3-yl]amino]-3,4-dihydropyrimidin-4-one trifluoroacetic acid | 47 | 562 M + H |
| 332 | 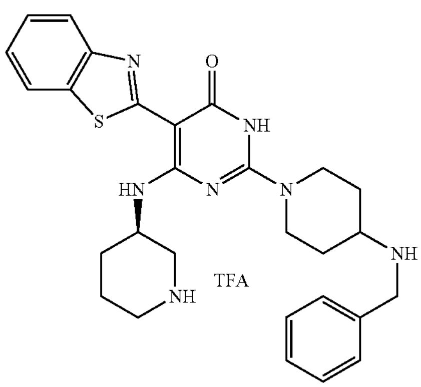 [SMILES: O=c1[nH]c(N2CCC(NCc3ccccc3)CC2)nc(N[C@@H]2CCCNC2)c1-c1nc2ccccc2s1] | 5-(1,3-benzothiazol-2-yl)-2-[4-(benzylamino)piperidin-1-yl]-6-[[(3R)-piperidin-3-yl]amino]-3,4-dihydropyrimidin-4-one trifluoroacetic acid | 110 | 516 M + H |
| 333 | 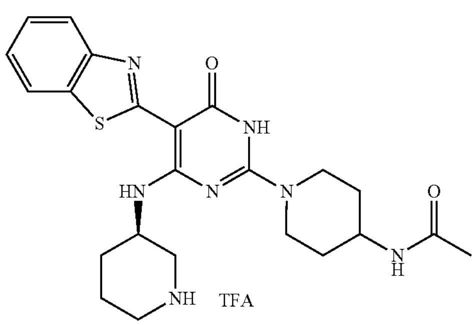 [SMILES: CC(=O)NC1CCN(c2nc(N[C@@H]3CCCNC3)c(-c3nc4ccccc4s3)c(=O)[nH]2)CC1] | N-[1-[5-(1,3-benzothiazol-2-yl)-6-oxo-4-[[(3R)-piperidin-3-yl]amino]-1,6-dihydropyrimidin-2-yl]piperidin-4-yl]acetamide trifluoroacetic acid | 94 | 468 M + H |

| Exple | Structure | Name | IC$_{50}$ (nM) | MS (m/z) |
|---|---|---|---|---|
| 334 | 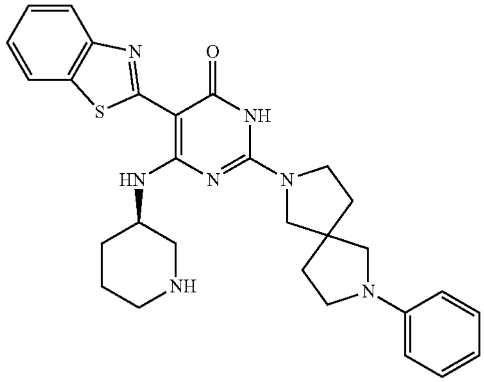 [SMILES: O=c1[nH]c(N2CCC3(CCN(c4ccccc4)C3)C2)nc(N[C@@H]2CCCNC2)c1-c1nc2ccccc2s1] | 5-(1,3-benzothiazol-2-yl)-2-[7-phenyl-2,7-diazaspiro[4.4]nonan-2-yl]-6-[[(3R)-piperidin-3-yl]amino]-3,4-dihydropyrimidin-4-one | 21 | 528 M + H |
| 335 | 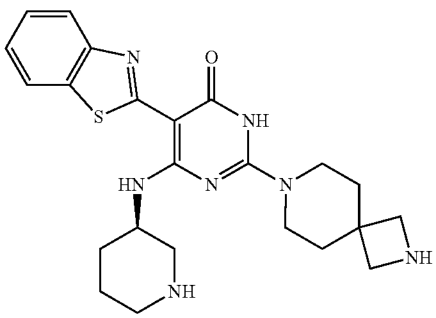 [SMILES: O=c1[nH]c(N2CCC3(CC2)CNC3)nc(N[C@@H]2CCCNC2)c1-c1nc2ccccc2s1] | 3-(1,3-benzothiazol-2-yl)-6-[2,7-diazaspiro[3.5]nonan-7-yl]-4-[[(3R)-piperidin-3-yl]amino]-1,2-dihydropyridin-2-one | 40 | 452 M + H |
| 336 | 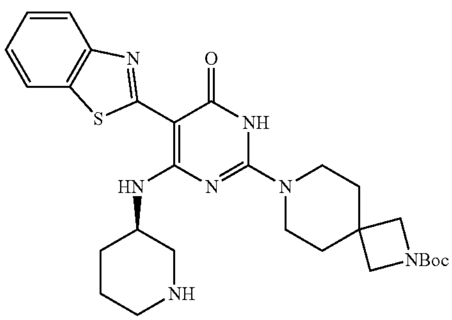 [SMILES: CC(C)(C)OC(=O)N1CC2(CCN(c3nc(N[C@@H]4CCCNC4)c(-c4nc5ccccc5s4)c(=O)[nH]3)CC2)C1] | tert-butyl 7-[5-(1,3-benzothiazol-2-yl)-6-oxo-4-[[(3R)-piperidin-3-yl]amino]-1,6-dihydropyridin-2-yl]-2,7-diazaspiro[3.5]nonane-2-carboxylate | 27 | 552 M + H |

NMR Data for the above Examples are:

Example 285

$^1$H-NMR (300 MHz, DMSO-d$_6$): δ ppm 1.71-2.08(br, 4H), 2.78-3.62(m, 10H), 3.82-3.94(m, 2H), 4.12-4.43(m, 4H), 7.23-7.28 (t,1H, J=7.5 Hz), 7.38-7.43(t, 1H, J=7.2 Hz), 7.75-7.78(d, 1H, J=8.1 Hz), 7.93-7.96(d, 1H, J=7.5 Hz), 8.25(s, 1H), 10.83-10.86(m,1H)

Example 286

1.79-1.83(m, 2H), 2.00(s, 1H), 2.14(s, 1H), 2.92-3.14(m, 4H), 3.25(d, J=10.8 Hz, 1H), 3.31(s, 3H), 3.39-3.66(m, 6H), 3.92(d, J=9.6 Hz, 1H), 4.32(d, J=14.2 Hz, 3H), 7.25-7.29(m, 1H), 7.40-7.44(m, 1H), 7.77(d, J=7.6 Hz, 1H), 7.95(d, J=8.0 Hz, 1H), 8.74(s, 1H), 8.75(s, 1H), 10.82(d, J=7.2 Hz, 1H), 11.18(s, 1H)

Example 287

$^1$H-NMR(400 MHz, DMSO-d6): ppm δ 1.60~1.75(m, 2H), 1.75~1.90(m, 1H), 1.95~2.05(m, 1H), 2.63~2.65(d, J=4.8 Hz, 3H), 2.75~3.05(m, 3H), 3.05~3.35(m, 3H), 3.62~3.68(t, J=9.2 Hz, 1H), 3.90~4.05(m, 2H), 4.20~4.35(m, 2H), 4.51~4.58(t, J=14.0 Hz, 1H), 7.24~7.28(m, 1H), 7.38~7.43(m, 1H), 7.75~7.77(d, J=8.0 Hz, 1H), 7.90~7.96 (m, 2H), 8.30(s, br, 1H), 10.88(s, br, 1H)

Example 288

$^1$H-NMR(400 MHz, DMSO-d$_6$): δppm 1.77-1.85(m, 3H), 1.85-2.05(m, 3H), 2.10-2.15 (m, 1H), 3.05-3.10 (m, 1H), 3.15-3.25 (m, 2H), 3.40-3.50 (m, 1H), 3.85-3.95(m, 2H), 4.20-4.29(m, 1H), 7.22-7.28(m, 1H), 7.35-7.45(m, 1H), 7.75-7.80(m, 1H), 7.95-7.97(m, 1H), 8.14(s, 1H), 8.68-8.80(br, 2H), 10.85(d, J=6.8 Hz, 1H).

Example 289

$^1$H-NMR(400 MHz, DMSO-d6): δ ppm 1.62-1.73 (m, 2H), 1.81 (s, 1H), 2.01 (s, 1H), 2.71-2.79 (m, 2H), 2.93 (d, J=12.0 Hz, 1H), 3.13 (s, 6H), 3.24 (d, J=11.6 Hz, 1H), 4.25 (s, 1H), 7.22 (t, J=7.4 Hz, 1H), 7.37 (t, J=7.6 Hz, 1H), 7.73 (d, J=8.0 Hz, 1H), 7.92 (d, J=7.6 Hz, 1H), 8.29 (s, 1H), 10.81 (d, J=7.2 Hz, 1H).

Example 290

¹H-NMR(400 MHz, DMSO-d6): δ ppm 0.926 (s, 3H), 1.19-1.24 (m, 2H), 1.45-1.48(m, 1H), 1.61-1.87(m, 6H), 2.05 (s, 1H), 2.67-2.76(m, 1H), 2.80-2.85(m, 2H), 2.96-3.03(m, 3H), 4.25-4.40(m, 3H), 7.23(t, J=7.6 Hz, 1H), 7.38(t, J=7.6 Hz, 1H), 7.74(d, J=8 Hz, 1H), 7.93(d, J=7.6 Hz, 1H), 10.80(d, J=6.8 Hz, 1H).

Example 291

¹H-NMR (400 MHz, DMSO-$d_6$): δ ppm 1.50~2.00 (m, 4H), 2.65~2.86(m, 4H), 3.15~3.26(m, 2H), 4.17(m, 1H), 4.35~4.23(m, 1H), 5.31(t, J=9.6 Hz, 1H), 7.19~7.27(m, 5H), 7.36~7.42(m, 1H), 7.60~7.75(m, 2H), 7.92~7.95(d, J=10.4 Hz, 1H), 8.34(s, 0.34H), 10.98(m, 1H).

Example 292

¹H-NMR(400 MHz, DMSO-d6): δ ppm 1.77-2.00(m, 3H), 2.15(m, 1H), 2.95-3.10(m, 2H), 3.18-3.34(m, 5H), 3.63(m, 1H), 3.69(m, 3H), 3.75(m, 1H), 4.43(br, 1H), 4.97-4.99 (br, 1H), 7.24-7.29(t, J=7.6 Hz, 1H), 7.39-7.43(t, J=7.6 Hz, 1H), 7.76-7.78(d, J=8.0 Hz, 1H), 7.95-7.97 (d, J=8.0 Hz, 1H), 8.79-9.24(br, 2H), 10.74-10.82(m, 2H);

Example 293

1H-NMR(300 MHz, DMSO-d6): δ ppm 1.47-1.50(m, 2H), 1.79-2.14(m, 6H), 2.95-2.99(br, 2H), 3.22-3.33(m, 3H), 3.48 (br, 4H), 3.99(br, 2H), 4.39(br, 1H), 7.24-7.28 (t, J=6.9 Hz, 1H), 7.39-7.44(t, J=7.2 Hz, 1H), 7.75-7.78(d, J=8.1 Hz, 1H), 7.94-7.97(d, J=7.5 Hz, 1H), 8.81-8.82(br, 1H), 9.15(br, 1H), 10.75-10.77(d, J=6.6 Hz, 1H), 11.08(s, 1H);

Example 294

¹H-NMR (400 MHz, DMSO-$d_6$): δ ppm 1.13-1.14(d, J=6.0 Hz, 6H), 1.63-1.81(m, 3H), 1.95-2.02(m, 1H), 2.50-2.75(m, 4H), 2.88-2.92(m, 1H), 3.17-3.20(d, J=11.2 Hz, 1H), 3.52-3.69(m, 3H), 4.15-4.20(m, 1H), 4.36-4.39(d, J=12.8 Hz, 2H), 7.22-7.26 (t, J=7.6 Hz, 1H), 7.37-7.41(t, J=7.6 Hz, 1H), 7.73-7.75(d, J=8 Hz, 1H), 7.92-7.94(d, J=7.6 Hz, 1H), 8.27(s, 1H), 10.85-10.87(d, J=6.4 Hz, 1H);

Example 295

¹H-NMR (400 MHz, DMSO-$d_6$): δ ppm 1.72-2.15(m, 9H), 2.95-3.11(m, 2H), 3.14-3.25(m, 1H), 3.50-3.74(m, 5H), 4.35-4.45(m, 1H), 7.22-7.27 (t, J=9.6 Hz, 1H), 7.38-7.42(t, J=9.6 Hz, 1H), 7.74-7.76(d, J=10.0 Hz, 1H), 7.93-7.95(d, J=10.0 Hz, 1H), 8.73-8.77(br, 1H), 8.90-9.00(br, 1H), 10.75-10.77 (d, J=8.4 Hz, 1H), 11.00(s, 1H);

Example 296

¹H-NMR (400 MHz, DMSO-$d_6$): δ ppm 0.82-0.93 (m, 6H), 1.58 (s, 2H), 1.79-1.86 (m, 3H), 2.00 (brs, 1H), 2.14 (m, 1H), 2.43 (s, 1H), 2.89-3.51 (m, 6H), 4.32-4.51 (m, 3H), 7.24 (t, J=7.6 Hz, 1H), 7.39 (t, J=7.4 Hz, 1H), 7.75 (d, J=8.0 Hz, 1H), 7.79 (d, J=8.0 Hz, 1H), 8.69 (brs, 1H), 8.73 (brs, 1H), 10.77 (d, J=6.4 Hz, 1H), 11.06 (s, 1H)

Example 297

¹H-NMR (400 MHz, DMSO-$d_6$); δ ppm 0.84 (m, 3H), 1.09-1.15(m, 2H), 1.52-1.70(m, 6H), 1.95 (s, 1H), 2.61-2.66 (m, 2H), 2.70-2.79(m, 1H), 2.91-2.98(t, J=12.8 Hz, 2H), 3.10-3.33(m, 1H), 4.138(s, 1H), 4.42-4.45(d, J=12.8 Hz, 2H), 7.22(t, J=7.2 Hz, 7.6 Hz, 1H), 7.37(t, J=7.6 Hz, 1H), 7.72 (d, J=8 Hz, 1H), 7.92(d, J=8 Hz, 1H), 10.85(d, J=7.2 Hz, 1H)

Example 298

¹H-NMR (400 MHz, DMSO-$d_6$); δ ppm 1.50-2.05(m, 4H), 2.70-2.90(m, 4H), 3.10-3.25(m, 2H), 4.25(brs, 1H), 4.58(m, 1H), 5.50(m, 1H), 7.19-7.30(m, 6H), 7.41(t, J=7.6 Hz, 1H), 7.75-7.77(d, J=8.0 Hz, 1H), 7.94-7.96(d, J=7.6 Hz, 1H), 8.28 (s, 1H), 11.01-11.03(d, J=7.2 Hz, 1H)

Example 299

¹H-NMR (400 MHz, DMSO-$d_6$); δ ppm 1.50-2.05 (m, 4H), 2.70-2.90(m, 4H), 3.10-3.20(m, 2H), 4.23(m, 1H), 4.59 (m, 1H), 5.48(m, 1H), 7.19-7.30(m, 6H), 7.41(t, J=7.6 Hz, 1H), 7.75-7.77(d, J=8.0 Hz, 1H), 7.94-7.96(d, J=8.0 Hz, 1H), 8.26(s, 1H), 11.04-1.06(d, J=7.2 Hz, 1H);

Example 300

¹H-NMR (400 MHz, D$_2$O-d$_2$): δ ppm 1.61-1.80 (m, 2H), 1.90 (s, 4H), 2.07-2.18 (m, 2H), 2.89-3.05 (m, 2H), 3.17 (brs, 3H), 3.29-3.40 (m, 1H), 3.51-3.80 (m, 2H), 3.99 (s, 1H), 4.48 (s, 2H), 7.16-7.18 (t, J=7.2 Hz, 1H), 7.29-7.33 (t, J=7.2 Hz, 1H), 7.58-7.60 (d, J=8.0 Hz, 1H), 7.69-7.71 (d, J=8.0 Hz, 1H)

Example 301

¹H-NMR (400 MHz, CD$_3$OD-d$_4$): δ ppm 1.40-1.59 (m, 2H), 1.77 (brs, 4H), 2.03-2.10 (m, 4H), 2.29-2.30 (m, 2H), 3.02-3.09 (m, 3H), 3.15-3.18 (m, 2H), 3.40-3.45 (m, 1H), 3.50-3.65 (m, 2H), 4.40-4.47 (brs, 2H), 7.26-7.30 (t, J=7.6 Hz, 1H), 7.40-7.44 (t, J=6.8 Hz, 1H), 7.80-7.82 (d, J=8.0 Hz, 1H), 7.88-7.90 (d, J=8.0 Hz, 1H)

Example 302

¹H-NMR (400 MHz, D$_2$O-d$_2$): δ ppm 1.91-2.05(m, 4H), 3.17-3.23(m, 4H), 3.54-3.59(m, 2H), 3.90-4.00 (m, 1H), 7.15-7.25(m, 1H), 7.25-7.35(m, 1H), 7.55-7.65(m, 1H), 7.75-7.84(m, 1H)

Example 303

¹H-NMR (300 MHz, DMSO-$d_6$) δ ppm 1.31~1.60(m, 2H), 1.62-1.93 (m,2H), 1.97-2.14 (m, 1H), 2.58-2.97 (m,7H), 3.71-3.84(brs, 1H),4.29-4.46(m, 1H),7.16-7.37(m, 7H), 7.70-7.72 (d, J=7.8 Hz, 1H), 7.90-7.93 (d, J=7.8 Hz, 1H), 10.00(s, 1H), 10.89-10.92 (m, 1H)

Example 304

¹H-NMR (300 MHz, DMSO-$d_6$) δ ppm 1.31-1.60(m, 2H), 1.62-1.93 (m,2H), 1.97-2.14 (m, 1H), 2.58-2.97 (m,7H), 3.71-3.84(m,1H),4.29-4.46(m, 1H),7.16-7.37(m, 7H), 7.70-7.72 (m, 1H), 7.90-7.93 (m, 1H), 10.00(s, 1H), 10.89-10.92 (m, 1H)

Example 305

¹H-NMR (300 MHz, DMSO-$d_6$): δ ppm 1.03-1.23(m, 2H), 1.47-1.76 (m, 6H), 1.90-2.10 (m, 1H), 2.60-2.79(m, 3H), 2.90-3.07(m, 2H), 3.10-3.16(m, 1H), 3.25-3.32(m, 3H), 4.05-4.16 (m, 1H), 4.45-4.52 (m, 3H), 7.20-7.25 (m, 1H), 7.36-7.40(m, 1H), 7.71-7.74 (d, J=7.8 Hz, 1H), 7.91-7.93(d, J=7.5 Hz, 1H), 10.83-10.86(m, 1H)

Example 306

$^1$H-NMR(400 MHz, CD$_3$OD-d$_4$) δ ppm 1.95-2.20(m, 4H), 2.20-2.30(m, 2H), 3.20-3.30(m, 1H), 3.50-3.80(m, 4H), 4.48-4.89(m, 2H), 7.26-7.30(t, J=7.6 Hz, 1H), 7.40-7.44(t, J=7.6 Hz, 1H), 7.79-7.81(d, J=8.0 Hz, 1H), 7.88-7.90(d, J=7.6 Hz, 1H)

Example 307

$^1$H-NMR (400 MHz, DMSO-d$_6$) δ ppm 1.72-2.08(m, 4H), 2.92-2.94(m, 2H), 3.13-3.21(m, 4H), 3.33-3.38(brs, 1H), 4.44-4.45(br, 1H), 4.91 (s, 2H), 7.25-7.43 (m, 7H), 7.77-7.79 (d, J=7.6 Hz, 1H), 7.95-7.97(d, J=7.6 Hz, 1H), 9.05(br, 1H), 9.35(br, 1H), 10.78-10.79(d, J=6.8 Hz, 1H), 11.09(br, 1H);

Example 308

$^1$H-NMR (300 MHz, DMSO-d$_6$) δ ppm 1.69-1.73(m, 2H), 1.82(m, 1H), 1.95(m, 1H), 2.33(s, 3H), 2.70-2.72(m, 2H), 2.80-2.85(m, 1H), 3.11-3.14(m, 1H), 3.62-3.68(m, 8H), 4.13-4.15(m, 1H), 7.06-7.09(d, J=8.1 Hz, 1H), 7.56(s, 1H), 7.78-7.83(m, 1H), 8.35(s, 1H), 10.86-10.89(m, 1H);

Example 309

$^1$H-NMR (300 MHz, DMSO-d$_6$) δ ppm 1.57-1.63 (m, 6H), 1.81-1.87 (m, 2H), 1.92-2.13 (m, 2H), 2.95-3.02 (m, 2H), 3.21-3.25 (m, 1H), 3.45-3.56 (m, 1H), 3.72 (s, 4H), 4.38 (brs,1H), 7.23 (t, J=7.0 Hz, 1H), 7.38 (t, J=7.8 Hz, 1H), 7.75 (d, J=8.1 Hz, 1H), 7.91 (d, J=7.8 Hz, 1H), 8.81 (brs,1H), 9.10 (brs,1H), 10.74 (d, J=6.6 Hz, 1H), 11.00 (s, 1H);

Example 310

$^1$H-NMR (400 MHz, DMSO-d$_6$) δ ppm 1.78-1.82 (m, 2H), 1.97 (m, 1H), 2.08 (m, 1H), 2.93 (s, 3H), 2.98-3.06 (m, 2H), 3.22 (d, J=11.2 Hz, 1H), 3.57 (d, J=11.6 Hz, 1H), 3.98-4.06 (m, 2H), 4.37 (brs,1H), 5.03 (brs,1H), 6.04 (brs,1H), 7.23-7.44 (m, 7H), 7.76 (d, J=8.0 Hz, 1H), 7.95 (d, J=7.6 Hz, 1H), 8.67 (brs,1H), 8.75 (brs,1H), 10.76 (d, J=6.4 Hz, 1H), 10.99 (brs,1H)

Example 311

$^1$H-NMR (400 MHz, DMSO-d$_6$) δ ppm 1.80-1.84 (m, 2H), 2.00 (s, 1H), 2.13 (s, 1H), 3.01-3.09 (m, 2H), 3.22 (s, 1H), 3.49 (s, 4H), 3.58 (s, 2H), 4.36 (brs,1H), 4.93 (s, 1H), 6.94 (brs,1H), 7.24 (t, J=7.4 Hz, 1H), 7.39 (t, J=7.6 Hz, 1H), 7.75 (d, J=8.0 Hz, 1H), 7.94 (d, J=7.6 Hz, 1H), 8.63 (brs,1H), 8.72 (brs,1H), 10.62 (s, 1H), 10.90 (d, J=6.4 Hz, 1H)

Example 312

$^1$H-NMR(400 MHz, D2O) δ ppm 1.90-2.02(m, 6H), 2.02-2.12(m, 2H), 3.14-3.25(m, 3H), 3.31(m, 1H), 3.40-3.50(s, 4H), 4.01-0-4.05(m, 1H), 7.19-7.23(t, J=7.6 Hz, 1H), 7.33-7.37(t, J=7.6 Hz, 1H), 7.65-7.67(d, J=8.0 Hz, 1H), 7.74-7.76 (d, J=8.0 Hz, 1H)

Example 313

$^1$H-NMR (300 MHz, CD$_3$OD-d$_4$): δ ppm 1.06-1.42(m, 8H), 1.70-1.84(m, 5H), 1.95-2.03 (m, 2H), 2.25-2.29(m, 2H), 2.59-2.67(m, 1H), 2.98-3.33(m, 2H), 3.55-3.64(m, 2H), 4.27-4.31(m, 1H), 4.48-4.58(m, 2H), 7.26(t, J=7.2 Hz, 1H), 7.39(t, J=−6.9 Hz, J=7.2 Hz, 1H), 7.79-7.87 (m, 2H);

Example 314

$^1$H-NMR(400 MHz, DMSO-d$_6$+D$_2$O): δ ppm 1.184 (t, J=4.4 Hz, J=6.4 Hz, 3H), 1.40-1.83(m, 8H), 2.00(s, 1H), 2.12(s, 1H), 2.95-3.04(m, 3H), 3.20-3.24(m, 1H), 3.45-3.69 (m, 1H), 4.23-4.32 (m, 2H), 4.76-4.80 (m, 1H), 7.24 (t, J=7.6 Hz, 1H), 7.39 (t, J=7.2 Hz, J=8 Hz, 1H), 7.76 (d, J=8 Hz, 1H), 7.92 (d, J=8 Hz, 1H)

Example 315

$^1$H-NMR(400 MHz, CD$_3$OD-d$_4$) δ ppm 1.80-2.10(m, 4H), 2.10-2.30(m, 2H), 3.28-3.70(m, 8H), 4.15-4.30(m, 1H), 4.35-4.45(m, 1H), 7.25-7.29(t, J=7.2 Hz, 1H), 7.46-7.50(t, J=7.2 Hz, 1H), 7.74-7.76(d, J=8.0 Hz, 1H), 7.85-7.87(d, J=8.0 Hz, 1H)

Example 316

$^1$H-NMR(300 MHz, DMSO-d$_6$) δ ppm 1.55-1.74 (m, 3H), 1.88-1.96(m, 1H), 2.05(s, 3H), 2.64-2.91(m, 3H), 3.09-3.16 (m, 1H), 3.50-3.60(s, 4H), 3.69-3.76(m, 4H), 4.10-4.16(m, 1H), 7.20-7.26(t, J=7.2 Hz, 1H), 7.37-7.41(t, J=7.2 Hz, 1H), 7.72-7.75(d, J=8.4 Hz, 1H), 7.92-7.94(d, J=8.4 Hz, 1H), 10.88-10.90 (d, J=7.5 Hz, 1H);

Example 317

$^1$H-NMR(400 MHz, DMSO-d$_6$) δ ppm 1.59-1.61 (m, 1H), 1.62-1.65 (m, 1H), 1.72-1.76 (m, 1H), 1.93 (s, 1H), 2.59-2.77 (m, 2H), 3.05-3.08 (d, J=12 Hz, 1H), 4.15-4.17 (m, 1H), 4.29 (s, 4H), 4.70 (s, 4H), 7.22-7.25 (t, J=7.6 Hz, 1H), 7.36-7.40 (t, J=7.6 Hz, 1H), 7.66-7.74 (m, 1H), 7.91-7.93 (d, J=8.0 Hz, 1H), 10.97-10.99 (d, J=7.2 Hz, 1H);

Example 318

$^1$H-NMR(400 MHz, DMSO-d$_6$) δ ppm 1.56-1.58 (m, 2H), 1.78-2.14 (m, 6H), 2.43-2.44(m, 1H), 2.96-3.09(m, 4H), 3.23-3.26(m, 1H), 3.47-3.50(m, 1H), 4.40-4.51 (m, 3H), 6.85 (s, 1H), 7.24(t, J=7.6 Hz, 1H), 7.34 (s, 1H), 7.39(t, J=8 Hz, J=7.2 Hz, 1H), 7.76(d, J=8 Hz, 1H), 7.94(d, J=8 Hz, 1H), 8.80 (s, 1H), 10.75 (d, J=6.8 Hz, 1H), 11.07 (s, 1H);

Example 319

$^1$H-NMR(300 MHz, DMSO-d$_6$) δ ppm 1.45 (s, 3H), 1.71-2.01 (m, 3H), 2.10-2.20 (m, 1H), 2.90-3.05 (m, 2H), 3.15-3.25(m, 1H), 3.45-3.92(m, 5H), 4.45-4.55(m, 1H), 7.21-7.32 (m, 1H), 7.42-7.48(m, 3H), 7.53-7.59 (m, 2H), 7.77-7.80 (d, J=8.1 Hz, 1H), 7.95-7.97(d, J=7.5 Hz, 1H), 8.83 (m, 1H), 9.32 (m, 1H), 10.82-10.86 (m, 1H), 11.20 (m, 1H);

Example 320

$^1$H-NMR (400 MHz, DMSO-d$_6$) δ ppm 1.79 (m, 2H,), 2.00-2.10(m, 2H), 2.94 (m, 2H), 3.18-3.20(d, J=10.0 Hz, 1H), 3.29-3.60 (m, 4H), 3.74-3.95 (m,2H), 4.05-4.30(m, 3H), 7.25-7.28(t, J=7.6 Hz, 1H), 7.38-7.42(t, J=7.6 Hz, 1H), 7.78-7.80 (d, J=8.0 Hz, 1H), 7.87-7.89 (d, J=8.0 Hz, 1H)

Example 321

$^1$H-NMR (300 MHz, DMSO-d) δ ppm 1.20-1.25 (t, J=6.9 Hz, 3H), 1.83-2.14(m, 4H), 3.01-3.08(m, 2H), 3.23-3.27(m, 1H), 3.51-3.75(m, 4H), 3.93-4.02 (m, 3H), 4.13-4.27 (m, 3H), 4.35-4.39 (m, 2H), 7.25-7.30 (t, J=7.5 Hz, 1H), 7.40-7.45(t, J=7.2 Hz, 1H), 7.77-7.80 (d, J=8.1 Hz, 1H), 7.95-7.98 (d, J=7.8 Hz, 1H), 8.53-8.92 (m, 2H), 10.83-10.86(d, J=6.3 Hz, 1H), 11.31(s, 1H)

Example 322

$^1$H-NMR (400 MHz, D$_2$O) δ ppm 1.47-1.55 (m, 2H), 1.95-2.00 (m, 4H), 2.12-2.15 (m, 2H), 2.71-2.82 (m, 2H), 3.21-3.38 (m, 5H), 4.05-4.25 (m, 3H), 7.23 (m, 1H), 7.29 (m, 1H), 7.67 (m, 1H), 7.77 (m, 1H)

Example 323

$^1$H-NMR (400 MHz, DMSO-d$_6$) δ ppm 1.41-1.43 (m, 2H), 1.80-1.96 (m, 4H), 2.00-2.13 (m, 2H), 2.95-3.01 (m, 2H), 3.17-3.28 (m, 3H), 3.37-3.52 (m, 1H), 3.67-3.69 (m, 1H), 4.32-4.36 (m, 3H), 5.03 (s, 2H), 7.25-7.27 (m, 1H), 7.31-7.38 (m, 6H), 7.40-7.43 (m, 1H), 7.76-7.78 (d, J=8.0 Hz, 1H), 7.95-7.97 (d, J=7.6 Hz, 1H), 8.65-8.80 (m, 2H), 10.78-10.79 (d, J=6.8 Hz, 1H), 11.10 (s, 1H)

Example 324

$^1$H-NMR (300 MHz, D$_2$O) δ ppm 1.80-2.20(m, 8H), 3.05-3.40(m, 8H), 3.50-4.05(m, 5H), 6.74-6.80(m, 1H), 7.10-7.18 (m, 1H), 7.26-7.32 (m, 1H), 7.61-7.70 (m, 2H), 8.30-8.45 (m, 2H)

Example 325

$^1$H-NMR (300 MHz, DMSO-d$_6$) δ ppm 1.43~1.59(m, 2H), 1.68~1.83(m, 3H), 1.88~2.01(m, 3H), 2.21(s, 3H), 2.27~2.43 (m, 3H), 2.55~2.66(m, 3H), 2.68~2.82(m, 2H), 3.06~3.16(m, 1H), 3.51~3.59(m, 3H), 4.10~4.27(m, 1H), 7.18~7.27(m, 1H), 7.32~7.43(m, 1H), 7.69~7.73(m, 1H), 7.90~7.94(m, 1H), 10.87~10.92(m, 1H)

Example 326

$^1$H-NMR (300 MHz, DMSO-d$_6$) δ ppm 1.23 (S, 1H), 1.42-1.78(m, 3H), 1.82-2.02(m, 9H), 2.60-2.82 (m, 3H), 3.04-3.12 (m, 1H), 3.42-3.72(m, 7H), 4.18(s, 1H), 7.18-7.24(m, 1H), 7.32-7.40(m, 1H), 7.73(m, 1H), 7.93(m, 1H), 10.92-10.95(m, 1H)

Example 327

$^1$H-NMR (400 MHz, CD$_3$CD) δ ppm 2.02-2.33(m, 8H), 3.10-3.80(m, 12H), 4.47-4.56(m, 3H), 7.27-7.31 (t, J=7.6 Hz, 1H), 7.41-7.44(t, J=7.2 Hz, 1H), 7.52-7.59(m, 5H), 7.80-7.82 (d, J=8.0 Hz, 1H), 7.88-7.90(d, J=7.2 Hz, 1H)

Example 328

$^1$H-NMR (400 MHz, DMSO-d$_6$) δ ppm 1.68-1.82 (m, 6h), 2.00-2.12 (m, 2H), 2.97-3.02 (m, 2H), 3.13-3.34 (m, 5H), 3.42-3.51 (m, 5H), 4.34 (m, 1H), 7.24-7.28 (t, J=8.0 Hz, 1H), 7.39-7.41 (m, 1H), 7.65-7.67 (m, 2H), 7.69-7.75 (m, 2H), 7.76-7.77 (m, 2H), 7.94-7.96 (d, J=7.6 Hz, 1H), 8.86-8.87 (m, 2H), 10.80-11.10 (m, 2H)

Example 329

$^1$H-NMR (400 MHz, DMSO-d$_6$) δ ppm 1.76-1.89 (m, 2H), 2.03-2.06 (m, 1H), 2.14-2.16 (m, 1H), 2.77-2.89 (m, 2H), 2.95-3.10 (m, 2H), 3.26-3.29 (m, 1H), 3.51-3.53 (m, 1H), 3.90-4.00 (m, 2H), 4.35-4.45 (m, 1H), 4.85 (m, 2H), 6.70-6.85 (m, 2H), 7.05-7.15(m, 1H), 7.25-7.29 (m 1H), 7.40-7.42 (m, 1H), 7.77-7.79 (d, J=8.0 Hz, 1H), 7.95-7.97 (d, J=7.6 Hz, 1H), 8.74-8.91 (m, 2H), 10.83-10.84 (d, J=6.4 Hz, 1H), 11.16 (s, 1H)

Example 330

$^1$H-NMR (400 MHz, DMSO-d6) δ ppm 1.24(s, 1H), 1.57-1.78(m, 3H), 2.0(m, 5H), 2.74 (m, 2H), 3.30(m, 3H), 3.65(m, 7H), 4.22(s, 1H), 6.51(d, J=9.2 MHz, 2H), 6.81(d, J=8.8 MHz, 2H), 7.22-7.26(t, J=8.0 Hz, 1H), 7.37-7.41(t, J=7.2 Hz, 1H), 7.73(d, J=8.0 MHz, 1H), 7.93(d, J=7.6 MHz, 1H)

Example 331

$^1$H-NMR (300 MHz, CD$_3$OD) δ ppm 1.90-2.15(m, 6H), 2.15-2.30(m, 2H), 3.19-3.64(m, 12H), 4.40-4.50(m, 1H), 6.52-6.57(m, 2H), 7.13-7.17(m, 2H), 7.26-7.32(m, 1H), 7.40-7.46(m, 1H), 7.79-7.87(m, 2H)

Example 332

$^1$H-NMR (400 MHz, D$_2$O) δ ppm 1.51-1.59(m, 2H), 1.85-2.00(m, 2H), 2.05-2.15(m, 4H), 2.67-2.79 (m, 2H), 3.15-3.25 (m, 3H), 3.31-3.49 (m, 2H), 4.07-4.18 (m, 3H), 4.21 (s, 2H), 7.20-7.24 (m, 1H), 7.29-7.50 (m, 6H), 7.68-7.70 (d, J=7.6 Hz, 1H), 7.76-7.78 (d, J=8.0 Hz, 1H)

Example 333

$^1$H-NMR (300 MHz, CD$_3$OD) δ ppm 1.40-1.56 (m, 2H), 1.90-2.10(m, 8H), 2.20-2.35 (m, 2H), 3.08-3.35 (m, 4H), 3.58-3.64 (m, 1H), 3.91-3.99 (m, 1H), 4.32-4.47 (m, 3H), 7.27-7.33 (m, 1H), 7.40-7.46 (m, 1H), 7.79-7.88 (m, 2H)

Example 334

$^1$H-NMR (300 MHz, DMSO-d$_6$) δ ppm 1.69-2.10(m, 8H), 2.75-3.05(m, 4H), 3.25-3.34 (m, 4H), 3.50-3.80(m, 4H), 4.20-4.30(m, 1H), 6.50-6.60(m, 3H), 7.10-7.26(m, 3H), 7.369(t, J=7.5 Hz, J=7.2 Hz, 1H), 7.73(d, J=8.1 Hz, 1H), 7.92 (d, J=7.8 Hz, 1H), 10.85 (d, J=5.7 Hz, 1H)

Example 335

$^1$H-NMR (400 MHz, DMSO-d$_6$) δ ppm 1.50-1.65 (m, 2H), 1.75 (s, 5H), 1.95 (m, 1H), 2.59-2.63 (m, 1H), 2.68-2.70 (m, 1H), 2.77-2.80 (m, 1H), 3.03-3.08 (m, 1H), 3.53-3.64 (m, 3H), 3.80-3.85 (m, 5H), 4.12 (m, 1H), 7.21-7.25 (t, J=8.0 Hz, 1H), 7.37-7.41 (t, J=8.0 Hz, 1H), 7.72-7.74 (d, J=8.4 Hz, 1H), 7.92-7.94 (d, J=8.0 Hz, 1H), 10.85-10.86 (d, J=5.6 Hz, 1H)

Example 336

$^1$H-NMR (400 Hz, DMSO-d6,): δ ppm 1.40 (s, 9H), 1.62-1.64 (m, 2H), 1.73 (s, 5H), 1.95 (m, 1H), 2.60-2.69 (m, 2H), 2.72-2.80 (m, 1H), 3.08-3.10 (m, 1H), 3.55-3.75 (m, 8H), 4.13-4.14 (m, 1H), 7.22-7.26 (t, J=7.2 Hz, 1H), 7.37-7.41 (t, J=7.6 Hz, 1H), 7.73-7.75 (d, J=8.0 Hz, 1H), 7.92-7.94 (d, J=8.0 Hz, 1H), 10.87-10.89 (d, J=6.8 Hz, 1H)

Example 337

2-(morpholin-4-yl)-6-[[(3R)-piperidin-3-yl]amino]-5-[5-(trifluoromethyl)-1,3-benzothiazol-2-yl]-3,4-dihydropyrimidin-4-one

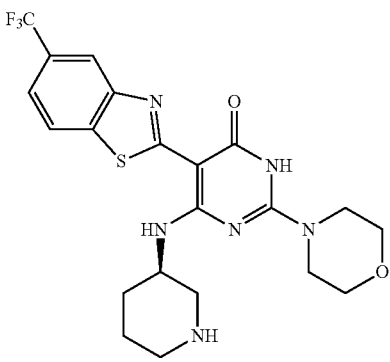 [SMILES: O=c1[nH]c(N2CCOCC2)nc(N[C@@H]2CCCNC2)c1-c1nc2cc(C(F)(F)F)ccc2s1]

Step 1. 5-(trifluoromethyl)-1,3-benzothiazole-2-thiol (Compound 59)

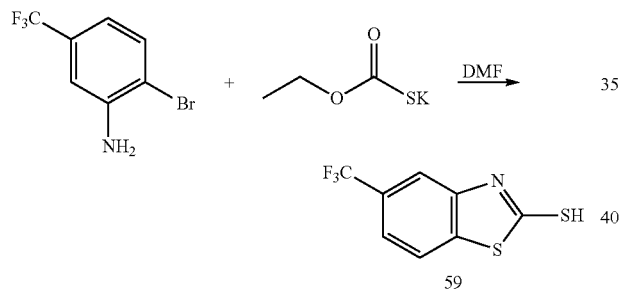

Into a solution of 2-bromo-5-(trifluoromethyl)aniline (1.5 g, 6.25 mmol, 1.00 equiv) in N,N-dimethylformamide (10.0 mL) was added ethoxy(potassiosulfanyl)methanethione (2.2 g, 13.72 mmol, 2.20 equiv) under nitrogen. The resulting mixture was heated for 4 h at 120° C. in an oil bath. After cooled down, water (70.0 mL) and hydrogen chloride (15.0 mL, 1 mol/L) were added. The solid was collected by filtration, dissolved in ethyl acetate and dried over anhydrous sodium sulfate. Filtration and evaporation of the solvent afforded the title compound. as a gray white solid. MS m/z [M+H]$^+$ (ESI): 236

Step 2. 5-(trifluoromethyl)-1,3-benzothiazole (Compound 60)

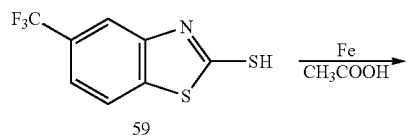

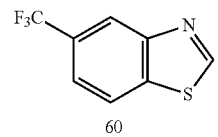

Into a solution of 5-(trifluoromethyl)-1,3-benzothiazole-2-thiol (500 mg, 2.13 mmol, 1.00 equiv) in acetic acid (15.0 mL) was added Fe (1.2 g, 10.00 equiv). The resulting solution was heated for 3 h at 110° C. in an oil bath. The solid was filtered out and washed with ethyl acetate. The filtrate was concentrated under reducing pressure, dissolved in 30 mL of ethyl acetate, washed with 50 mL of saturated sodium bicarbonate solution and 50 mL of brine respectively and dried over anhydrous sodium sulfate. Filtration and evaporation of the solvent provided 0.45 g (crude) of the title compound, which was used for next step without further purification. MS m/z [M+H]$^+$ (ESI): 204

Step 3. (3R)-tert-butyl 3-(6-methoxy-2-morpholino-5-(5-(trifluoromethyl)benzo[d]thiazol-2-yl)pyrimidin-4-ylamino)piperidine-1-carboxylate (Compound 61)

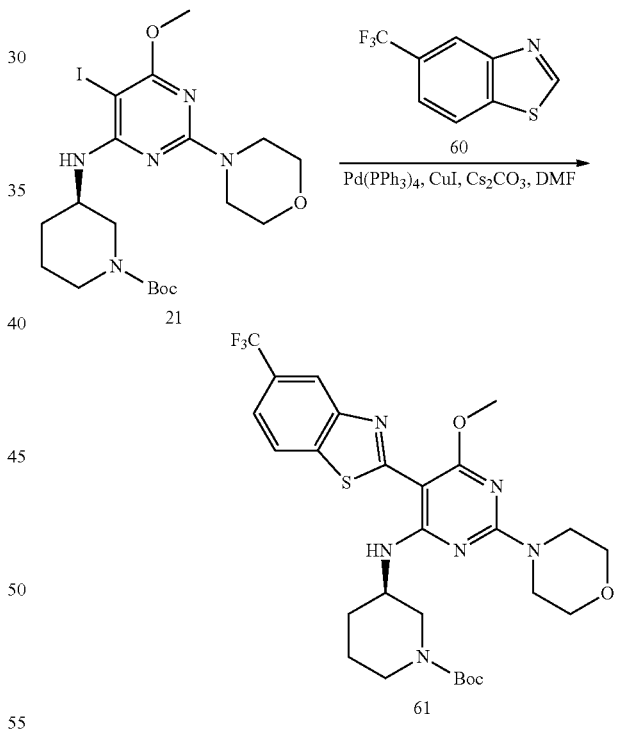

Into a 25-mL round-bottom flask purged and maintained with an inert atmosphere of nitrogen was placed a solution of 5-(trifluoromethyl)-1,3-benzothiazole (100 mg, 0.49 mmol, 1.80 equiv) in N,N-dimethylformamide (5.0 mL), tert-butyl 3-[[5-iodo-6-methoxy-2-(morpholin-4-yl)pyrimidin-4-yl]amino]piperidine-1-carboxylate (140.2 mg, 0.27 mmol, 1.00 equiv), Cesium Carbonate (534.3 mg, 6.00 equiv), Tetrakis (triphenylphosphine)palladium (57.8 mg, 0.05 mmol, 0.18 equiv), and Copper (I) iodide (9.5 mg, 0.05 mmol, 0.18 equiv). The resulting mixture was heated for 2.5 h at 85° C. in an oil bath, cooled down, quenched by the addition of 15 mL of water and then extracted with ethyl acetate (4×15 mL). The combined organic layers were washed with brine (20 mL) and dried over anhydrous sodium sulfate. After filtration and concentration under reducing pressure, the residue was purified by chromatography on a silica gel column eluting with petroleum ether/ethyl acetate (10:1-3:1) to afford the title compound as a gray white solid. MS m/z [M+H]⁺ (ESI): 595

Step 4. 2-(morpholin-4-yl)-6-[[(3R)-piperidin-3-yl]amino]-5-[5-(trifluoromethyl)-1,3-benzothiazol-2-yl]-3,4-dihydropyrimidin-4-one (Example 337)

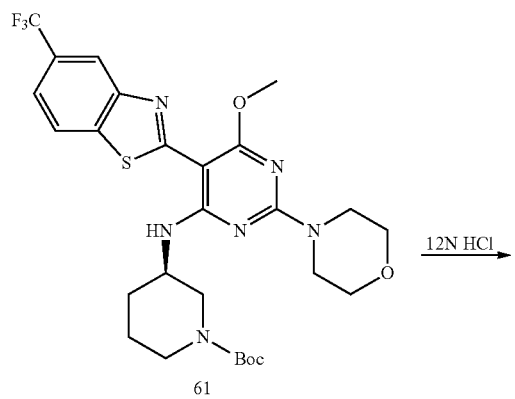

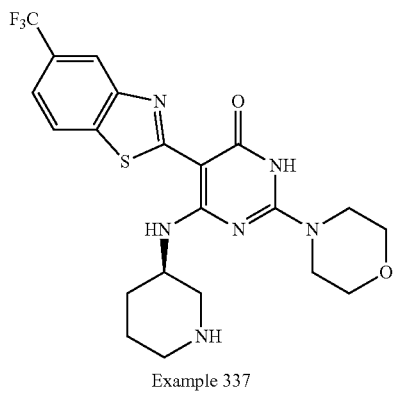
Example 337

(3R)-tert-butyl 3-(6-methoxy-2-morpholino-5-(5-(trifluoromethyl)benzo[d]thiazol-2-yl)pyrimidin-4-ylamino)piperidine-1-carboxylate (40.0 mg, 0.07 mmol, 1.00 equiv) was added to concentrated hydrochloric acid (3.0 mL, 12N). The resulting solution was stirred for 2 h at 80° C. in an oil bath. After concentrated under reducing pressure, the residue was washed with 30 mL of methanol. The solid was collected by filtration and dissolved in 5 ml of water. After adjusted the pH value to 11 with 1N sodium hydroxide (aq.), the solid was collected by filtration and dried in vacuo to provide the title compound as a yellow solid. ¹H-NMR (400 MHz, DMSO-d₆): δ ppm 1.58-1.86(m, 3H), 1.95-1.96(m, 1H), 2.58-2.67 (m, 2H), 2.78-2.81(m, 1H), 3.11-3.13(m, 1H), 3.65-3.67 (m, 8H), 4.08-4.12(m, 1H), 7.445-7.466(d, J=8.4 Hz, 1H), 7.943- 7.980(d, J=14.8 Hz, 1H), 8.072-8.092 (d, J=8.0 Hz, 1H), 10.347-10.364(m, 1H); MS m/z [M+H]⁺ (ESI): 481. IRAK4 IC₅₀=70 nM Example 338

(R)-2-morpholino-6-(piperidin-3-ylamino)-5-(7-(trifluoromethyl)benzo[d]thiazol-2-yl)pyrimidin-4(3H)-one

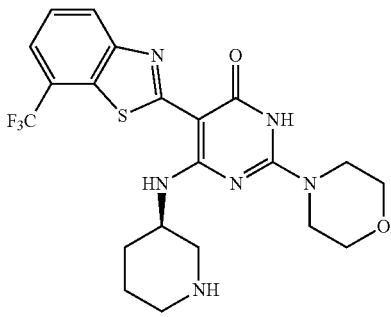 [SMILES: O=c1[nH]c(N2CCOCC2)nc(N[C@@H]2CCCNC2)c1-c1nc2cccc(C(F)(F)F)c2s1]

Step 1: 7-(trifluoromethyl)benzo[d]thiazole-2-thiol (Compound 62)

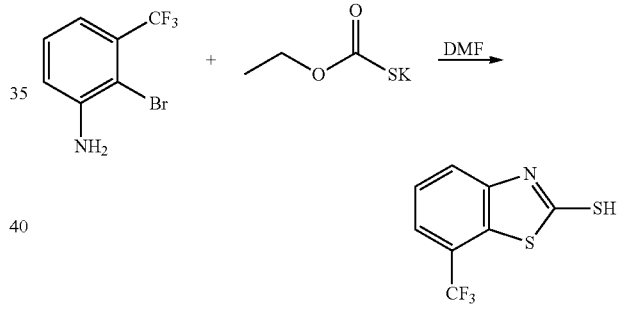

Following the same procedure as in step 1 of Example 337 using 2-bromo-3-(trifluoromethyl)aniline (1.0 g, 4.17 mmol, 1.00 equiv) and potassium O-ethyl carbonothioate (1.5 g, 9.36 mmol, 2.20 equiv) in N,N-dimethylformamide (8.0 mL). The solid was collected by filtration, washed with water and dried in vacuo to provide the title compound as a gray white solid.

Step 2: 7-(trifluoromethyl)benzo[d]thiazole (Compound 63)

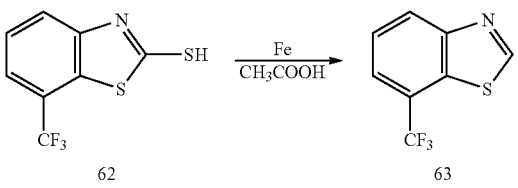

Following the same procedure as in step 2 of Example 337 using 7-(trifluoromethyl)-1,3-benzothiazole-2-thiol (300 mg, 1.28 mmol, 1.00 equiv) and iron powder (710 mg, 10.00 equiv) in acetic acid (12.0 mL). 210 mg of the title compound was obtained as a crude product as a gray-white solid, which was used directly for next step without further purification.

Step 3: (3R)-tert-butyl 3-(6-methoxy-2-morpholino-5-(7-(trifluoromethyl)benzo[d]thiazol-2-1)pyrimidin-4-ylamino)piperidine-1-carboxylate (Compound 64)

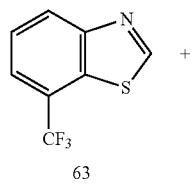
63

+

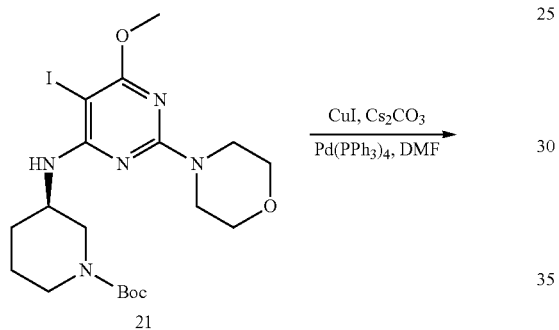
21

Following the same procedure as in step 3 of Example 337 using 7-(trifluoromethyl)-1,3-benzothiazole (100 mg, 0.49 mmol, 1.80 equiv) tert-butyl (3R)-3-[[5-iodo-6-methoxy-2-(morpholin-4-yl)pyrimidin-4-yl]amino]piperidine-1-carboxylate (140.2 mg, 0.27 mmol, 1.00 equiv), cesium carbonate (534.3 mg, 1.64 mmol, 6.00 equiv), tetrakis(triphenylphosphine)palladium (57.8 mg, 0.05 mmol, 0.18 equiv) and copper (I) iodide (9.5 mg, 0.05 mmol, 0.18 equiv) in DMF (5.0 mL). The crude product was purified by flash chromatography on silica gel, eluting with ethyl acetate/petroleum ether (1:10-1:3) to give the title compound (white solid).

Step 4: 2-(morpholin-4-yl)-6-[[(3R)-piperidin-3-yl]amino]-5-[7-(trifluoromethyl)-1,3-benzothiazol-2-yl]-3,4-dihydropyrimidin-4-one (Example 338)

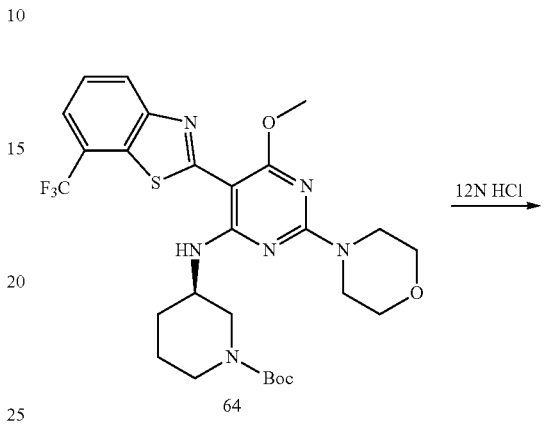
64

12N HCl →

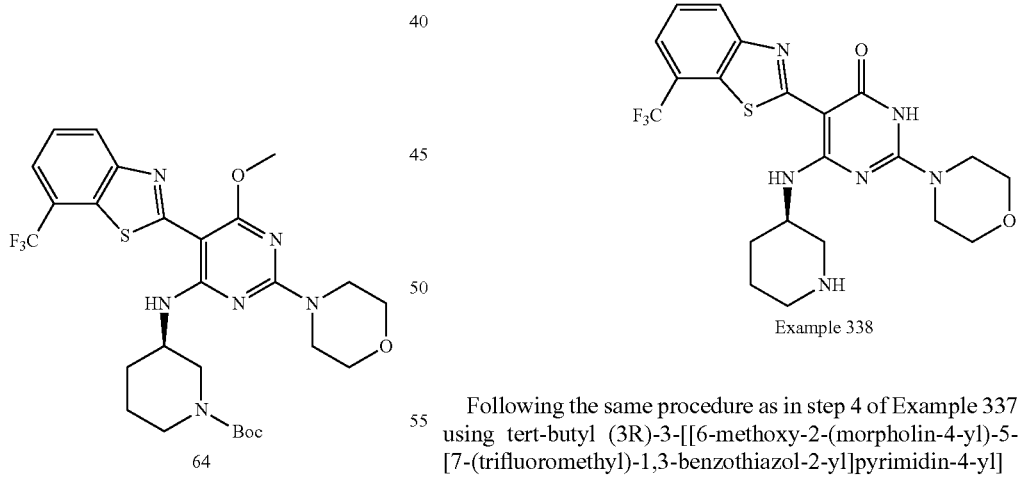
Example 338

Following the same procedure as in step 4 of Example 337 using tert-butyl (3R)-3-[[6-methoxy-2-(morpholin-4-yl)-5-[7-(trifluoromethyl)-1,3-benzothiazol-2-yl]pyrimidin-4-yl]amino]piperidine-1-carboxylate (40.0 mg, 0.07 mmol, 1.00 equiv) and conc. hydrochloric acid (3.0 mL). The crude product was triturated in methanol and dissolved in 5.0 ml of water. The pH value of the solution was adjusted to 11 with sodium hydroxide (1 M). The solid was collected by filtration and dried in vacuo to afford the title compound. Yield: 16.1 mg (50%). $^1$H-NMR (400 MHz, DMSO-$d_6$): ppm 1.54-1.57 (m, 1H), 1.63-1.73(m, 2H), 1.94(m, 1H), 2.64-2.82(m, 3H), 3.08-3.11(m, 1H), 3.69-3.70(m, 8H), 4.17-4.18(m, 1H), 7.57-7.63(m, 2H), 8.00-8.02(d, J=7.6 Hz, 1H), 10.69-10.71(m, 1H); $^{19}$F-NMR (300 MHz, DMSO-d6): ppm −61.57; MS m/z [M+H]$^+$ (ESI): 481. IRAK4 IC$_{50}$=520 nM Example 339

(R)-5-(7-chlorobenzo[d]thiazol-2-yl)-2-morpholino-6-(piperidin-3-ylamino)pyrimidin-4(3H)-one

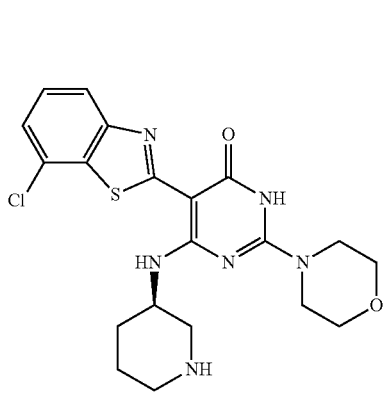 [SMILES: O=c1[nH]c(N2CCOCC2)nc(N[C@@H]2CCCNC2)c1-c1nc2cccc(Cl)c2s1]

Step 1: 7-chlorobenzo[d]thiazole-2-thiol (Compound 65)

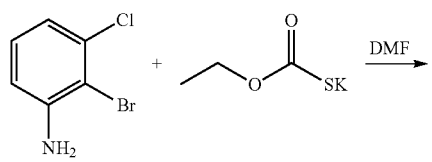

Following the same procedure as in step 1 of Example 337 using 2,3-dichloroaniline (2.0 g, 12.34 mmol, 1.00 equiv) and potassium O-ethyl carbonothioate (4.4 g, 27.45 mmol, 2.20 equiv) in DMF (15.0 mL). Yield: 1 g (84%) gray white solid.

Step 2: 7-chlorobenzo[d]thiazole (Compound 66)

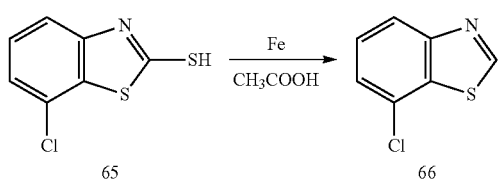

Following the same procedure in step 2 of Example 337 using 7-chloro-1,3-benzothiazole-2-thiol (700 mg, 3.47 mmol, 1.00 equiv) and iron powder (1.94 g, 10.00 equiv) in acetic acid (20.0 mL) (gray white solid).

Step 3: (3R)-tert-butyl 3-(5-(7-chlorobenzo[d]thiazol-2-yl)-6-methoxy-2-morpholinopyrimidin-4-ylamino)piperidine-1-carboxylate (Compound 67)

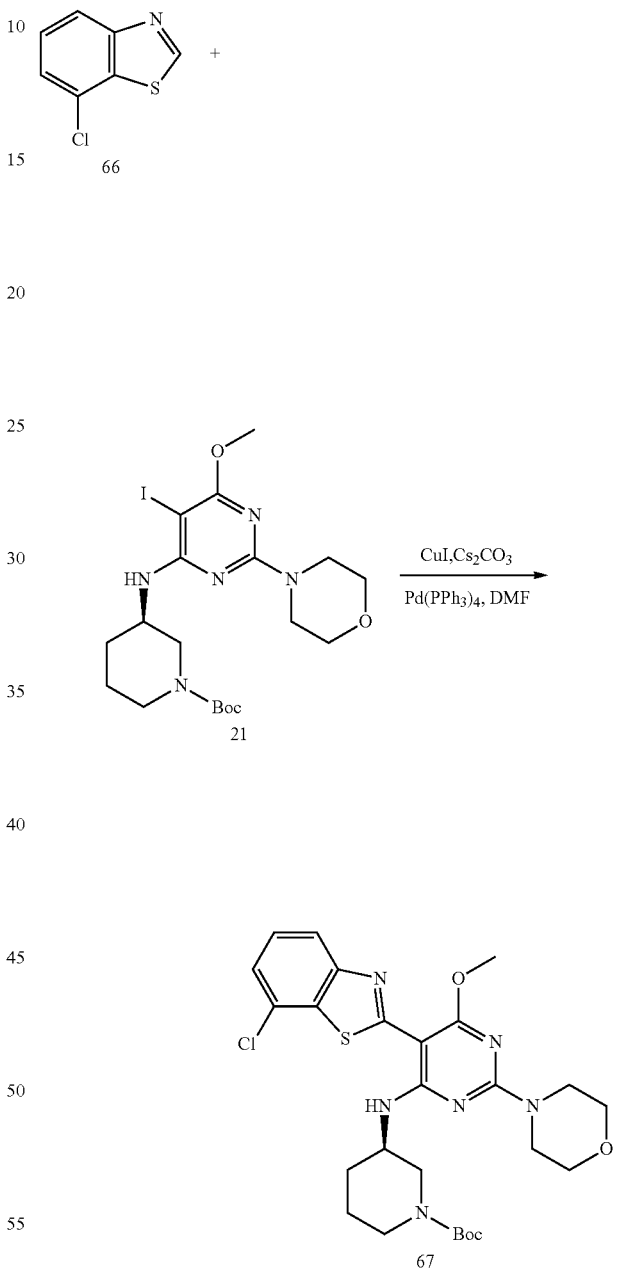

Following the same procedure as in step 3 of Example 337 using 7-chloro-1,3-benzothiazole (58.8 mg, 0.35 mmol, 1.80 equiv), tert-butyl (3R)-3-[[5-iodo-6-methoxy-2-(morpholin-4-yl)pyrimidin-4-yl]amino]piperidine-1-carboxylate (100.0 mg, 0.19 mmol, 1.00 equiv), cesium carbonate (371.4 mg, 6.00 equiv), tetrakis(triphenylphosphine)palladium (40.4 mg, 0.03 mmol, 0.18 equiv) and copper (I) iodide (6.7 mg, 0.04 mmol, 0.18 equiv) in N,N-dimethylformamide (4.0 mL). The crude product was purified through a silica gel column, eluting with ethyl acetate/petroleum ether (1:10-1:3) to provide the title compound as a white solid.

Step 4: (R)-5-(7-chlorobenzo[d]thiazol-2-yl)-2-morpholino-6-(piperidin-3-ylamino)pyrimidin-4(3H)-one (Example 339)

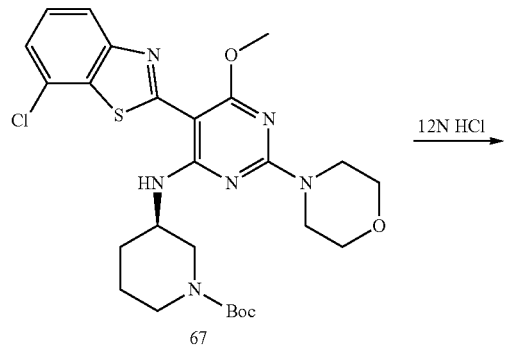

Example 339

Following the same procedure as in step 4 of Example 337 using tert-butyl (3R)-3-[[5-(7-chloro-1,3-benzothiazol-2-yl)-6-methoxy-2-(morpholin-4-yl)pyrimidin-4-yl]amino]piperidine-1-carboxylate (40.0 mg, 0.07 mmol, 1.00 equiv) and 12 N hydrochloric acid (3.0 ml). The solid was collected by filtration and dried in vacuo to give the title compound as an off-white solid. $^1$H-NMR (400 MHz, DMSO-$d_6$): ppm 1.611-1.736(m, 3H), 1.935(m, 1H), 2.621-2.819(m, 3H), 3.079-3.114(m, 1H), 3.687-3.698(m, 8H), 4.157-4.167(m, 1H), 7.306-7.325(d, J=7.6 Hz, 1H), 7.399-7.419(d, J=8.0 Hz, 1H), 7.686-7.706(d, J=8.0 Hz, 1H), 10.667-10.685(m, 1H). MS m/z [M+H]$^+$ (ESI): 447. IRAK4 IC$_{50}$=180 nM

Example 340

5-(7-methylbenzo[d]thiazol-2-yl)-2-morpholino-6-(piperidin-3-ylamino)pyrimidin-4(3H)-one

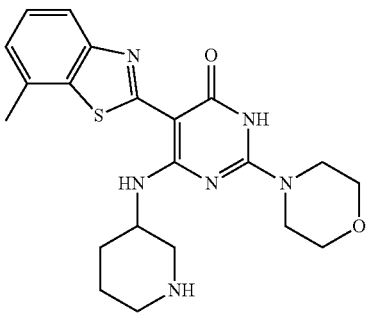 [SMILES: Cc1cccc2nc(-c3c(NC4CCCNC4)nc(N4CCOCC4)[nH]c3=O)sc12]

Step 1: 7-methylbenzo[d]thiazole-2-thiol (Compound 68)

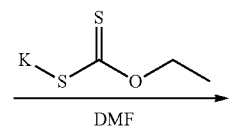

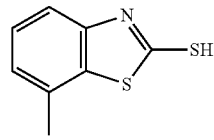

68

Following the same procedure as in step 1 of Example 337 using 2-bromo-3-methylaniline (5 g, 26.87 mmol, 1.00 equiv) and potassium O-ethyl carbonothioate (9.46 g, 59.01 mmol, 2.20 equiv) in DMF (40 mL) as a yellow solid.

Step 2: 7-methylbenzo[d]thiazole (Compound 69)

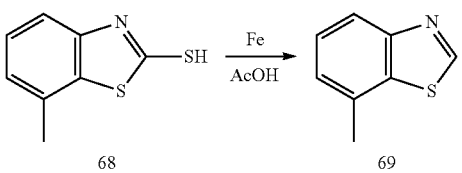

Following the same procedure as in step 2 of Example 337 using 7-methyl-1,3-benzothiazole-2-thiol (3.8 g, 20.96 mmol, 1.00 equiv) and iron powder (9.28 g, 171.85 mmol, 8.20 equiv) in acetic acid (24 mL) as a yellow oil.

Step 3: tert-butyl 3-(6-methoxy-5-(7-methylbenzo[d]thiazol-2-yl)-2-morpholino-1,6-dihydropyrimidin-4-ylamino)piperidine-1-carboxylate (Compound 70)

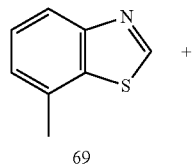

69

+

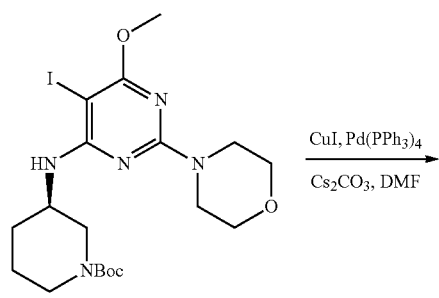

21

CuI, Pd(PPh₃)₄
Cs₂CO₃, DMF
→

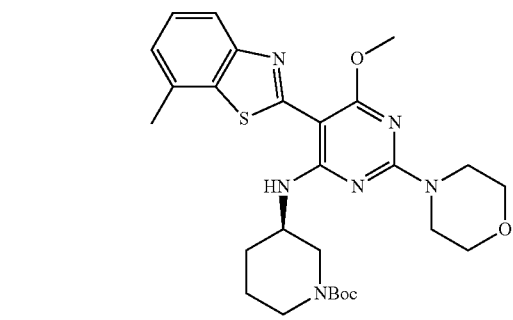

67

Following the same procedure as in step 3 of Example 337 using tert-butyl (3R)-3-[[5-iodo-6-methoxy-2-(morpholin-4-yl)-1,6-dihydropyrimidin-4-yl]amino]piperidine-1-carboxylate (30 mg, 0.06 mmol, 1.00 equiv), 7-methyl-1,3-benzothiazole (15.5 mg, 0.10 mmol, 1.81 equiv), tetrakis(triphenylphosphane) palladium (12 mg, 0.01 mmol, 0.18 equiv), iodocopper (2 mg, 0.01 mmol, 0.18 equiv), and cesium Carbonate (112.8 mg, 0.35 mmol, 6.00 equiv) in N,N-dimethylformamide (2.5 mL). The crude product was purified through a silica gel column with ethyl acetate/petroleum ether (1:10-1:5) to afford the title compound as a brown solid.

Step 4: (R)-5-(7-methylbenzo[d]thiazol-2-yl)-2-morpholino-6-(piperidin-3-ylamino)pyrimidin-4(3H)-one (Example 340)

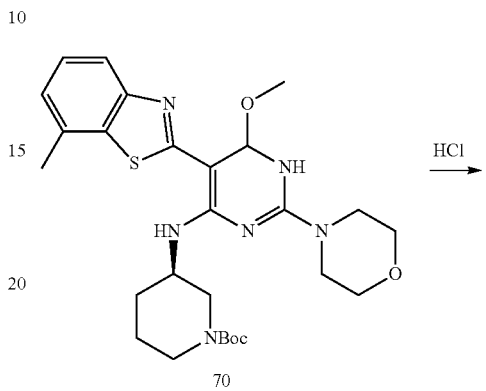

70

HCl
→

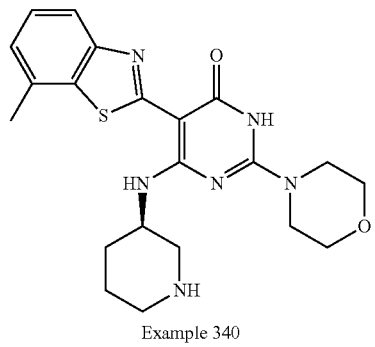

Example 340

Following the same procedure as in step 4 of Example 337 using tert-butyl (3R)-3-[[6-methoxy-5-(7-methyl-1,3-benzothiazol-2-yl)-2-(piperidin-4-yl)-1,6-dihydropyrimidin-4-yl]amino]piperidine-1-carboxylate (100 mg, 0.18 mmol, 1.00 equiv) and conc. Hydrochloric acid (3 mL). The crude product was purified by Prep-HPLC with the following conditions (1#-Pre-HPLC-001(SHIMADZU)): Column, SunFire Prep C18 OBD Column, 5 um, 19*150 mm,; mobile phase, water with 0.05% TFA and CH₃CN (23% CH₃CN up to 37% in 7 min, up to 100% in 2 min, down to 23% in 1 min); Detector, Waters 2489 254&220 nm to afford the title compound as the corresponding TFA salt as a white solid. ¹H-NMR (400 MHz, DMSO-d6): ppm 1.79-1.83 (m, 2H), 1.99-2.02 (m, 1H), 2.12 (s, 1H), 2.50 (s, 3H), 2.95-3.00 (m, 2H), 3.25-3.33 (m, 1H), 3.41-3.48 (m, 1H), 3.70-3.87 (m, 8H), 4.37 (s, 1H), 7.09-7.10 (d, J=7.2 Hz, 1H), 7.32-7.36 (t, J=7.6 Hz, 1H), 7.61-7.67 (m, 1H), 8.81-9.00 (br, 2H), 10.82-

10.84 (d, J=6.8 Hz, 1H), 11.02-11.22 (br, 1H); MS m/z [M+H]+ (ESI): 427. IRAK4 IC$_{50}$=580 nM

Example 341

5-(5-methyl-1,3-benzothiazol-2-yl)-2-(morpholin-4-yl)-6-[[(3R)-piperidin-3-yl]amino]-3,4-dihydropyrimidin-4-one formic acid

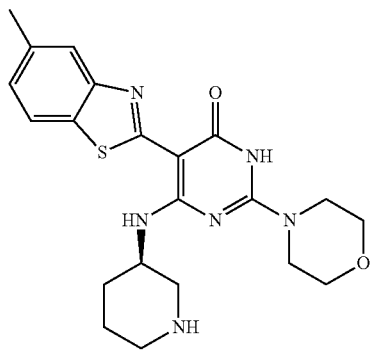 [SMILES: Cc1ccc2sc(-c3c(N[C@@H]4CCCNC4)nc(N4CCOCC4)[nH]c3=O)nc2c1]

Step 1. tert-butyl (3R)-3-[[6-methoxy-5-(5-methyl-1,3-benzothiazol-2-yl)-2-(morpholin-4-yl)pyrimidin-4-yl]amino]piperidine-1-carboxylate (Compound 71)

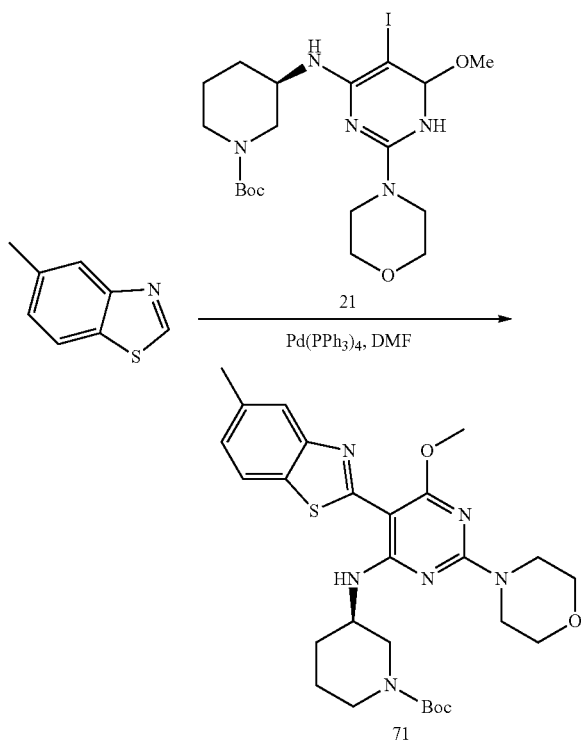

Following the same procedure as in step 3 of Example 337 using 5-methyl-1,3-benzothiazole (52.2 mg, 0.35 mmol, 1.80 equiv), tert-butyl (3R)-3-[[5-iodo-6-methoxy-2-(morpholin-4-yl)pyrimidin-4-yl]amino]piperidine-1-carboxylate (100.0 mg, 0.19 mmol, 1.00 equiv), cesium Carbonate (0.37 g, 6.00 equiv), Pd(PPh$_3$)$_4$ (40.4 mg, 0.03 mmol, 0.18 equiv) and copper (I) iodide (6.7 mg, 0.09 mmol, 0.18 equiv) in DMF (6 mL). The crude product was purified by chromatography on a silica gel column eluting with petroleum ether/ethyl acetate (15:1-3:1) to afford the title compound as a light yellow solid. MS m/z [M+H]+ (ESI): 541.

Step 2. 5-(5-methyl-1,3-benzothiazol-2-yl)-2-(morpholin-4-yl)-6-[[(3R)-piperidin-3-yl]amino]-3,4-dihydropyrimidin-4-one; formic acid (Example 341)

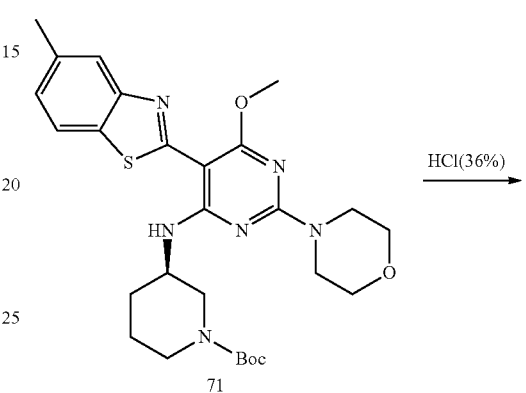

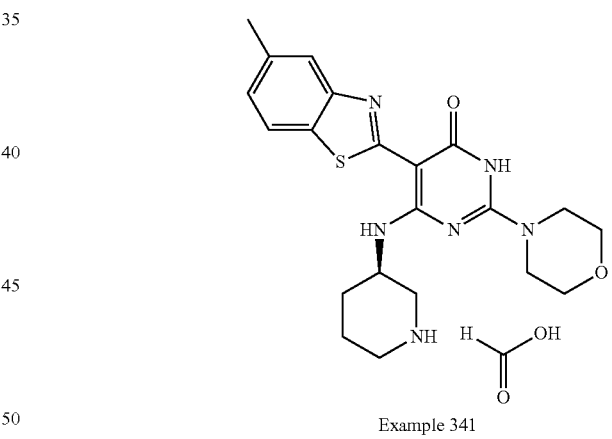

Example 341

Following the same procedure as in step 4 of Example 337 using tert-butyl (3R)-3-[[6-methoxy-5-(5-methyl-1,3-benzothiazol-2-yl)-2-(morpholin-4-yl)pyrimidin-4-yl]amino] piperidine-1-carboxylate (70.0 mg, 0.13 mmol, 1.00 equiv) in conc. hydrochloric acid (5.0 mL). The crude product was purified by Prep-HPLC with the following conditions (1#-Pre-HPLC-001(SHIMADZU)): Column, SunFire Prep C18 OBD Column, 5 um, 19*150 mm,; mobile phase, water with 0.1% FA and CH$_3$CN (17.0% CH$_3$CN up to 31.0% in 7 min, up to 100.0% in 4 min, down to 17.0% in 1 min); Detector, Waters 2489 254&220 nm to afford the title compound as the corresponding FA salt as a white solid. $^1$H-NMR (300 MHz, DMSO-d$_6$) δ ppm 1.69-1.73(m, 2H), 1.82(m, 1H), 1.95(m, 1H), 2.33(s, 3H), 2.70-2.72(m, 2H), 2.80-2.85(m, 1H), 3.11-3.14(m, 1H), 3.62-3.68(m, 8H), 4.13-4.15(m, 1H), 7.06-7.09

(d, J=8.1 Hz, 1H), 7.56(s, 1H), 7.78-7.83(m, 1H), 8.35(s, 1H), 10.86-10.89(m, 1H); MS m/z [M+H]+ (ESI): 427. IRAK4 IC$_{50}$=50 nM

Example 342

(R)-5-(5-tert-butylbenzo[d]thiazol-2-yl)-2-morpholino-6-(piperidin-3-ylamino)pyrimidin-4(3H)-one

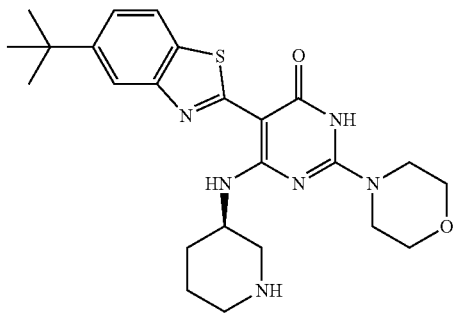 [SMILES: CC(C)(C)c1ccc2sc(-c3c(N[C@@H]4CCCNC4)nc(N4CCOCC4)[nH]c3=O)nc2c1]

Step 1: 1-bromo-4-tert-butyl-2-nitrobenzene (Compound 72)

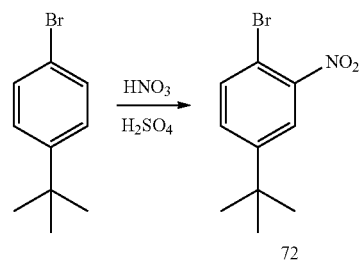

A mixture of sulfuric acid (5.79 g, 59.03 mmol, 2.25 equiv) and nitric acid (2.48 g, 39.37 mmol, 1.50 equiv) was added into 1-bromo-4-tert-butylbenzene (5.6 g, 26.28 mmol, 1.00 equiv) while maintaining the temperature below 10° C. The resulting solution was stirred for 20 h at 25° C., poured into water and extracted with ether. The organic phase was dried over anhydrous sodium sulfate. After filtered and concentrated under reduced pressure, the residue was purified through a silica gel column with ethyl acetate/petroleum ether (1:200-1:50) to afford the title compound as a yellow liquid. $^1$H-NMR (400 MHz, DMSO-d6): δ ppm 1.361(s, 9H), 7.454 (dd, J=2.4 Hz, J=8.4 Hz, 1H), 7.65(d, J=8.4 Hz, 1H), 7.848(d, J=2.4 Hz, 1H).

Step 2: 2-bromo-5-tert-butylbenzenamine (Compound 73)

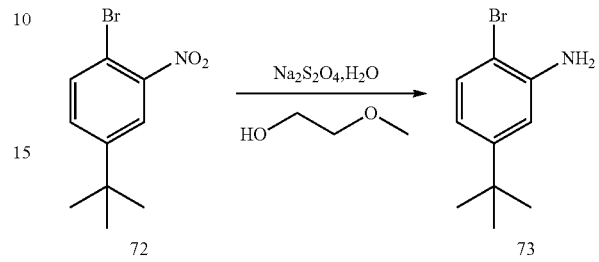

Into a 100-mL round-bottom flask purged and maintained with an inert atmosphere of nitrogen, was placed 1-bromo-4-tert-butyl-2-nitrobenzene (2.1 g, 8.14 mmol, 1.00 equiv), sodium hyposulfite (6.6 g, 37.91 mmol, 3.50 equiv) and a solution of 2-methoxyethan-1-ol (12 mL) in water (12 mL). The resulting solution was stirred overnight at 130° C. Water (11 ml) and concentrated hydrochloric acid (11 ml) were added to the warm solution. After heated under reflux for 30 min, the reaction mixture was poured into ice water (25 ml), adjusted the pH value of the solution to 8-9 with sodium carbonate(s) and extracted with ether (3×50 mL). The combined organic layers were washed with brine and dried over anhydrous sodium sulfate. Filtration and concentration under reduced pressure gave the title compound, which was used directly for next step without further purification as a yellow liquid. $^1$H-NMR(400 MHz, DMSO-d6): δ ppm 1.298(s, 9H), 4.097(s, 2H), 6.682(dd, J=2 Hz, J=8.4 Hz, 1H), 6.827(d, J=2.4 Hz, 1H), 7.33(d, J=8.4 Hz, 1H).

Step 3: 5-tert-butylbenzo[d]thiazole-2-thiol (Compound 74)

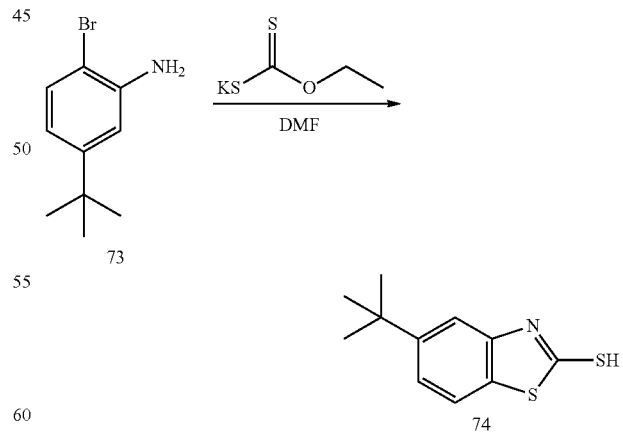

Following the same procedure as in step 1 of Example 337 using 2-bromo-5-tert-butylaniline (500 mg, 2.19 mmol, 1.00 equiv) and potassium O-ethyl carbonothioate (1.406 g, 8.77 mmol, 4.00 equiv) in N,N-dimethylformamide (25 mL). 0.5 g (crude) of the title compound was obtained as a yellow solid, which was used directly for next step without further purification. ¹H-NMR(300 MHz, CDCl₃): δ ppm 1.345(s, 9H), 7.313-7.406 (m, 3H), 11.48(s, 1H); MS m/z [M+H]+ (ESI): 224.

Step 4: 5-tert-butylbenzo[d]thiazole (Compound 75)

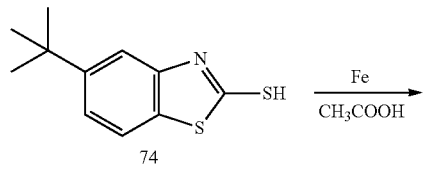

Following the same procedure as in step 2 of Example 337 using 5-tert-butyl-1,3-benzothiazole-2-thiol (1.2 g, 5.36 mmol, 1.00 equiv), and iron powder (3.0 g, 53.57 mmol, 10.00 equiv) in acetic acid (60 mL). 1.12 g (crude) of the title compound was obtained as a yellow liquid, which was used directly for next step without further purification. ¹H-NMR (400 MHz, DMSO-d6): δ ppm δ 1.459(s, 9H), 7.544(dd, J=1.6 Hz, J=8.8 Hz, 1H), 7.897(d, J=8.8 Hz, 1H), 8.187(d, J=1.6 Hz, 1H), 9.00(s, 1H).

Step 5: 5-tert-butylbenzo[d]thiazole (Compound 76)

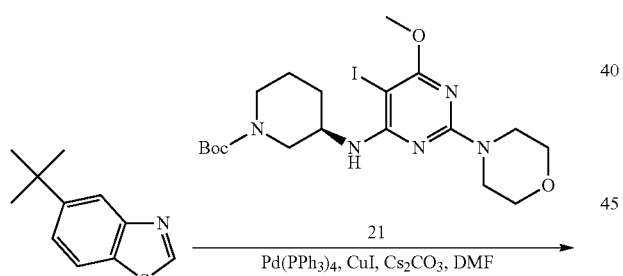

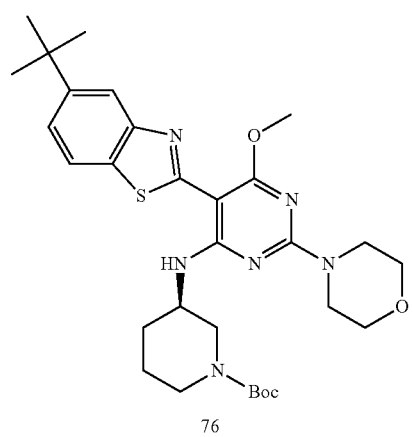

Following the same procedure as in step 3 of Example 337 using 5-tert-butyl-1,3-benzothiazole (77.4 mg, 0.40 mmol, 1.00 equiv), tert-butyl (3R)-3-[[5-iodo-6-methoxy-2-(morpholin-4-yl)pyrimidin-4-yl]amino]piperidine-1-carboxylate (117 mg, 0.23 mmol, 1.00 equiv), Pd(PPh₃)-4 (46.9 mg, 0.04 mmol, 0.18 equiv), copper (I) iodide (7.7 mg, 0.04 mmol, 0.18 equiv) and cesium carbonate (440 mg, 1.35 mmol, 6.00 equiv) in N,N-dimethylformamide (12 mL). The crude product was purified through a silica gel column with dichloromethane/methanol (50:1) to give the title compound as a yellow solid.

Step 6: (R)-5-(5-tert-butylbenzo[d]thiazol-2-yl)-2-morpholino-6-(piperidin-3-ylamino)pyrimidin-4 (3H)-one (Example 342)

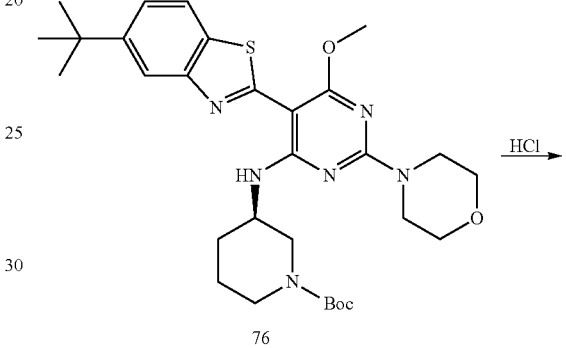

Example 342

Following the same procedure as in step 4 of Example 337 using tert-butyl (3R)-3-[[5-(5-tert-butyl-1,3-benzothiazol-2-yl)-6-methoxy-2-(morpholin-4-yl)pyrimidin-4-yl]amino]piperidine-1-carboxylate (101.6 mg, 0.17 mmol, 1.00 equiv) and hydrochloric acid (10 mL, 6M). The crude product was purified by Prep-HPLC with the following conditions (1#-Pre-HPLC-001(SHIMADZU)): Column, SunFire Prep C18 OBD Column, 5 um, 19*150 mm,; mobile phase, water with 0.05% TFA and CH₃CN (30.0% CH₃CN up to 44.0% in 7 min, up to 100.0% in 5 min, down to 30.0% in 1 min); Detector, Waters 2489 254&220 nm to afford the title compound as the corresponding FTA salt as a white solid. ¹H-NMR(400 MHz, DMSO-d6): □δ ppm 1.239 (s, 1H), 1.375 (s, 9H), 1.837(d, J=9.2 Hz, 2H), 2.0(d, J=6 Hz, 1H), 2.126 (s, 1H), 2.936-3.01 (m, 2H), 3.272(d, J=11.2 Hz, 1H), 3.489(d, J=9.6 Hz, 1H), 3.706-3.726(m, 8H), 4.375(d, J=5.2 Hz, 1H), 7.349(t, J=1.6 Hz, J=8.4 Hz, 1H), 7.752(d, J=1.6 Hz, 1H), 7.849(d, J=8.4 Hz, 1H), 8.733(br, 1H), 8.866 (br, 1H), 10.768(d, J=6.8 Hz, 1H), 11.133 (s, 1H); $^{19}$F-NMR (400 MHz, DMSO-d6): δ ppm −74.25; MS m/z [M+H]+ (ESI): 469. IRAK4 IC$_{50}$=1300 nM

Example 343

(R)-5-(5-chlorobenzo[d]thiazol-2-yl)-2-morpholino-6-(piperidin-3-ylamino)pyrimidin-4(3H)-one

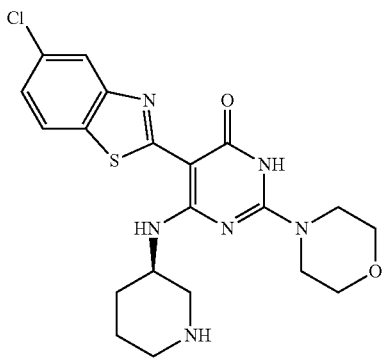 [SMILES: O=c1[nH]c(N2CCOCC2)nc(N[C@@H]2CCCNC2)c1-c1nc2cc(Cl)ccc2s1]

Step 1: 5-chlorobenzo[d]thiazole-2-thiol (Compound 77)

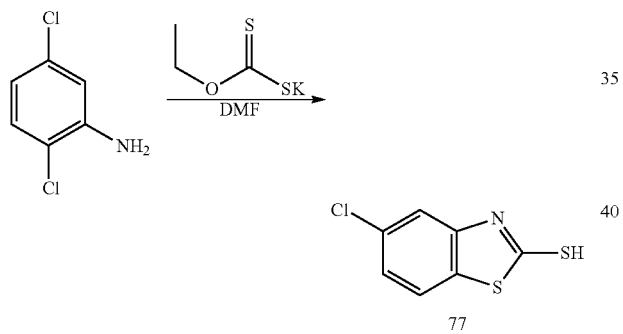

Following the same procedure as in step 1 of Example 337 using 2,5-dichloroaniline (3.0 g, 18.52 mmol, 1.00 equiv) and potassium O-ethyl carbonothioate (6.6 g, 41.17 mmol, 2.00 equiv) in N,N-dimethylformamide (18.0 mL). 2.3 g (62%) of the title compound was obtained as a crude product, which was used directly for next step without further purification.

Step 2: 5-chlorobenzo[d]thiazole (Compound 78)

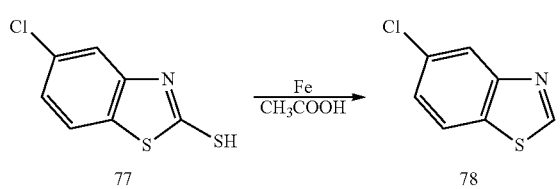

Following the same procedure as in step 2 of Example 337 using 5-chloro-1,3-benzothiazole-2-thiol (1.0 g, 4.96 mmol, 1.00 equiv) and iron powder (2.8 g, 10.00 equiv) in acetic acid (15.0 mL). The crude product was purified through a silica gel column with ethyl acetate/petroleum ether (1:50-1:10) to afford the title compound as a white solid.

Step 3: tert-butyl (3R)-3-(5-(5-chlorobenzo[d]thiazol-2-yl)-6-methoxy-2-morpholinopyrimidin-4-ylamino)piperidine-1-carboxylate (Compound 79)

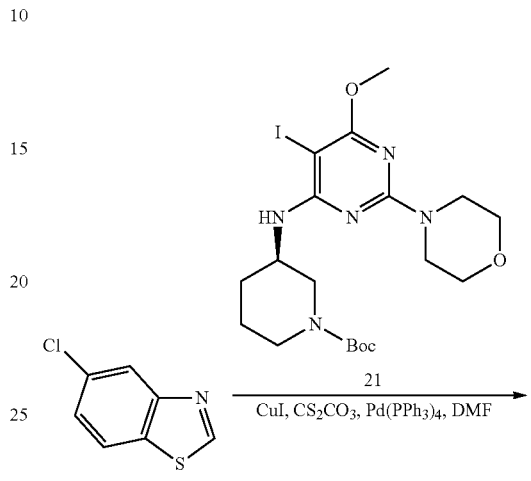

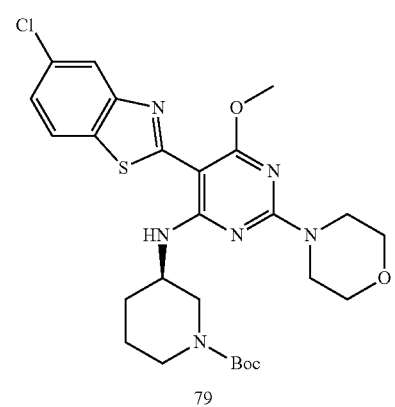

Following the same procedure as in step 3 of Example 337 using 5-chloro-1,3-benzothiazole (59.4 mg, 0.35 mmol), tert-butyl (3R)-3-[[5-iodo-6-methoxy-2-(morpholin-4-yl)pyrimidin-4-yl]amino]piperidine-1-carboxylate (100 mg, 0.19 mmol), cesium carbonate (0.37 mg), tetrakis(triphenylphosphine)palladium (40.4 mg, 0.03 mmol, 0.18 equiv) and copper (I) iodide (6.7 mg, 0.04 mmol) in DMF (5.0 mL). The crude product was purified by chromatography on a silica gel column with ethyl acetate/petroleum ether (1:10-1:3) to afford the title compound as a light yellow solid.

Step 4: (R)-5-(5-chlorobenzo[d]thiazol-2-yl)-2-morpholino-6-(piperidin-3-ylamino)pyrimidin-4(3H)-one (Example 343)

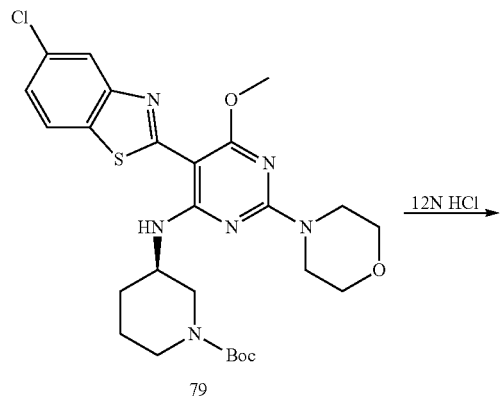

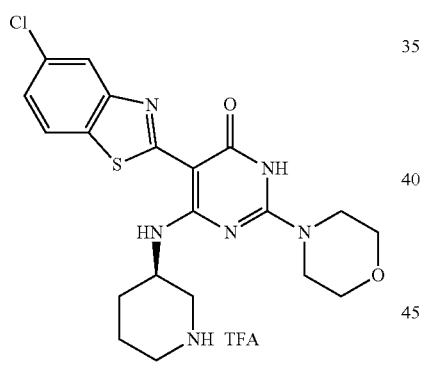

Example 343

Following the same procedure as in step 4 of Example 337 using tert-butyl (3R)-3-[[5-(5-chloro-1,3-benzothiazol-2-yl)-6-methoxy-2-(morpholin-4-yl)pyrimidin-4-yl]amino]piperidine-1-carboxylate (90.0 mg, 0.16 mmol, 1.00 equiv) and 12 N hydrochloric acid (6.0 mL,). The crude product was purified by Prep-HPLC with the following conditions (1#-Pre-HPLC-001(SHIMADZU)): Column, SunFire Prep C18 OBD Column, 5 um, 19*150 mm,; mobile phase, water with 0.05% TFA and CH₃CN (24% CH₃CN up to 38% in 7 min, up to 100% in 3 min, down to 24% in 1 min); Detector, Waters 2489 254&220 nm to afford the title compound as the corresponding TFA salt as a white solid. $^1$H-NMR(300 MHz, DMSO-d6): δ ppm 1.82-1.89(m, 2H), 1.98-2.08(m, 2H), 2.93-2.97(m, 2H), 3.16-3.20(m, 1H), 3.43-3.46(m, 1H), 3.72-3.84(m, 8H), 4.39-4.42(m, 1H), 7.28-7.31(dd, J=2.1, 8.4 Hz, 1H), 7.85-7.86(d, J=1.8 Hz, 1H), 7.97-8.00(d, J=8.4 Hz, 1H), 8.65-8.74(br, 2H), 10.68-10.70(m, 1H), 11.19(s, 1H); $^{19}$H-NMR(300 MHz, DMSO-d6): δ ppm −73.45; MS m/z [M+H]$^+$ (ESI): 447, [M+Na]$^+$ (ESI): 469. IRAK4 IC$_{50}$=8 nM Example 344

5-(7-cyclopropyl-1,3-benzothiazol-2-yl)-2-(morpholin-4-yl)-6-[[(3R)-piperidin-3-yl]amino]-3,4-dihydropyrimidin-4-one trifluoroacetic acid

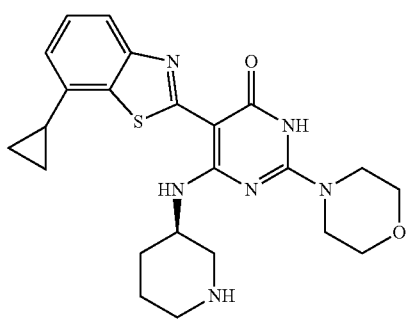 [SMILES: O=c1[nH]c(N2CCOCC2)nc(N[C@@H]2CCCNC2)c1-c1nc2cccc(C3CC3)c2s1]

Step 1. 7-cyclopropyl-1,3-benzothiazole (Compound 80)

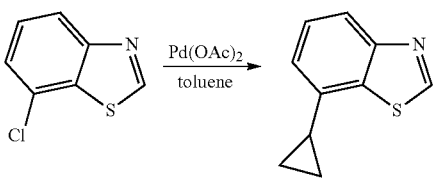

Into a solution of 7-chloro-1,3-benzothiazole (390 mg, 2.30 mmol, 1.00 equiv), cyclopropylboronic acid (300 mg, 3.49 mmol, 2.00 equiv) and potassium phosphate (2.2 g, 4.50 equiv) in a mixture toluene (12 mL) and water (1.2 mL) was added Pd(OAc)₂ (51.6 mg, 0.23 mmol, 0.10 equiv) and PCy₃HBF₄ (0.17 g, 0.20 equiv). After degassed under vacuum and flushed with nitrogen, the resulting mixture was heated for 6 h at 100° C. in an oil bath under nitrogen atmosphere, cooled down to room temperature, quenched by the addition of 20.0 mL of water and extracted with ethyl acetate (3×20 mL). The combined organic layers were washed with brine and dried over anhydrous sodium sulfate. Upon filtration and concentration under reduced pressure, the residue was purified by flash chromatography on silica gel, eluting with petroleum ether/ethyl acetate (10:1-5:1) to provide the title compound as purple oil. MS m/z [M+H]+ (ESI): 176.

Step 2. Tert-butyl (3R)-3-[[5-(7-cyclopropyl-1,3-benzothiazol-2-yl)-6-methoxy-2-(morpholin-4-yl)pyrimidin-4-yl]amino]piperidine-1-carboxylate (Compound 81)

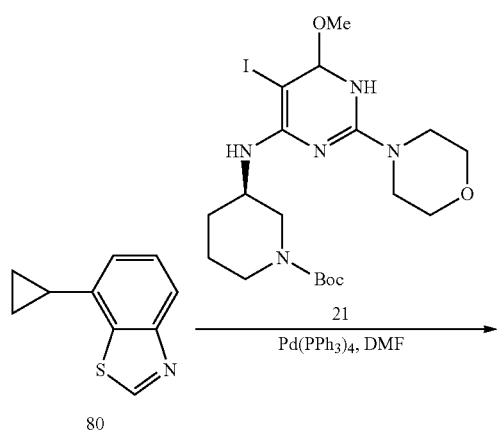

Following the same procedure as in step 3 of Example 337 using 7-cyclopropyl-1,3-benzothiazole (61.4 mg, 0.35 mmol, 1.80 equiv), tert-butyl (3R)-3-[[5-iodo-6-methoxy-2-(morpholin-4-yl)pyrimidin-4-yl]amino]piperidine-1-carboxylate (100.0 mg, 0.19 mmol, 1.00 equiv) and cesium carbonate (370 mg, 1.14 mmol, 6.00 equiv), Pd(PPh₃)₄ (40.4 mg, 0.03 mmol, 0.18 equiv) and copper (I) iodide (6.7 mg, 0.04 mmol, 0.18 equiv) in DMF (6 mL). The crude product was purified by flash chromatography on silica gel, eluting with petroleum ether/ethyl acetate (15:1-5:1) to provide the title compound as a light yellow solid. MS m/z [M+H]+ (ESI): 567.

Step 3. 5-(7-cyclopropyl-1,3-benzothiazol-2-yl)-2-(morpholin-4-yl)-6-[[(3R)-piperidin-3-yl]amino]-3,4-dihydropyrimidin-4-one: trifluoroacetic acid (Example 344)

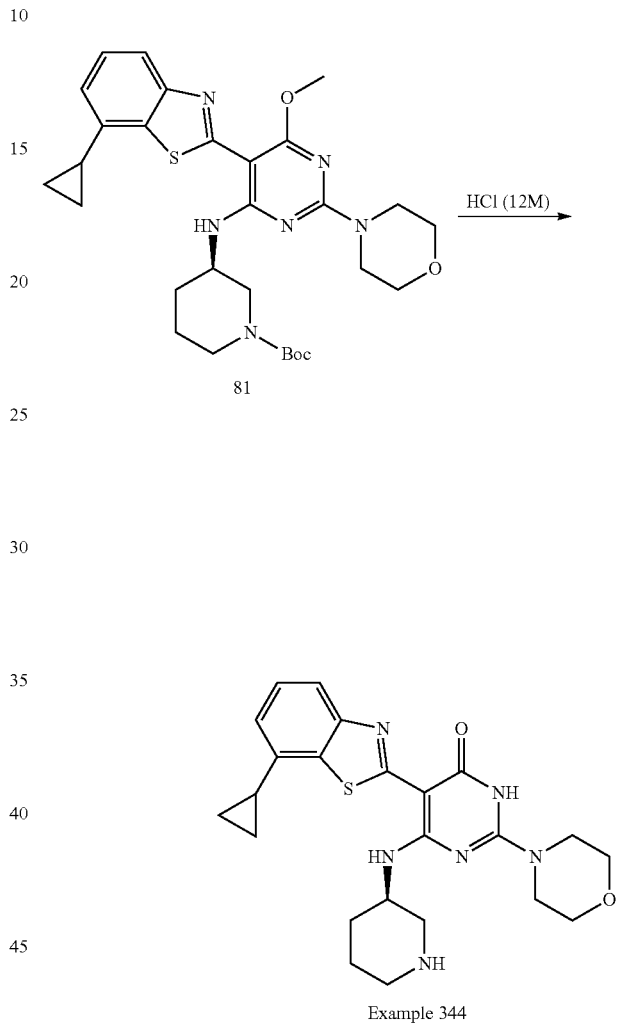

Following the same procedure as in step 4 of Example 337 using tert-butyl (3R)-3-[[5-(7-cyclopropyl-1,3-benzothiazol-2-yl)-6-methoxy-2-(morpholin-4-yl)pyrimidin-4-yl]amino]piperidine-1-carboxylate (60.0 mg, 0.11 mmol, 1.00 equiv) and conc. hydrochloric acid (6.0 mL). The crude product (100 mg) was purified by Prep-HPLC with the following conditions (1#-Pre-HPLC-001(SHIMADZU)): Column, SunFire Prep C18 OBD Column, 5 um, 19*150 mm,; mobile phase, water with 0.05% TFA and CH₃CN (26.0% CH₃CN up to 38.0% in 8 min, up to 100.0% in 5 min, down to 26.0% in 1 min); Detector, Waters 2489 254&220 nm to afford the title compound as the corresponding TFA salt as a white solid. ¹H-NMR(400 MHz, DMSO-d₆) δ ppm 0.79-0.86(m, 2H), 1.03-1.07(m, 2H), 1.79-1.83(m, 2H), 1.94-2.09(m, 1H), 2.11-2.12(m, 2H), 2.97-3.00(m, 2H), 3.16-3.18(m, 1H), 3.47-3.49 (m, 1H), 3.73-3.81(m, 8H), 6.89-6.90(d, J=7.2 Hz, 1H), 7.31-7.7.35(m, 1H), 7.59-7.61(d, J=8.0 Hz, 1H), 8.66(s, 1H), 8.86

(s, 1H), 10.85-10.86(m, 1H), 11.14(s, 1H); ¹⁹F-NMR(400 MHz, DMSO-d₆) δ ppm −73.48; MS m/z [M+H]⁺ (ESI): 453. IRAK4 IC$_{50}$=4500 nM

Example 345

5-(5-bromo-1,3-benzothiazol-2-yl)-2-(morpholin-4-yl)-6-[[(3R)-piperidin-3-yl]amino]-3,4-dihydropyrimidin-4-one

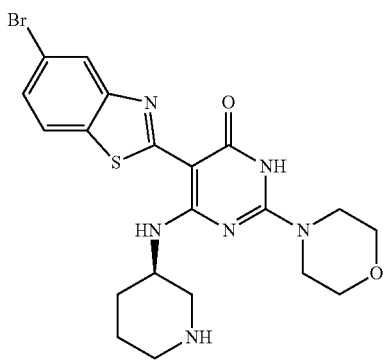 [SMILES: O=c1[nH]c(N2CCOCC2)nc(N[C@@H]2CCCNC2)c1-c1nc2cc(Br)ccc2s1]

Step 1. tert-butyl (3R)-3-[[5-(5-bromo-1,3-benzothiazol-2-yl)-6-methoxy-2-(morpholin-4-yl)pyrimidin-4-yl]amino]piperidine-1-carboxylate (Compound 82)

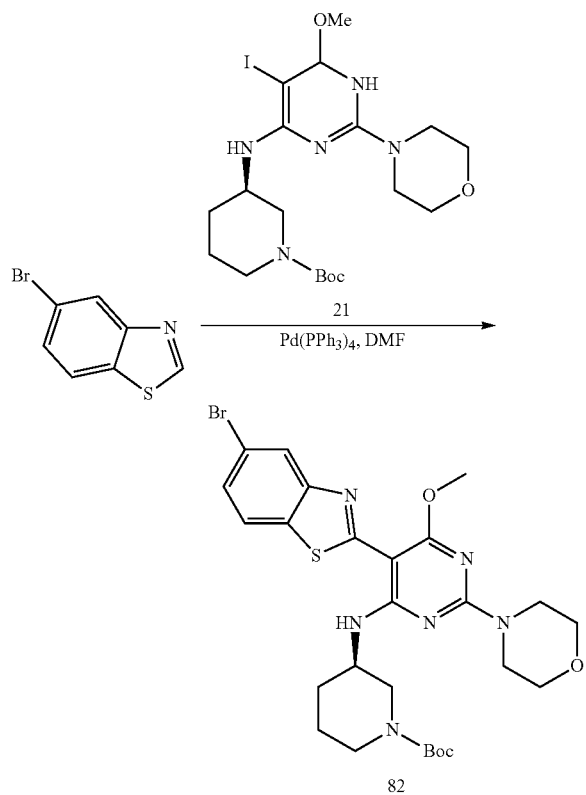

Following the same procedure as in step 3 of Example 337 using 5-bromo-1,3-benzothiazole (74.9 mg, 0.35 mmol, 1.80 equiv), tert-butyl (3R)-3-[[5-iodo-6-methoxy-2-(morpholin-4-yl)pyrimidin-4-yl]amino]piperidine-1-carboxylate (100.0 mg, 0.19 mmol, 1.00 equiv), cesium carbonate (370 mg, 1.14 mmol, 6.00 equiv), Pd(PPh₃)₄ (40.4 mg, 0.035 mmol, 0.18 equiv), copper (I) iodide (6.7 mg, 0.035 mmol, 0.18 equiv) in DMF (5.0 mL). The crude product was purified by flash chromatography on silica gel, eluting with petroleum ether/ethyl acetate (10:1-5:1) to provide the title compound as a light yellow solid. MS m/z [M+H]⁺ (ESI): 605

Step 2. 5-(5-bromo-1,3-benzothiazol-2-yl)-2-(morpholin-4-yl)-6-[[(3R)-piperidin-3-yl]amino]-3,4-dihydropyrimidin-4-one (Example 345)

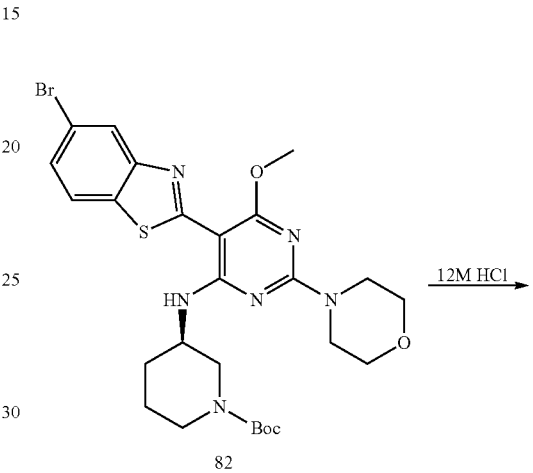

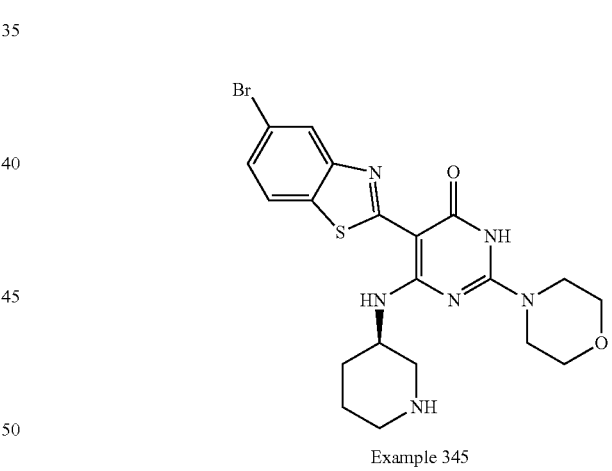

Example 345

Following the same procedure as in step 4 of Example 337 using tert-butyl (3R)-3-[[5-(5-bromo-1,3-benzothiazol-2-yl)-6-methoxy-2-(morpholin-4-yl)pyrimidin-4-yl]amino]piperidine-1-carboxylate (60.0 mg, 0.10 mmol, 1.00 equiv) and conc. hydrochloric acid (4.0 mL). The crude product (100 mg) was purified by Prep-HPLC with the following conditions (1#-Pre-HPLC-001 (SHIMADZU)): Column, SunFire Prep C18 OBD Column, 5 um, 19*150 mm,; mobile phase, water with 50 mmol NH₄HCO₃ and CH₃CN (38.0% CH₃CN up to 53.0% in 7 min, up to 100.0% in 5 min, down to 38.0% in 1 min); Detector, Waters 2489 254&220 nm to afford the title compound as a white solid. ¹H-NMR(400 MHz, DMSO-d₆) δ ppm 1.54-1.72(m, 3H), 1.92-1.93(m, 1H), 2.65-2.75(m, 2H), 2.86(m, 1H), 3.10-3.13(m, 1H), 3.62-3.69(m, 8H), 4.17

(m, 1H), 7.37-7.39(d, J=8.4 Hz, 1H), 7.89-7.94(m, 2H), 10.74-10.75(m, 1H); MS m/z [M+H]+ (ESI): 492. IRAK4 IC$_{50}$=19 nM

Example 346

5-(5-cyclopropyl-1,3-benzothiazol-2-yl)-2-(morpholin-4-yl)-6-[[(3R)-piperidin-3-yl]amino]-3,4-dihydropyrimidin-4-one trifluoroacetic acid

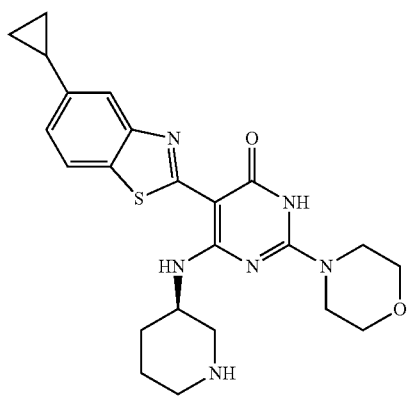 [SMILES: O=c1[nH]c(N2CCOCC2)nc(N[C@@H]2CCCNC2)c1-c1nc2cc(C3CC3)ccc2s1]

Step 1. 5-cyclopropyl-1,3-benzothiazole (Compound 83)

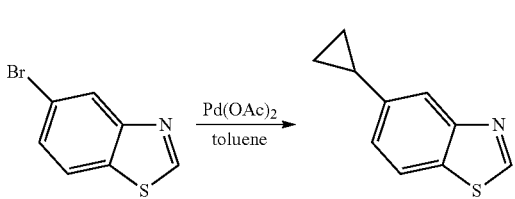

Following the same procedure in step 1 of Example 344 using 5-bromo-1,3-benzothiazole (500 mg, 2.34 mmol, 1.00 equiv), cyclopropylboronic acid (300 mg, 3.49 mmol, 1.50 equiv), potassium phosphate (2.2 g, 10.36 mmol, 4.50 equiv), palladium acetate (51.6 mg, 0.10 equiv), and PCy$_3$.HBF$_4$ (0.17 g, 0.20 equiv) in a mixture of toluene (12 mL) and water (1.2 mL). The crude product was purified by flash chromatography on silica gel, eluting with petroleum ether/ethyl acetate (10:1-5:1) to provide the title compound as a purple oil. MS m/z [M+H]+ (ESI): 176.

Step 2. Tert-butyl (3R)-3-[[5-(5-cyclopropyl-1,3-benzothiazol-2-yl)-6-methoxy-2-(morpholin-4-yl)pyrimidin-4-yl]amino]piperidine-1-carboxylate (Compound 84)

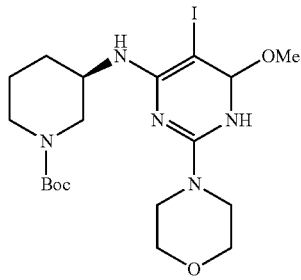

Following the same procedure as in step 3 of Example 337 using 5-cyclopropyl-1,3-benzothiazole (61.4 mg, 0.35 mmol, 1.80 equiv), tert-butyl (3R)-3-[[5-iodo-6-methoxy-2-(morpholin-4-yl)pyrimidin-4-yl]amino]piperidine-1-carboxylate (100 mg, 0.19 mmol, 1.00 equiv), cesium carbonate (0.37 g, 6.00 equiv, 1.14 mmol), Pd(PPh$_3$)$_4$ (40.4 mg, 0.035 mmol, 0.18 equiv) and copper iodide (6.7 mg, 0.035 mmol, 0.18 equiv) in DMF (6.0 mL). The crude product was purified by flash chromatography on silica gel, eluting with petroleum ether/ethyl acetate (20:1-5:1) to provide the title compound as a white solid. MS m/z [M+H]+ (ESI): 567.

Step 3. 5-(5-cyclopropyl-1,3-benzothiazol-2-yl)-2-(morpholin-4-yl)-6-[[(3R)-piperidin-3-yl]amino]-3,4-dihydropyrimidin-4-one; trifluoroacetic acid (Example 346)

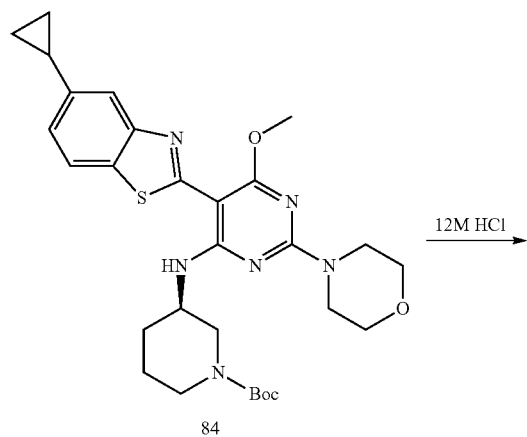

Following the same procedure in step 4 of Example 337 using tert-butyl (3R)-3-[[5-(5-cyclopropyl-1,3-benzothiazol-2-yl)-6-methoxy-2-(morpholin-4-yl)pyrimidin-4-yl]amino]piperidine-1-carboxylate (50 mg, 0.09 mmol, 1.00 equiv) in 5 mL of 12 M HCl The crude product was purified by Prep-HPLC with the following conditions (1#-Pre-HPLC-001 (SHIMADZU)): Column, SunFire Prep C18 OBD Column, 5 um, 19*150 mm,; mobile phase, water with 0.05% TFA and CH$_3$CN (25% CH$_3$CN up to 39% in 9 min, up to 100% in 3 min, down to 25% in 1 min); Detector, Waters 2489 254&220 nm to afford the title compound as the corresponding TFA salt as a white solid. $^1$H-NMR(400 MHz, DMSO-d$_6$) δ ppm 0.70-0.75(m, 2H), 0.98-1.01(m, 2H), 1.78-1.87(m, 2H), 1.99-2.09 (m, 3H), 2.95-3.19(m, 2H), 3.22-3.29(m, 1H), 3.47-3.49(m, 1H), 3.72-3.78(m, 8H), 4.37(m, 1H), 7.02-7.04(d, J=8.4 Hz, 1H), 7.48(s, 1H), 7.79-7.81(d, J=Hz, 1H), 8.68-8.84(m, 2H), 10.79-10.81(m, 1H), 11.12(s, 1H); F-NMR (400 MHz, DMSO-d$_6$) δ ppm −73.5; MS m/z [M+H]+ (ESI): 453. IRAK4 IC$_{50}$=330 nM Example 347

(R)-2-(2-morpholino-6-oxo-4-(piperidin-3-ylamino)-1,6-dihydropyrimidin-5-yl)benzo[d]thiazole-5-carboxamide

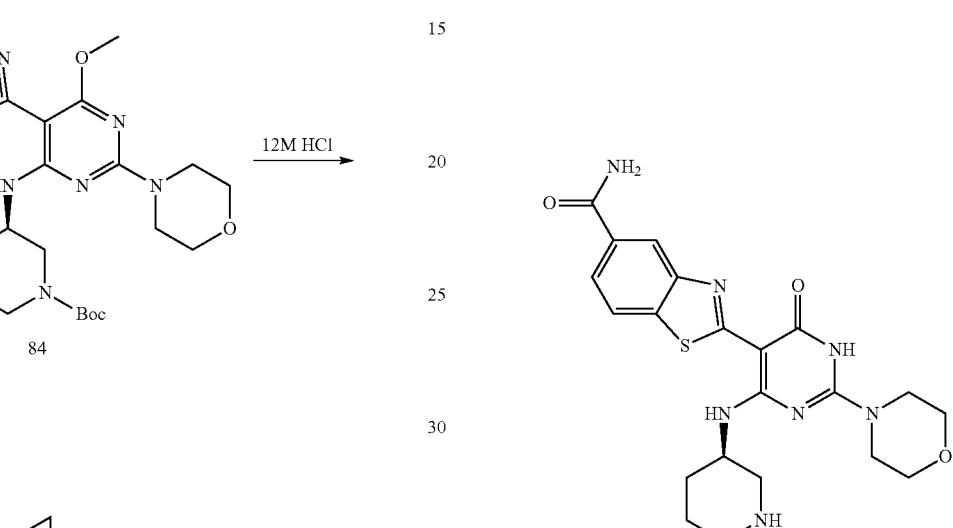

Step 1. 1,3-benzothiazole-5-carboxamide (Compound 85)

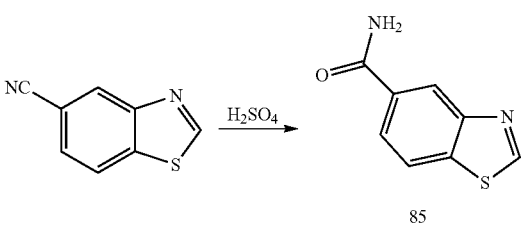

A solution of 1,3-benzothiazole-5-carbonitrile (100 mg, 0.62 mmol, 1.00 equiv) in sulfuric acid (3.0 mL) was heated for 2 h at 45° C. After cooling down, the reaction mixture was poured into 15 mL of water. The pH value of the solution was adjusted to 7 with saturated aqueous sodium bicarbonate. The resulting solution was extracted with of ethyl acetate (5×10.0 mL). The combined organic layers were washed with brine, dried over anhydrous sodium sulfate, filtered and then concentrated under vacuum. This resulted in 60.0 mg of the title compound as a crude product, which was used directly for next step without further purification. MS m/z [M+H]+ (ESI): 179.

Step 2. tert-butyl (3R)-3-[[5-(5-carbamoyl-1,3-benzothiazol-2-yl)-6-methoxy-2-(morpholin-4-yl)pyrimidin-4-yl]amino]piperidine-1-carboxylate (Compound 86)

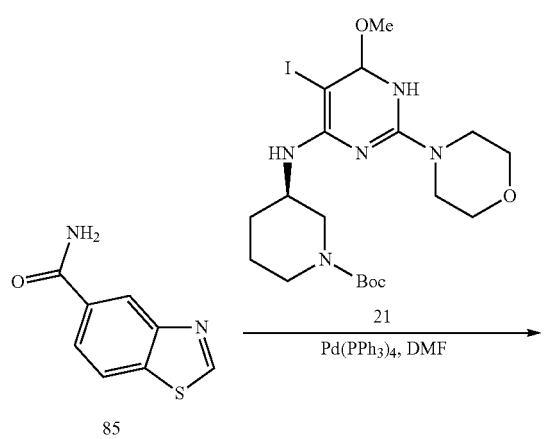

Step 3. 2-[2-(morpholin-4-yl)-6-oxo-4-[[(3R)-piperidin-3-yl]amino]-1,6-dihydropyrimidin-5-yl]-1,3-benzothiazole-5-carboxamide (Example 347)

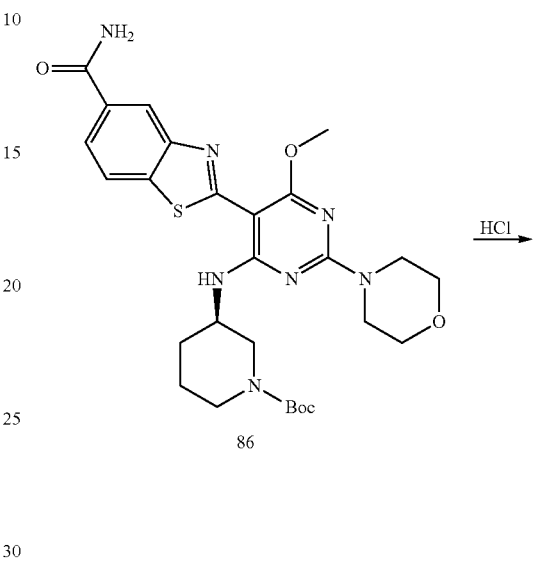

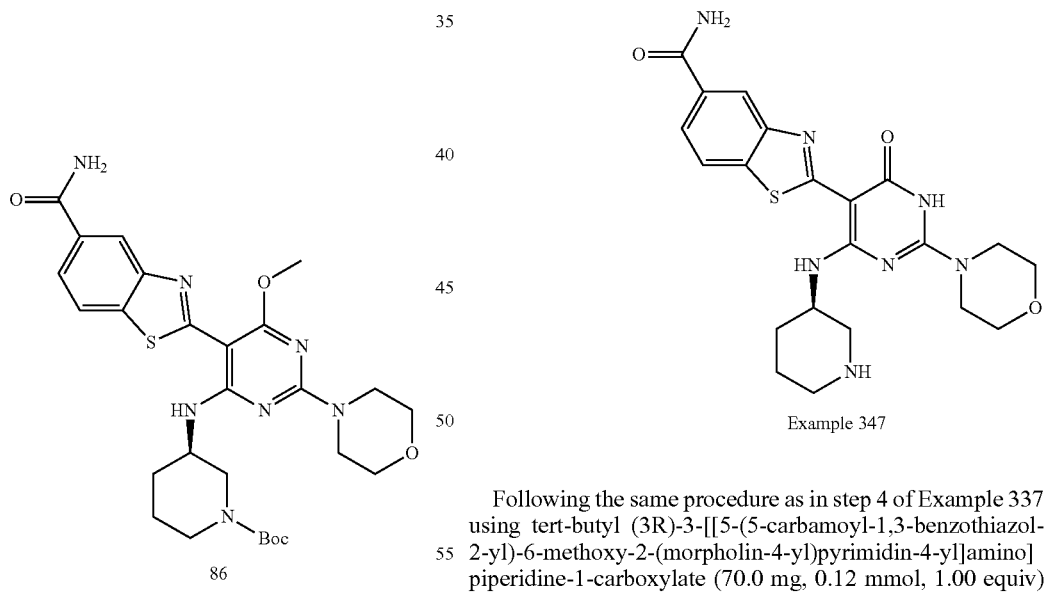

Following the same procedure as in step 3 of Example 337 using 1,3-benzothiazole-5-carboxamide (60.6 mg, 0.34 mmol, 1.80 equiv), tert-butyl (3R)-3-[[5-iodo-6-methoxy-2-(morpholin-4-yl)pyrimidin-4-yl]amino]piperidine-1-carboxylate (100.0 mg, 0.19 mmol, 1.00 equiv), cesium carbonate (0.38 g, 6.00 equiv), Pd(PPh3)4 (39.3 mg, 0.034 mmol, 0.18 equiv) and copper iodide (6.5 mg, 0.034 mmol, 0.18 equiv) in DMF (5.0 mL). The crude product was purified by flash chromatography on a silica gel column eluting with ethyl acetate/petroleum ether (1:15-1:1) to provide the title compound as a white solid. MS m/z [M+H]+ (ESI): 570.

Following the same procedure as in step 4 of Example 337 using tert-butyl (3R)-3-[[5-(5-carbamoyl-1,3-benzothiazol-2-yl)-6-methoxy-2-(morpholin-4-yl)pyrimidin-4-yl]amino]piperidine-1-carboxylate (70.0 mg, 0.12 mmol, 1.00 equiv) and conc. hydrochloric acid (4.0 mL). The crude product was purified by Prep-HPLC with the following conditions (1#-Pre-HPLC-001(SHIMADZU)): Column, XBridge Shield RP18 OBD Column, 5 um, 19*150 mm,; mobile phase, water 0.03% NH3H2O and CH3CN (14% CH3CN up to 27% in 7 min, up to 100% in 2 min, down to 14% in 1 min); Detector, Waters 2489 254&220 nm to afford the title compound as a white solid. 1H-NMR(400 MHz, DMSO-d6) δ ppm 1.54-1.66 (m, 2H), 1.75(m, 1H), 1.99(m, 1H), 2.61-2.73(m, 2H), 2.80-2.85(m, 1H), 3.14-3.16(m, 1H), 3.69(m, 8H), 4.15-4.16(m, 1H), 7.38(s, 1H), 7.75-7.77(m, 1H), 7.97-8.00(m, 1H), 8.08

(s, 1H), 8.26(s, 1H), 10.77-10.79(d, J=7.6 Hz, 1H). MS m/z [M+H]⁺ (ESI): 456. IRAK4 $IC_{50}$=10 nM

Example 348

2-[2-(morpholin-4-yl)-6-oxo-4-[[(3R)-piperidin-3-yl]amino]-1,6-dihydropyrimidin-5-yl]-1,3-benzothiazole-5-carbonitrile

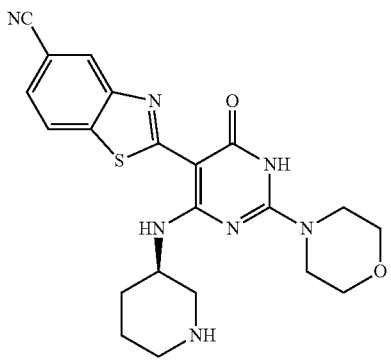 [SMILES: N#Cc1ccc2sc(-c3c(N[C@@H]4CCCNC4)nc(N4CCOCC4)[nH]c3=O)nc2c1]

Step 1. 1,3-benzothiazole-5-carbonitrile (Compound 87)

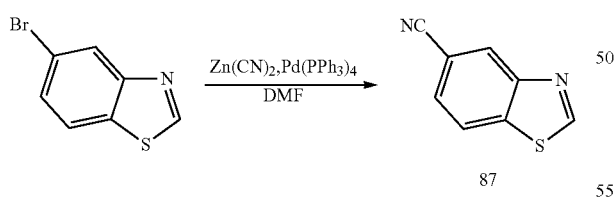

Into a mixture of 5-bromo-1,3-benzothiazole (300 mg, 1.40 mmol, 1.00 equiv) and zinc cyanide (131.6 mg, 0.80 equiv) in N,N-dimethylformamide (6.0 mL) was added Pd(PPh₃)₄ (80.9 mg, 0.07 mmol, 0.05 equiv) and nitrogen was bubbled for 5 min. The resulting mixture was heated overnight at 80° C., quenched by water (15.0 mL), and extracted with ethyl acetate (3×15 mL). The combined organic layers were washed with brine (2×15 mL) and dried over Na₂SO₄. After filtered and concentrated under reduced pressure, the residue was purified by flash chromatography on silica gel, eluting with a mixture of 5-10% ethyl acetate in petroleum ether to afford the title compound as a light yellow solid. MS m/z [M+H]⁺ (ESI): 161.

Step 2. tert-butyl (3R)-3-[[5-(5-cyano-1,3-benzothiazol-2-yl)-6-methoxy-2-(morpholin-4-yl)pyrimidin-4-yl]amino]piperidine-1-carboxylate (Compound 88)

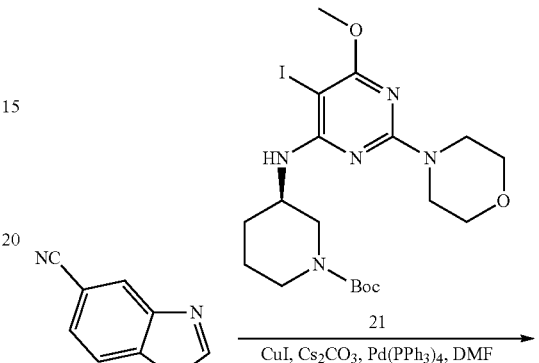

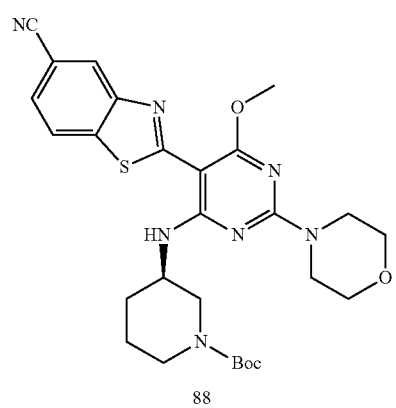

Following the same procedure as in step 3 of Example 121 using 1,3-benzothiazole-5-carbonitrile (56.1 mg, 0.35 mmol, 1.80 equiv), tert-butyl (3R)-3-[[5-iodo-6-methoxy-2-(morpholin-4-yl)pyrimidin-4-yl]amino]piperidine-1-carboxylate (100 mg, 0.19 mmol, 1.00 equiv), copper iodide (6.7 mg, 0.035 mmol, 0.18 equiv), cesium Carbonate (0.37 g, 6.00 equiv, 1.14 mmol) and Pd(PPh₃)₄ (40.4 mg, 0.035 mmol, 0.18 equiv) in DMF (6.0 mL). The crude product was purified by flash chromatography on silica gel, eluting with a mixture of 10-20% ethyl acetate in petroleum ether to give the title compound as a white solid. MS m/z [M+H]+ (ESI): 552.

Step 3. 2-[2-(morpholin-4-yl)-6-oxo-4-[[(3R)-piperidin-3-yl]amino]-1,6-dihydropyrimidin-5-yl]-1,3-benzothiazole-5-carbonitrile (Example 348)

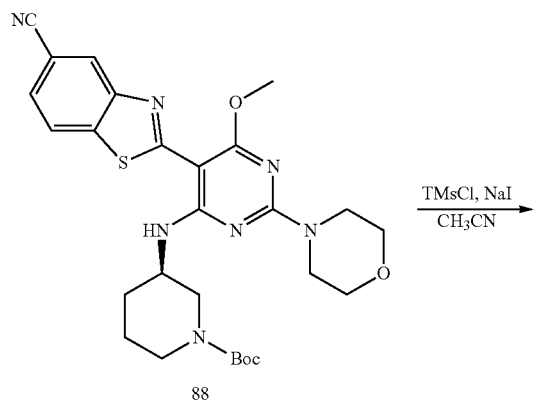

Following the same procedure as Example 80 using tert-butyl (3R)-3-[[5-(5-cyano-1,3-benzothiazol-2-yl)-6-methoxy-2-(morpholin-4-yl)pyrimidin-4-yl]amino]piperidine-1-carboxylate (90.0 mg, 0.16 mmol, 1.00 equiv), sodium iodide (49.5 mg, 0.33 mmol, 2.00 equiv) and trimethylchlorosilane (38.4 mg, 0.35 mmol, 2.00 equiv) in acetonitrile (6 mL). The crude product was purified by Prep-HPLC with the following conditions (1#-Pre-HPLC-001(SHIMADZU)): Column, SunFire Prep C18 OBD Column, 5 um, 19*150 mm,; mobile phase, water with 0.05% TFA and CH3CN (21% CH3CN up to 34% in 7 min, up to 100% in 4 min, down to 21% in 1 min); Detector, Waters 2489 254&220 nm to afford the title compound as the corresponding TFA salt as a light yellow solid. 1H-NMR(400 MHz, DMSO-d$_6$) δ ppm 1.78-1.83(m, 2H), 1.95-2.15(m, 2H), 2.92-3.02(m, 2H), 3.25-3.28(m, 1H), 3.44-3.46(m, 1H), 3.70-3.81(m, 8H), 4.38-4.40(m, 1H), 7.63-7.66 (m, 1H), 8.18-8.20(d, J=8.0 Hz, 1H), 8.27(s, 1H), 8.62-8.78 (m, 1H), 10.62-10.64(d, J=6.8 Hz, 1H). 19F-NMR(400 MHz, DMSO-d$_6$) δ ppm −73.427; MS m/z [M+H]+ (ESI): 460. IRAK4 IC$_{50}$=5 nM Example 349

[4-(4-fluorophenyl)-1,3-thiazol-2-yl-6-[(3R)-piperidin-3-yl]amino]-2-[4-(pyridin-3-yl)piperazin-1-yl]-3,4-dihydropyrimidin-4-one

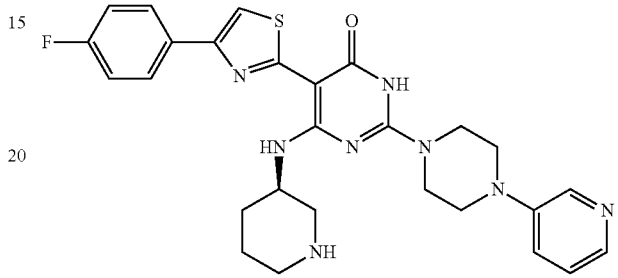

Step 1. Tert-butyl (3R)-3-([5-[4-(4-fluorophenyl)-1,3-thiazol-2-yl]-6-methoxy-2-(methylsulfanyl pyrimidin-4-yl]amino)piperidine-1-carboxylate (Compound 89)

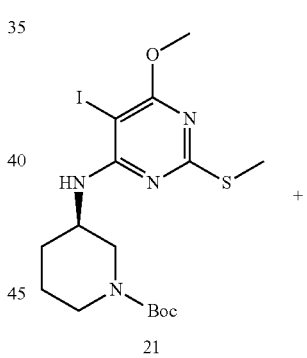

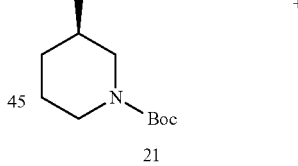

-continued

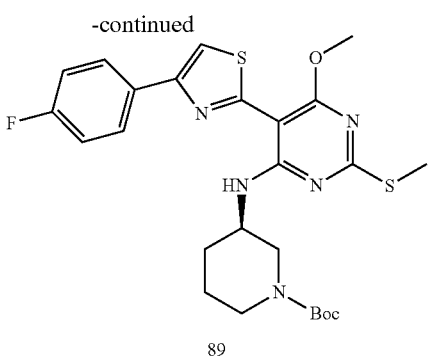

89

Into a mixture of tert-butyl (3R)-3-[[5-iodo-6-methoxy-2-(methylsulfanyl)pyrimidin-4-yl]amino]piperidine-1-carboxylate (750 mg, 1.56 mmol, 1.00 equiv), 4-(4-fluorophenyl)-1,3-thiazole (500 mg, 2.79 mmol, 1.80 equiv) and Cs$_2$CO$_3$ (3.0 g, 9.18 mmol, 6.00 equiv) in DMF (15.0 mL) was added tetrakis(triphenylphosphane) palladium (320 mg, 0.28 mmol, 0.18 equiv) and iodocopper (53.4 mg, 0.28 mmol, 0.18 equiv) and nitrogen was bubbled in for 5 min. The resulting mixture was heated for 2 h at 95° C. in an oil bath under an inert atmosphere of nitrogen, cooled down, quenched by the addition of 50 mL of water, and extracted with ethyl acetate (3×50 mL). The combined organic layers were washed with brine and dried over Na$_2$SO$_4$. After filtered and concentrated under reduced pressure, the residue was purified by flash chromatography on silica gel, eluting with a mixture of 5-20% ethyl acetate in petroleum ether to give the title compound as a yellow solid. MS m/z [M+H]$^+$ (ESI): 532.

Step 2. tert-butyl (3R)-3-([5-[4-(4-fluorophenyl)-1,3-thiazol-2-yl]-2-methanesulfonyl-6-methoxypyrimidin-4-yl]amino)piperidine-1-carboxylate (Compound 90)

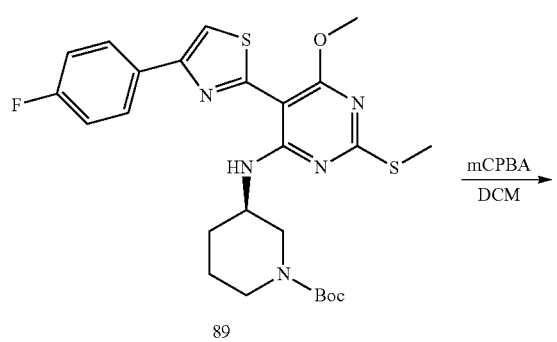

Into a solution of tert-butyl (3R)-3-([5-[4-(4-fluorophenyl)-1,3-thiazol-2-yl]-6-methoxy-2-(methylsulfanyl)pyrimidin-4-yl]amino)piperidine-1-carboxylate (200 mg, 0.38 mmol, 1.00 equiv) in dichloromethane (2.0 mL) was added 3-chlorobenzoperoxoic acid (162.4 mg, 0.94 mmol, 2.50 equiv) in portions at 0° C. The resulting solution was stirred for 1 h at 25° C., quenched by the addition of 3.0 mL of sodium bicarbonate (e.q), and extracted with dichloromethane (3×20.0 mL). The combined organic layers were washed with brine and dried over Na$_2$SO$_4$. Filtration and concentration under reduced pressure gave the title compound as a yellow solid. MS m/z [M+H]$^+$ (ESI): 564.

Step 3. tert-butyl (3R)-3-([5-[4-(4-fluorophenyl)-1,3-thiazol-2-yl]-6-methoxy-2-[4-(pyridin-3-yl)piperazin-1-yl]pyrimidin-4-yl]amino)piperidine-1-carboxylate (Compound 91)

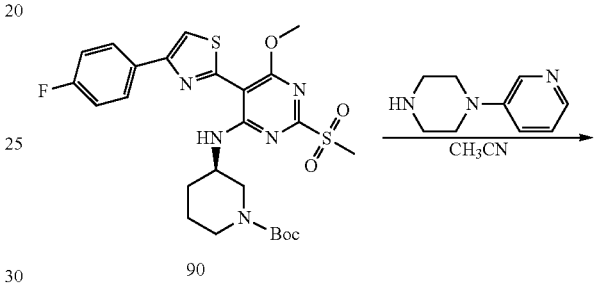

90

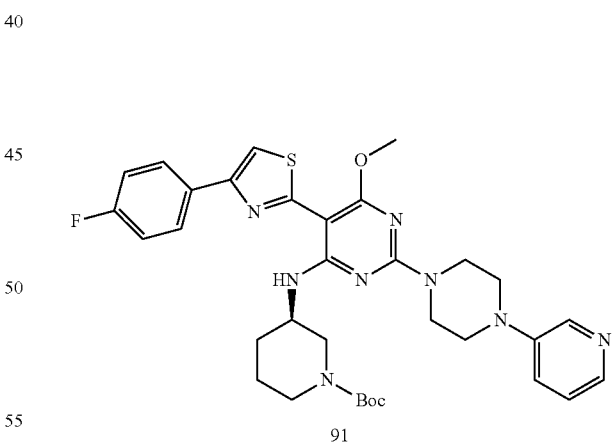

91

A solution of tert-butyl (3R)-3-([5-[4-(4-fluorophenyl)-1,3-thiazol-2-yl]-2-methanesulfonyl-6-methoxypyrimidin-4-yl]amino)piperidine-1-carboxylate (45.0 mg, 0.08 mmol, 1.00 equiv), 1-(pyridin-3-yl)piperazine (15.6 mg, 0.10 mmol, 1.20 equiv) and N-ethyl-N-isopropylpropan-2-amine (20.7 mg, 0.16 mmol, 2.00 equiv) in CH$_3$CN (6.0 mL) was heated for 15 h at 100° C. in an oil bath. Concentration under reduced pressure gave 80.0 mg (crude) of the title compound, which was used directly for next step without further purification. MS m/z [M+H]$^+$ (ESI): 647.

Step 4. 5-[4-(4-fluorophenyl)-1,3-thiazol-2-yl]-6-[[(3R)-piperidin-3-yl]amino]-2-[4-(pyridin-3-yl)piperazin-1-yl]-3,4-dihydropyrimidin-4-one (Example 349)

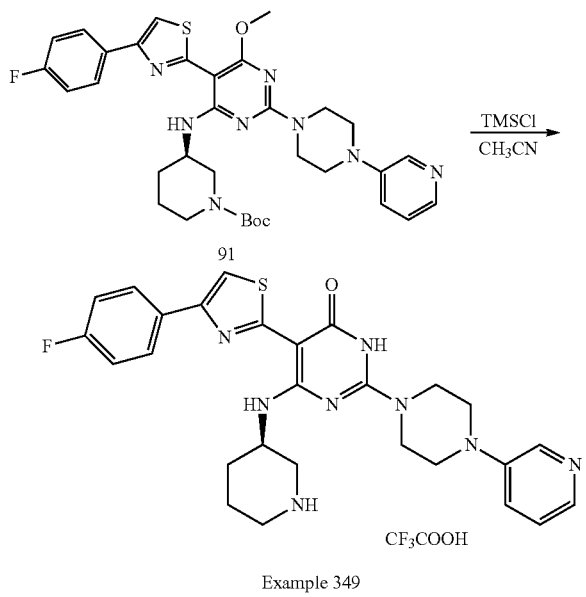

Example 349

Into a mixture of tert-butyl (3R)-3-([5-[4-(4-fluorophenyl)-1,3-thiazol-2-yl]-6-methoxy-2-[4-(pyridin-3-yl)piperazin-1-yl]pyrimidin-4-yl]amino)piperidine-1-carboxylate (100.0 mg, 0.15 mmol, 1.00 equiv) and NaI (45.0 mg, 0.32 mmol, 2.00 equiv) in acetonitrile (10.0 mL) was added chlorotrimethylsilane (35.3 mg, 0.32 mmol, 2.00 equiv). The resulting mixture was heated for 2 h at 55° C. in an oil bath. After removed the solvent, the residue (150 mg) was purified by Prep-HPLC with the following conditions (1#-Pre-HPLC-001(SHIMADZU)): Column, SunFire Prep C18 OBD Column, 5 um, 19*150 mm,; mobile phase, WATER WITH 0.05% TFA and methanol (34.0% methanol up to 48.0% in 10 min, hold 48.0% in 1 min, up to 100.0% in 2 min, down to 34.0% in 2 min); Detector, Waters 2489 254&220 nm to afford the title compound as the corresponding TFA salt as a yellow solid. $^1$H-NMR (400 Hz, CD$_3$OD,): δ ppm 1.97-2.04 (m, 2H), 2.22-2.92(m, 2H), 3.15-3.23(m, 3H), 3.40(m, 1H), 3.61-3.62(m, 3H), 3.63-3.73(m, 1H), 3.96-4.04(m, 4H), 4.51 (m, 1H), 7.19-7.23(t, J=8.8 Hz, 2H), 7.23(s, 1H), 7.78-7.81 (m, 1H), 7.91-7.97(m, 2H), 8.01-8.05(m, 1H), 8.16-8.17(m, 1H), 8.41(s, 1H); $^{19}$F-NMR (400 Hz, CD$_3$OD,): δ ppm −76.981, −116.654. MS m/z [M+H]F (ESI): 533. IRAK4 IC$_{50}$=20 nM The following examples were synthesized in a route similar to that used for Example 349.

| Exple | Structure | Name | IC$_{50}$ (nM) | MS (m/z) | NMR |
|---|---|---|---|---|---|
| 350 | (structure) | 5-[4-(4-fluorophenyl)-1,3-thiazol-2-yl]-6-[[(3R)-piperidin-3-yl]amino]-2-[4-(pyrimidin-2-yl)piperazin-1-yl]-3,4-dihydropyrimidin-4-one; trifluoroacetic acid | 21 | 534 M + H | $^1$H-NMR (400 Hz, DMSO-d6) δ ppm 1.84-1.89 (m, 2H), 2.02-2.04 (m, 1H), 2.20-2.34 (m, 1H), 1.90-3.05 (m, 2H), 3.25-3,30 (m, 2H), 3.80-3.90 (m, 8H), 4.32-4.34 (m, 1H), 6.70-6.72 (t, J$_1$ = 4.8 Hz, 1H), 7.29-7.34 (m, 2H), 7.75 (s, 1H), 7.94-7.97 (m, 2H), 8.42-8.43 (d, J = 4.8 Hz, 2H), 8.66-8.84 (m, 2H), 10.47-10.48 (m, 1H), 11.15-11.18 (m, 1H); (400 Hz, DMSO-d6 + D$_2$O-d2): 1.80-1.90 (m, 2H), 2.00-2.08 (m, 1H), 2.15-2.13 (m, 1H), 2.95-3.02 (m, 2H), 3.21-3.28 (m, 1H), 3.51 (m, 1H), 3.80-3.90 (m, 8H), 4.34 (m, 1H), 6.71 (m, 1H), 7.31 (m, 2H), 7.71 (8, 1H), 7.95 (m, 1H), 8.41-8.42 (m, 2H) |

| Exple | Structure | Name | IC$_{50}$ (nM) | MS (m/z) | NMR |
|---|---|---|---|---|---|
| 351 | 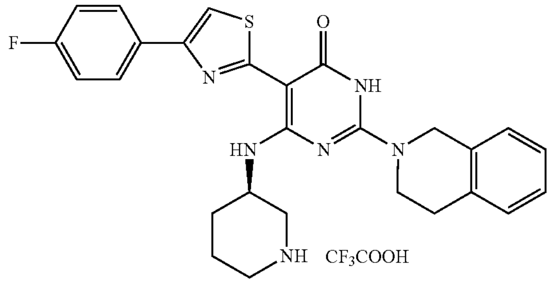 [SMILES: O=c1[nH]c(N2CCc3ccccc3C2)nc(N[C@@H]2CCCNC2)c1-c1nc(-c2ccc(F)cc2)cs1 ; "CF3COOH"] | 5-[4-(4-fluorophenyl)-1,3-thiazol-2-yl]-6-[[(3R)-piperidin-3-yl]amino]-2-(1,2,3,4-tetrahydroisoquinolin-2-yl)pyrimidin-4-ol; trifluoroacetic acid | 57 | 534 M + H | $^1$H-NMR (400 Hz, DMSO-d6,) δ ppm 1.80-195 (m, 2H), 1.95-2.10 (m, 1H), 2.15-2.20 (m, 1H), 2.94-3.10 (m, 5H), 3.20-3.26 (m, 2H), 3.90-4.00 (m, 2H), 4.30-4.40 (m, 1H), 4.86-4.89 (m, 2H), 7,18-7.30 (m, 6H), 7.72 (s, 1H), 7.85-7.95 (m, 2H), 8.60-8.86 (m, 2H), 10.48 (m, 1H), 11.14 (s, 1H); (400 Hz, DMSO-d6 + D$_2$O-d2): 1.80-1.90 (m, 2H), 1.95-2.10 (m, 1H), 2.10-2.20 (m, 1H), 2.94-3.05 (m, 4H), 3.25-3.29 (m, 1H), 3.58 (m, 1H), 3.92 (m, 2H), 4.34-4.37 (m, 1H), 4.85-4.87 (m, 2H), 7.19-7.33 (m, 6H), 7.70 (s, 1H), 7.92-7.96 (m, 2H) |

Examples 352 and 353

5-(4-[[(trans. rac)-2-aminocyclohexyl]amino]-1,3-benzothiazol-2-yl)-2-(morpholin-4-yl)-6-[[(3R)-piperidin-3-yl]amino]-3,4-dihydropyrimidin-4-one and 5-[(cis, rac)4-[(2-aminocyclohexyl)amino]-1,3-benzothiazol-2-yl]-2-(morpholin-4-yl)-6-[[(3R)-piperidin-3-yl]amino]-3,4-dihydropyrimidin-4-one Example 352

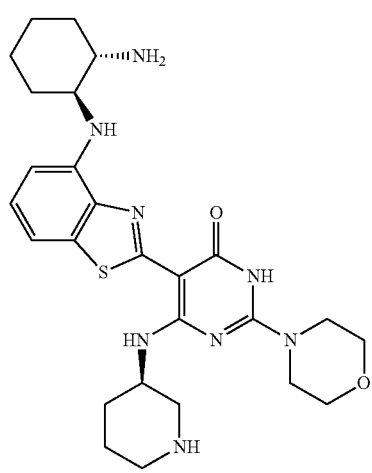

-continued

Example 353

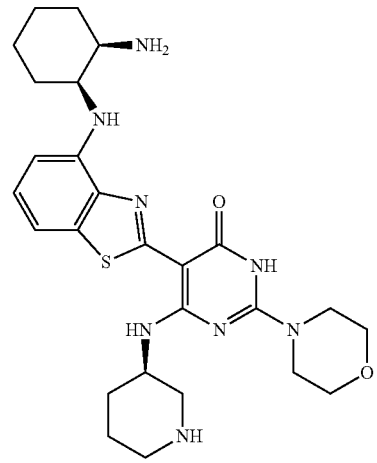

Step 1: tert-butyl (3R)-3-[(5-[4-[(2-aminocyclohexyl)amino]-1,3-benzothiazol-2-yl]-6-methoxy-2-(morpholin-4-yl)pyrimidin-4-yl)amino]piperidine-1-carboxylate (Compound 92)

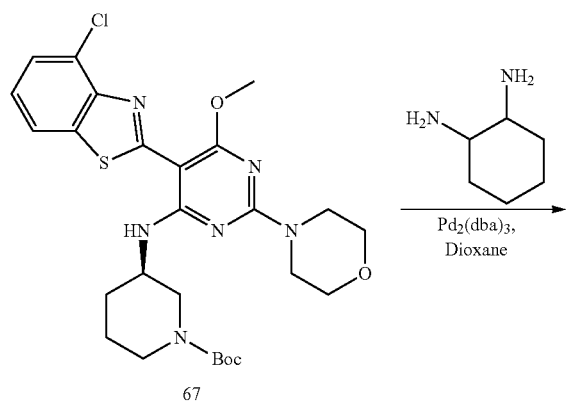

Step 2: 5-(4-[[(trans, rac)-2-aminocyclohexyl]amino]-1,3-benzothiazol-2-yl)-2-(morpholin-4-yl)-6-[[(3R)-piperidin-3-yl]amino]-3,4-dihydropyrimidin-4-one (Example 352) and 5-[4-[(cis, rac)-(2-aminocyclohexyl)amino]-1,3-benzothiazol-2-yl]-2-(morpholin-4-yl)-6-[[(3R)-piperidin-3-yl]amino]-3,4-dihydropyrimidin-4-one (Example 353)

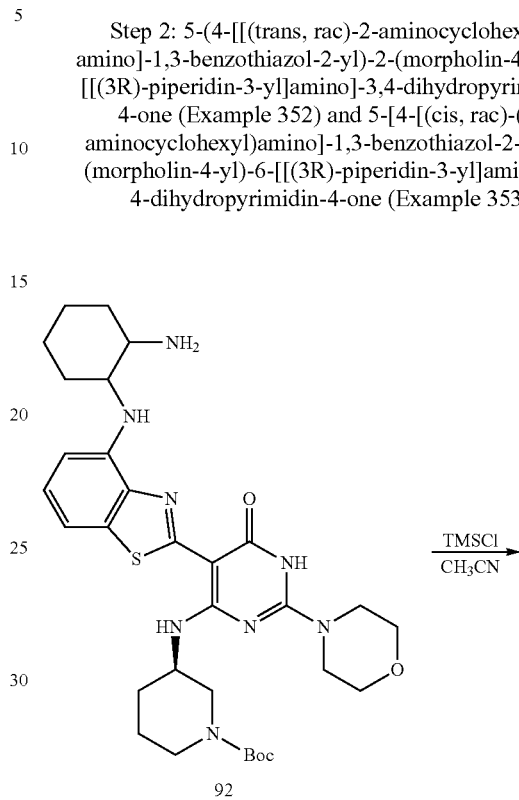

tert-Butyl (3R)-3-[[5-(4-chloro-1,3-benzothiazol-2-yl)-6-methoxy-2-(morpholin-4-yl)pyrimidin-4-yl]amino]piperidine-1-carboxylate (200 mg, 0.36 mmol, 1.00 equiv), cyclohexane-1,2-diamine (112.9 mg, 0.99 mmol, 3.00 equiv), NaOBu-t (63.4 mg, 0.66 mmol, 2.00 equiv), tris(dibenzylideneacetone)dipalladium (30.2 mg, 0.03 mmol, 0.10 equiv) and O-biphenyl(t-Bu)$_2$P (11.8 mg, 0.04 mmol, 0.12 equiv) in toluene (12.0 mL) were dissolved in dioxane (2 mL) and heated to reflux for 18 h. The mixture was cooled to room temperature and concentrated. The crude product was purified by flash chromatography on silica gel, eluting with a mixture of 6-50% ethyl acetate in petroleum ether (15:1-2:1) to provide the title compound as a yellow solid. MS, m/z:[M+H]$^+$ (ESI): 639.

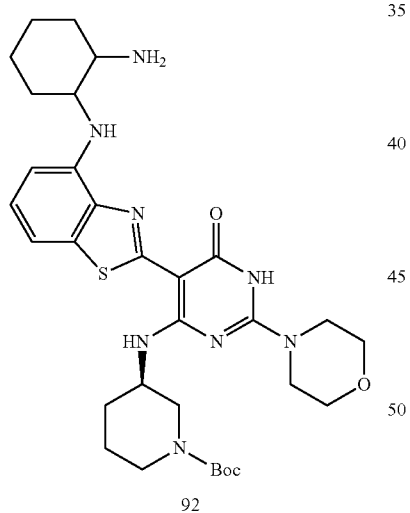

92

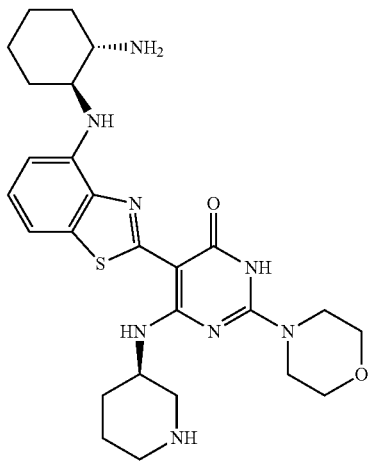

Example 352

+

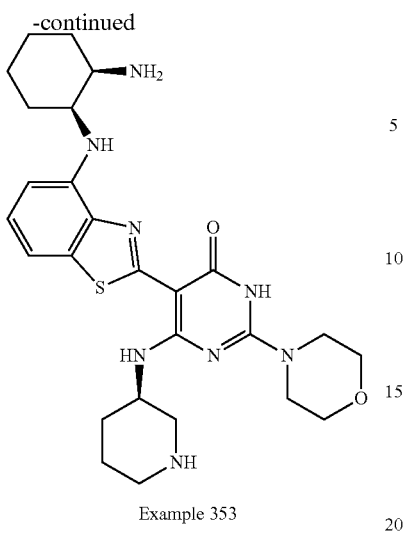

Example 353

Following the same procedure as Example 348 using tert-butyl (3R)-3-[(5-[4-[(2-aminocyclohexyl)amino]-1,3-benzothiazol-2-yl]-6-methoxy-2-(morpholin-4-yl)pyrimidin-4-yl)amino]piperidine-1-carboxylate (50 mg, 0.08 mmol, 1.00 equiv), chlorotrimethylsilane (17.0 mg, 0.16 mmol, 2.00 equiv), and sodium iodide (24.0 mg, 0.16 mmol, 2.00 equiv) in acetonitrile (5.0 mL). The crude product (100 mg) was purified by Prep-HPLC with the following conditions (1#-Pre-HPLC-001(SHIMADZU)): Column, SunFire Prep C18 OBD Column, 5 um, 19*150 mm,; mobile phase, WATER WITH 0.05% TFA and $CH_3CN$ (8% $CH_3CN$ up to 22% in 10 min, hold 22% in 2 min, up to 27% in 3 min, up to 100% in 4 min, down to 8% in 1 min); Detector, Waters 2489 254&220 nm to afford two title compounds as the corresponding the TFA salts.

5-(4-[[(trans, rac)-2-aminocyclohexyl]amino]-1,3-benzothiazol-2-yl)-2-(morpholin-4-yl)-6-[[(3R)-piperidin-3-yl]amino]-3,4-dihydropyrimidin-4-one (Isomer 1) (Example 352) (off-white solid)

$^1$H-NMR (400 MHz, DMSO-$d_6$): δ Ppm 1.29-1.53(m, 4H), 1.73-1.81(m, 4H), 1.99-2.19(m, 4H), 2.90-3.07(m, 3H), 3.55 (m, 2H), 3.71-3.72(m, 8H), 4.33(m, 1H), 5.18-5.20(d, J=10.0 Hz, 1H), 6.73-6.75(d, J=7.6 Hz, 1H), 7.11-7.15(t, J=7.6 Hz, 1H), 7.23-7.24(d, J=7.2 Hz, 1H), 7.95(s, 3H), 8.65-8.85(m, 2H), 10.33-10.34(d, J=6.4 Hz, 1H), 11.14(s, 1H); $^{19}$F-NMR (400 MHz, DMSO-$d_6$): δ ppm −73.61; MS, m/z [M+H]$^+$ (ESI): 525. IRAK4 IC$_{50}$=5400 nM 5-[4-[(cis, rac)-(2-aminocyclohexyl)amino]-1,3-benzothiazol-2-yl]-2-(morpholin-4-yl)-6-[[(3R)-piperidin-3-yl]amino]-3,4-dihydropyrimidin-4-one (Isomer 2) (Example 353)

Yield: 4.3 mg (7%) purple solid. $^1$H-NMR (400 MHz, DMSO-$d_6$): δ ppm 1.24-1.48(m, 4H), 1.72-1.78(m, 5H), 1.91-1.94(m, 2H), 2.12-2.19(m, 2H), 2.67-3.06(m, 2H), 3.64-3.71(m, 2H), 3.72-3.73(m, 8H), 4.10(s, 1H), 4.31(m, 1H), 5.10-5.15(m, 1H), 6.74-6.76(d, J=7.6 Hz, 1H), 7.10-7.16(m, 1H), 7.23-7.26(m, 1H), 7.97-8.03(m, 3H), 8.90(m, 2H), 10.20-10.34(m, 1H), 11.14-11.17(d, J=11.2 Hz, 1H). $^{19}$F-NMR (400 MHz, DMSO-$d_6$): δ ppm −73.52; MS m/z [M+H]$^+$ (ESI): 525. IRAK4 IC$_{50}$=24 nM Example 354 and 355

5-(4-((1S,2R)-2-aminocyclohexylamino)benzo[d]thiazol-2-yl)-2-morpholino-6-((R)-piperidin-3-ylamino)pyrimidin-4(3H)-one and 5-(4-((1R,2S)-2-aminocyclohexylamino)benzo[d]thiazol-2-yl)-2-morpholino-6-((R)-piperidin-3-ylamino)pyrimidin-4(3H)-one

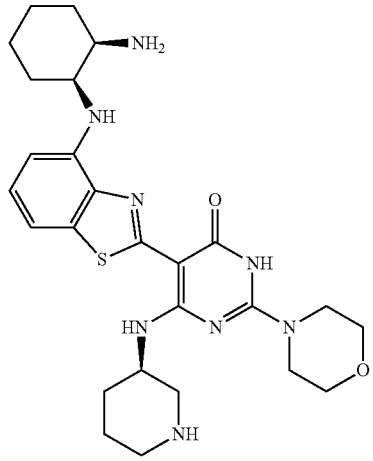

Example 354

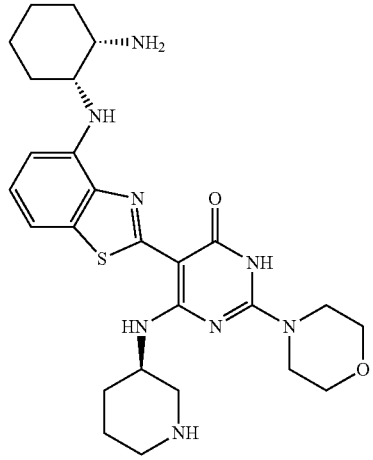

Example 355

Step 1: (R)-tert-butyl 3-(5-(4-(cis-2-aminocyclohexylamino)benzo[d]thiazol-2-yl)-6-methoxy-2-morpholinopyrimidin-4-ylamino)piperidine-1-carboxylate (Compound 93)

Step 2: 5-(4-((1S,2R)-2-aminocyclohexyl amino)benzo[d]thiazol-2-yl)-2-morpholino-6-((R)-piperidin-3-ylamino)pyrimidin-4(3H)-one (Isomer A) (Example 354) and 5-(4-((1R,2S)-2-amino cyclohexylamino)benzo[d]thiazol-2-yl)-2-morpholino-6-((R)-piperidin-3-ylamino)pyrimidin-4(3H)-one (Isomer B) (Example 355)

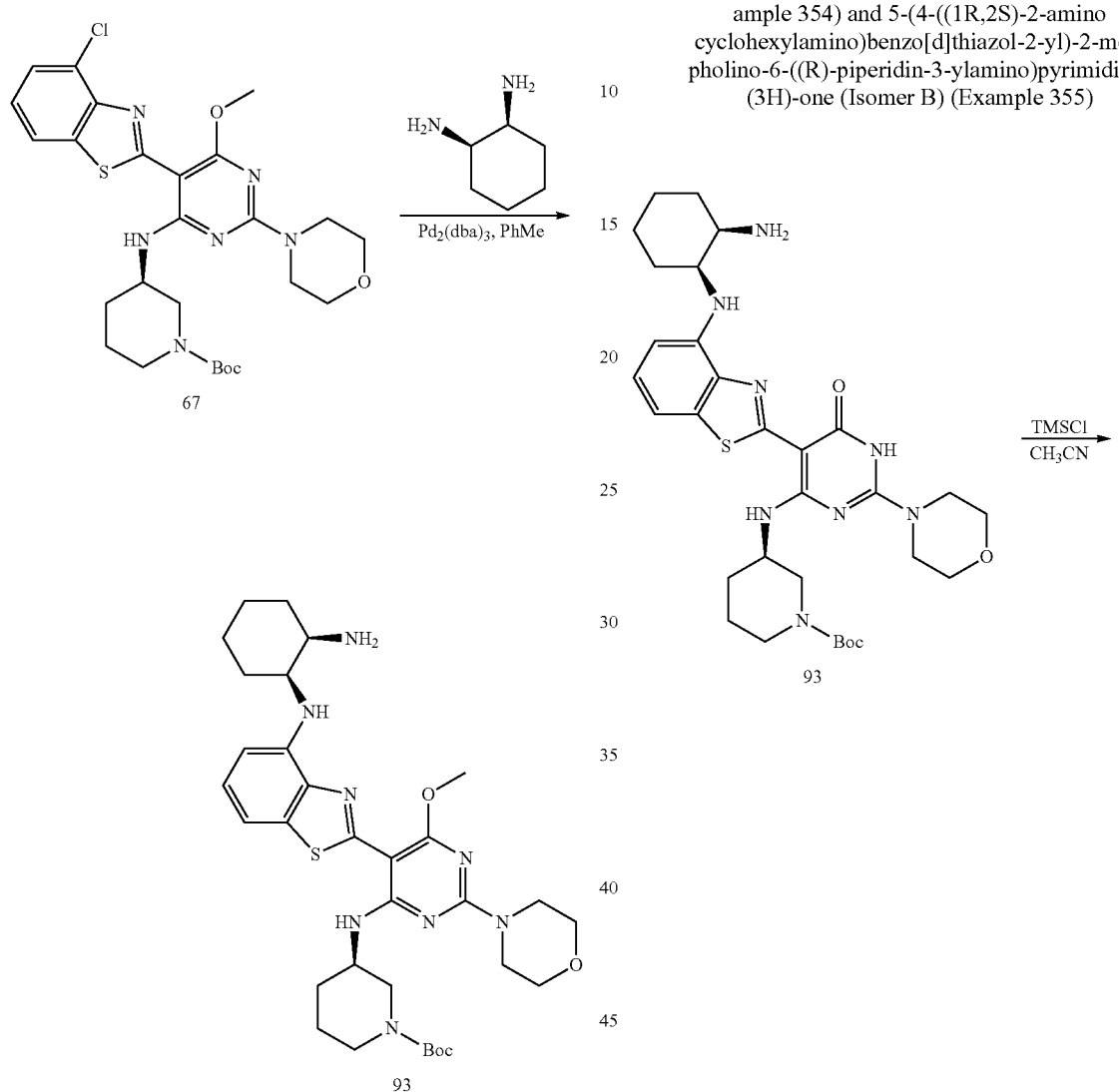

Into a 50-mL round-bottom flask purged and maintained with an inert atmosphere of nitrogen was placed tert-butyl (3R)-3-[[5-(4-chloro-1,3-benzothiazol-2-yl)-6-methoxy-2-(morpholin-4-yl)pyrimidin-4-yl]amino]piperidine-1-carboxylate (180.0 mg, 0.32 mmol, 1.00 equiv), cis-1,2-diaminocyclohexane (109.9 mg, 0.96 mmol, 3.00 equiv), sodium 2-methylpropan-2-olate (61.5 mg, 0.64 mmol, 2.00 equiv) and toluene (8.0 mL). tris(dibenzylideneacetone)dipalladium (30.0 mg, 0.03 mmol, 0.10 equiv), and o-biphenyl(t-Bu)$_2$P (19.1 mg, 0.06 mmol, 0.20 equiv) were added. And nitrogen was bubbled in for 5 min. The resulting mixture was stirred for 12 h at 95° C. in an oil bath. After cooled down, the reaction mixture was quenched by the addition of 30.0 mL of water, and extracted with ethyl acetate (3×30.0 mL). The combined organic layers were washed with brine and dried over anhydrous sodium sulfate. After filtered and concentrated under reduced pressure, the residue was purified by flash chromatography on silica gel, eluting with a mixture of 10-100% ethyl acetate in petroleum ether to give the title compounds as a white solid. MS m/z [M+H]$^+$ (ESI): 639.

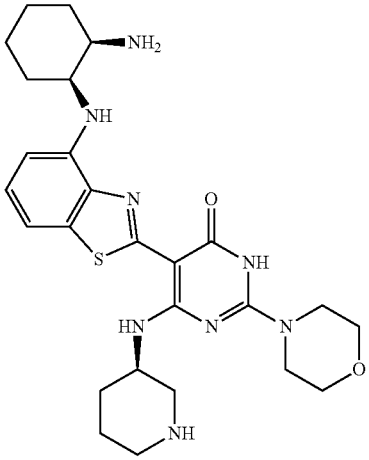

Example 354

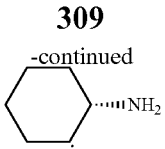

Example 355

Into a mixture of (R)-tert-butyl 3-(5-(4-(cis-2-aminocyclohexylamino)benzo[d]thiazol-2-yl)-6-methoxy-2-morpholinopyrimidin-4-ylamino)piperidine-1-carboxylate (70.0 mg, 0.11 mmol, 1.00 equiv), sodium iodide (33.0 mg, 0.22 mmol, 2.00 equiv) in acetonitrile (6.0 mL) was chlorotrimethylsilane (23.9 mg, 0.22 mmol, 2.00 equiv). The reaction mixture was stirred for 2 h at 70° C. in an oil bath. After removal of the solvent, the residue (100 mg) was purified by Prep-HPLC with the following conditions (1#-Pre-HPLC-001(SHIMADZU)): Column, SunFire Prep C18 OBD Column, 5 um, 19*150 mm,; mobile phase, WATER WITH 0.05% TFA and CH₃CN (8.0% CH₃CN up to 22.0% in 10 min, hold 22.0% in 2 min, up to 27.0% in 3 min, up to 100.0% in 4 min, down to 8.0% in 1 min); Detector, Waters 2489 254&220 nm to afford the title compounds as the corresponding TFA salts.

5-(4-[[(1S,2R)-2-aminocyclohexyl]amino]-1,3-benzothiazol-2-yl)-2-(morpholin-4-yl)-6-[[(3R)-piperidin-3-yl]amino]-3,4-dihydropyrimidin-4-one (Isomer A) (Example 354)

(off-white solid). $^1$H-NMR (300 MHz, DMSO-d$_6$): δ ppm 1.47-1.94(m, 11H), 2.27-2.31(m, 1H), 2.72-2.83(m, 2H), 3.51-3.59(m, 2H), 3.70-3.72(m, 8H), 4.01(s, 1H), 4.37-4.38 (m, 1H), 5.08-5.11(d, J=8.7 Hz, 1H), 6.74-6.77(d, J=7.8 Hz, 1H), 7.10-7.16(t, J=7.8 Hz, 1H), 7.23-7.26(d, J=7.5 Hz, 1H), 7.94(s, 1H), 8.68-8.92(m, 2H), 10.18-10.20(m, 1H), 11.15(s, 1H); $^{19}$F-NMR (300 MHz, DMSO-d6,): δ ppm −73.50 MS m/z [M+H]$^+$ (ESI): 639. IRAK4 IC$_{50}$=70 nM 5-(4-[[(1R,2S)-2-aminocyclohexyl]amino]-1,3-benzothiazol-2-yl)-2-(morpholin-4-yl)-6-[[(3R)-piperidin-3-yl]amino]-3,4-dihydropyrimidin-4-one(isomer B) (Example 355)

(off-white solid). $^1$H-NMR (300 MHz, DMSO-d$_6$,): δ ppm 1.48-1.94(m, 3H), 1.71-1.93(m, 8H), 2.19-2.27(m, 1H), 2.69-2.72(m, 2H), 3.42(m, 1H), 3.57-3.93(m, 10H), 4.10-4.15(m, 1H), 4.37-4.45(m, 1H), 5.06-5.09(d, J=9.3 Hz, 1H), 6.74-6.77(d, J=7.5 Hz, 1H), 7.11-7.16(t, J=7.8 Hz, 1H), 7.23-7.26 (d, J=7.5 Hz, 1H), 7.95(s, 3H), 8.86-9.05(m, 2H), 10.17-10.19(m, 1H), 11.17-11.24(m, 1H); $^{19}$F-NMR (300 MHz, DMSO-d$_6$,): δ ppm −73.501; MS m/z [M+H]$^+$ (ESI): 639. IRAK4 IC$_{50}$=2 nM Example 356

5-[4-[(2-aminoethyl)amino]-1,3-benzothiazol-2-yl]-2-(morpholin-4-yl)-6-[[(3R)-piperidin-3-yl]amino]-3,4-dihydropyrimidin-4-one

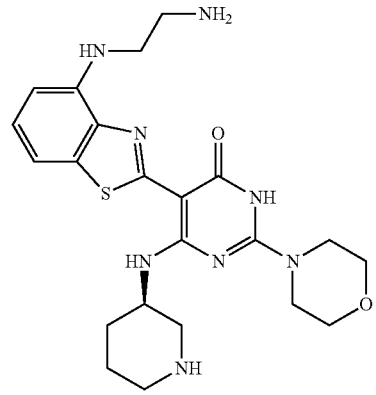 [SMILES: NCCNc1cccc2sc(-c3c(N[C@@H]4CCCNC4)nc(N4CCOCC4)[nH]c3=O)nc12]

Step 1: tert-butyl (3R)-3-[(5-[4-[(2-aminoethyl)amino]-1,3-benzothiazol-2-yl]-6-methoxy-2-(morpholin-4-yl)pyrimidin-4-yl)amino]piperidine-1-carboxylate (Compound 94)

311
-continued

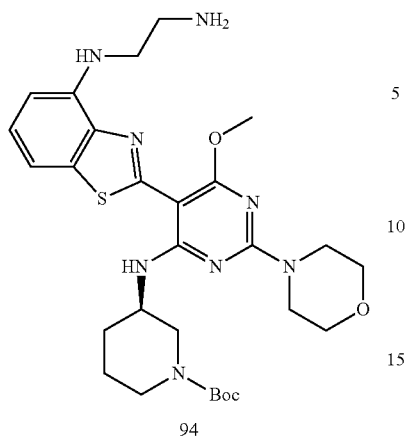

94

Into a mixture of tert-butyl (3R)-3-[[5-(4-chloro-1,3-benzothiazol-2-yl)-6-methoxy-2-(morpholin-4-yl)pyrimidin-4-yl]amino]piperidine-1-carboxylate (150 mg, 0.25 mmol, 1.00 equiv), ethane-1,2-diamine (48.0 mg, 0.80 mmol, 3.00 equiv), sodium 2-methylpropan-2-olate (52.0 mg, 0.54 mmol, 2.00 equiv) and o-biphenyl(t-Bu)$_2$P (10.7 mg, 0.04 mmol, 0.12 equiv) in toluene (6.0 mL) was added tris(dibenzylideneacetone) dipalladium (30.0 mg, 0.03 mmol, 0.10 equiv) and nitrogen was bubbled in for 5 min. The resulting mixture was heated for 12 h at 90° C. in an oil bath. After removed the solvent, the residue was purified by flash chromatography on silica gel, eluting with a mixture of 10% MeOH in CH$_2$Cl$_2$ to give the title compound as a yellow solid. MS m/z [M+H]$^+$ (ESI): 585.

Step 2: 5-[4-[(2-aminoethyl)amino]-1,3-benzothiazol-2-yl]-2-(morpholin-4-yl)-6-[[(3R)-piperidin-3-yl]amino]-3,4-dihydropyrimidin-4-one (Example 356)

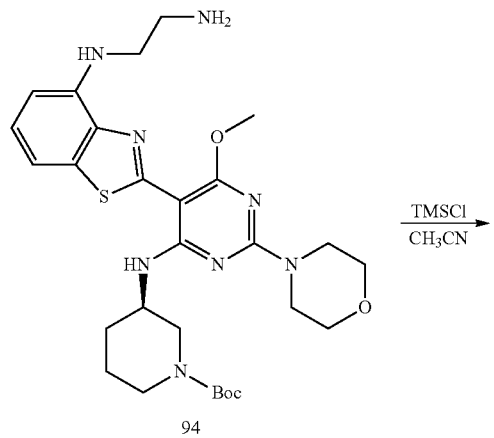

94

312
-continued

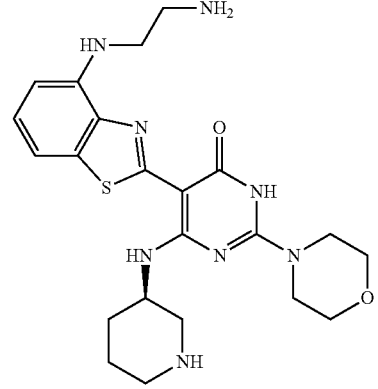

Example 356

Into a mixture of tert-butyl (3R)-3-[(5-[4-[(2-aminoethyl)amino]-1,3-benzothiazol-2-yl]-6-methoxy-2-(morpholin-4-yl)pyrimidin-4-yl)amino]piperidine-1-carboxylate (50.0 mg, 0.09 mmol, 1.00 equiv) and sodium iodide (25.5 mg, 0.17 mmol, 2.00 equiv) in acetonitrile (5.0 mL) was added chlorotrimethylsilane (18.6 mg, 0.17 mmol, 2.00 equiv). The resulting solution was heated for 2 h at 70° C. in an oil bath. After removed the solvent, the residue (60 mg) was purified by Prep-HPLC with the following conditions (2#-Gilson Gx 281(HPLC-37)): Column, SunFire Prep C18 OBD Column, 5 um, 19*150 mm,; mobile phase, CH$_3$CN and water (0.05% CF$_3$COOH) up to 22% in 7 min, hold 22% in 0.5 min, up to 100% in 2.5 min, down to 10% in 1 min); Detector, Waters 2489 254&220 nm to afford the title compound as the corresponding TFA salt as a purple solid. $^1$H-NMR (300 MHz, CD$_3$OD-d$_4$): δ ppm 1.94-2.05(m, 2H), 2.17-2.21(m, 1H), 2.31-2.34(m, 1H), 3.07-3.29(m, 3H), 3.68-3.80(m, 11H), 4.44-4.50(m, 1H), 6.73-6.75(d, J=6.9 Hz, 1H), 7.16-7.22(t, J=7.8 Hz, 1H), 7.22-7.26(m, 1H); $^{19}$F-NMR (300 Hz, CD$_3$OD-d$_4$): δ ppm −76.933; MS m/z [M+H]$^+$ (ESI): 471. IRAK4 IC$_{50}$=16 nM

What is claimed is:

1. A compound of Formula (I), or a pharmaceutically acceptable salt thereof;

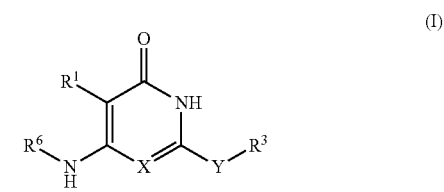

wherein;
X is —N═;
Y is —NR$^2$—, wherein R$^2$ and R$^3$ together with the nitrogen to which they are attached form a 4- to 6-membered heterocyclic ring selected from

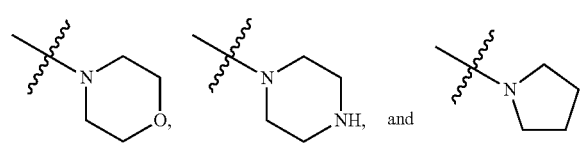 [SMILES: *N1CCOCC1 ; *N1CCNCC1 ; *N1CCCC1]

and optionally substituted with 1 to 3 substituents independently selected from methyl, ethyl, propyl, hydroxy, halogen, methoxy, and ethoxy;

$R^1$ is selected from the group consisting of: $C_{1-6}$ alkyl, $C_{3-6}$ cycloalkyl, aryl, and heterocyclyl; and $R^6$ is selected from the group consisting of: $C_{1-6}$ alkyl, $C_{3-6}$ cycloalkyl, aryl, and heterocyclyl;

wherein each of the $C_{1-6}$ alkyl, $C_{3-6}$ cycloalkyl, aryl and heterocyclyl of $R^1$ and $R^6$ are optionally substituted with 1-3 substituents independently selected from the group consisting of $C_{1-4}$ alkyl, $C_{1-4}$ alkoxy, oxo, and halogen.

2. A compound of Formula (I), or a pharmaceutically acceptable salt thereof;

(I)

wherein;

X is —N═;

Y is —NR²—, wherein R² and R³ together with the nitrogen to which they are attached form a 4- to 6-membered heterocyclic ring; wherein the 4- to 6-membered heterocyclic ring is optionally substituted with 1 to 3 substituents independently selected from R⁷ groups;

$R^1$ is selected from the group consisting of phenyl, pyridinyl, pyrimidinyl, wherein each of the foregoing $R^1$ group is optionally substituted with 1-3 substituents independently selected from methyl, ethyl, propyl, hydroxy, halogen, methoxy, ethoxy, oxo, and phenyl optionally substituted with 1 or 2 groups independently selected from methyl and halogen;

$R^6$ is selected from the group consisting of: $C_{1-6}$ alkyl, $C_{3-6}$ cycloalkyl, aryl, and heterocyclyl; and $R^7$ is selected from the group consisting of: hydrogen, $C_{1-6}$ alkyl, $C_{3-6}$ cycloalkyl, aryl, and heteroaryl;

wherein each of the $C_{1-6}$ alkyl, $C_{3-6}$ cycloalkyl, aryl and heterocyclyl of $R^6$ and $R^7$ are optionally substituted with 1-3 substituents independently selected from the group consisting of $C_{1-4}$ alkyl, $C_{1-4}$ alkoxy, oxo, and halogen.

3. A compound selected from the group consisting of:

5-(benzo[d]thiazol-2-yl)-2-(cyclobutylamino)-6-((1R,2S,3R,4R)-2,3-dihydroxy-4-(hydroxymethyl)cyclopentylamino)pyrimidin-4(3H)-one, 2-amino-5-(benzo[d]thiazol-2-yl)-6-((1R,2S,3R,4R)-2,3-dihydroxy-4-(hydroxymethyl)cyclopentylamino)pyrimidin-4(3H)-one, 5-(benzo[d]thiazol-2-yl)-2-(cyclopropylamino)-6-((1R,2S,3R,4R)-2,3-dihydroxy-4-(hydroxymethyl)cyclopentylamino)pyrimidin-4(3H)-one, 5-(benzo[d]thiazol-2-yl)-2-(cyclopentylamino)-6-((1R,2S,3R,4R)-2,3-dihydroxy-4-(hydroxymethyl)cyclopentylamino)pyrimidin-4(3H)-one, 5-(benzo[d]thiazol-2-yl)-6-((1R,2S,3R,4R)-2,3-dihydroxy-4-(hydroxymethyl)cyclopentylamino)-2-(isopropylamino)pyrimidin-4(3H)-one, 5-(benzo[d]thiazol-2-yl)-2-(cyclohexylamino)-6-((1R,2S,3R,4R)-2,3-dihydroxy-4-(hydroxymethyl)cyclopentylamino)pyrimidin-4(3H)-one, 5-(benzo[d]thiazol-2-yl)-6-((1R,2S,3R,4R)-2,3-dihydroxy-4-(hydroxymethyl)cyclopentylamino)pyrimidine-2,4(1H,3H)-dione, 5-(benzo[d]thiazol-2-yl)-6-((1R,2S,3R,4R)-2,3-dihydroxy-4-(hydroxymethyl)cyclopentylamino)-2-(tetrahydro-2H-pyran-4-ylamino)pyrimidin-4(3H)-one, 5-(benzo[d]thiazol-2-yl)-2-(3,3-difluorocyclobutylamino)-6-((1R,2S,3R,4R)-2,3-dihydroxy-4-(hydroxymethyl)cyclopentylamino)pyrimidin-4(3H)-one, 5-(benzo[d]thiazol-2-yl)-6-((1R,2S,3R,4R)-2,3-dihydroxy-4-(hydroxymethyl)cyclopentylamino)-2-(1-(methylsulfonyl)piperidin-4-ylamino)pyrimidin-4(3H)-one, 5-(benzo[d]thiazol-2-yl)-6-((1R,2S,3R,4R)-2,3-dihydroxy-4-(hydroxymethyl)cyclopentylamino)-2-(oxetan-3-ylamino)pyrimidin-4(3H)-one, 5-(benzo[d]thiazol-2-yl)-6-((1R,2S,3R,4R)-2,3-dihydroxy-4-(hydroxymethyl)cyclopentylamino)-2-(4-(methylsulfonyl)piperazin-1-yl)pyrimidin-4(3H)-one, 5-(benzo[d]thiazol-2-yl)-6-((1R,2S,3R,4R)-2,3-dihydroxy-4-(hydroxymethyl)cyclopentylamino)-2-(2-oxa-6-azaspiro[3.3]heptan-6-yl)pyrimidin-4(3H)-one, 5-(benzo[d]thiazol-2-yl)-6-((1R,2S,3R,4R)-2,3-dihydroxy-4-(hydroxymethyl)cyclopentylamino)-2-(6-(methylsulfonyl)-2,6-diazaspiro[3.3]heptan-2-yl)pyrimidin-4(3H)-one, 5-(benzo[d]thiazol-2-yl)-2-cyclobutoxy-6-((1R,2S,3R,4R)-2,3-dihydroxy-4-(hydroxymethyl)cyclopentylamino)pyrimidin-4(3H)-one, 5-(benzo[d]thiazol-2-yl)-6-((1R,2S,3R,4R)-2,3-dihydroxy-4-(hydroxymethyl)cyclopentylamino)-2-(2,6-diazaspiro[3.3]heptan-2-yl)pyrimidin-4(3H)-one, 5-(benzo[d]thiazol-2-yl)-6-((1R,2S,3R,4R)-2,3-dihydroxy-4-(hydroxymethyl)cyclopentylamino)-2-(1-methylcyclobutylamino)pyrimidin-4(3H)-one, 6-((1R,2S,3R,4R)-2,3-dihydroxy-4-(hydroxymethyl)cyclopentylamino)-2-morpholino-5-(quinolin-2-yl)pyrimidin-4(3H)-one, 6-((1R,2S,3R,4R)-2,3-dihydroxy-4-(hydroxymethyl)cyclopentylamino)-2-(piperidin-1-yl)-5-(quinolin-2-yl)pyrimidin-4(3H)-one, 2-(cyclobutylamino)-6-((1R,2S,3R,4R)-2,3-dihydroxy-4-(hydroxymethyl)cyclopentylamino)-5-(quinolin-2-yl)pyrimidin-4(3H)-one, 2-(cyclobutylamino)-6-((1R,2S,3R,4R)-2,3-dihydroxy-4-(hydroxymethyl)cyclopentylamino)-5-(pyridin-2-yl)pyrimidin-4(3H)-one, 2-(cyclobutylamino)-6-((1R,2S,3R,4R)-2,3-dihydroxy-4-(hydroxymethyl)cyclopentylamino)-5-(thiazol-2-yl)pyrimidin-4(3H)-one, 2-(cyclobutylamino)-6-((1R,2S,3R,4R)-2,3-dihydroxy-4-(hydroxymethyl)cyclopentylamino)-5-(thiazol-4-yl)pyrimidin-4(3H)-one, 5-(benzo[d]thiazol-2-yl)-6-(((1R,2S,3R,4R)-2,3-dihydroxy-4-(hydroxymethyl)cyclopentyl)amino)-2-morpholinopyrimidin-4(3H)-one, 5-(benzo[d]thiazol-2-yl)-6-(((1R,2S,3R,4R)-2,3-dihydroxy-4-(hydroxymethyl)cyclopentyl)amino)-2-(pyrrolidin-1-yl)pyrimidin-4(3H)-one, 5-(benzo[d]thiazol-2-yl)-6-(((1R,2S,3R,4R)-2,3-dihydroxy-4-(hydroxymethyl)cyclopentyl)amino)-2-(piperidin-1-yl)pyrimidin-4(3H)-one, 5-(benzo[d]thiazol-2-yl)-2-(4,4-difluoropiperidin-1-yl)-6-(((1R,2S,3R,4R)-2,3-dihydroxy-4-(hydroxymethyl)cyclopentyl)amino)pyrimidin-4(3H)-one, 5-(benzo[d]thiazol-2-yl)-6-(((1R,2S,3R,4R)-2,3-dihydroxy-4-(hydroxymethyl)cyclopentyl)amino)-2-(4-methyl)piperazin-1-yl)pyrimidin-4(3H)-one, 5-(benzo[d]thiazol-2-yl)-2-(3,4-dihydroisoquinolin-2(1H)-yl)-6-(((1R,2S,3R,4R)-2,3-dihydroxy-4-(hydroxymethyl)cyclopentyl)amino)pyrimidin-4(3H)-one, 5-(benzo[d]thiazol-2-yl)-6-(((1R,2S,3R,4R)-2,3-dihydroxy-4-(hydroxymethyl)cyclopentyl)amino)-2-(dimethylamino)pyrimidin-4(3H)-one, 2-(azetidin-1-yl)-5-(benzo[d]thiazol-2-yl)-6-(((1R,2S,3R,4R)-2,3-dihydroxy-4-(hydroxymethyl)cyclopentyl)amino)pyrimidin-4(3H)-one, 6-(((1R,2S,3R,4R)-2,3-dihydroxy-4-(hydroxymethyl)cyclopentyl)amino)-5-(4-methyl)thiazol-2-yl)-2-morpholinopyrimidin-4(3H)-one, 6-(((1R,2S,3R,4R)-2,3-dihydroxy-4-(hydroxymethyl)cyclopentyl)amino)-5-(4-methyl)thiazol-2-yl)-2-(4-(trifluoromethyl)piperidin-1-yl)pyrimidin-4(3H)-one, 6-(((1R,2S,3R,4R)-2,3-dihydroxy-4-(hydroxymethyl)cyclopentyl)amino)-5-(6-methyl)pyridin-2-yl)-2-morpholinopyrimidin-4(3H)-one, 6-(((1R,2S,3R,4R)-2,3-dihydroxy-4-(hydroxymethyl)cyclopentyl)amino)-5-(6-methyl)pyridin-2-yl)-2-(piperidin-1-yl)pyrimidin-4(3H)-one, 2-(azetidin-3-ylamino)-5-(benzo[d]thiazol-2-yl)-6-(((1R,2S,3R,4R)-2,3-dihydroxy-4-(hydroxymethyl)cyclopentyl)amino)pyrimidin-4(3H)-one, 5-(benzo[d]thiazol-2-yl)-6-(((1R,2S,3R,4R)-2,3-dihydroxy-4-(hydroxymethyl)cyclopentylamino)-2-(pyrrolidin-3-ylamino)pyrimidin-4(3H)-one, 5-(benzo[d]thiazol-2-yl)-6-(((1R,2S,3R,4R)-2,3-dihydroxy-4-(hydroxymethyl)cyclopentylamino)-2-((R)-piperidin-3-ylamino)pyrimidin-4(3H)-one, 5-(benzo[d]thiazol-2-yl)-6-(((1R,2S,3R,4R)-2,3-dihydroxy-4-(hydroxymethyl)cyclopentyl)amino)-2-((S)-piperidin-3-ylamino)pyrimidin-4(3H)-one, 5-(benzo[d]thiazol-2-yl)-6-(((1R,2S,3R,4R)-2,3-dihydroxy-4-(hydroxymethyl)cyclopentyl)amino)-2-((3-methoxypropyl)amino)pyrimidin-4(3H)-one, 5-(benzo[d]thiazol-2-yl)-2-(cyclobutylamino)-6-((1R,2S,3R,4R)-2,3-dihydroxy-4-(hydroxymethyl)-2-methylcyclopentylamino)pyrimidin-4(3H)-one, 5-(benzo[d]thiazol-2-yl)-6-((1R,2S,3R,4R)-2,3-dihydroxy-4-isopropylcyclopentylamino)-2-morpholinopyrimidin-4(3H)-one, 5-(benzo[d]thiazol-2-yl)-6-((1R,2S,3R,4R)-2,3-dihydroxy-4-isopropylcyclopentylamino)pyrimidin-4(3H)-one, 5-(benzo[d]thiazol-2-6-((1R,2S,3R,4R)-2,3-dihydroxy-4-isopropylcyclopentylamino)-2-(4-(pyrimidin-5-yl)piperidin-1-yl)pyrimidin-4(3H)-one, 5-(benzo[d]thiazol-2-yl)-2-(cyclobutylamino)-6-((1R,2S,3R,4S)-2,3-dihydroxy-4-(2-hydroxypropan-2-yl)cyclopentylamino)pyrimidin-4(3H)-one, 6-((1R,2S,3R,4S)-2,3-dihydroxy-4-methylcyclopentylamino)-2-morpholino-5-(quinolin-2-yl)pyrimidin-4(3H)-one, 5-(benzo[d]thiazol-2-yl)-6-((1R,2S,3R,4S)-2,3-dihydroxy-4-methylcyclopentylamino)-2-morpholinopyrimidin-4(3H)-one, 5-(benzo[d]thiazol-2-yl)-2-(cyclobutylamino)-6-((1R,2S,3R)-2,3-dihydroxycyclopentylamino)pyrimidin-4(3H)-one, (S)-5-(benzo[d]thiazol-2-yl)-2-(cyclobutylamino)-6-(2,3-dihydroxypropylamino)pyrimidin-4(3H)-one, 5-(benzo[d]thiazol-2-yl)-6-((1R,2S,3R,4R)-2,3-dihydroxy-4-(hydroxymethyl)cyclopentyl)amino)-2-((2,6-dimethyl)pyridin-4-ylamino)pyrimidin-4(3H)-one, 5-(benzo[d]thiazol-2-yl)-6-((1R,2S,3R,4R)-2,3-dihydroxy-4-(hydroxymethyl)cyclopentyl)amino)-2-(pyrimidin-5-ylamino)pyrimidin-4(3H)-one, 5-(benzo[d]thiazol-2-yl)-6-((1R,2S,3R,4R)-2,3-dihydroxy-4-(hydroxymethyl)cyclopentylamino)-2-(4-fluorophenylamino)pyrimidin-4(3H)-one, 5-(benzo[d]thiazol-2-yl)-6-((1R,2S,3R,4R)-2,3-dihydroxy-4-(hydroxymethyl)cyclopentyl)amino)-2-(phenylamino)pyrimidin-4(3H)-one, 5-(benzo[d]thiazol-2-yl)-6-((1R,2S,3R,4R)-2,3-dihydroxy-4-(hydroxymethyl)cyclopentyl)amino)-2-(pyridin-4-ylamino)pyrimidin-4(3H)-one, 2-(cyclobutylamino)-6-((1R,2S,3R,4R)-2,3-dihydroxy-4-(hydroxymethyl)cyclopentylamino)-5-(thiazolo[4,5-c]pyridin-2-yl)pyrimidin-4(3H)-one, 6-(((1R,2S,3R,4R)-2,3-dihydroxy-4-(hydroxymethyl)cyclopentyl)amino)-5-(4-methylthiazolo[4,5-c]pyridin-2-yl)-2-morpholinopyrimidin-4(3H)-one, 6-(((1R,2S,3R,4R)-2,3-dihydroxy-4-(hydroxymethyl)cyclopentyl)amino)-5-(4,6-dimethylthiazolo[4,5-c]pyridin-2-yl)-2-morpholinopyrimidin-4(3H)-one, 6-(((1R,2S,3R,4R)-2,3-dihydroxy-4-(hydroxymethyl)cyclopentyl)amino)-5-(4-(4-fluorophenyl)thiazol-2-yl)-2-morpholinopyrimidin-4(3H)-one, 6-(((1R,2S,3R,4R)-2,3-dihydroxy-4-(hydroxymethyl)cyclopentyl)amino)-5-(4-(4-fluorophenyl)thiazol-2-yl)-2-(piperidin-1-yl)pyrimidin-4(3H)-one, 5-(benzo[d]thiazol-2-yl)-6-((1R,2S,3R,4R)-2,3-dihydroxy-4-(hydroxymethyl)cyclopentylamino)-2-(methylthio)pyrimidin-4(3H)-one, 5-(benzo[d]thiazol-2-yl)-6-((1R,2S,3R,4R)-2,3-dihydroxy-4-(hydroxymethyl)cyclopentylamino)-2-ethylpyrimidin-4(3H)-one, 5-(benzo[d]thiazol-2-yl)-6-((1R,2S,3R,4R)-2,3-dihydroxy-4-(hydroxymethyl)cyclopentylamino)-2-methylpyrimidin-4(3H)-one, 5-(benzo[d]thiazol-2-yl)-6-((1R,2S,3R,4R)-2,3-dihydroxy-4-(hydroxymethyl)cyclopentylamino)-2-(4-(pyridin-3-yl)piperazin-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(pyrimidin-5-yl)piperidin-1-yl)pyrimidin-4(3H)-one,
5-(benzo[d]thiazol-2-yl)-2-(3,4-dihydro-2,7-naphthyridin-2(1H)-yl)-6-((1R,2S,3R,4R)-2,3-dihydroxy-4-(hydroxymethyl)cyclopentylamino)pyrimidin-4(3H)-one,
8-(5-(benzo[d]thiazol-2-yl)-4-((1R,2S,3R,4R)-2,3-dihydroxy-4-(hydroxymethyl)cyclopentylamino)-6-oxo-1,6-dihydropyrimidin-2-yl)-2-methyl-2,8-diazaspiro[4.5]decan-1-one,
2-(4-(1H-1,2,3-triazol-1-yl)piperidin-1-yl)-5-(benzo[d]thiazol-2-yl)-6-((1R,2S,3R,4R)-2,3-dihydroxy-4-(hydroxymethyl)cyclopentylamino)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(pyridin-2-yl)piperazin-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(pyrazin-2-yl)piperidin-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(pyridin-3-yl)piperidin-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(3-(methylsulfonyl)azetidin-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(pyridin-4-yl)piperidin-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(1-methyl-1H-1,2,3-triazol-4-yl)piperidin-1-yl)pyrimidin-4(3H)-one,
5-(benzo[d]thiazol-2-yl)-2-(3,4-dihydro-2,6-naphthyridin-2(1H)-yl)-6-((1R,2S,3R,4R)-2,3-dihydroxy-4-(hydroxymethyl)cyclopentylamino)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(thiazol-2-yl)methyl)-1,4-diazepan-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(3-(pyridin-4-yl)pyrrolidin-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(methylsulfonyl)-1,4-diazepan-1-yl)pyrimidin-4(3H)-one,
5-(benzo[d]thiazol-2-yl)-6-((1R,2S,3R,4R)-2,3-dihydroxy-4-(hydroxymethyl)cyclopentylamino)-2-(4-(pyridin-2-yl)piperidin-1-yl)pyrimidin-4(3H)-one,
N-((1-(5-(benzo[d]thiazol-2-yl)-4-((1R,2S,3R,4R)-2,3-dihydroxy-4-(hydroxymethyl)cyclopentylamino)-6-oxo-1,6-dihydropyrimidin-2-yl)piperidin-4-yl)methyl)acetamide,
2-(4-((1H-pyrazol-1-yl)methyl)piperidin-1-yl)-5-(benzo[d]thiazol-2-yl)-6-((1R,2S,3R,4R)-2,3-dihydroxy-4-(hydroxymethyl)cyclopentylamino)pyrimidin-4(3H)-one,
8-(5-(benzo[d]thiazol-2-yl)-4-((1R,2S,3R,4R)-2,3-dihydroxy-4-(hydroxymethyl)cyclopentylamino)-6-oxo-1,6-dihydropyrimidin-2-yl)-3-oxa-1,8-diazaspiro[4.5]decan-2-one,
5-(benzo[d]thiazol-2-yl)-6-((1R,2S,3R,4R)-2,3-dihydroxy-4-(hydroxymethyl)cyclopentylamino)-2-(3-(pyridin-3-yl)pyrrolidin-1-yl)pyrimidin-4(3H)-one,
(R)-5-(benzo[d]thiazol-2-yl)-2-morpholino-6-(piperidin-3-ylamino)pyrimidin-4(3H)-one,
(S)-5-(benzo[d]thiazol-2-yl)-2-morpholino-6-(piperidin-3-ylamino)pyrimidin-4(3H)-one,
5-(benzo[d]thiazol-2-yl)-2-morpholino-6-(pyrrolidin-3-ylamino)pyrimidin-4(3H)-one,
(S)-5-(benzo[d]thiazol-2-yl)-2-morpholino-6-(pyrrolidin-3-ylamino)pyrimidin-4(3H)-one,
(R)-5-(benzo[d]thiazol-2-yl)-2-morpholino-6-(pyrrolidin-3-ylamino)pyrimidin-4(3H)-one,
5-(benzo[d]thiazol-2-yl)-2-morpholino-6-(piperidin-4-ylamino)pyrimidin-4(3H)-one,
(R)-5-(benzo[d]thiazol-2-yl)-2-morpholino-6-(6-oxopiperidin-3-ylamino)pyrimidin-4(3H)-one,
6-(3-aminocyclohexylamino)-5-(benzo[d]thiazol-2-yl)-2-morpholinopyrimidin-4(3H)-one,
(R)-3-(5-(benzo[d]thiazol-2-yl)-2-morpholino-6-oxo-1,6-dihydropyrimidin-4-ylamino)azepan-2-one,
6-(azepan-3-ylamino)-5-(benzo[d]thiazol-2-yl)-2-morpholinopyrimidin-4(3H)-one,
(R)-2-morpholino-6-(piperidin-3-ylamino)-5-(quinolin-2-yl)pyrimidin-4(3H)-one,
(R)-5-(4-methyl)thiazol-2-yl)-2-morpholino-6-(piperidin-3-ylamino)pyrimidin-4(3H)-one,
(R)-5-(benzo[d]thiazol-2-yl)-6-(1-methylpiperidin-3-ylamino)-2-morpholinopyrimidin-4(3H)-one,
5-(benzo[d]thiazol-2-yl)-6-(3-hydroxycyclohexylamino)-2-morpholinopyrimidin-4(3H)-one,
(R)-5-(5-fluorobenzo[d]thiazol-2-yl)-2-morpholino-6-(piperidin-3-ylamino)pyrimidin-4(3H)-one,
(R)-5-(4-(4-fluorophenyl)thiazol-2-yl)-2-morpholino-6-(piperidin-3-ylamino)pyrimidin-4(3H)-one,
(R)-5-(4-methylthiazolo[4,5-c]pyridin-2-yl)-2-morpholino-6-(piperidin-3-ylamino)pyrimidin-4(3H)-one,
(R)-5-(4-cyclopropyl)thiazol-2-yl)-2-morpholino-6-(piperidin-3-ylamino)pyrimidin-4(3H)-one,
(R)-2-morpholino-6-(piperidin-3-ylamino)-5-(thiazol-2-yl)pyrimidin-4(3H)-one,
(R)-5-(5-methyl)thiazol-2-yl)-2-morpholino-6-(piperidin-3-ylamino)pyrimidin-4(3H)-one,
(R)-2-morpholino-6-(piperidin-3-ylamino)-5-(4-(4-(trifluoromethoxy)phenyl)thiazol-2-yl)pyrimidin-4(3H)-one,
(R)-6-(azepan-3-ylamino)-5-(benzo[d]thiazol-2-yl)-2-morpholinopyrimidin-4(3H)-one,
5-(benzo[d]thiazol-2-yl)-6-(((3R,5R)-5-hydroxypiperidin-3-ylamino)-2-morpholinopyrimidin-4(3H)-one,
5-(benzo[d]thiazol-2-yl)-2-morpholino-6-(piperidin-3-ylamino)pyrimidin-4(3H)-one,
6-((6-methyl)piperidin-3-ylamino)-2-morpholino-5-(quinolin-2-yl)pyrimidin-4(3H)-one,
5-(benzo[d]thiazol-2-yl)-6-(((1R,3R)-3-hydroxycyclohexyl)amino)-2-morpholinopyrimidin-4(3H)-one,
(R)-5-(6-methyl)pyridin-2-yl)-2-morpholino-6-(piperidin-3-ylamino)pyrimidin-4(3H)-one,
(R)-5-(5-methyl)pyridin-2-yl)-2-morpholino-6-(piperidin-3-ylamino)pyrimidin-4(3H)-one,
(R)-5-(4-cyclopropyl)thiazolo[4,5-c]pyridin-2-yl)-2-morpholino-6-(piperidin-3-ylamino)pyrimidin-4(3H)-one,
(R)-5-(6-fluorobenzo[d]thiazol-2-yl)-2-morpholino-6-(piperidin-3-ylamino)pyrimidin-4(3H)-one, (R)-2-morpholino-6-(piperidin-3-ylamino)-5-(thiazolo[4,5-c]pyridin-2-yl)pyrimidin-4(3H)-one, (R)-6-(piperidin-3-ylamino)-2-(pyrrolidin-1-yl)-5-(quinolin-2-yl)pyrimidin-4(3H)-one,
(R)-2-(piperidin-1-yl)-6-(piperidin-3-ylamino)-5-(quinolin-2-yl)pyrimidin-4(3H)-one, (R)-2-(4-methyl)piperazin-1-yl)-6-(piperidin-3-ylamino)-5-(quinolin-2-yl)pyrimidin-4(3H)-one,
(R)-5-(4-cyclopropyl)thiazolo[4,5-c]pyridin-2-yl)-2-(piperidin-1-yl)-6-(piperidin-3-ylamino)pyrimidin-4(3H)-one,
(R)-5-(4-cyclopropyl)thiazolo[4,5-c]pyridin-2-yl)-6-(piperidin-3-ylamino)-2-(pyrrolidin-1-yl)pyrimidin-4(3H)-one,
(R)-5-(4-cyclopropyl)thiazolo[4,5-c]pyridin-2-yl)-2-(4-(methylsulfonyl)piperazin-1-yl)-6-(piperidin-3-ylamino)pyrimidin-4(3H)-one,
(R)-5-(4-cyclopropyl)thiazolo[4,5-c]pyridin-2-yl)-2-(4-methyl)piperazin-1-yl)-6-(piperidin-3-ylamino)pyrimidin-4(3H)-one,
6-(methyl)piperidin-3-yl)amino-2-morpholino-5-(quinolin-2-yl)pyrimidin-4(3H)-one,
6-(methyl)piperidin-3-yl)amino-2-morpholino-5-(quinolin-2-yl)pyrimidin-4(3H)-one,
5-(benzo[d]thiazol-2-yl)-6-((6-methyl)piperidin-3-ylamino)-2-morpholinopyrimidin-4(3H)-one,
5-(benzo[d]thiazol-2-yl)-6-((6-methyl)piperidin-3-ylamino)-2-morpholinopyrimidin-4(3H)-one,
5-(benzo[d]thiazol-2-yl)-2-(3-(hydroxymethyl)morpholino)-6-((R)-piperidin-3-ylamino)pyrimidin-4(3H)-one,
5-(benzo[d]thiazol-2-yl)-2-(2-methylmorpholino)-6-((R)-piperidin-3-ylamino)pyrimidin-4(3H)-one,
5-(benzo[d]thiazol-2-yl)-2-((R)-3-methylmorpholino)-6-((R)-piperidin-3-ylamino)pyrimidin-4(3H)-one,
5-(benzo[d]thiazol-2-yl)-2-((S)-3-methylmorpholino)-6-((R)-piperidin-3-ylamino)pyrimidin-4(3H)-one,
5-(benzo[d]thiazol-2-yl)-2-(2-(2-hydroxyethyl)morpholino)-6-((R)-piperidin-3-ylamino)pyrimidin-4(3H)-one,
5-(benzo[d]thiazol-2-yl)-6-((R)-piperidin-3-ylamino)-2-(2-(trifluoromethyl)morpholino)pyrimidin-4(3H)-one,
(R)-5-(benzo[d]thiazol-2-yl)-2-(2,2-dimethylmorpholino)-6-(piperidin-3-ylamino)pyrimidin-4(3H)-one,
(R)-5-(benzo[d]thiazol-2-yl)-6-(piperidin-3-ylamino)-2-(4-(pyridin-2-yl)piperazin-1-yl)pyrimidin-4(3H)-one,
(R)-5-(benzo[d]thiazol-2-yl)-2-(4-(3-chloro-5-(trifluoromethyl)pyridin-2-yl)piperazin-1-yl)-6-(piperidin-3-ylamino)pyrimidin-4(3H)-one,
(R)-5-(benzo[d]thiazol-2-yl)-6-(piperidin-3-ylamino)-2-(4-(pyrazin-2-yl)piperazin-1-yl)pyrimidin-4(3H)-one,
(R)-5-(benzo[d]thiazol-2-yl)-6-(piperidin-3-ylamino)-2-(4-(5-(trifluoromethyl)pyridin-2-yl)piperazin-1-yl)pyrimidin-4(3H)-one,
(R)-5-(benzo[d]thiazol-2-yl)-6-(piperidin-3-ylamino)-2-(4-(pyrimidin-2-yl)piperazin-1-yl)pyrimidin-4(3H)-one,
(R)-5-(benzo[d]thiazol-2-yl)-2-(4-(6-chloropyridin-2-yl)piperazin-1-yl)-6-(piperidin-3-ylamino)pyrimidin-4(3H)-one,
(R)-5-(benzo[d]thiazol-2-yl)-6-(piperidin-3-ylamino)-2-(4-(pyridin-3-yl)piperazin-1-yl)pyrimidin-4(3H)-one,
(R)-5-(benzo[d]thiazol-2-yl)-2-(4-(4-methyl-1,2,5-oxadiazol-3-yl)piperazin-1-yl)-6-(piperidin-3-ylamino)pyrimidin-4(3H)-one,
(R)-5-(benzo[d]thiazol-2-yl)-6-(piperidin-3-ylamino)-2-(2-(trifluoromethyl)-5,6-dihydroimidazo[1,2-a]pyrazin-7(8H)-yl)pyrimidin-4(3H)-one,
(R)-5-(benzo[d]thiazol-2-yl)-2-(4-(5-methoxypyridin-2-yl)piperazin-1-yl)-6-(piperidin-3-ylamino)pyrimidin-4(3H)-one,
(R)-5-(benzo[d]thiazol-2-yl)-2-(4-(4-methoxypyridin-2-yl)piperazin-1-yl)-6-(piperidin-3-ylamino)pyrimidin-4(3H)-one,
(R)-5-(benzo[d]thiazol-2-yl)-2-(4-(6-methoxypyridin-2-yl)piperazin-1-yl)-6-(piperidin-3-ylamino)pyrimidin-4(3H)-one,
(R)-5-(benzo[d]thiazol-2-yl)-2-(4-(5-chloropyridin-2-yl)piperazin-1-yl)-6-(piperidin-3-ylamino)pyrimidin-4(3H)-one,
(R)-5-(benzo[d]thiazol-2-yl)-2-(4-(4-chloropyridin-2-yl)piperazin-1-yl)-6-(piperidin-3-ylamino)pyrimidin-4(3H)-one,
(R)-5-(benzo[d]thiazol-2-yl)-2-(4-(2-fluorophenyl)piperazin-1-yl)-6-(piperidin-3-ylamino)pyrimidin-4(3H)-one,
(R)-5-(benzo[d]thiazol-2-yl)-2-(4-(2-chloro-4-(methylsulfonyl)phenyl)piperazin-1-yl)-6-(piperidin-3-ylamino)pyrimidin-4(3H)-one,
(R)-5-(benzo[d]thiazol-2-yl)-6-(piperidin-3-ylamino)-2-(4-(2-(trifluoromethyl)phenyl)piperazin-1-yl)pyrimidin-4(3H)-one,
(R)-5-(benzo[d]thiazol-2-yl)-6-(piperidin-3-ylamino)-2-(4-(thiazol-2-yl)piperazin-1-yl)pyrimidin-4(3H)-one,
(R)-5-(benzo[d]thiazol-2-yl)-2-(4-(4-fluoro-2-(methylsulfonyl)phenyl)piperazin-1-yl)-6-(piperidin-3-ylamino)pyrimidin-4(3H)-one,
(R)-5-(benzo[d]thiazol-2-yl)-2-(4-(2-chlorophenyl)piperazin-1-yl)-6-(piperidin-3-ylamino)pyrimidin-4(3H)-one,
(R)-5-(benzo[d]thiazol-2-yl)-6-(piperidin-3-ylamino)-2-(4-(3-(trifluoromethyl)phenyl)piperazin-1-yl)pyrimidin-4(3H)-one,
(R)-5-(benzo[d]thiazol-2-yl)-2-(4-(3,4-dichlorophenyl)piperazin-1-yl)-6-(piperidin-3-ylamino)pyrimidin-4(3H)-one,
(R)-5-(benzo[d]thiazol-2-yl)-2-(4-(4-methoxyphenyl)piperazin-1-yl)-6-(piperidin-3-ylamino)pyrimidin-4(3H)-one,
(R)-2-(4-(benzo[d][1,3]dioxol-5-yl)piperazin-1-yl)-5-(benzo[d]thiazol-2-yl)-6-(piperidin-3-ylamino)pyrimidin-4(3H)-one,
(R)-5-(benzo[d]thiazol-2-yl)-2-(4-(2-(methylsulfonyl)phenyl)piperazin-1-yl)-6-(piperidin-3-ylamino)pyrimidin-4(3H)-one,
(R)-5-(benzo[d]thiazol-2-yl)-2-(4-(3-methylisothiazol-5-yl)piperazin-1-yl)-6-(piperidin-3-ylamino)pyrimidin-4(3H)-one,
(R)-5-(benzo[d]thiazol-2-yl)-2-(4-(3-methyl)pyridin-4-yl)piperazin-1-yl)-6-(piperidin-3-ylamino)pyrimidin-4(3H)-one,
(R)-5-(benzo[d]thiazol-2-yl)-2-(4-(1-methyl-1H-pyrazol-4-yl)piperazin-1-yl)-6-(piperidin-3-ylamino)pyrimidin-4(3H)-one,
(R)-5-(benzo[d]thiazol-2-yl)-2-(4-(3,6-dimethyl)pyrazin-2-yl)piperazin-1-yl)-6-(piperidin-3-ylamino)pyrimidin-4(3H)-one,
(R)-5-(benzo[d]thiazol-2-yl)-2-(4-(2,5-dimethoxyphenyl)piperazin-1-yl)-6-(piperidin-3-ylamino)pyrimidin-4(3H)-one,
(R)-5-(benzo[d]thiazol-2-yl)-2-(4-(5-cyclopropyl)-1,3,4-oxadiazol-2-yl)piperazin-1-yl)-6-(piperidin-3-ylamino)pyrimidin-4(3H)-one,
(R)-2-(4-(1,3,4-thiadiazol-2-yl)piperazin-1-yl)-5-(benzo[d]thiazol-2-yl)-6-(piperidin-3-ylamino)pyrimidin-4(3H)-one,
2-((R)-3-(dimethylamino)pyrrolidin-1-yl)-6-((R)-piperidin-3-ylamino)-5-(quinolin-2-yl)pyrimidin-4(3H)-one, N-(1-(6-oxo-4-((R)-piperidin-3-ylamino)-5-(quinolin-2-yl)-1,6-dihydropyrimidin-2-yl)pyrrolidin-3-yl)acetamide,
2-((S)-3-(dimethylamino)pyrrolidin-1-yl)-6-((R)-piperidin-3-ylamino)-5-(quinolin-2-yl)pyrimidin-4(3H)-one,
2-(3-hydroxypyrrolidin-1-yl)-6-((R)-piperidin-3-ylamino)-5-(quinolin-2-yl)pyrimidin-4(3H)-one,
2-(3-azabicyclo[3.1.0]hexan-3-yl)-6-((R)-piperidin-3-ylamino)-5-(quinolin-2-yl)pyrimidin-4(3H)-one,
(R)-2-(3-(methylsulfonyl)azetidin-1-yl)-6-(piperidin-3-ylamino)-5-(quinolin-2-yl)pyrimidin-4(3H)-one,
(R)-2-(3-hydroxy-3-(trifluoromethyl)azetidin-1-yl)-6-(piperidin-3-ylamino)-5-(quinolin-2-yl)pyrimidin-4(3H)-one,
(R)-2-(3-hydroxy-3-methyl)azetidin-1-yl)-6-(piperidin-3-ylamino)-5-(quinolin-2-yl)pyrimidin-4(3H)-one,
(R)-2-(3-(2-hydroxypropan-2-yl)azetidin-1-yl)-6-(piperidin-3-ylamino)-5-(quinolin-2-yl)pyrimidin-4(3H)-one,
2-((3S,4S)-3-hydroxy-4-methoxypyrrolidin-1-yl)-6-((R)-piperidin-3-ylamino)-5-(quinolin-2-yl)pyrimidin-4(3H)-one,
2-(3,3-dioxido-3-thia-6-azabicyclo[3.2.1]octan-6-yl)-6-((R)-piperidin-3-ylamino)-5-(quinolin-2-yl)pyrimidin-4(3H)-one,
2-((3S,4S)-3,4-difluoropyrrolidin-1-yl)-6-((R)-piperidin-3-ylamino)-5-(quinolin-2-yl)pyrimidin-4(3H)-one,
(R)-2-(3-methoxy-3-methyl)azetidin-1-yl)-6-(piperidin-3-ylamino)-5-(quinolin-2-yl)pyrimidin-4(3H)-one,
2-((S)-3-fluoropyrrolidin-1-yl)-6-((R)-piperidin-3-ylamino)-5-(quinolin-2-yl)pyrimidin-4(3H)-one,
2-((S)-3-methoxypyrrolidin-1-yl)-6-((R)-piperidin-3-ylamino)-5-(quinolin-2-yl)pyrimidin-4(3H)-one,
2-((R)-3-(hydroxymethyl)pyrrolidin-1-yl)-6-((R)-piperidin-3-ylamino)-5-(quinolin-2-yl)pyrimidin-4(3H)-one,
2-((S)-3-(hydroxymethyl)pyrrolidin-1-yl)-6-((R)-piperidin-3-ylamino)-5-(quinolin-2-yl)pyrimidin-4(3H)-one,
2-(3-hydroxy-3-methyl)pyrrolidin-1-yl)-6-((R)-piperidin-3-ylamino)-5-(quinolin-2-yl)pyrimidin-4(3H)-one,
6-((R)-piperidin-3-ylamino)-2-(2-(pyridin-4-yl)pyrrolidin-1-yl)-5-(quinolin-2-yl)pyrimidin-4(3H)-one,
2-((S)-2-(fluoromethyl)pyrrolidin-1-yl)-6-((R)-piperidin-3-ylamino)-5-(quinolin-2-yppyrimidin-4(3H)-one,
2-(3-(2-hydroxypropan-2-yl)pyrrolidin-1-yl)-6-((R)-piperidin-3-ylamino)-5-(quinolin-2-yl)pyrimidin-4(3H)-one,
2-(6-methyl)octahydro-1H-pyrrolo[2,3-c]pyridin-1-yl)-6-((R)-piperidin-3-ylamino)-5-(quinolin-2-yl)pyrimidin-4(3H)-one,
2-(3-methoxypyrrolidin-1-yl)-6-((R)-piperidin-3-ylamino)-5-(quinolin-2-yl)pyrimidin-4(3H)-one, (R)-2-(4-phenyl)piperidin-1-yl)-6-(piperidin-3-ylamino)-5-(quinolin-2-yl)pyrimidin-4(3H)-one, (R)-6-(piperidin-3-ylamino)-5-(quinolin-2-yl)-2-(4-(o-tolyl)piperidin-1-yl)pyrimidin-4(3H)-one, (R)-2-(4-(2-methoxyphenyl)piperidin-1-yl)-6-(piperidin-3-ylamino)-5-(quinolin-2-yl)pyrimidin-4(3H)-one,
(R)-6-(piperidin-3-ylamino)-5-(quinolin-2-yl)-2-(4-(2-(trifluoromethyl)phenyl)piperidin-1-yl)pyrimidin-4(3H)-one,
(R)-2-(4-(3-methyl-1,2,4-thiadiazol-5-yl)piperidin-1-yl)-6-(piperidin-3-ylamino)-5-(quinolin-2-yl)pyrimidin-4(3H)-one,
(R)-2-(4-(3-methyl-1H-pyrazol-5-yl)piperidin-1-yl)-6-(piperidin-3-ylamino)-5-(quinolin-2-yl)pyrimidin-4(3H)-one,
(R)-2-(4-(6-fluoropyridin-2-yl)piperidin-1-yl)-6-(piperidin-3-ylamino)-5-(quinolin-2-yl)pyrimidin-4(3H)-one,
2-(2,5-diazabicyclo[2.2.1]heptan-2-yl)-6-((R)-piperidin-3-ylamino)-5-(quinolin-2-yl)pyrimidin-4(3H)-one,
2-(5-(4-methoxyphenyl)-2,5-diazabicyclo[2.2.1]heptan-2-yl)-6-((R)-piperidin-3-ylamino)-5-(quinolin-2-yl)pyrimidin-4(3H)-one,
(R)-5-(benzo[d]oxazol-2-yl)-2-morpholino-6-(piperidin-3-ylamino)pyrimidin-4(3H)-one,
(R)-5-(6-(tert-butyl)pyridin-2-yl)-2-morpholino-6-(piperidin-3-ylamino)pyrimidin-4(3H)-one,
(R)-5-(6-(1H-pyrrol-1-yl)pyrazin-2-yl)-2-morpholino-6-(piperidin-3-ylamino)pyrimidin-4(3H)-one,
(R)-2-morpholino-6-(piperidin-3-ylamino)-5-(pyridin-2-yl)pyrimidin-4(3H)-one,
(R)-2-morpholino-6-(piperidin-3-ylamino)-5-(4-(3-(trifluoromethyl)phenyl)thiazol-2-yl)pyrimidin-4(3H)-one,
(R)-5-(4-(2-fluorophenyl)thiazol-2-yl)-2-morpholino-6-(piperidin-3-ylamino)pyrimidin-4(3H)-one,
(R)-5-(4-(4-chlorophenyl)thiazol-2-yl)-2-morpholino-6-(piperidin-3-ylamino)pyrimidin-4(3H)-one,
(R)-5-(4-(3,5-difluorophenyl)thiazol-2-yl)-2-morpholino-6-(piperidin-3-ylamino)pyrimidin-4(3H)-one,
(R)-5-(4-(3-fluorophenyl)thiazol-2-yl)-2-morpholino-6-(piperidin-3-ylamino)pyrimidin-4(3H)-one,
(R)-5-(4-(2,5-difluorophenyl)thiazol-2-yl)-2-morpholino-6-(piperidin-3-ylamino)pyrimidin-4(3H)-one,
(R)-2-morpholino-6-(piperidin-3-ylamino)-5-(4-(5-(trifluoromethyl)pyridin-2-yl)thiazol-2-yl)pyrimidin-4(3H)-one,
(R)-2-morpholino-6-(piperidin-3-ylamino)-5-(4-(pyridin-2-yl)thiazol-2-yl)pyrimidin-4(3H)-one,
5-(benzo[d]thiazol-2-yl)-2-morpholino-6-(quinuclidin-3-ylamino)pyrimidin-4(3H)-one,
5-(benzo[d]thiazol-2-yl)-6-(((3R,5S)-5-methyl)pyrrolidin-3-ylamino)-2-morpholinopyrimidin-4(3H)-one,
5-(benzo[d]thiazol-2-yl)-6-(((3R,5R)-5-methyl)pyrrolidin-3-ylamino)-2-morpholinopyrimidin-4(3H)-one,
6-((1S,4R,6R)-2-azabicyclo[2.2.1]heptan-6-ylamino)-5-(benzo[d]thiazol-2-yl)-2-morpholinopyrimidin-4(3H)-one,
(R)-5-(benzo[d]thiazol-2-yl)-6-((5,5-difluoropiperidin-3-ylamino)-2-morpholinopyrimidin-4(3H)-one,
5-(benzo[d]thiazol-2-yl)-6-(((3S,4S)-4-fluoropiperidin-3-ylamino)-2-morpholinopyrimidin-4(3H)-one,
(R)-5-(2-(1H-pyrrol-1-yl)thiazol-4-yl)-2-morpholino-6-(piperidin-3-ylamino)pyrimidin-4(3H)-one,
(R)-5-(6-(1H-pyrrol-1-yl)pyridin-2-yl)-2-morpholino-6-(piperidin-3-ylamino)pyrimidin-4(3H)-one,
(R)-2-morpholino-5-(6-(2-oxopyrrolidin-1-yl)pyridin-2-yl)-6-(piperidin-3-ylamino)pyrimidin-4(3H)-one,
(R)-5-(2-(1H-pyrazol-1-yl)thiazol-4-yl)-2-morpholino-6-(piperidin-3-ylamino)pyrimidin-4(3H)-one,
(R)-2-morpholino-5-(2-phenylthiazol-4-yl)-6-(piperidin-3-ylamino)pyrimidin-4(3H)-one,
(R)-5-(2-(1H-imidazol-1-yl)thiazol-4-yl)-2-morpholino-6-(piperidin-3-ylamino)pyrimidin-4(3H)-one,
(R)-5-fluoro-2'-morpholino-6'-(piperidin-3-ylamino)-[2,5'-bipyrimidin]-4'(3'H)-one,
(R)-6-(2-morpholino-6-oxo-4-(piperidin-3-ylamino)-1,6-dihydropyrimidin-5-yl)picolinonitrile,
(R)-2-(2-morpholino-6-oxo-4-(piperidin-3-ylamino)-1,6-dihydropyrimidin-5-yl)isonicotinonitrile, (R)-6-(2-morpholino-6-oxo-4-(piperidin-3-ylamino)-1,6-dihydropyrimidin-5-yl)nicotinonitrile, (R)-5-(5-cyclopropylpyridin-2-yl)-2-morpholino-6-(piperidin-3-ylamino)pyrimidin-4(3H)-one, (R)-5-(isoquinolin-3-yl)-2-morpholino-6-(piperidin-3-ylamino)pyrimidin-4(3H)-one, (R)-5-(1,3-benzothiazol-2-yl)-2-(1-methylpiperidin-4-yl)-6-[[(3R)-piperidin-3-yl]amino]-3,4-dihydropyrimidin-4-one,
(R)-N-[1-(2,4-difluorophenyl)-3-[4-(methylsulfamoyl)phenyl]-1H-pyrazol-5-yl]pyrazolo[1,5-a]pyrimidine-3-carboxamide,
(R)-5-(1,3-benzothiazol-2-yl)-6-[[(3R)-piperidin-3-yl]amino]-2-[1-(propan-2-yl)piperidin-4-yl]-3,4-dihydropyrimidin-4-one,
5-(1,3-benzothiazol-2-yl)-2-[1-(cyclopropylmethyl)piperidin-4-yl]-6-[[(3R)-piperidin-3-yl]amino]-3,4-dihydropyrimidin-4-one,
(R)-5-(1,3-benzothiazol-2-yl)-2-(1-cyclobutylpiperidin-4-yl)-6-[(piperidin-3-yl)amino]-3,4-dihydropyrimidin-4-one,
5-(1,3-benzothiazol-2-yl)-2-(1-cyclopentylpiperidin-4-yl)-6-[[(3R)-piperidin-3-yl]amino]-3,4-dihydropyrimidin-4-one,
(R)-5-(1,3-benzothiazol-2-yl)-2-(1-cyclohexylpiperidin-4-yl)-6-[(piperidin-3-yl)amino]-3,4-dihydropyrimidin-4-one,
5-(1,3-benzothiazol-2-yl)-2-[1-(oxolan-3-yl)piperidin-4-yl]-6-[[(3R)-piperidin-3-yl]amino]pyrimidin-4-ol,
(R)-5-(benzo[d]thiazol-2-yl)-6-(piperidin-3-ylamino)-2-(1-(tetrahydro-2H-pyran-4-yl) piperidin-4-yl) pyrimidin-4(3H)-one,
(R) 5-(1,3-benzothiazol-2-yl)-2-(1-methanesulfonylpiperidin-4-yl)-6-[[(3R)-piperidin-3-yl]amino]-3,4-dihydropyrimidin-4-one,
5-(1,3-benzothiazol-2-yl)-2-[1-(ethanesulfonyl)piperidin-4-yl]-6-[[(3R)-piperidin-3-yl]amino]-3,4-dihydropyrimidin-4-one,
5-(1,3-benzothiazol-2-yl)-6-[[(3R)-piperidin-3-yl]amino]-2-[1-(propane-2-sulfonyl)piperidin-4-y1]-3,4-dihydropyrimidin-4-one,
(R)-5-(1,3-benzothiazol-2-yl)-2-[1-(cyclopropanesulfonyl)piperidin-4-yl]-6-[(piperidin-3-yl)amino]-3,4-dihydropyrimidin-4-one,
methyl) 4-[(R)-5-(1,3-benzothiazol-2-yl)-6-oxo-4-[[(3R)-piperidin-3-yl]amino]-1,6-dihydropyrimidin-2-yl]piperidine-1-carboxylate,
(R)-4-[5-(1,3-benzothiazol-2-yl)-6-oxo-4-[[(3R)-piperidin-3-yl]amino]-1,6-dihydropyrimidin-2-yl]-N-methylpiperidine-1-carboxamide,
2-(1-acetylpiperidin-4-yl)-5-(1,3-benzothiazol-2-yl)-6-[[(3R)-piperidin-3-yl]amino]-4,5-dihydropyrimidin-4-one,
(R)-5-(benzo[d]thiazol-2-yl)-6-(piperidin-3-ylamino)-2-(1-(pyridin-2-yl)piperidin-4-yl)pyrimidin-4(3H)-one,
(R)-5-(benzo[d]thiazol-2-yl)-6-(piperidin-3-ylamino)-2-(1-(pyrazin-2-yl)piperidin-4-yl)pyrimidin-4(3H)-one,
(R)-5-(benzo[d]thiazol-2-yl)-6-(piperidin-3-ylamino)-2-(1-(pyrimidin-2-yl)piperidin-4-yl)pyrimidin-4(3H)-one,
(R)-5-(benzo[d]thiazol-2-yl)-6-(piperidin-3-ylamino)-2-(1-(pyridin-3-yl)piperidin-4-yl)pyrimidin-4(3H)-one,
5-(1,3-benzothiazol-2-yl)-6-[(2,3-dihydroxypropyl)amino]-2-(morpholin-4-yl)-3,4-dihydropyrimidin-4-one,
6-[[(1R,2S)-2-aminocyclopropyl]amino]-5-(1,3-benzothiazol-2-yl)-2-(morpholin-4-yl)-3,4-dihydropyrimidin-4-one,
5-(1,3-benzothiazol-2-yl)-6-[(3-methylpiperidin-3-yl)amino]-2-(morpholin-4-yl)-3,4-dihydropyrimidin-4-one,
2-[[5-(1,3-benzothiazol-2-yl)-2-(morpholin-4-yl)-6-oxo-1,6-dihydropyrimidin-4-yl]amino]acetamide,
2-[[5-(1,3-benzothiazol-2-yl)-2-(morpholin-4-yl)-6-oxo-1,6-dihydropyrimidin-4-yl]amino]ethanimidamide,
5-(benzo[d]thiazol-2-yl)-6-(2-(2-hydroxyethylamino)ethylamino)-2-morpholinopyrimidin-4(3H)-one,
5-(1,3-benzothiazol-2-yl)-6-[(1-methylpiperidin-3-yl)amino]-2-(morpholin-4-yl)-3,4-dihydropyrimidin-4-one,
6-[(azetidin-3-yl)amino]-5-(1,3-benzothiazol-2-yl)-2-(morpholin-4-yl)-3,4-dihydropyrimidin-4-one,
5-(1,3-benzothiazol-2-yl)-2-(morpholin-4-yl)-6-[(piperidin-2-yl)methyl)amino]-3,4-dihydropyrimidin-4-one,
5-(1,3-benzothiazol-2-yl)-6-[[(1-ethylpyrrolidin-2-yl)methyl]amino]-2-(morpholin-4-yl)-3,4-dihydropyrimidin-4-one,
5-(1,3-benzothiazol-2-yl)-2-(morpholin-4-yl)-6-[[2-(piperazin-1-yl)ethyl]amino]-3,4-dihydropyrimidin-4-one,
5-(1,3-benzothiazol-2-yl)-2-(morpholin-4-yl)-6-[[2-(piperidin-1-yl)ethyl]amino]-3,4-dihydropyrimidin-4-one,
5-(1,3-benzothiazol-2-yl)-6-[[2-(4-hydroxypiperidin-1-yl)ethyl]amino]-2-(morpholin-4-yl)-3,4-dihydropyrimidin-4-one,
5-(1, 3-benzothiazol-2-yl)-2-(morpholin-4-yl)-6-[[2-(pyrrolidin-1-yl) ethyl]amino]-3,4-dihydropyrimidin-4-one,
5-(1,3-benzothiazol-2-yl)-6-[[2-(dimethylamino)ethyl]amino]-2-(morpholin-4-yl)-3,4-dihydropyrimidin-4-one,
N-(2-[[5-(1,3-benzothiazol-2-yl)-2-(morpholin-4-yl)-6-oxo-1,6-dihydropyrimidin-4-yl]amino]ethyl)acetamide,
5-(benzo[d]thiazol-2-yl)-6-(1-hydroxybutan-2-ylamino)-2-morpholinopyrimidin-4(3H)-one,
6-(2-aminocyclohexylamino)-5-(benzo[d]thiazol-2-yl)-2-morpholinopyrimidin-4(3H)-one,
6-(2-(1H-imidazol-2-yl)ethylamino)-5-(benzo[d]thiazol-2-yl)-2-morpholinopyrimidin-4(3H)-one, 5-(benzo[d]thiazol-2-yl)-6-(2-hydroxypropylamino)-2-morpholinopyrimidin-4(3H)-one,
(R)-5-(benzo[d]thiazol-2-yl)-6-(1-hydroxy-4-methylpentan-2-ylamino)-2-morpholinopyrimidin-4(3H)-one,
5-(benzo[d]thiazol-2-yl)-6-((1S,2R)-2-hydroxy-2,3-dihydro-1H-inden-1-ylamino)-2-morpholinopyrimidin-4(3H)-one,
5-(benzo[d]thiazol-2-yl)-6-(4-hydroxycyclohexylamino)-2-morpholinopyrimidin-4(3H)-one,
5-(benzo[d]thiazol-2-yl)-6-(2-hydroxycyclohexylamino)-2-morpholinopyrimidin-4(3H)-one,
5-(benzo[d]thiazol-2-yl)-6-(1,3-dihydroxypropan-2-ylamino)-2-morpholinopyrimidin-4(3H)-one,
5-(1,3-benzothiazol-2-yl)-2-(morpholin-4-yl)-6-[(piperidin-4-ylmethyl)amino]-3,4-dihydropyrimidin-4-one,
6-[[2-(dimethylamino)ethyl]amino]-2-(morpholin-4-yl)-5-(quinolin-2-yl)-3,4-dihydropyrimidin-4-one,
6-([2-[(2-hydroxyethyl)amino]ethyl]amino)-2-(morpholin-4-yl)-5-(quinolin-2-yl)-3,4-dihydropyrimidin-4-one,
6-[(1-methyl)piperidin-3-yl)amino]-2-(morpholin-4-yl)-5-(quinolin-2-yl)-3,4-dihydropyrimidin-4-one,
6-[(azetidin-3-yl)amino]-2-(morpholin-4-yl)-5-(quinolin-2-yl)-3,4-dihydropyrimidin-4-one,
2-morpholino-6-(piperidin-2-ylmethylamino)-5-(quinolin-2-yl)pyrimidin-4(3H)-one,
6-((l-ethyl)pyrrolidin-2-ylmethylamino)-2-morpholino-5-(quinolin-2-yl)pyrimidin-4(3H)-one,
2-(morpholin-4-yl)-6-[[2-(piperidin-1-yl)ethyl]amino]-5-(quinolin-2-yl)-3,4-dihydropyrimidin-4-one, 2-(morpholin-4-yl)-6-[[2-(pyrrolidin-1-yl)ethyl]amino]-5-(quinolin-2-yl)-3,4-dihydropyrimidin-4-one,
6-[(3-methylpiperidin-3-yl)amino]-2-(morpholin-4-yl)-5-(quinolin-2-yl)-3,4-dihydropyrimidin-4-one,
6-[(2,3-dihydroxypropyl)amino]-2-(morpholin-4-yl)-5-(quinolin-2-yl)-3,4-dihydropyrimidin-4-one,
6-[[2-(4-hydroxypiperidin-1-yl)ethyl]amino]-2-(morpholin-4-yl)-5-(quinolin-2-yl)-3,4-dihydropyrimidin-4-one,
2-(morpholin-4-yl)-6-[[2-(pyrrolidin-1-yl)ethyl]amino]-5-(quinolin-2-yl)-3,4-dihydropyrimidin-4-one,
5-(1,3-benzothiazol-2-yl)-2-(oxan-4-yl)-6-[[(3R)-piperidin-3-yl]amino]-4,5-dihydropyrimidin-4-one,
5-(1,3-benzothiazol-2-yl)-2-[2-(hydroxymethyl)morpholin-4-yl]-6-[[(3R)-piperidin-3-yl]amino]-3,4-dihydropyrimidin-4-one,
5-(benzo[d]thiazol-2-yl)-2-(2-(methoxymethyl)morpholino)-6-((R)-piperidin-3-ylamino)pyrimidin-4(3H)-one,
4-(5-(benzo[d]thiazol-2-yl)-6-oxo-4-((R)-piperidin-3-ylamino)-1,6-dihydropyrimidin-2-yl)-N-methylmorpholine-2-carboxamide,
(R)-2-(azetidin-1-yl)-5-(benzo[d]thiazol-2-yl)-6-(piperidin-3-ylamino)pyrimidin-4(3H)-one,
(R)-5-(benzo[d]thiazol-2-yl)-2-(dimethylamino)-6-(piperidin-3-ylamino)pyrimidin-4(3H)-one,
5-(benzo[d]thiazol-2-yl)-2-(3-methylpiperidin-1-yl)-6-((R)-piperidin-3-ylamino)pyrimidin-4(3H)-one,
5-(benzo[d]thiazol-2-yl)-2-((1S,2S)-2-hydroxy-2,3-dihydro-1H-inden-1-ylamino)-6-((R)-piperidin-3-ylamino)pyrimidin-4(3H)-one,
(R)-5-(benzo[d]thiazol-2-yl)-2-((2-hydroxyethyl)(methylamino)-6-(piperidin-3-ylamino)pyrimidin-4(3H)-one,
(R)-5-(benzo[d]thiazol-2-yl)-2-(4-methoxypiperidin-1-yl)-6-(piperidin-3-ylamino)pyrimidin-4(3H)-one,
5-(benzo[d]thiazol-2-yl)-2-(2,6-dimethylmorpholino)-6-((R)-piperidin-3-ylamino)pyrimidin-4(3H)-one,
5-(benzo[d]thiazol-2-yl)-2-(2,6-dimethylmorpholino)-6-((R)-piperidin-3-ylamino)pyrimidin-4(3H)-one,
5-(1,3-benzothiazol-2-yl)-2-(3,5-dimethylpiperidin-1-yl)-6-[[(3R)-piperidin-3-yl]amino]-3,4-dihydropyrimidin-4-one,
5-(1,3-benzothiazol-2-yl)-2-(4-methylpiperidin-1-yl)-6-[[(3R)-piperidin-3-yl]amino]-3,4-dihydropyrimidin-4-one,
5-(1,3-benzothiazol-2-yl)-2-[[(1S,2R)-2-hydroxy-2,3-dihydro-1H-inden-1-yl]amino]-6-[[(3R)-piperidin-3-yl]amino]pyrimidin-4-ol,
5-(1,3-benzothiazol-2-yl)-2-[[(1R,2S)-2-hydroxy-2,3-dihydro-1H-inden-1-yl]amino]-6-[[(3R)-piperidin-3-yl]amino]pyrimidin-4-ol,
5-(1,3-benzothiazol-2-yl)-2-[8-oxa-3-azabicyclo[3.2.1]octan-3-yl]-6-[[(3R)-piperidin-3-yl]amino]-3,4-dihydropyrimidin-4-one,
5-(1,3-benzothiazol-2-yl)-2-[(4-hydroxycyclohexyl)(methyl)amino]-6-[[(3R)-piperidin-3-yl]amino]-3,4-dihydropyrimidin-4-one,
(R)-2-(5-(benzo[d]thiazol-2-yl)-6-oxo-4-(piperidin-3-ylamino)-1,6-dihydropyrimidin-2-ylamino)acetamide,
(S)-4-(5-(benzo[d]thiazol-2-yl)-6-oxo-4-((R)-piperidin-3-ylamino)-1,6-dihydropyrimidin-2-ylamino)-4,5-dihydro-1H-benzo[b]azepin-2(3H)-one,
(R)-4-(5-(benzo[d]thiazol-2-yl)-6-oxo-4-((R)-piperidin-3-ylamino)-1,6-dihydropyrimidin-2-ylamino)-4,5-dihydro-1H-benzo[b]azepin-2(3H)-one,
5-(1,3-benzothiazol-2-yl)-2-[4-(hydroxymethyl)piperidin-1-yl]-6-[[(3R)-piperidin-3-yl]amino]-3,4-dihydropyrimidin-4-one,
5-(benzo[d]thiazol-2-yl)-2-((S)-3-hydroxypyrrolidin-1-yl)-6-((R)-piperidin-3-ylamino)pyrimidin-4(3H)-one,
5-(1,3-benzothiazol-2-yl)-2-[benzyl(methyl)amino]-6-[[(3R)-piperidin-3-yl]amino]-3,4-dihydropyrimidin-4-one,
5-(5-methyl-1,3-benzothiazol-2-yl)-2-(morpholin-4-yl)-6-[[(3R)-piperidin-3-yl]amino]-3,4-dihydropyrimidin-4-one, 5-(1,3-benzothiazol-2-yl)-2-(piperidin-1-yl)-6-[[(3R)-piperidin-3-yl]amino]-3,4-dihydropyrimidin-4-one,
5-(1,3-benzothiazol-2-yl)-2-[[(1S)-2-hydroxy-1-phenylethyl](methyl)amino]-6-[[(3R)-piperidin-3-yl]amino]-3,4-dihydropyrimidin-4-one,
5-(1,3-benzothiazol-2-yl)-2-[(2-hydroxyethyl)amino]-6-[[(3R)-piperidin-3-yl]amino]-3,4-dihydropyrimidin-4-one,
(R)-5-(benzo[d]thiazol-2-yl)-2-(4,4-difluoropiperidin-1-yl)-6-(piperidin-3-ylamino)pyrimidin-4(3H)-one,
5-(1,3-benzothiazol-2-yl)-2-(decahydroisoquinolin-2-yl)-6-[[(3R)-piperidin-3-yl]amino]-3,4-dihydropyrimidin-4-one,
5-(1,3-benzothiazol-2-yl)-2-(2-methylpiperidin-1-yl)-6-[[(3R)-piperidin-3-yl]amino]-3,4-dihydropyrimidin-4-one,
5-(1,3-benzothiazol-2-yl)-2-[(3R)-3-hydroxypyrrolidin-1-yl]-6-[[(3R)-piperidin-3-yl]amino]-3,4-dihydropyrimidin-4-one,
2-(4-acetylpiperazin-1-yl)-5-(1,3-benzothiazol-2-yl)-6-[[(3R)-piperidin-3-yl]amino]-3,4-dihydropyrimidin-4-one,
5-(1,3-benzothiazol-2-yl)-2-[2-oxa-6-azaspiro[3.3]heptan-6-yl]-6-[[(3R)-piperidin-3-yl]amino]-3,4-dihydropyrimidin-4-one,
1-[5-(1,3-benzothiazol-2-yl)-6-oxo-4-[[(3R)-piperidin-3-yl]amino]-1,6-dihydropyrimidin-2-yl]piperidine-4-carboxamide,
5-(benzo[d]thiazol-2-yl)-2-(2-(4-chlorophenyl)-2-methylmorpholino)-6-((R)-piperidin-3-ylamino)pyrimidin-4(3H)-one,
4-[5-(1,3-benzothiazol-2-yl)-6-oxo-4-[[(3R)-piperidin-3-yl]amino]-1,6-dihydropyrimidin-2-yl]morpholine-2-carboxylic acid,
ethyl 4-[5-(1,3-benzothiazol-2-yl)-6-oxo-4-[[(3R)-piperidin-3-yl]amino]-1,6-dihydropyrimidin-2-yl]morpholine-2-carboxylate,
2-(4-aminopiperidin-1-yl)-5-(1,3-benzothiazol-2-yl)-6-[[(3R)-piperidin-3-yl]amino]-3,4-dihydropyrimidin-4-one,
Benzyl N-[1-[5-(1,3-benzothiazol-2-yl)-6-oxo-4-[[(3R)-piperidin-3-yl]amino]-1,6-dihydropyrimidin-2-yl]piperidin-4-yl]carbamate,
5-(1,3-benzothiazol-2-yl)-6-[[(3R)-piperidin-3-yl]amino]-2-[7-(pyrimidin-2-yl)-2,7-diazaspiro[4.4]nonan-2-yl]-3,4-dihydropyrimidin-4-one,
5-(1,3-benzothiazol-2-yl)-2-[7-methyl-2,7-diazaspiro[4.4]nonan-2-yl]-6-[[(3R)-piperidin-3-yl]amino]-3,4-dihydropyrimidin-4-one,
2-[7-acetyl-2,7-diazaspiro[4.4]nonan-2-yl]-5-(1,3-benzothiazol-2-yl)-6-[[(3R)-piperidin-3-yl]amino]-3,4-dihydropyrimidin-4-one,
5-(1,3-benzothiazol-2-yl)-2-[7-benzyl-2,7-diazaspiro[4.4]nonan-2-yl]-6-[[(3R)-piperidin-3-yl]amino]-3,4-dihydropyrimidin-4-one, 6-[4-[7-(benzenesulfonyl)-2,7-diazaspiro[4.4]nonan-2-yl]piperidin-1-yl]-3-(1,3-benzothiazol-2-yl)-4-[[(3R)-piperidin-3-yl]amino]-1,2-dihydropyridin-2-one, 6-(7-amino-1,2,3,4-tetrahydroisoquinolin-2-yl)-3-(1,3-benzothiazol-2-yl)-4-[[(3R)-piperidin-3-yl]amino]-1,2-dihydropyridin-2-one, 5-(1,3-benzothiazol-2-yl)-2-[7-(4-methoxyphenyl)-2,7-diazaspiro[4.4]nonan-2-yl]-6-[[(3R)-piperidin-3-yl]amino]-3,4-dihydropyrimidin-4-one, 5-(1,3-benzothiazol-2-yl)-2-[7-(4-chlorophenyl)-2,7-diazaspiro[4.4]nonan-2-yl]-6-[[(3R)-piperidin-3-yl]amino]-3,4-dihydropyrimidin-4-one, 5-(1,3-benzothiazol-2-yl)-2-[(benzylamino)piperidin-1-yl]-6-[[(3R)-piperidin-3-yl]amino]-3,4-dihydropyrimidin-4-one, N-[1-[5-(1,3-benzothiazol-2-yl)-6-oxo-4-[[(3R)-piperidin-3-yl]amino]-1,6-dihydropyrimidin-2-yl]piperidin-4-yl]acetamide, 5-(1,3-benzothiazol-2-yl)-2-[7-phenyl-2,7-diazaspiro[4.4]nonan-2-yl]-6-[[(3R)-piperidin-3-yl]amino]-3,4-dihydropyrimidin-4-one, 3-(1,3-benzothiazol-2-yl)-6-[2,7-diazaspiro[3.5]nonan-7-yl]-4-[[(3R)-piperidin-3-yl]amino]-1,2-dihydropyridin-2-one, tert-butyl 7-[5-(1,3-benzothiazol-2-yl)-6-oxo-4-[[(3R)-piperidin-3-yl]amino]-1,6-dihydropyridin-2-yl]-2,7-diazaspiro[3.5]nonane-2-carboxylate, 2-(morpholin-4-yl)-6-[[(3R)-piperidin-3-yl]amino]-5-[5-(trifluoromethyl)-1,3-benzothiazol-2-y1]-3,4-dihydropyrimidin-4-one, 2-(morpholin-4-yl)-6-[[(3R)-piperidin-3-yl]amino]-5-[7-(trifluoromethyl)-1,3-benzothiazol-2-yl]-3,4-dihydropyrimidin-4-one, (R)-5-(7-chlorobenzo[d]thiazol-2-yl)-2-morpholino-6-(piperidin-3-ylamino)pyrimidin-4(3H)-one, (R)-5-(7-methylbenzo[d]thiazol-2-yl)-2-morpholino-6-(piperidin-3-ylamino)pyrimidin-4(3H)-one, 5-(5-methyl-1,3-benzothiazol-2-yl)-2-(morpholin-4-yl)-6-[[(3R)-piperidin-3-yl]amino]-3,4-dihydropyrimidin-4-one, (R)-5-(5-tert-butylbenzo[d]thiazol-2-yl)-2-morpholino-6-(piperidin-3-ylamino)pyrimidin-4(3H)-one, (R)-5-(5-chlorobenzo[d]thiazol-2-yl)-2-morpholino-6-(piperidin-3-ylamino)pyrimidin-4(3H)-one, 5-(7-cyclopropyl-1,3-benzothiazol-2-yl)-2-(morpholin-4-yl)-6-[[(3R)-piperidin-3-yl]amino]-3,4-dihydropyrimidin-4-one, 5-(5-bromo-1,3-benzothiazol-2-yl)-2-(morpholin-4-yl)-6-[[(3R)-piperidin-3-yl]amino]-3,4-dihydropyrimidin-4-one, 5-(5-cyclopropyl-1,3-benzothiazol-2-yl)-2-(morpholin-4-yl)-6-[[(3R)-piperidin-3-yl]amino]-3,4-dihydropyrimidin-4-one, (R)-2-(2-morpholino-6-oxo-4-(piperidin-3-ylamino)-1,6-dihydropyrimidin-5-yl)benzo[d]thiazole-5-carboxamide, 2-[2-(morpholin-4-yl)-6-oxo-4-[[(3R)-piperidin-3-yl]amino]-1,6-dihydropyrimidin -5-yl]-1,3-benzothiazole-5-carbonitrile,

[4-(4-fluorophenyl)-1,3-thiazol-2-yl]-6-[[(3R)-piperidin-3-yl]amino]-2[4-(pyridin-3-yl)piperazin-1-yl]-3,4-dihydropyrimidin-4-one, 5-[4-(4-fluorophenyl)-1,3-thiazol -2-yl]-6-[[(3R)-piperidin-3-yl]amino]-2-[4-(pyrimidin-2-yl)piperazin-1-yl]-3,4-dihydropyrimidin-4-one, 5-[4-(4-fluorophenyl)-1,3-thiazol-2-yl]-6-[[(3R)-piperidin-3-yl]amino]-2-(1,2,3,4-tetrahydroisoquinolin-2-yl)pyrimidin-4-ol, 5-(4-[[(trans, rac)-2-aminocyclohexyl]amino]-1,3-benzothiazol-2-yl)-2-(morpholin-4-yl)-6-[[(3R)-piperidin-3-yl]amino]-3,4-dihydropyrimidin-4-one, 5-[(cis, rac)4-[(2-aminocyclohexyl)amino]-1,3-benzothiazol-2-yl]-2-(morpholin-4-yl)-6-[[(3R)-piperidin-3-yl]amino]-3,4-dihydropyrimidin-4-one, 5-(4-((1S,2R)-2-aminocyclohexylamino)benzo[d]thiazol-2-yl)-2-morpholino-6-((R)-piperidin-3-ylamino)pyrimidin-4(3H)-one, 5-(4-((1R,2S)-2-aminocyclohexylamino)benzo[d]thiazol-2-yl)-2-morpholino-6-((R)-piperidin-3-ylamino) pyrimidin-4(3H)-one, and 5-[4-[(2-aminoethyl)amino]-1,3-benzothiazol-2-yl]-2-(morpholin-4-yl)-6-[[(3R)-piperidin-3-yl]amino]-3,4-dihydropyrimidin-4-one;

or a pharmaceutically acceptable salt thereof.

* * * * *